US012747218B2

(12) United States Patent
Padia et al.

(10) Patent No.: US 12,747,218 B2
(45) **Date of Patent: *Sep. 29, 2026**

(54) DERIVATIVES OF SUBSTITUTED MORPHOLINES AND USES THEREOF

(71) Applicant: Supernus Pharmaceuticals, Inc., Rockville, MD (US)

(72) Inventors: Janak Khimchand Padia, Germantown, MD (US); Chungping Yu, Gaithersburg, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/740,059

(22) Filed: Jun. 11, 2024

(65) Prior Publication Data

US 2024/0343699 A1 Oct. 17, 2024

Related U.S. Application Data

(63) Continuation of application No. 18/617,255, filed on Mar. 26, 2024.

(60) Provisional application No. 63/454,930, filed on Mar. 27, 2023.

(51) Int. Cl.

| | |
|---|---|
| ***C07D 265/30*** | (2006.01) |
| ***A61K 31/5375*** | (2006.01) |
| ***A61K 31/5377*** | (2006.01) |
| ***C07D 413/14*** | (2006.01) |

(52) U.S. Cl.

CPC ........ *C07D 265/30* (2013.01); *A61K 31/5375* (2013.01); *A61K 31/5377* (2013.01); *C07D 413/14* (2013.01)

(58) Field of Classification Search

None

See application file for complete search history.

(56) References Cited

U.S. PATENT DOCUMENTS

| | | | |
|---|---|---|---|
| 8,748,472 | B2 | 6/2014 | Chang et al. |
| 8,957,206 | B2 | 2/2015 | Hanbauer et al. |
| 9,403,783 | B2 | 8/2016 | Liang et al. |
| 9,434,703 | B2 | 9/2016 | Liang et al. |
| 9,562,011 | B2 | 2/2017 | Hanbauer et al. |
| 9,744,137 | B2 | 8/2017 | Nangia et al. |
| 9,802,893 | B2 | 10/2017 | Hanbauer et al. |
| 10,005,743 | B2 | 6/2018 | Liang et al. |
| 10,081,595 | B2 | 9/2018 | Hanbauer et al. |
| 10,149,853 | B2 | 12/2018 | Chang et al. |
| 10,160,733 | B2 | 12/2018 | Liang et al. |
| 10,676,432 | B2 | 6/2020 | Hanbauer et al. |
| 11,077,114 | B2 | 8/2021 | Chang et al. |
| 11,117,862 | B2 | 9/2021 | Hanbauer et al. |
| 11,324,753 | B2 | 5/2022 | Breder |
| 11,458,143 | B2 | 10/2022 | Breder |
| 11,634,415 | B2 | 4/2023 | Padia |
| 11,919,889 | B2 | 3/2024 | Padia |
| 11,964,951 | B2 | 4/2024 | Sun et al. |
| 12,121,523 | B2 | 10/2024 | Breder |
| 2010/0069390 | A1 | 3/2010 | Breder |
| 2013/0289035 | A1 | 10/2013 | Breder |
| 2015/0290202 | A1 | 10/2015 | Breder |
| 2017/0312289 | A1 | 11/2017 | Dugan Stocks et al. |
| 2019/0300492 | A1 | 10/2019 | Liang et al. |
| 2020/0246348 | A1 | 8/2020 | Dugan Stocks et al. |
| 2021/0322429 | A1 | 10/2021 | Chang et al. |
| 2022/0016128 | A1 | 1/2022 | Stocks et al. |
| 2022/0024885 | A1 | 1/2022 | Liang et al. |
| 2022/0298150 | A1 | 9/2022 | Padia |
| 2023/0295100 | A1 | 9/2023 | Sun et al. |
| 2024/0182458 | A1 | 6/2024 | Padia |

FOREIGN PATENT DOCUMENTS

| | | | | |
|---|---|---|---|---|
| GB | 1243991 A * | 8/1971 | ........... C07D 211/22 |
| WO | WO-9822110 A1 * | 5/1998 | ................ C07F 9/59 |
| WO | WO-2008/027557 A2 | 3/2008 | |
| WO | WO-2010/028207 A2 | 3/2010 | |
| WO | WO-2011/123497 A1 | 10/2011 | |
| WO | WO-2011/130194 A2 | 10/2011 | |
| WO | WO-2014/042688 A1 | 3/2014 | |
| WO | WO-2017/189892 A1 | 11/2017 | |
| WO | WO-2022/198062 A2 | 9/2022 | |
| WO | WO-2023/177845 A1 | 9/2023 | |

OTHER PUBLICATIONS

Callahan et al., "Differential effects of alkaloids on memory in rodents," Scientific Reports, 2021, 11(1):9843, 1-9.

Callahan et al., "Effects of the nicotinic alpha7 receptor partial agonist GTS-21 on NMDA-glutamatergic receptor related deficits in sensorimotor gating and recognition memory in rats," Psychopharmacology, 2014, 231, 3695-3706.

(Continued)

*Primary Examiner* — Jeffrey S Lundgren
*Assistant Examiner* — Eric Tran
(74) *Attorney, Agent, or Firm* — Foley & Lardner LLP

(57) ABSTRACT

A compound of Formula I includes a stereoisomer thereof and/or a salt thereof; wherein $R^1$ is a substituted alkane group, a heterocylic group, or a pyridine group; X is hydrogen, a halogen, an amino acid residue, a substituted amino acid residue, an alkyl group, or an ester. Such compounds may be used in pharmaceutical compositions and for the treatment of central nervous system (CNS) disorders:

(I)

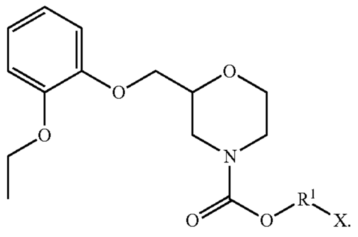

19 Claims, 110 Drawing Sheets

(56) References Cited

OTHER PUBLICATIONS

Callahan et al., "Positive allosteric modulator of alpha 7 nicotinic-acetylcholine receptors, PNU-120596 augments the effects of donepezil on learning and memory in aged rodents and non-human primates," Neuropharmacology, 2013, 67:201-212.
Callahan et al., "Tropisetron sensitizes alpha7 containing nicotinic receptors to low levels of acetylcholine in vitro and improves memory-related task performance in young and aged animals," Neuropharmacology, 2017, 117:422-433.
Floresco et al., "Inactivation of the medial prefrontal cortex of the rat impairs strategy set-shifting, but not reversal learning, using a novel, automated procedure," Behav. Brain Res., Jun. 26, 2008, 190:85-96.
Gazarini et al., "Protein synthesis in dorsal hippocampus supports the drug tolerance induced by prior elevated plus-maze experience," Neuroscience. 2011, 179:179-187.
Mork et al., "Vortioxetine (Lu AA21004), a novel multimodal antidepressant, enhances memory in rats," Pharmacology, Biochemistry and Behavior, 2013, 105:41-50.
Pehrson et al., "Task- and Treatment Length-Dependent Effects of Vortioxetine on Scopolamine-Induced Cognitive Dysfunction and Hippocampal Extracellular Acetylcholine in Rats," J. Pharmacol. Exp. Ther., Sep. 2016, 358:472-482.
Terry et al., "R=(+( and S-(−) Isomers of Cotinine Augments Cholinergic Responses In Vitro and In Vivo," The Journal of Pharmacology and Experimental Therapeutics, Feb. 2015, 352(2),:405-418.
Guilleminault et al., "Viloxane Hydrochloride in Narcolepsy: A Preliminary Report," Sleep, Mar. 1, 1986, 9(1):275-279.
Kayki-Mutlu et al., "A year in pharmacology: new drugs approved by the US Food and Drug Administration in 2021," Naunyn-Schmiedeberg's Archives of Pharmacology, May 11, 2022, 395(8):867-885.
Melloni et al., "Potential antidepressant agents. alpha-Aryloxy-benzyl derivatives of ethanolamine and morpholine," Eur. J. Med., Chem.—Chim. Ther., 1984, 235-242.
U.S. Appl. No. 17/358,920, filed Jun. 25, 2021, Chang et al.
U.S. Appl. No. 18/891,542, filed Sep. 20, 2024, Breder, Christopher D.

* cited by examiner

Percent Remaining of COMPOUND A in Human Plasma

Percent Remaining of COMPOUND B in Human Plasma

Percent Remaining of COMPOUND C in Human Plasma

Hemolytic Potential in Human Blood after Exposure to COMPOUND A
0 min Dosing, 60 min Incubation Hemolytic Potential in Human Blood after Exposure to Ampotericin B
0 min Dosing, 60 min Incubation Hemolytic Potential in Rat Blood after Exposure to COMPOUND A
0 min Dosing, 60 min Incubation Hemolytic Potential in Rat Blood after Exposure to Amphotericin B
0 min Dosing, 60 min Incubation

| Treatment | [illegible] | [illegible] | [illegible] | [illegible] | [illegible] | [illegible] |
|---|---|---|---|---|---|---|
| Discrimination | 95% | 95% | 95% | 95% | 95% | 95% |
| Proximity | 37% | 26% | 11% | 36% | 27% | 52% |
| Unique Features | 12% | 10% | 6% | 10% | 12% | 13% |

| Treatment | [illegible] | [illegible] | [illegible] | [illegible] | [illegible] | [illegible] |
|---|---|---|---|---|---|---|
| Discrimination | 99% | 99% | 99% | 99% | 99% | 99% |
| Proximity | 62% | 51% | 28% | 57% | 57% | 76% |
| Unique Features | 7% | 5% | 4% | 4% | 7% | 6% |

| Treatment | [illegible] | [illegible] | [illegible] | [illegible] | [illegible] | [illegible] |
|---|---|---|---|---|---|---|
| Discrimination | 99% | 99% | 99% | 99% | 99% | 99% |
| Proximity | 50% | 41% | 23% | 47% | 45% | 77% |
| Unique Features | 5% | 2% | 2% | 3% | 4% | 5% |

| Treatment | [illegible] | [illegible] | [illegible] | [illegible] | [illegible] | [illegible] |
|---|---|---|---|---|---|---|
| Discrimination | 95% | 95% | 95% | 95% | 95% | 95% |
| Proximity | 34% | 20% | 2% | 31% | 22% | 51% |
| Unique Features | 3% | 3% | 2% | 4% | 4% | 4% |

| Treatment | [illegible] | [illegible] | [illegible] | [illegible] | [illegible] | [illegible] |
|---|---|---|---|---|---|---|
| Discrimination | 99% | 99% | 99% | 99% | 99% | 99% |
| Proximity | 71% | 54% | 28% | 28% | 70% | 79% |
| Unique Features | 3% | 4% | 6% | 6% | 5% | 4% |

| Treatment | [illegible] | [illegible] | [illegible] | [illegible] | [illegible] | [illegible] |
|---|---|---|---|---|---|---|
| Discrimination | 99% | 99% | 99% | 99% | 99% | 99% |
| Proximity | 67% | 57% | 35% | 65% | 70% | 74% |
| Unique Features | 4% | 3% | 3% | 3% | 3% | 7% |

| Treatment | [illegible] | COMPOUND D | COMPOUND E | COMPOUND A | COMPOUND B | COMPOUND C |
|---|---|---|---|---|---|---|
| Discrimination | 99% | 99% | 99% | 99% | 99% | 99% |
| Proximity | 65% | 53% | 29% | 58% | 60% | 76% |
| Unique Features | 1% | 2% | 1% | 1% | 1% | 2% |

| Treatment | [illegible] | COMPOUND D | COMPOUND E | COMPOUND A | COMPOUND B | COMPOUND C |
|---|---|---|---|---|---|---|
| Discrimination | 93% | 93% | 93% | 93% | 93% | 93% |
| Proximity | 64% | 51% | 30% | 58% | 62% | 77% |
| Unique Features | 10% | 3% | 4% | 4% | 5% | 6% |

| Treatment | [illegible] | Compound D | Compound E | Compound A | Compound B | Compound C |
|---|---|---|---|---|---|---|
| Discrimination | 100% | 100% | 100% | 100% | 100% | 100% |
| Proximity | 47% | 36% | 19% | 41% | 46% | 51% |
| Unique Features | 3% | 3% | 3% | 3% | 3% | 3% |

| Treatment | [illegible] | Compound D | Compound E | Compound A | Compound B | Compound C |
|---|---|---|---|---|---|---|
| Discrimination | 99% | 99% | 99% | 99% | 99% | 99% |
| Proximity | 75% | 58% | 33% | 66% | 74% | 92% |
| Unique Features | 1% | 1% | 3% | 1% | 1% | 3% |

| Treatment | [illegible] | [illegible] | [illegible] | [illegible] | [illegible] | [illegible] |
|---|---|---|---|---|---|---|
| Discrimination | 100% | 100% | 100% | 100% | 100% | 100% |
| Proximity | 37% | 33% | 15% | 34% | 37% | 54% |
| Unique Features | 8% | 5% | 4% | 6% | 6% | 9% |

| Treatment | [illegible] | [illegible] | [illegible] | [illegible] | [illegible] | [illegible] |
|---|---|---|---|---|---|---|
| Discrimination | 86% | 86% | 86% | 86% | 86% | 86% |
| Proximity | 71% | 53% | 31% | 61% | 69% | 69% |
| Unique Features | 9% | 4% | 5% | 6% | 5% | 15% |

| Dose | 30 | 60 | 90 | 120 |
|---|---|---|---|---|
| Discrimination | 99% | 99% | 99% | 99% |
| Proximity | 54% | 57% | 74% | 78% |
| Unique Features | 4% | 3% | 2% | 2% |

| Dose | 30 | 60 | 90 | 120 |
|---|---|---|---|---|
| Discrimination | 100% | 100% | 100% | 100% |
| Proximity | 37% | 27% | 44% | 33% |
| Unique Features | 2% | 7% | 8% | 7% |

Vehicle
Donepezil
COMPOUND A Doses

| Dose | 30 | 60 | 90 | 120 |
|---|---|---|---|---|
| Discrimination | 99% | 99% | 99% | 99% |
| Proximity | 40% | 47% | 62% | 68% |
| Unique Features | 4% | 9% | 12% | 3% |

Vehicle
Thioperamide
COMPOUND C Doses

| Dose | 60 | 90 | 120 | 150 |
|---|---|---|---|---|
| Discrimination | 99% | 99% | 99% | 99% |
| Proximity | 70% | 68% | 100% | 100% |
| Unique Features | 2% | 2% | 92% | 4% |

| Dose | 60 | 90 | 120 | 150 |
|---|---|---|---|---|
| Discrimination | 100% | 100% | 100% | 100% |
| Proximity | 44% | 30% | 95% | 69% |
| Unique Features | 9% | 7% | 5% | 18% |

| Dose | 60 | 90 | 120 | 150 |
|---|---|---|---|---|
| Discrimination | 99% | 99% | 99% | 99% |
| Proximity | 61% | 52% | 72% | 99% |
| Unique Features | 7% | 9% | 7% | 5% |

| Dose | 30 | 60 | 90 |
|---|---|---|---|
| Discrimination | 100% | 100% | 100% |
| Proximity | 24% | 35% | 57% |
| Unique Features | 4% | 9% | 12% |

| Dose1 | 30 | 60 | 90 |
|---|---|---|---|
| Discrimination | 99% | 99% | 99% |
| Proximity | 45% | 79% | 100% |
| Unique Features | 2% | 1% | 2% |

| Dose | 30 | 60 | 90 |
|---|---|---|---|
| Discrimination | 99% | 99% | 99% |
| Proximity | 36% | 74% | 99% |
| Unique Features | 4% | 7% | 6% |

S

DERIVATIVES OF SUBSTITUTED MORPHOLINES AND USES THEREOF

PRIORITY

The present application is a Continuation of U.S. application Ser. No. 18/617,255, filed Mar. 26, 2024, which claims priority to U.S. provisional patent application No. 63/454,930 filed Mar. 27, 2023, which are incorporated herein by reference in their entireties.

FIELD

The present technology generally relates to derivatives of substituted morpholines and their uses in pharmaceutical compositions and for the treatment of central nervous system (CNS) disorders.

BACKGROUND (R,S)-2-[(2-ethoxyphenoxy)methyl]morpholine

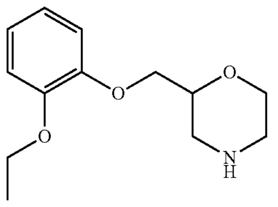 [SMILES: CCOc1ccccc1OCC1CNCCO1]

is a bicyclic morpholine derivative, assigned CAS No. 46817-91-8 (CAS No. 35604-67-2 for the HCl salt). It is characterized by the formula $C_{13}H_{19}NO_3$, with a molecular mass of 237.295 g/mol.

2-((2-ethoxyphenoxy)methyl)morpholine is known to have several desirable pharmacologic uses, including treatment of depression, nocturnal enuresis, narcolepsy, sleep disorders, and alcoholism, among others. 2-((2-ethoxyphenoxy)methyl)morpholine was previously marketed in several European countries for the treatment of major depressive disorder (MDD). 2-((2-ethoxyphenoxy)methyl) morpholine is an inhibitor of the reuptake of norepinephrine ("NRI"), but may also enhance the release of serotonin from neuronal stores.

However, treatment with 2-((2-ethoxyphenoxy)methyl) morpholine has been associated with numerous side effects including nausea, vomiting, loss of appetite, increased erythrocyte sedimentation, EKG and EEG anomalies, epigastric pain, diarrhea, constipation, vertigo, orthostatic hypotension, edema of the lower extremities, dysarthria, tremor, psychomotor agitation, mental confusion, inappropriate secretion of antidiuretic hormone, increased transaminases, and seizure.

In order to minimize the side effects associated with 2-((2-ethoxyphenoxy)methyl)morpholine, chemists have synthesized derivatives and analogs that retain the pharmacologic properties of 2-((2-ethoxyphenoxy)methyl)morpholine. Derivatives of substituted morpholines have been previously disclosed in the art, for example in UK Patent 1 243 391 and UK Patent 1 260 886. In a different approach, the present inventors synthesize novel derivatives of substituted morpholines. Prodrugs are a class of derivatives that in many instances have little or no pharmacological activity, which are converted in vivo to therapeutically active compounds. In some instances, the prodrug itself may possess biological activity. Prodrug activation may occur by enzymatic or non-enzymatic cleavage of the temporary bond between the carrier and the drug molecule, or a sequential or simultaneous combination of both.

The newly synthesized derivatives of substituted morpholines, with the derivatization of the amine group of the morpholine in the structure of 2-((2-ethoxyphenoxy)methyl) morpholine produce chemically stable compounds to serve as novel compounds. These derivatives of 2-((2-ethoxyphenoxy)methyl)morpholine can be used in pharmaceutical compositions and for the treatment of central nervous system (CNS) disorders.

SUMMARY

In some aspects, treatment of a central nervous system ("CNS") disorder is provided, the treatment including administering to a subject in need thereof a pharmaceutical composition that includes a derivative of substituted morpholines, including of a compound of Formula I, II, III, or IV. In one aspect, derivatives of substituted morpholines are utilized, including a compound of Formula I, a stereoisomer thereof, or a salt thereof:

(I)

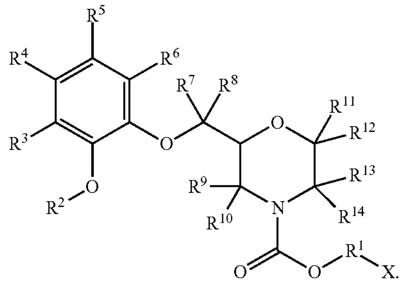

In Formula I, $R^1$ may be alkyl, heterocyclyl, or a pyridyl, $R^2$ may be alkyl, aryl, heteroaryl, or heterocyclyl, $R^3$-$R^{14}$ may be each independently H, F, Cl, Br, I, CN, $NO_2$, alkyl, aryl, heteroaryl, or heterocyclyl; and X may be H, F, Cl, Br, I, an amino acid residue, a substituted amino acid residue, alkyl, ester.

In some embodiments, the present technology relates to derivatives of substituted morpholines according to the compound of Formula II, stereoisomer thereof, and/or a salt thereof are utilized:

(II)

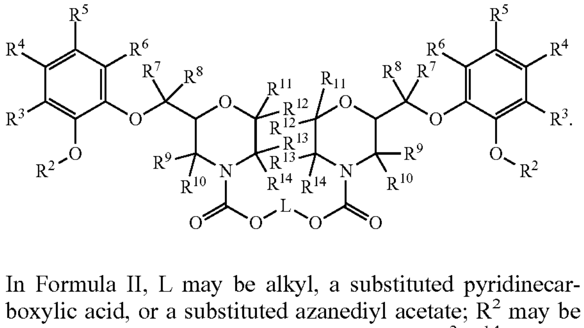

In Formula II, L may be alkyl, a substituted pyridinecarboxylic acid, or a substituted azanediyl acetate; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl.

In some embodiments, the present technology utilizes derivatives of substituted morpholines according to the compound of Formula III, a stereoisomer thereof, and/or a salt thereof:

(III)

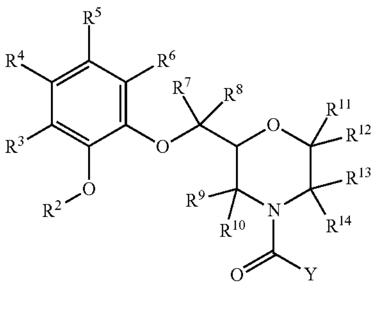

In Formula III, Y may be F, Cl, Br, I, an amino acid residue, a substituted amino acid residue, alkyl, or ester; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl.

In some embodiments, derivatives of substituted morpholines are utilized according to Formula IV, a stereoisomer thereof, and/or a salt thereof:

(IV)

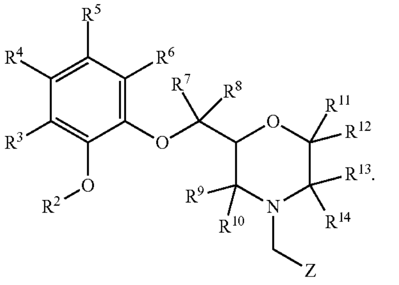

In Formula IV, Z may be H, F, Cl, Br, I, an amino acid residue, a substituted amino acid residue, or a nitrogen-containing group; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl.

In some aspects, the CNS disorder includes, but is not limited to, depression, attention deficit hyperactivity disorder (ADHD), sleep disorders (for example cataplexy, narcolepsy, REM sleep behavior disorder), apathy, cognition, anxiety, orthostatic hypotension, and pain, and also neurological disorders (for example Parkinson's disease, Alzheimer's disease, Lewy body dementia, multiple system atrophy). Preferably, the subject suffering from a CNS disorder is a human.

BRIEF DESCRIPTION OF THE DRAWINGS

FIG. 9*a* is expressed as peak area, FIG. 9*b* is expressed as percent change relative to control.

FIG. 10*a* is expressed as peak area, FIG. 10*b* is expressed as percent change relative to controls.

FIG. 11*a* is expressed as peak area, FIG. 11*b* is expressed as percent change relative to controls.

FIG. 12*a* is expressed as peak area, FIG. 12*b* is expressed as percent change relative to controls.

FIG. 13*a* is expressed as peak area, FIG. 13*b* is expressed as percent change relative to controls.

FIG. 14*a* is expressed as peak area, FIG. 14*b* is expressed as percent change relative to controls.

FIG. 15*a* is expressed as peak area, FIG. 15*b* is expressed as percent change relative to controls.

FIGS. 20*a*-20*b* show plasma concentration-time profiles of S(−)-(FIG. 20*a*) and R(+)-(FIG. 20*b*) viloxazine following administration of COMPOUND A to mice at 19.82 mg/kg. FIGS. 20*c*-20*d* show plasma concentration-time profiles of S(−)-(FIG. 20*c*) and R(+)-(FIG. 20*d*) following administration of COMPOUND B to mice at 21.03 mg/kg. FIGS. 20*e*-20*f* show plasma concentration-time profiles of S(−)-(FIG. 20*e*) and R(+)-(FIG. 20*f*) following administration of COMPOUND C to mice at 21.11 mg/kg. FIGS. 20*e*-20*f* show plasma concentration-time profiles of S(−)-(FIG. 20*g*) and R(+)-(FIG. 20*h*) following administration of racemic viloxazine to mice at 11.64 mg/kg.

(FIG. 70*b*) the % of time spent in the open arms, and (FIG. 70*c*) the total distance travelled are illustrated. In the insets, the effects of a single dose of the positive control compound midazolam (0.5 mg/kg i.p.) are illustrated. Bars represent mean±S.E.M. for each treatment (N=8-9). VEH=vehicle; S-VLX=S-Viloxazine, Mid=midazolam. *=significantly different (p<0.05) from the VEH-associated response; **=p<0.01.

Not enough REM occurred following some conditions to allow ANOVA to be performed. Top left panel: The average hourly power during REM in the delta frequency range. Top right panel: The average hourly power during REM in the theta frequency range. Middle left panel: The average hourly power during REM in the alpha frequency range. Middle right panel: The average hourly power during REM in the beta frequency range. Bottom left panel: The average hourly power during REM in the low gamma frequency range. Bottom right panel: The average hourly power during REM in the high gamma.

Figure 94:
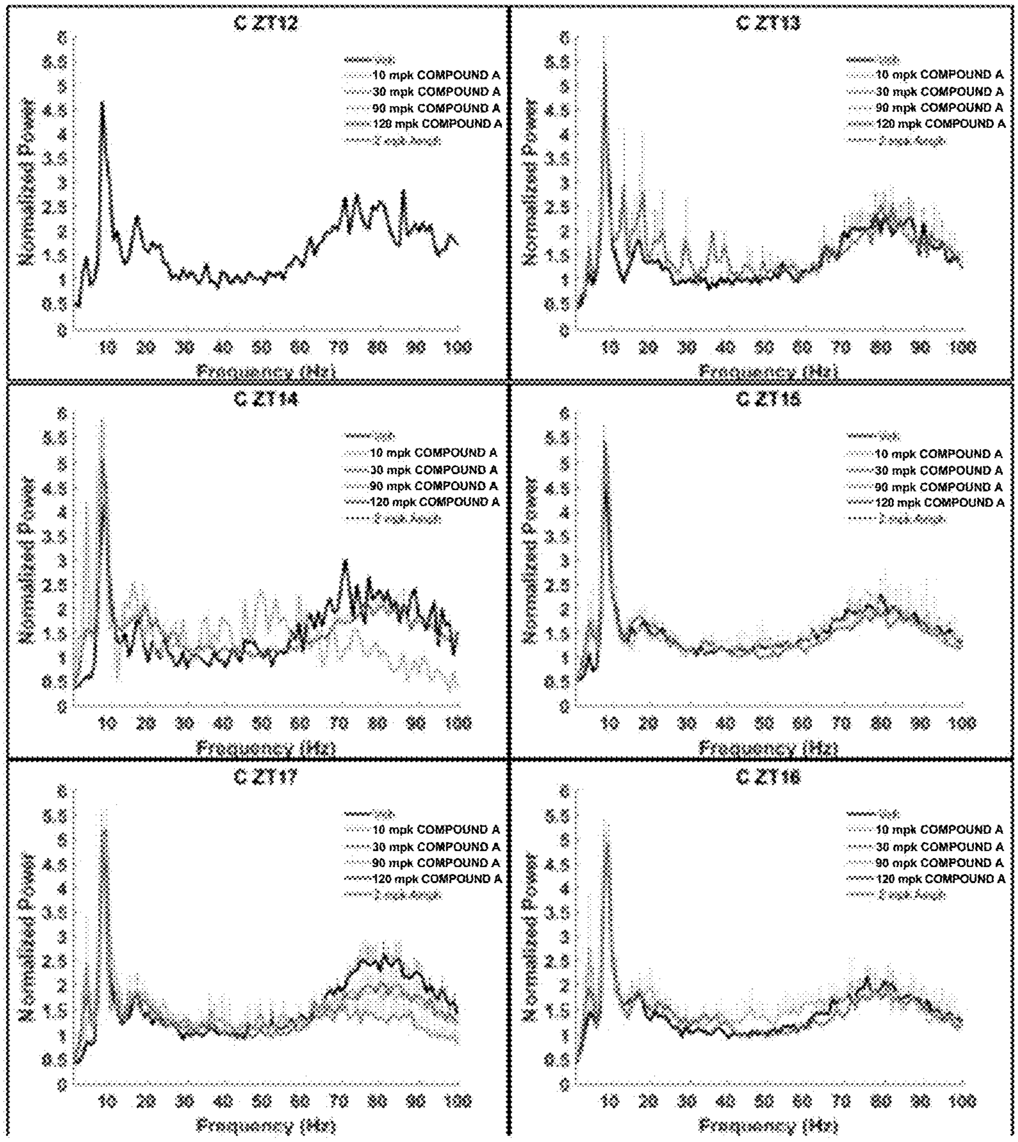

FIG. 94 shows the full normalized EEG spectrum (0.3-100 Hz) in C following Amph at 2 mg/kg and COMPOUND A at 10, 30, 90 and 120 mg/kg vs. Veh. Top left panel: The normalized C EEG spectrum for the 1st h following dosing. Top right panel: The normalized C EEG spectrum for the 2nd h following dosing. Middle left panel: The normalized C EEG spectrum for the 3rd h following dosing. Middle right panel: The normalized C EEG spectrum for the 4th h following dosing. Bottom left panel: The normalized C EEG spectrum for the 5th h following dosing. Bottom right panel: The normalized C EEG spectrum for the 6th h following dosing.

Figure 95:
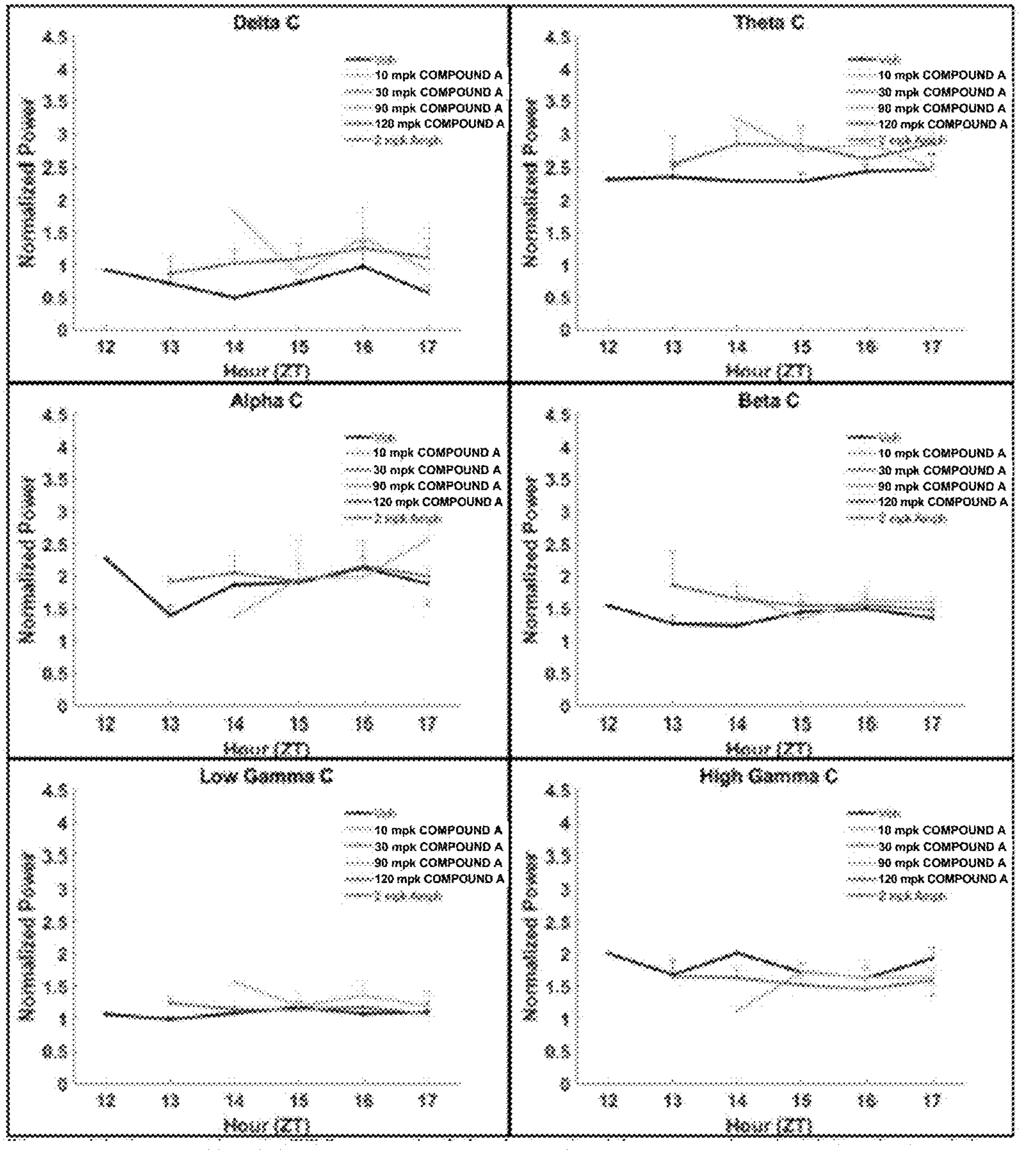

FIG. 95 shows average hourly EEG power in C for 6 standard frequency bands (delta, theta, alpha, beta, low gamma, and high gamma) following Amph at 2 mg/kg and COMPOUND A at 10, 30, 90 and 120 mg/kg vs. Veh. Data were normalized to the 6 h average following Veh control. Not enough C occurred following some conditions to allow ANOVA to be performed. Top left panel: The average hourly power during C in the delta frequency range. Top right panel: The average hourly power during C in the theta frequency range. Middle left panel: The average hourly power during C in the alpha frequency range. Middle right panel: The average hourly power during C in the beta frequency range. Bottom left panel: The average hourly power during C in the low gamma frequency range. Bottom right panel: The average hourly power during C in the high gamma.

Figure 96:
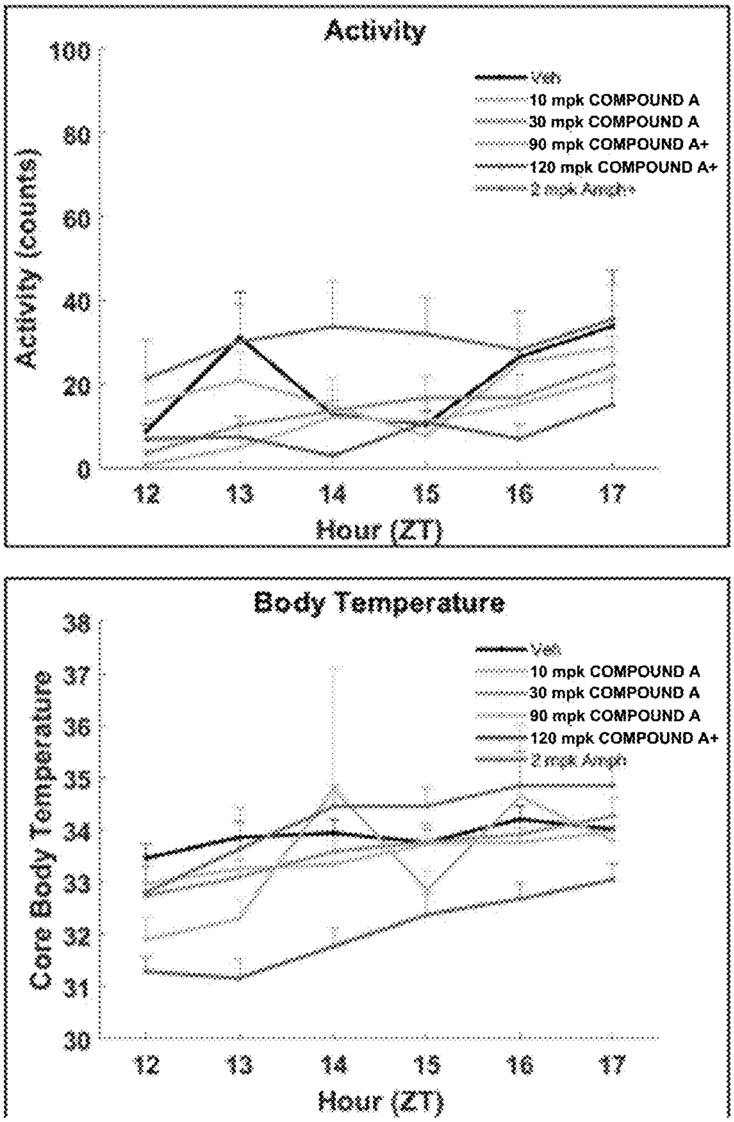

FIG. 96 shows average hourly LMA and Body Temperature following Amph at 2 mg/kg and COMPOUND A at 10, 30, 90 and 120 mg/kg vs. Veh. Dosing occurred just prior to the start of ZT12. The "+" in the legends represent overall condition effects with significant differences from Veh. Top panel: The average hourly Activity. ANOVA is significant for treatment only. Bottom panel: The average hourly Temperature. ANOVA is significant for treatment only.

Figure 97:
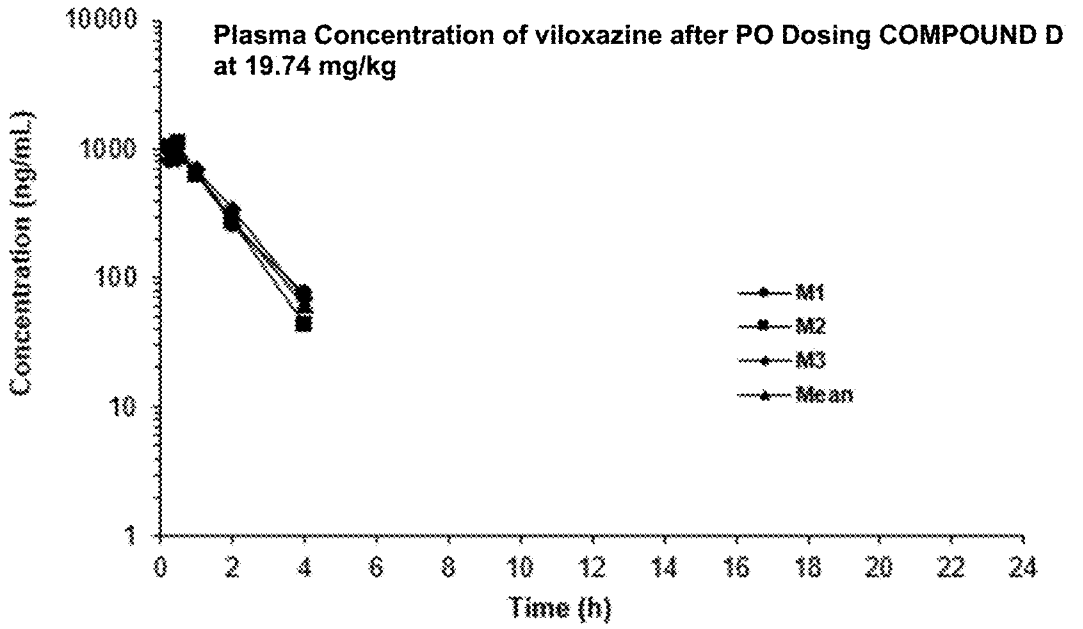

FIG. 97 shows plasma concentration of viloxazine after PO dosing COMPOUND D at 19.74 mg/kg.

Figure 98:
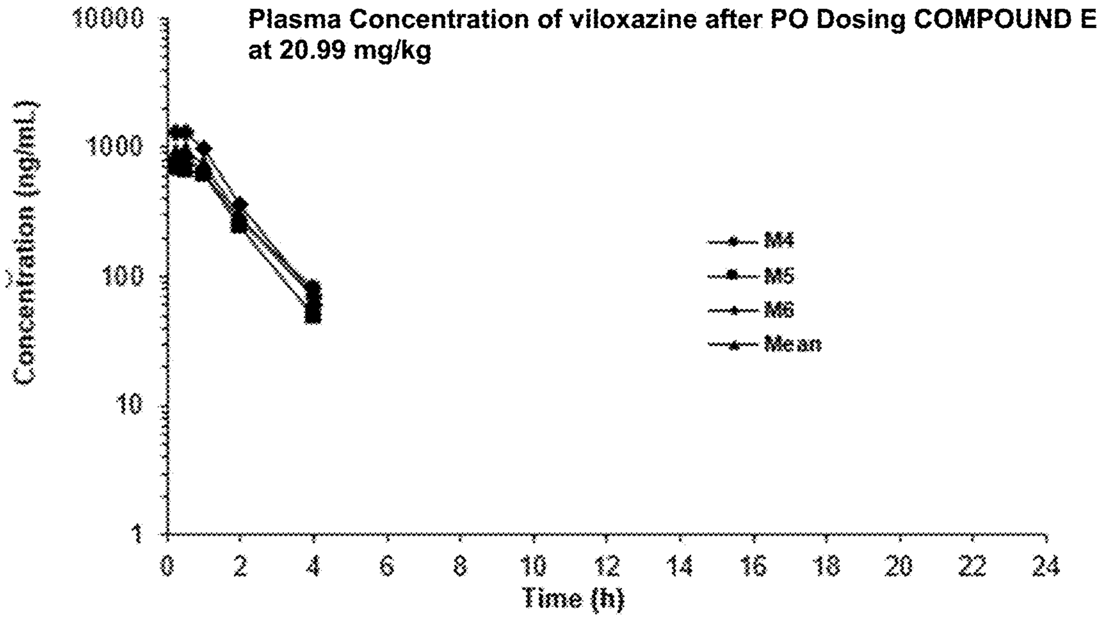

FIG. 98 shows plasma concentration of viloxazine after PO dosing COMPOUND E at 20.99 mg/kg.

Figure 99A:
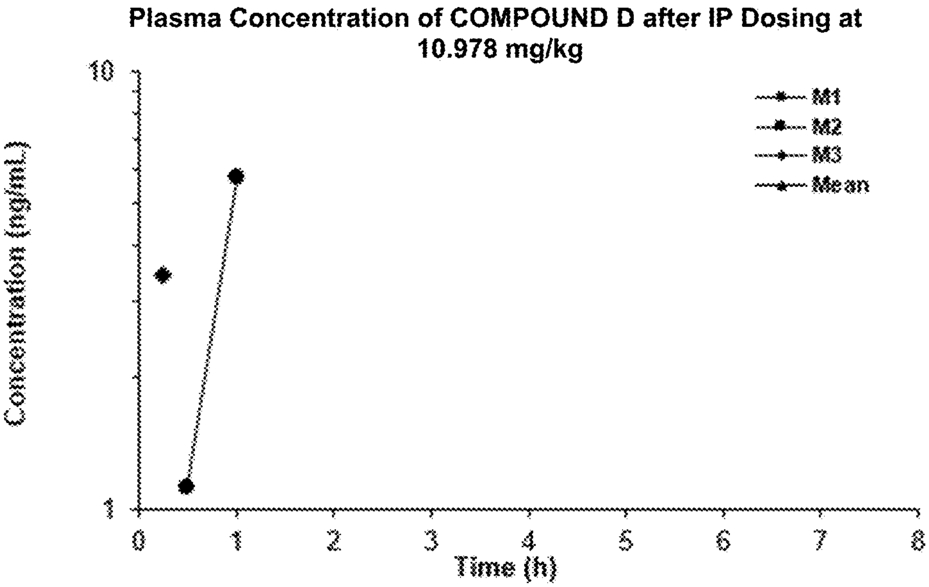
Figure 99B:
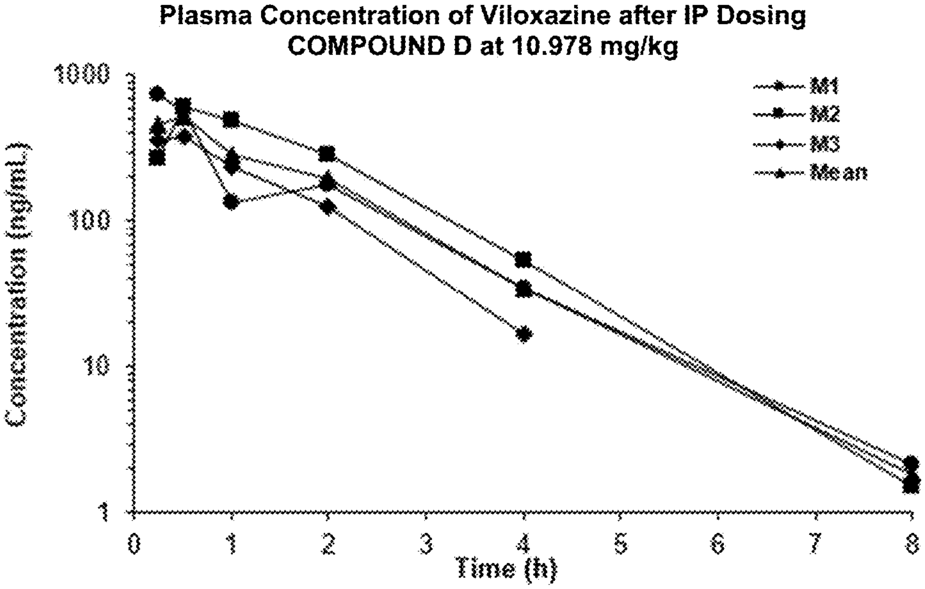
Figure 99C:
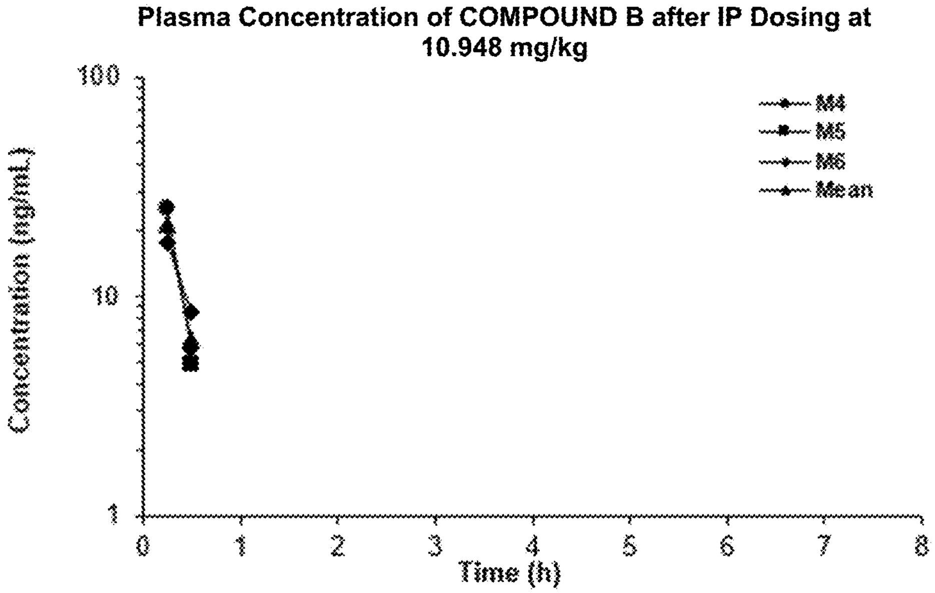
Figure 99D:
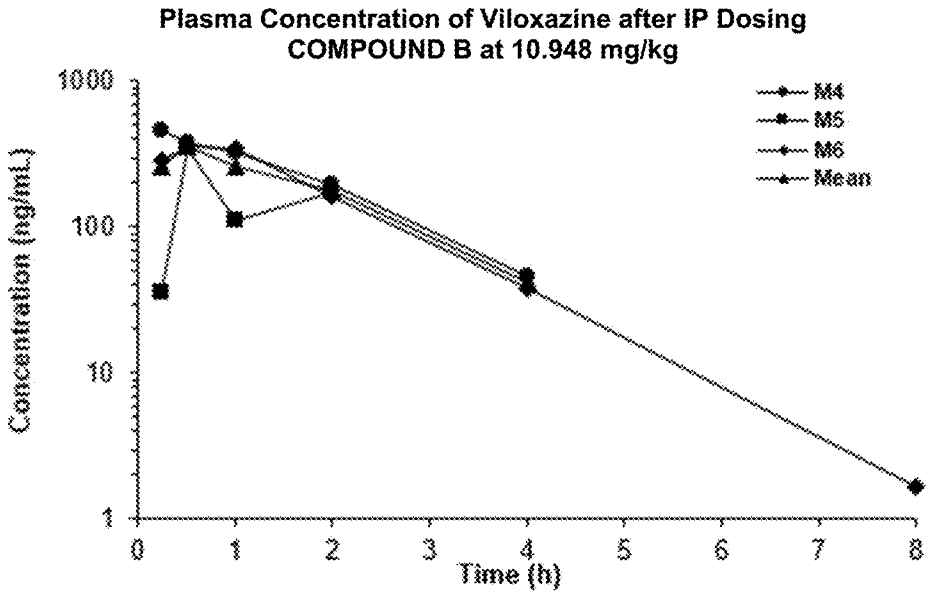
Figure 99E:
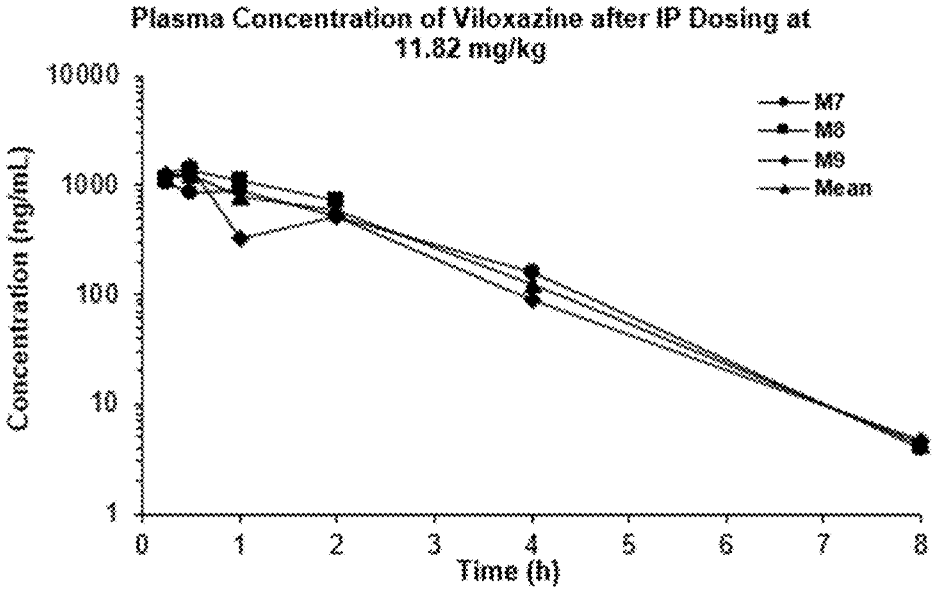
Figure 99F:
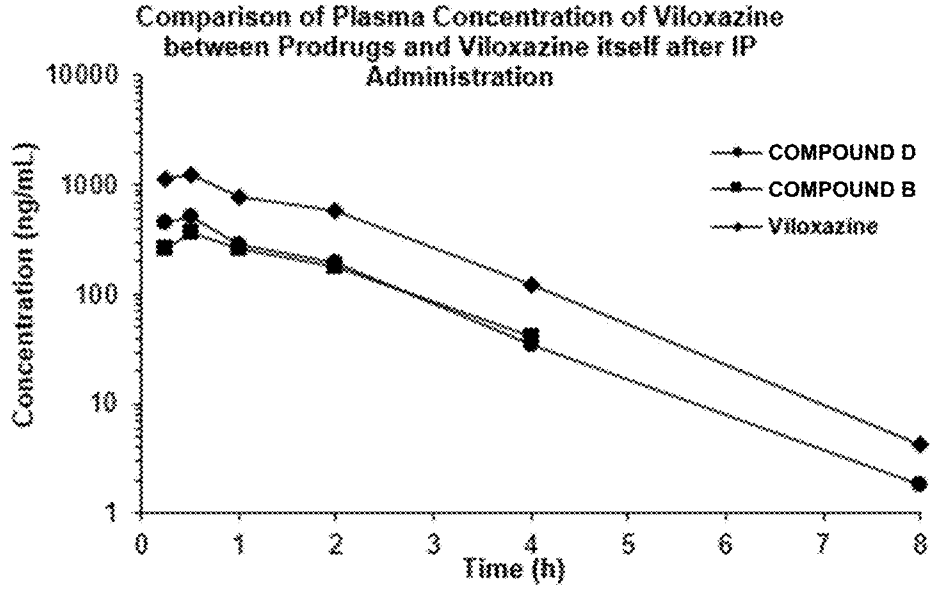
Figure 100A:
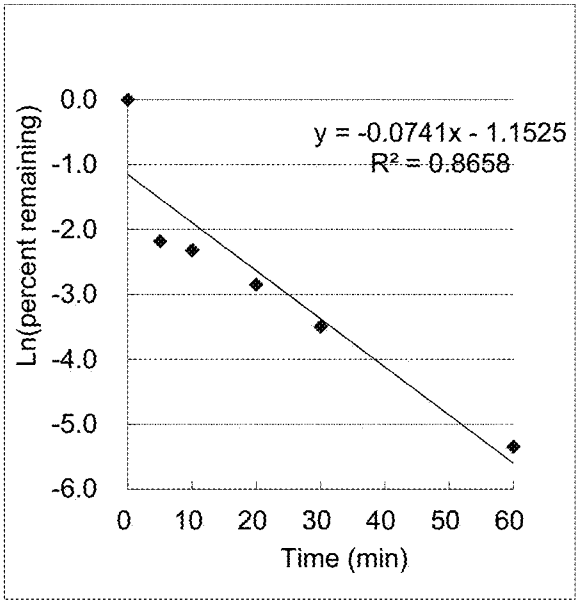
Figure 100B:
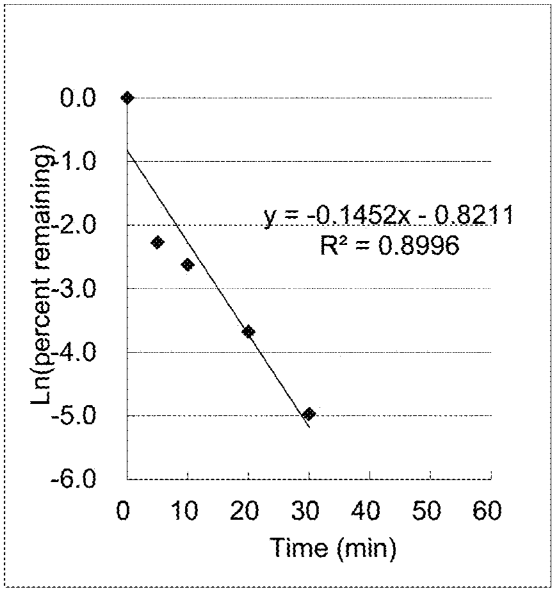
Figure 100C:
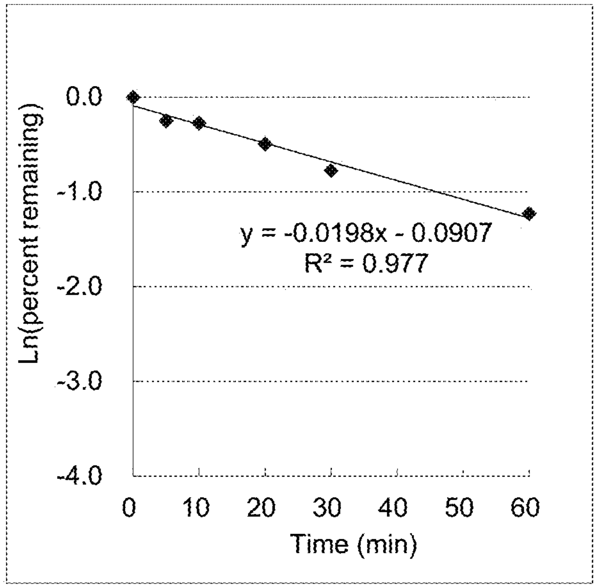
Figure 100D:
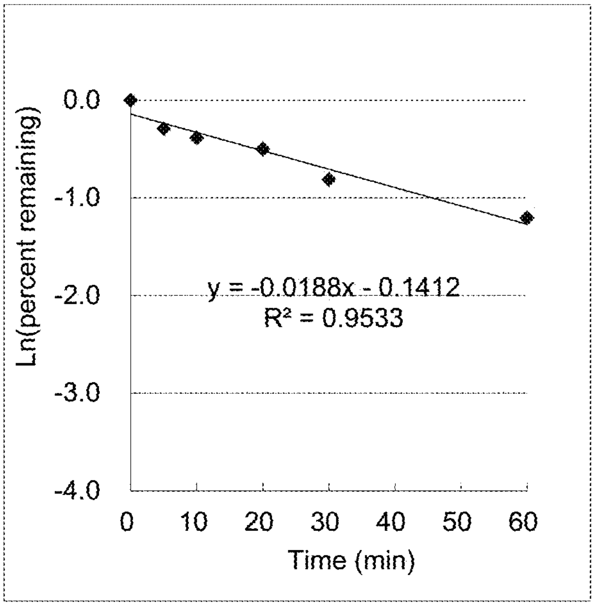
Figure 101A:
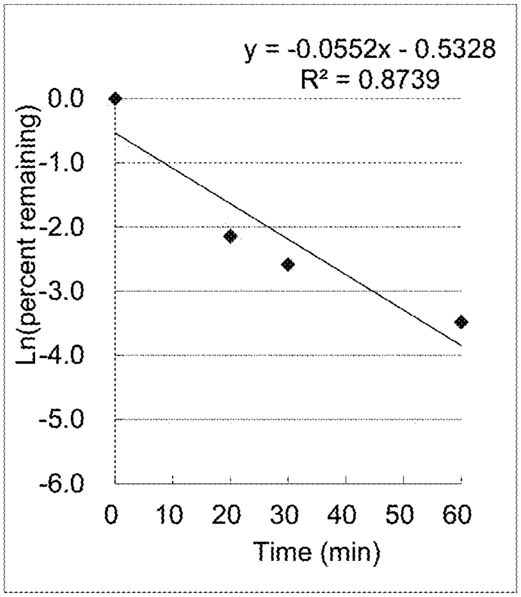
Figure 101B:
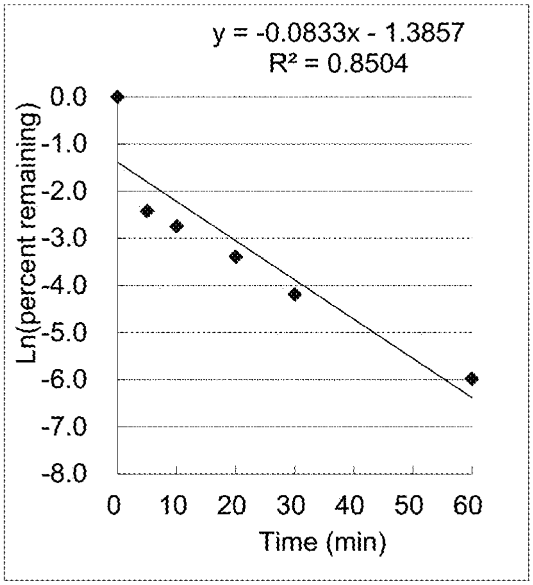
Figure 101C:
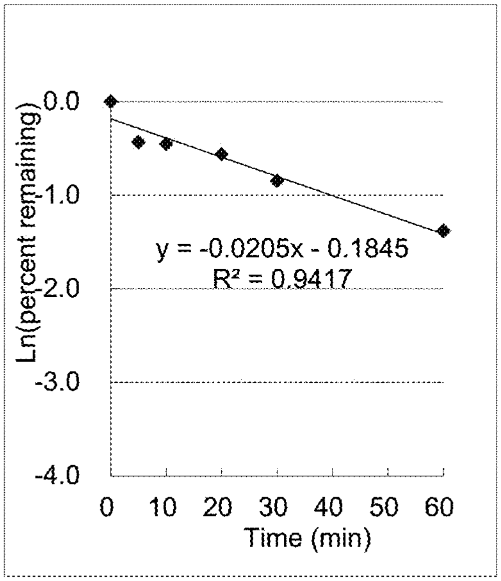
Figure 101D:
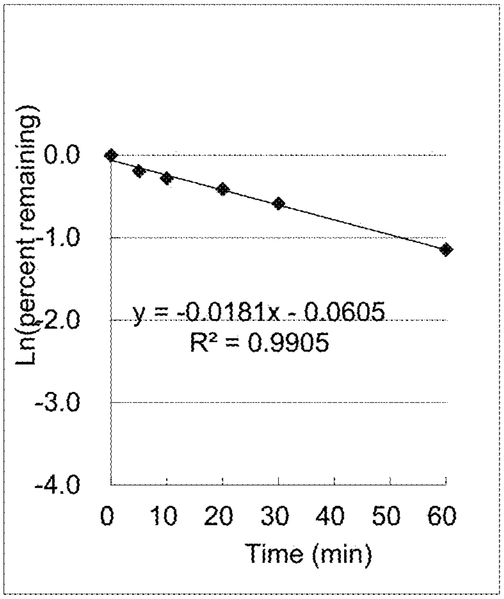
Figure 102A:
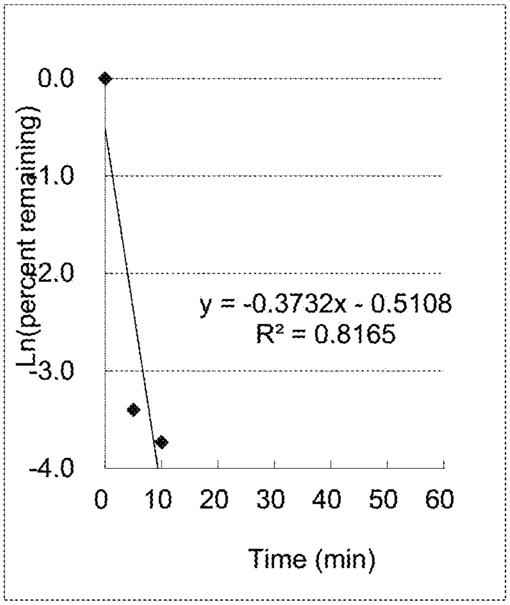
Figure 102B:
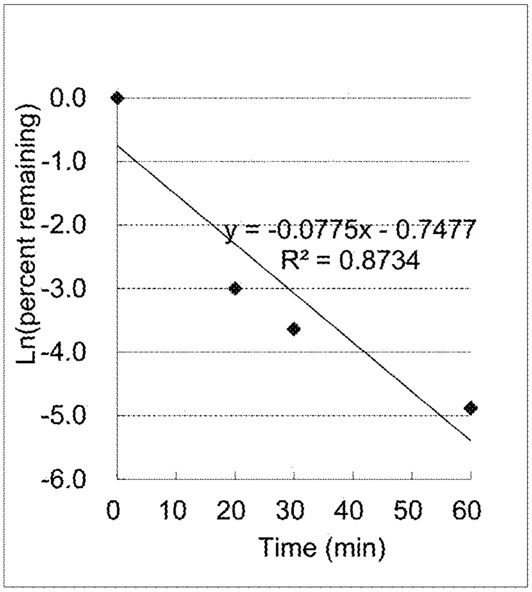
Figure 102C:
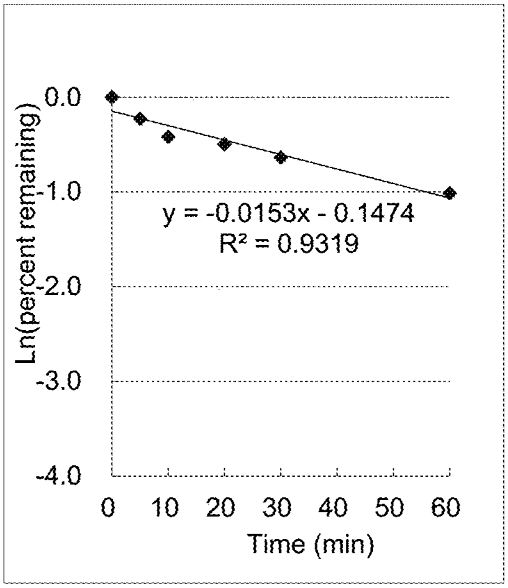
Figure 102D:
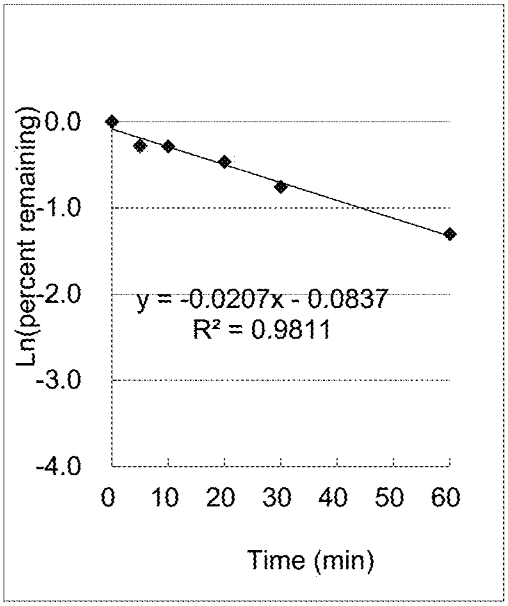

FIG. 99*a* shows plasma concentration of COMPOUND D after IP dosing at 10.978 mg/kg. FIG. 99*b* shows plasma concentration of viloxazine after IP dosing COMPOUND D at 10.978 mg/kg. FIG. 99*c* shows plasma concentration of COMPOUND B after IP dosing at 10.948 mg/kg. FIG. 99*d* shows plasma concentration of viloxazine after IP dosing COMPOUND B at 10.948 mg/kg. FIG. 99*e* shows plasma concentration of viloxazine after IP dosing at 11.82 mg/kg. FIG. 99*f* shows comparison of plasma concentration of viloxazine between prodrugs and viloxazine itself after IP administration.

FIGS. 100*a*-100*d* show stability in Rat Liver S9 Fractions for compounds: COMPOUND D (FIG. 100*a*), COMPOUND E (FIG. 100*b*), 7-EC (7-ethoxycoumarin) (FIG. 100*c*) and 7-HC (7-hydroxycoumarin) (FIG. 100*d*), respectively.

FIGS. 101*a*-101*d* show stability in Dog Liver S9 Fractions for compounds: COMPOUND D (FIG. 101*a*), COMPOUND E (FIG. 101*b*), 7-EC (7-ethoxycoumarin) (FIG. 101*c*) and 7-HC (7-hydroxycoumarin) (FIG. 101*d*), respectively.

FIGS. 102*a*-102*d* show stability in Human Liver S9 Fractions for compounds: COMPOUND D (FIG. 102*a*), COMPOUND E (FIG. 102*b*), 7-EC (7-ethoxycoumarin) (FIG. 103*c*) and 7-HC (7-hydroxycoumarin) (FIG. 103*d*), respectively.

Figure 103A:
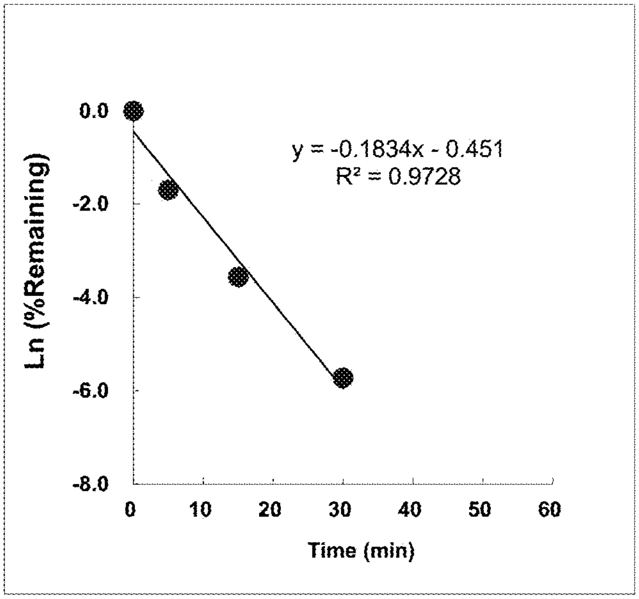
Figure 103B:
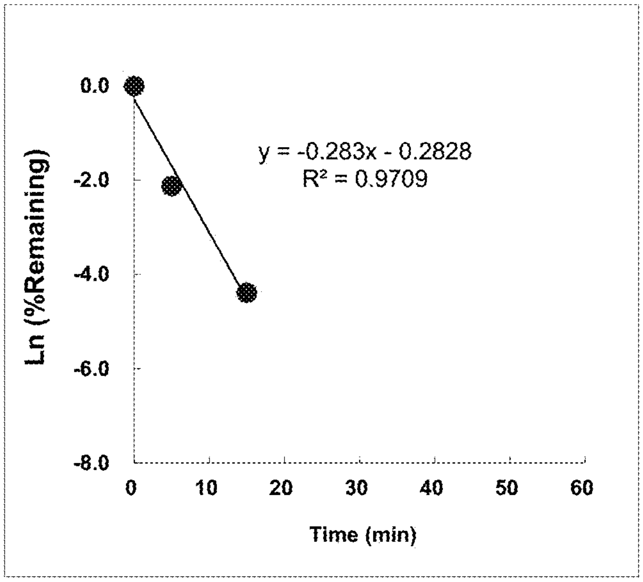
Figure 103C:
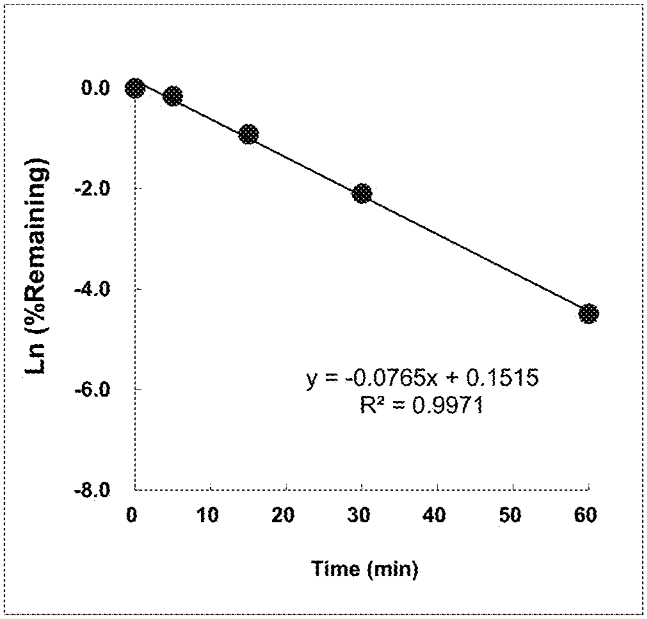
Figure 103D:
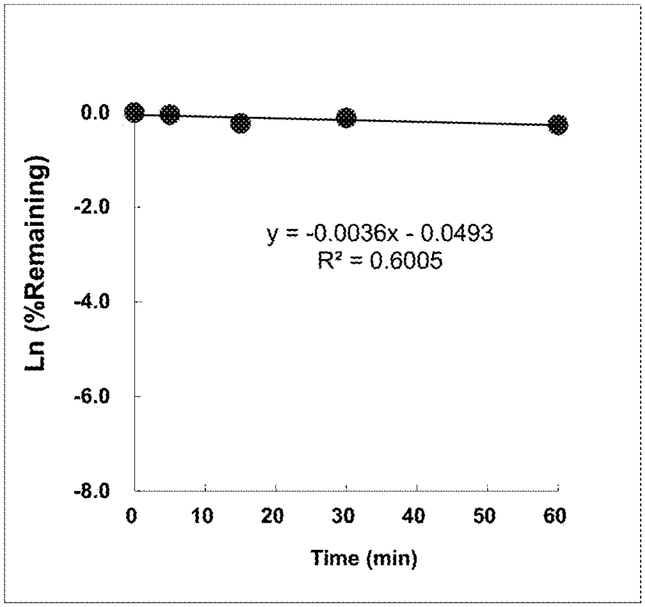
Figure 103E:
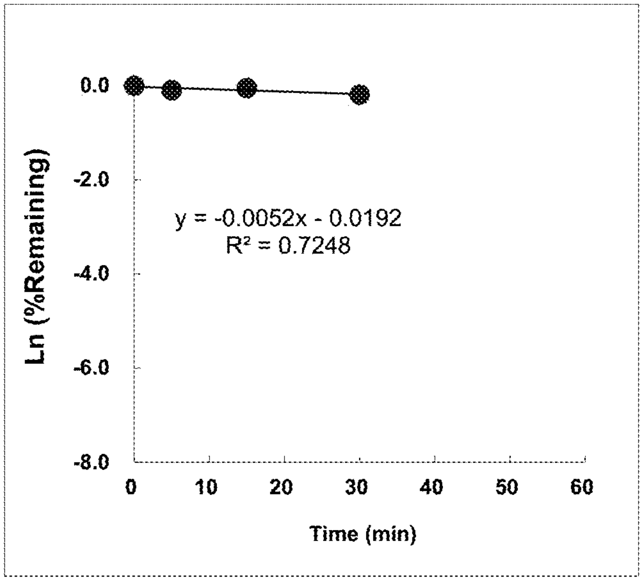
Figure 103F:
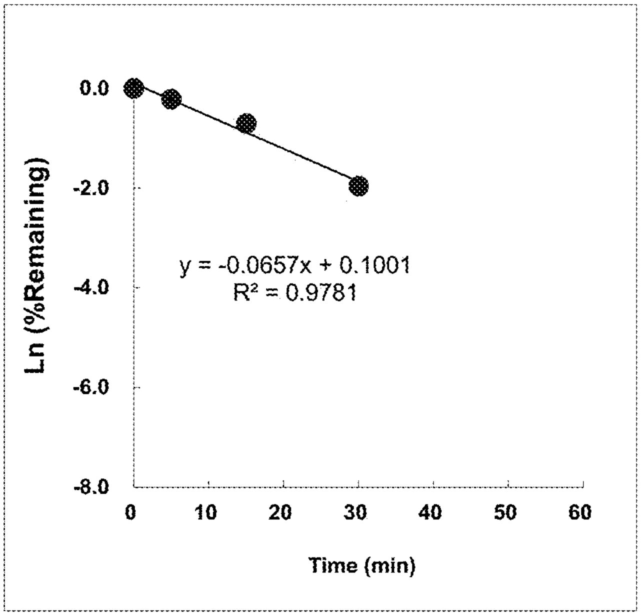

FIGS. 103*a*-103*f* show plasma stability of the test compounds. COMPOUND D stability in rat plasma is shown in FIG. 103*a*. COMPOUND E stability in rat plasma is shown in FIG. 103*b*. Stability of the positive control Enalapril in rat plasma is shown in FIG. 103*c*. COMPOUND D stability in human plasma is shown in FIG. 103*d*. COMPOUND E stability in human plasma is shown in FIG. 103*e*. Stability of the positive control Propantheline in human plasma is shown in FIG. 103*f*.

Figure 104A:
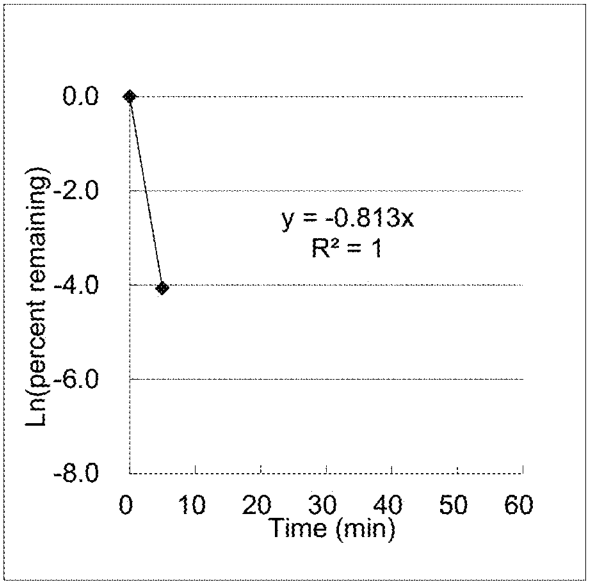
Figure 104B:
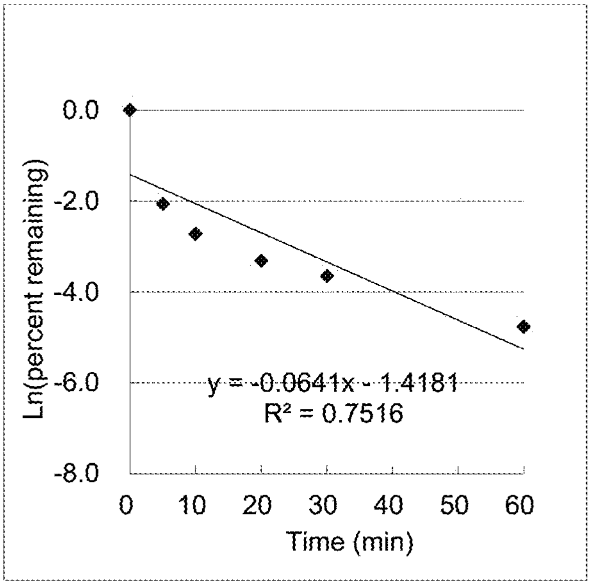
Figure 104C:
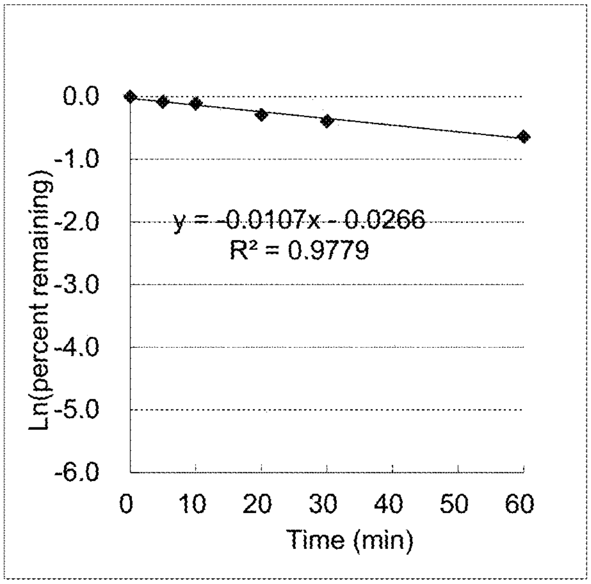
Figure 104D:
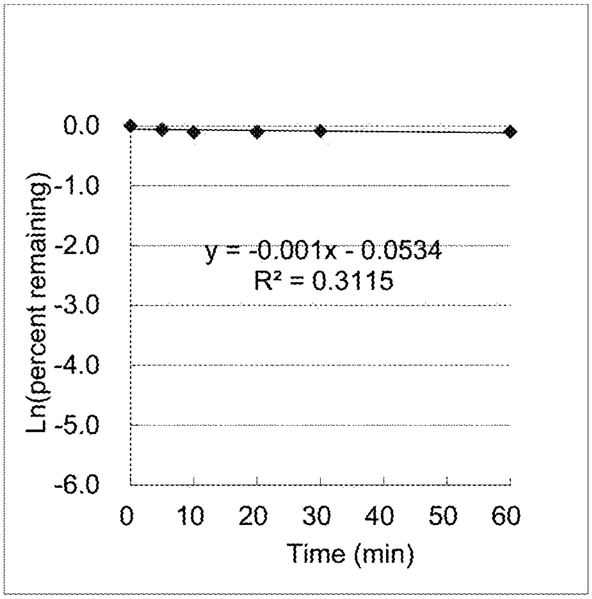

FIGS. 104*a*-104*d* show compound Stability in Human Intestinal homogenates. COMPOUND D stability Human Intestinal homogenates is shown in FIG. 104*a*. COMPOUND E stability in Human Intestinal homogenates is shown in FIG. 104*b*. Stability of the positive control Testosterone in Human Intestinal homogenates is shown in FIG. 104*c*. Stability of the positive control 7-HC (7-hydroxycoumarin) in Human Intestinal homogenates is shown in FIG. 104*d*.

DETAILED DESCRIPTION

Definitions. The following terms are used throughout as defined below.

As used herein, the term "viloxazine" or 2-((2-ethoxyphenoxy)methyl)morpholine means (R,S)-2-[(2-ethoxyphenoxy)methyl]morpholine] includes a pharmaceutically acceptable salt or ester thereof, including either a single (−) enantiomer or a single (+) enantiomer, or in the form of a racemic mixture or a non-racemic mixture of enantiomers with varying amounts of (−) and (+) enantiomers.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein merely intended to serve as shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$, and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

The term "carboxylate" as used herein refers to the conjugate base a carboxylic acid with the chemical formula —COO.

The term "ester" as used herein refers to $—COOR^2—$ and —C(O)O-G groups. $R^2$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., $C(O)NR^3R^4$, and —NRC(O)—R groups, respectively. $R^3$ and $R^4$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups ($—C(O)NH_2$) and formamide groups (NHC(O)H). In some embodiments, the amide is —NRC(O)—($C_1$-5 alkyl) and the group is termed "carbonylamino," and in others the amide is —NHC(O)-alkyl and the group is termed "alkanoylamino."

The term "amine" (or "amino") as used herein refers to $—NR^5R^6$ groups, wherein $R^5$ and $R^6$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is $NH_2$, methylamino, dimethylamino, ethylamino, diethylamino, propylamino, isopropylamino, phenylamino, or benzylamino.

The term "halogen" or "halo" as used herein refers to bromine (Br), chlorine (Cl), fluorine (F), or iodine (I). In some embodiments, the halogen is chlorine (Cl).

The term "polypeptide" or "peptide" as used herein refers to two or more amino acids linked by a peptide (i.e., amide) bond between the carboxyl terminus of one amino acid and the amino terminus of another. The term "peptide" may be combined with a prefix indicating the number of amino acids in the peptide, e.g., a "pentapeptide" is a peptide of five amino acids.

The term "amino acid" is recognized in the art and generally refers to a natural or unnatural alpha or beta amino acid. The term "amino acid" includes, but is not limited to, anyone of the twenty-one standard L-amino acids commonly found in naturally occurring peptides.

The term "amino acid residue with hydrophobic side chain" as used herein refers to the following amino acids: alanine (Ala), valine (Val), isoleucine (Ile), Leucine (Leu), methionine (Met), phenylalanine (Phe), tyrosine (Tyr), tryptophan (Trp). In some embodiment, the amino acid residue with hydrophobic side chain is valine (Val). In other embodiment, the amino acid residue with hydrophobic side chain is phenylalanine (Phe).

The term "acetyl" as used herein refers to a methyl group bonded to a carbonyl group ($CH_3CO—$).

The term "pyridine" group as used herein refers to a group with the heterocyclic organic compound with the chemical formula $C_5H_5N$.

The term "pyridinecarboxylic acid" as used herein refers to compound having a pyridine ring and a carboxyl group.

The term "azanediyl" as used herein refers to a functional group having the formula —NH; the group is bonded to the rest of the compound by two single bonds.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, or $Zn^{2+}$), ammonia or organic amines (e.g., dicyclohexylamine, trimethylamine, triethylamine, pyridine, picoline, ethanolamine, diethanolamine, or triethanolamine) or basic amino acids (e.g. arginine, lysine, or ornithine). Such salts can be prepared in situ during isolation and purification of the compounds or by separately reacting the purified compound in its free base or free acid form with a suitable acid or base, respectively, and isolating the salt thus formed.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The term "pharmaceutically acceptable excipient" refers to those substances that are well accepted by the industry and regulatory agencies such as those listed in monographs published in compendia such as USP-NF, Food Chemicals Codex, Code of Federal Regulations (CFR), FDA Inactive Ingredients Guide and in 21 CFR parts 182 and 184 that lists substances that are generally regarded as safe (GRAS) food ingredients.

In one aspect, a compound represented by Formula I is provided, or a stereoisomer thereof or a pharmaceutically acceptable salt thereof:

(I)

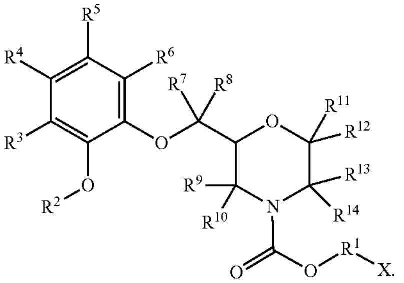

In the compound of Formula I, $R^1$ may be alkyl, heterocyclyl, or a pyridyl; $R^2$ may be alkyl, aryl, heteroaryl, or heterocyclyl; $R^3$-$R^{14}$ may be each independently H, F, Cl, Br, I, CN, $NO_2$, alkyl, aryl, heteroaryl, or heterocyclyl; and X may be H, halogen, an amino acid residue, a substituted amino acid residue, alkyl, ester. In some preferred embodiments, $R^2$ is ethyl. In any of the above embodiments, $R^1$ may be $CH_2$, $CH_2CH_2$, $CH_2CH_2CH_2$, $CH_2CH_2CH_2CH_2$, $(CH_3)_2C$, $(CH_3)_2CHCH_2$, or $(CH_3)_3CCH_2$. In any of the above embodiments, X may be an amino acid residue. In such embodiments, the amino acid residue may further include a hydrophobic side chain. In any of the above embodiments, the amino acid residue may be valine or phenylalanine. In any of the above embodiments, each of $R^3$-$R^{14}$ may be independently H, F, Cl, Br, I, or alkyl. In some such embodiments, each of $R^3$-$R^{14}$ may be independently H or $C_1$-$C_6$ alkyl. In some embodiments, $R^3$-$R^{14}$ are all H. In any of the above embodiments, $R^1$ may be $CH_2CH_2$ or $CH_2CH_2CH_2CH_2$. In various embodiments above, $R_1$ may be $CH_2$ or $C_2H_5$, and/or X may be an ester. In various embodiments above, $R^1$ may be a pyridyl group and X may be F, Cl, Br, or I.

In various embodiments, the compound represented by Formula I is one or more of the following compounds, with the understanding that where chiral centers are present each representation includes any R, S, or racemic structures as well:

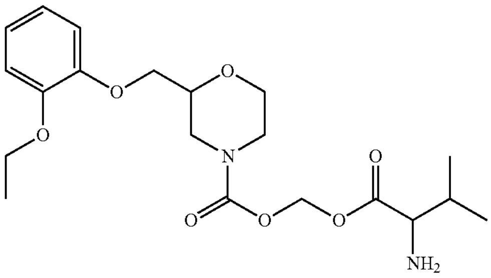
;

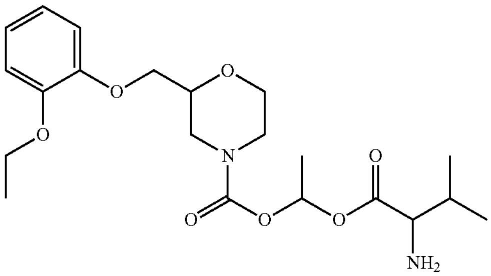
;

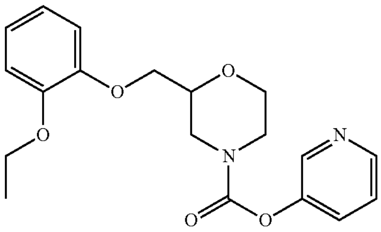
;

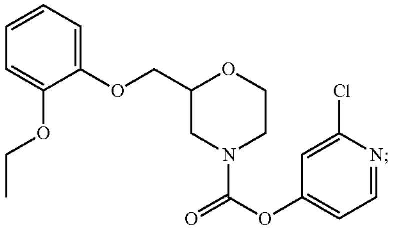

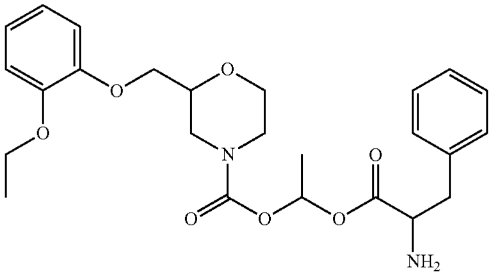
;

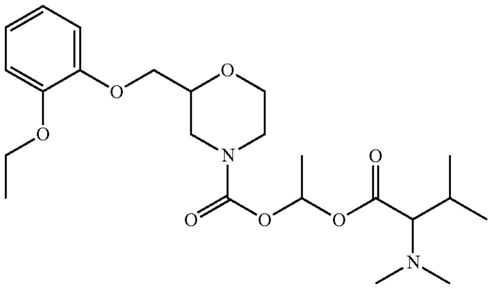
;

-continued

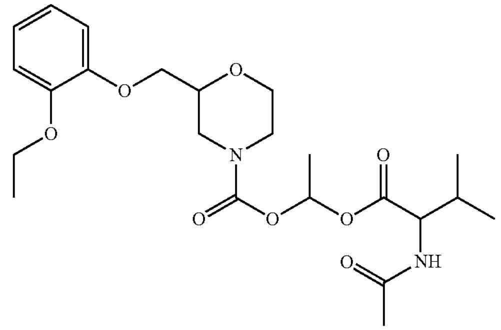

;

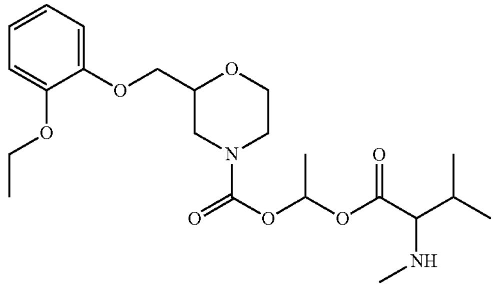

;

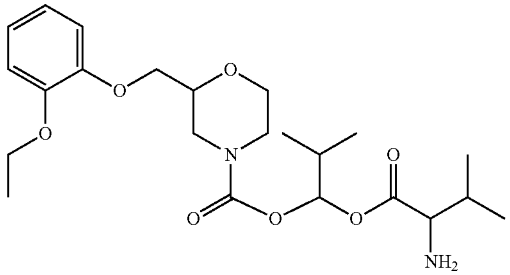

;

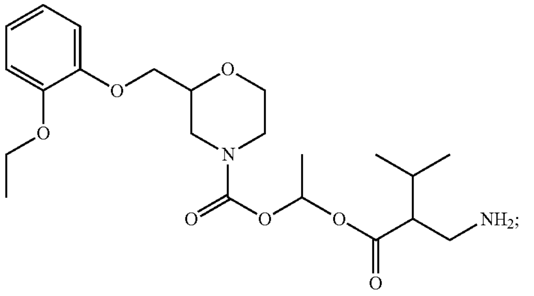

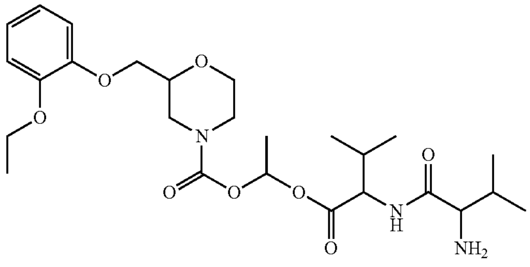

;

-continued

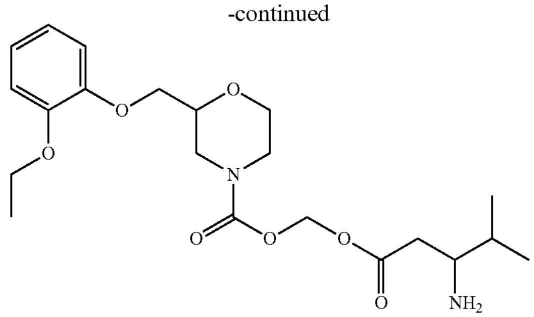

;

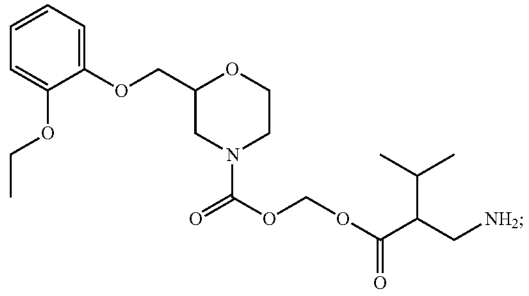

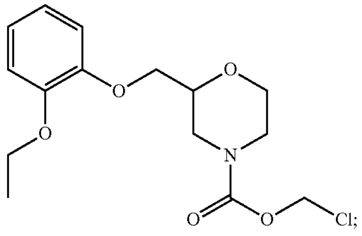

or

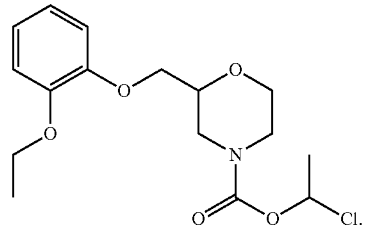

In some embodiments, the compound represented by Formula I is:

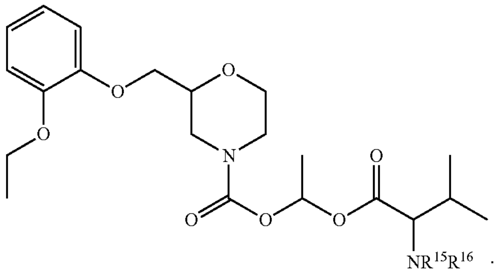

In the above formula, $R^{15}$ may be H, alkyl, or —C(O)OR$^{17}$; $R^{16}$ may be H, alkyl, or —C(O)OR$^{17}$; and $R^{17}$ may be H or alkyl. In some embodiments, $R^{15}$ may be alkyl and $R^{16}$ may be H or alkyl. In such embodiments, $R^{15}$ may be methyl and $R^{16}$ may be H or methyl. In some embodiments, $R^{15}$ and $R^{16}$ are methyl. In some embodiments, $R^{15}$ is —C(O)OR$^{17}$, $R^{16}$ is H, and $R^{17}$ is methyl.

In another aspect, a compound represented by Formula II is provided, or a stereoisomer thereof, and/or a salt thereof:

(II)

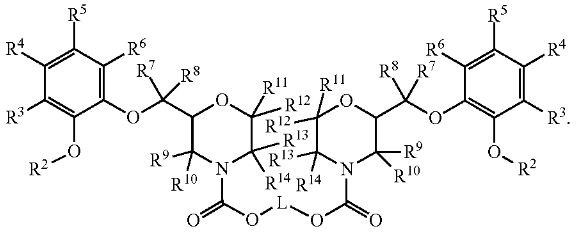

In Formula II, L is alkyl, a substituted pyridinecarboxylic acid, or a substituted azanediyl acetate; $R^2$ is alkyl, aryl, heteroaryl, or heterocyclyl; and $R^3$-$R^{14}$ are each independently H, F, Cl, Br, I, CN, $NO_2$, alkyl, aryl, heteroaryl, or heterocyclyl. In some embodiments, $R^2$ is ethyl.

In some embodiments, the compound represented by Formula II is:

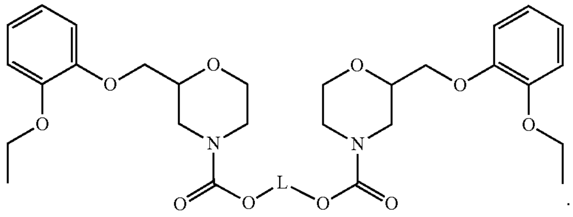

.

In various embodiments, the compound of Formula II is one or more of the following:

(SP-21)

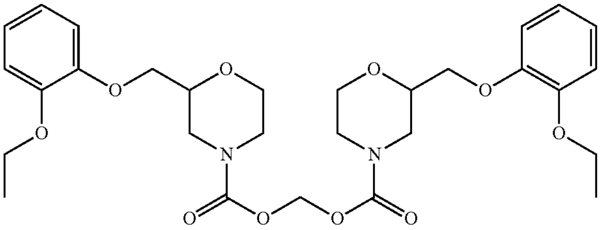

;

(SP-30)

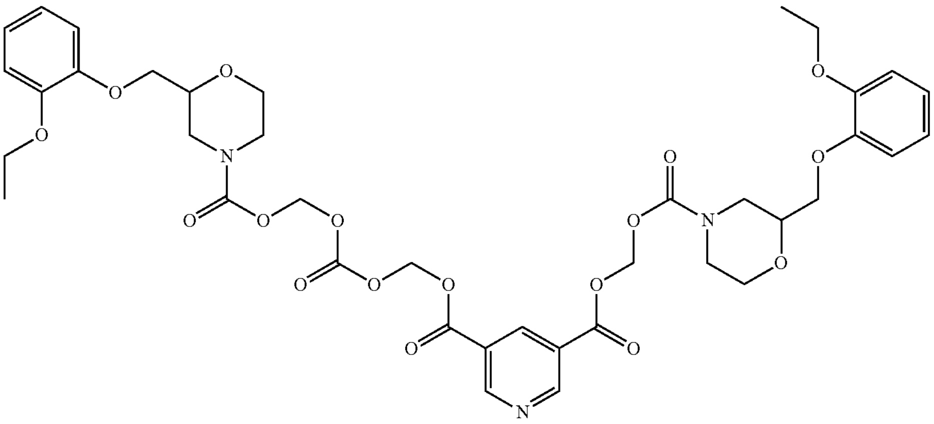

; or (SP-31)

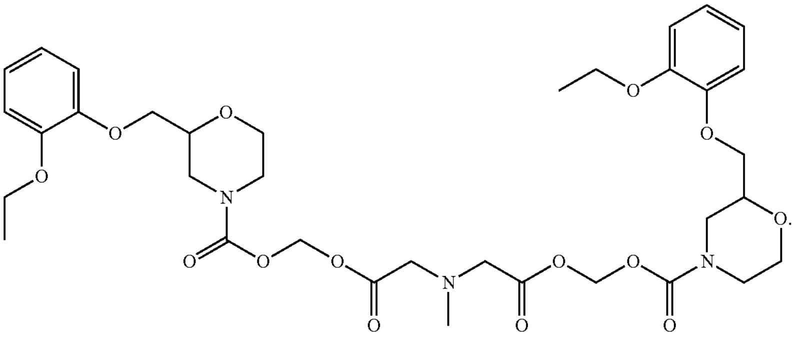

In another aspect, a compound represented by Formula III is provided, or a stereoisomer thereof, and/or a salt thereof:

(III)

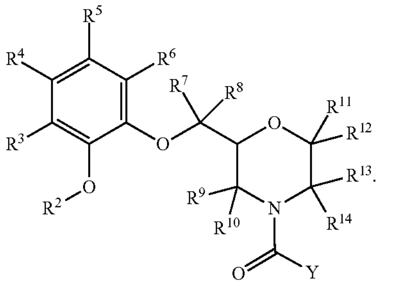

In Formula III, Y may be F, Cl, Br, I, an amino acid residue, a substituted amino acid residue, alkyl, or ester; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl. In some embodiments, $R^2$ is ethyl.

In some embodiments, the compound represented by Formula III is:

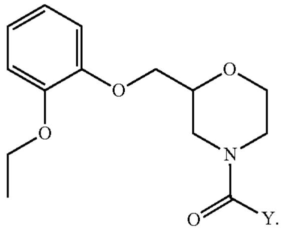

In some embodiments, the compound represented by Formula III is:

(Intermediate 1)

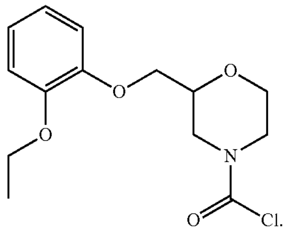

In another aspect, a compound represented by Formula IV is provided, or a stereoisomer thereof, and/or a salt thereof:

(III)

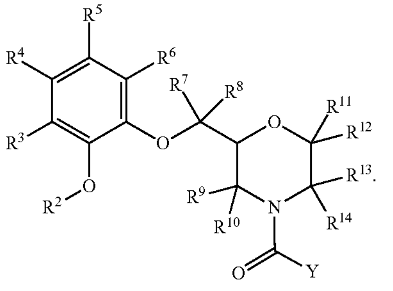

In Formula III, Z may be H, F, Cl, Br, I, an amino acid residue, a substituted amino acid residue, or a nitrogen-containing group; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl. In some embodiments, $R^2$ is ethyl.

In some embodiments, the compound represented by Formula IV is:

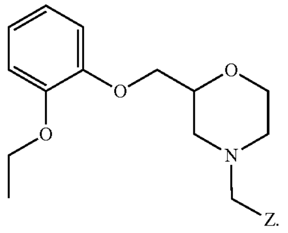

In some embodiments, the compound represented by Formula IV is:

(SP-18)

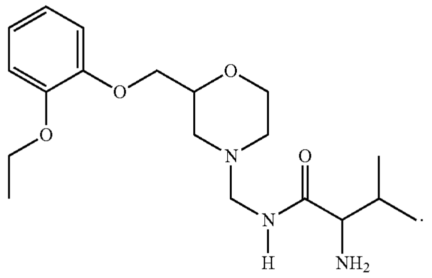

In some embodiments, a composition includes a derivative of substituted morpholines of Formula I, II, III, or IV, stereoisomers thereof, and/or salts thereof, and at least one pharmaceutically acceptable excipient or carrier.

In some embodiments, a pharmaceutical composition includes comprising a derivative of substituted morpholines of Formula I, II, III, or IV, stereoisomers thereof, and/or salts thereof with a pharmaceutically acceptable carrier or excipient. The pharmaceutical formulation may be in an appropriate dosage form. Illustrative dosage forms include, but are not limited to, injections, oral forms, suppositories, caches, pouches, transdermal, and the like.

In another aspect, treatment of a CNS disorder is provided by administering a composition including a derivative of substituted morpholines of Formulae I, II, III, or IV, or salts thereof as described herein to a subject in need thereof.

In another aspect, a method is provided for administering to a subject a composition including a compound of Formula I, II, III, or IV or salts thereof. In one aspect, the subject is a mammal. In further embodiments, the mammalian subject is a human. In particular embodiments, the mammalian subject is an adult human or a human child.

In some embodiments, the methods described herein include administering the derivative of substituted morpholines of Formula I, II, III, or IV, stereoisomers thereof, and/or salts thereof along with at least one additional pharmaceutical agent. In some embodiments, the at least one additional pharmaceutical agent is another agent for a CNS disorder. In further embodiments, the at least one additional pharmaceutical agent is 2-((2-ethoxyphenoxy)methyl)morpholine or a salt thereof.

In one embodiment, the derivative of substituted morpholines may be prepared from 2-((2-ethoxyphenoxy)methyl) morpholine or a salt thereof.

In one embodiment, the derivative of substituted morpholines may be prepared by reacting 2-((2-ethoxyphenoxy) methyl)morpholine or a salt thereof with sodium bicarbonate to form the intermediate 1 having the following structure:

(Intermediate 1)

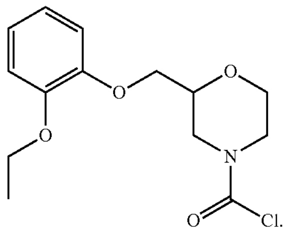

In one embodiment, the derivative of substituted morpholines may be prepared by reacting 2-((2-ethoxyphenoxy) methyl)morpholine or a salt thereof with 1-chloromethyl chloroformate forming the Intermediate 2 having the following structure:

(Intermediate 2)

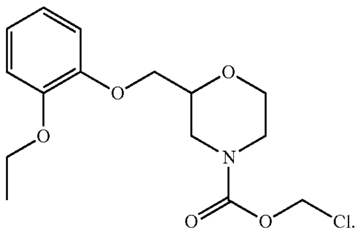

In one embodiment, the derivative of substituted morpholines can be prepared by reacting 2-((2-ethoxyphenoxy) methyl)morpholine or a salt thereof with 1-chloroethyl chloroformate forming the Intermediate 3 having the following structure:

(Intermediate 3)

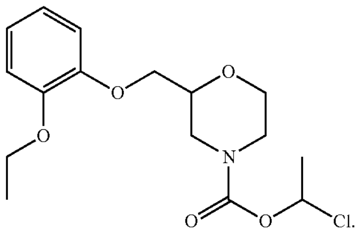

In one embodiment, the derivatives of substituted morpholines of Formula I, II, III, or IV are prepared by reacting 2-((2-ethoxyphenoxy)methyl)morpholine or a salt thereof with the Intermediate 1, Intermediate 2, or Intermediate 3.

In another embodiment, a method of making the derivatives of substituted morpholines of Formula I, II, III, or IV are provided.

The derivatives of substituted morpholines may be analyzed by liquid chromatography-mass spectrometry (LCMS) and nuclear magnetic resonance (NMR) spectroscopy.

The present invention, thus generally described, will be understood more readily by reference to the following examples, which are provided by way of illustration and are not intended to be limiting of the present invention.

EXAMPLES

Example 1. Preparation of Compounds of the Invention

Procedures for making the Intermediates. It is understood that while in some structures, chiral centers are indicated in either an R or S configuration, the other configuration is also disclosed herein.

Intermediate 1: Synthesis of 2-((2-ethoxyphenoxy)methyl)morpholine-4-carbonyl chloride

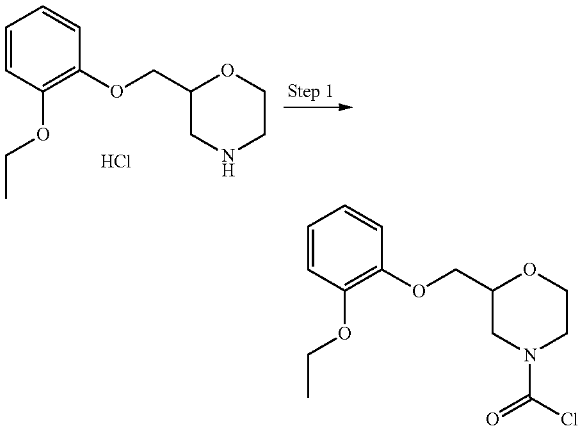

Intermediate 1

A solution of 2-((2-ethoxyphenoxy)methyl)-morpholine hydrochloride (500 mg, 1.83 mmol) in dichloromethane (50 ml) was added dropwise to a slurry of sodium bicarbonate (460 mg, 5.48 mmol). The reaction mixture was stirred for 30 minutes. A solution of triphosgene (358 mg, 1.21 mmol) in dichloromethane (25 ml) was added at 10-15° C. over 15 minutes. The reaction mixture was stirred at room temperature for 3 hours. The reaction mass was filtered to remove sodium chloride and the filtrate is concentrated under vacuum to give 438 mg of ethyl methyl carbamoyl chloride as a light-yellow oil (yield: 80%).

$^1H$ NMR ($CDCl_3$, 400 MHz): δ ppm 6.88-6.91 (m, 4H), 4.39-4.47 (br t, 1H), 3.96-4.25 (m, 6H), 3.83-3.87 (br t, 1H), 3.61-3.71 (br t, 1H), 3.03-3.38 (m, 2H), 1.44 (t, 3H).

Intermediate 2: chloromethyl 2-((2-ethoxyphenoxy) methyl)morpholine-4-carboxylate

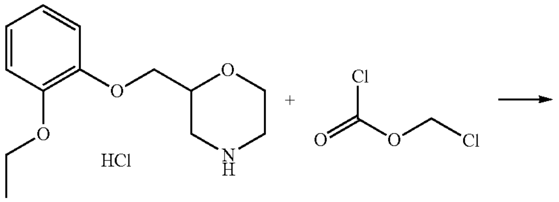

-continued

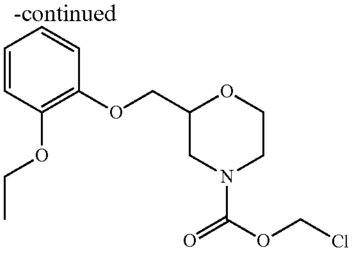

Intermediate 2

To a stirred ice cold mixture of 2-((2-ethoxyphenoxy) methyl)morpholine hydrochloride (1.3 gm, 4.52 mmol), trimethylamine (1.01 gm, 9.95 mmol) dichloromethane was added dropwise 1-chloromethyl chloroformate. The reaction mixture was stirred at 10-15° C., allowed to attain room temperature and stirred for 5 hours. The precipitated solids were filtered and the filtrate was concentrated. The crude product was purified by column chromatography (hexane: EtOAc 7:3) to afford 1.2 gm (80%) of white solid.

$^1$H NMR ($CDCl_3$, 400 MHz): δ ppm 1.46 (t, 3H), 1.59 (s, 4H), 3.05 (d, 2H), 3.63 (d, 1H), 3.92-4.02 (m, 2H), 4.04-4.15 (m, 4H), 4.23 (br. s., 1H), 5.76-5.86 (m, 2H), 6.84-7.00 (m, 4H).

Intermediate 3: 1-chloroethyl 2-((2-ethoxyphenoxy) methyl)morpholine-4-carboxylate

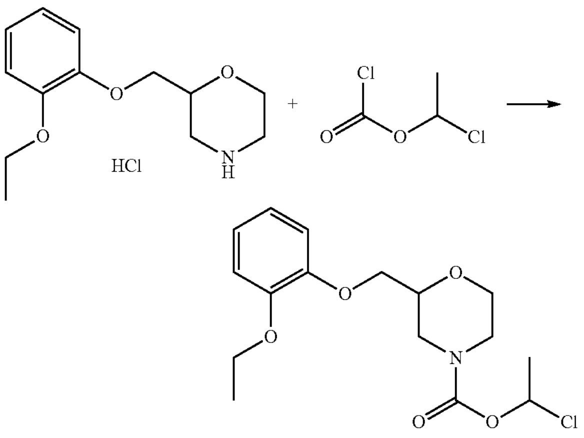

Intermediate 3

To a stirred ice cold mixture of 2-((2-ethoxyphenoxy)-methyl)morpholine hydrochloride (2 gm, 6.96 mmol), trimethylamine (1.01 g, 9.95 mmol) dichloromethane was added dropwise 1-chloroethyl chloroformate (1.19 g, 83.5 mmol). The reaction mixture was stirred at 10-15° C. and allowed to attain room temperature and stirred for 5 h. Precipitated solids were filtered, and the filtrate was concentrated. The crude product was purified by column chromatography (hexane:EtOAc 7:3) to afford 1.42 gm (59.3%) of white solid.

$^1$H NMR (400 MHz, $CDCl_3$): δ ppm 1.39-1.51 (m, 3H), 1.83 (d, 3H), 2.92-3.12 (m, 2H), 3.54-3.72 (m, 1H), 3.85 (br. s., 1H), 3.89-4.13 (m, 7H), 4.20 (d, 1H), 6.61 (m, 1H), 6.84-7.01 (m, 4H).

Procedures for Synthesizing the Compounds of Formula I, II, III or IV

SP-16: ((D-valyl)oxy)methyl 2-((2-ethoxyphenoxy) methyl)morpholine-4 carboxylate Step 1

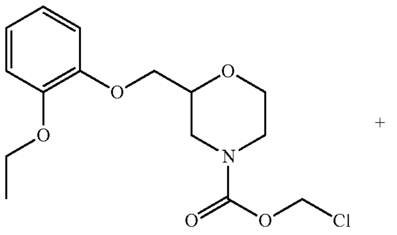

Intermediate 2

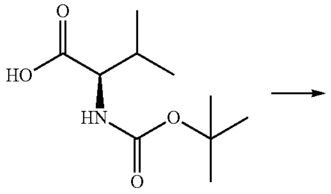

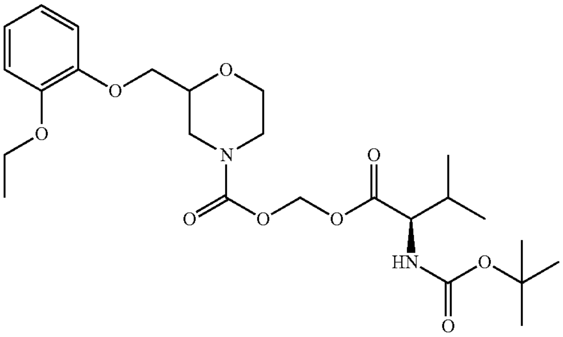

SP-16A

A reaction mixture of N-Boc-D-Valine (175 mg, 0.80 mmol), cesium carbonate (130 mg, 0.4 mmol), in methanol (3.3 ml) was stirred at room temperature for 3 hours, then methanol evaporated, residue reconstituted with DMF (1 ml). To the reaction mixture was added chloromethyl 2-((2-ethoxyphenoxy)methyl)morpholine-4-carb oxyl ate (Intermediate 2) (177 mg, 0.52 mmol). The resulting mixture was stirred at 80° C. for 20 hours. DMF was evaporated under vacuum, residue dissolved in chloroform and purified by column chromatography (hexane:EtOAc 1:1) to afford 112 mg (39.4%) of semi-solid oil.

Step 2

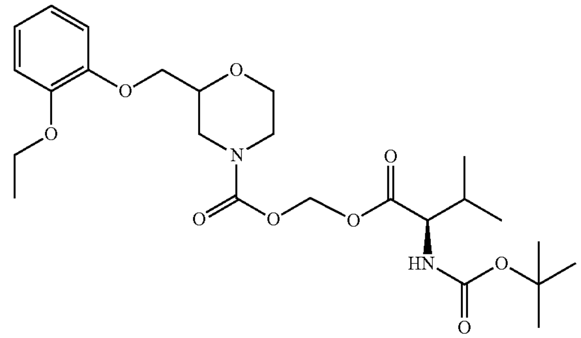

SP-16A

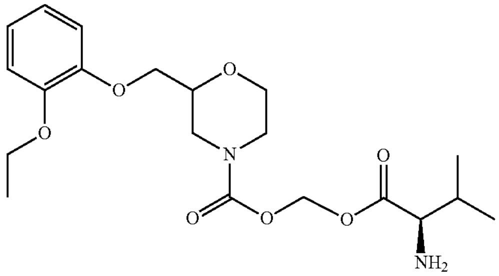

SP-16

A solution of SP-16A (65 mg, 0.12 mmol) and 2M HCl in dioxane stirred at room temperature overnight. Solvent was evaporated and dried under vacuum to obtain 50 mg (95.6%) of pure desired product (SP-16) as a brown semisolid. LCMS: Purity: 96.27% by ELS detector. MS: M+H=411.14. $^{1}$H NMR ($CDCl_3$, 400 MHz): δ ppm 1.12 (t, 6H), 1.44 (t, 3H), 2.46 (br. s, 1H), 2.90-3.10 (m, 2H), 3.52-3.66 (m, 1H), 3.85-420 (m, 10H), 5.83 (br. s, 1H), 5.95 (d, 1H), 6.85-6.96 (m, 4H), 8.24 (br. s, 2H).

SP-17: 1-((L-valyl)oxy)ethyl 2-((2-ethoxyphenoxy) methyl)morpholine-4 carboxylate Step 1

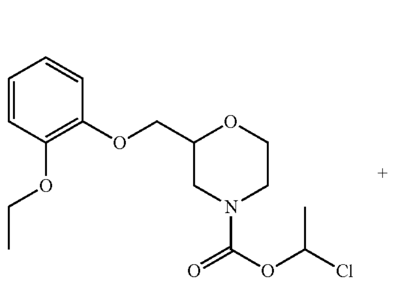

Intermediate 3

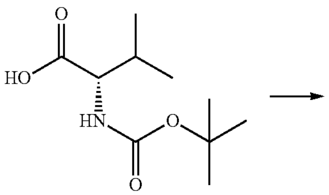

-continued

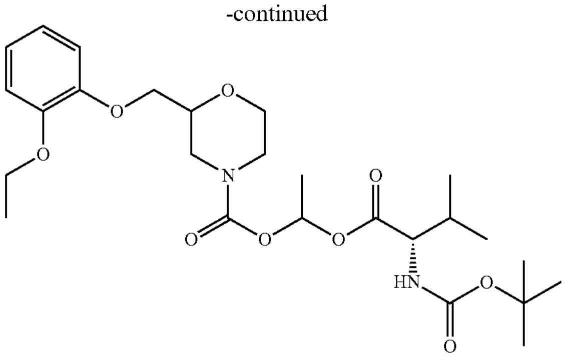

SP-17A

A reaction mixture of N-Boc-L-Valine (175 mg, 0.80 mmol), cesium carbonate (130 mg, 0.4 mmol), in methanol (3.3 ml) was stirred at room temperature for 3 hours, then methanol evaporated, residue reconstituted with DMF (1 ml). To the reaction mixture was added chloromethyl 2 1-chloroethyl 2-((2-ethoxyphenoxy)methyl)morpholine-4-carboxylate (Intermediate 3) (184 mg, 0.52 mmol). The resulting mixture was stirred at 80° C. for 20 hours. DMF was evaporated under vacuum, residue dissolved in chloroform and purified by column chromatography (hexane: EtOAc 8:2) to obtain 141 mg (48.3%) of semisolid oil.

Step 2

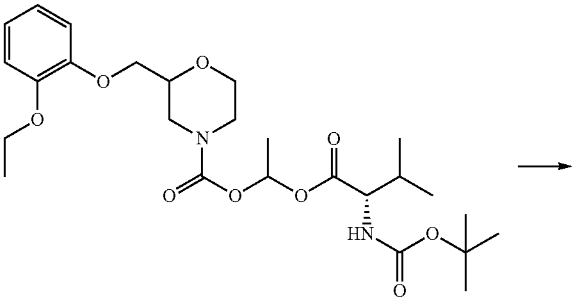

SP-17A

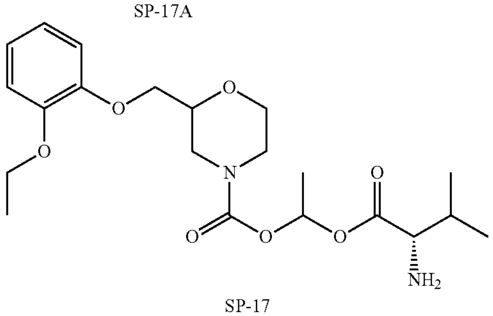

SP-17

A solution of SP-17A (65 mg, 0.11 mmol) and 2M HCl in dioxane stirred at room temperature overnight. The solvent was then evaporated and the product dried under vacuum to obtain 51 mg (92.4%) of pure desired product (SP-17) as a brown solid. LCMS: Purity: 100% by ELS detector. MS: M+H=425.17. $^{1}$H NMR ($CDCl_3$, 400 MHz): δ ppm 1.12 (t, 6H), 1.44 (t, 3H), 2.46 (br. s., 1H), 2.90-3.10 (m, 2H), 3.52-3.66 (m, 1H), 3.85-420 (m, 10H), 5.83 (br. s., 1H), 5.95 (d, 1H), 6.85-6.96 (m, 4H), 8.24 (br. s, 2H).

SP-18: (2R)-2-amino-N-((2-((2-ethoxyphenoxy) methyl)morpholino)methyl)-3-methylbutanamide bis hydrochloride salt Step 1

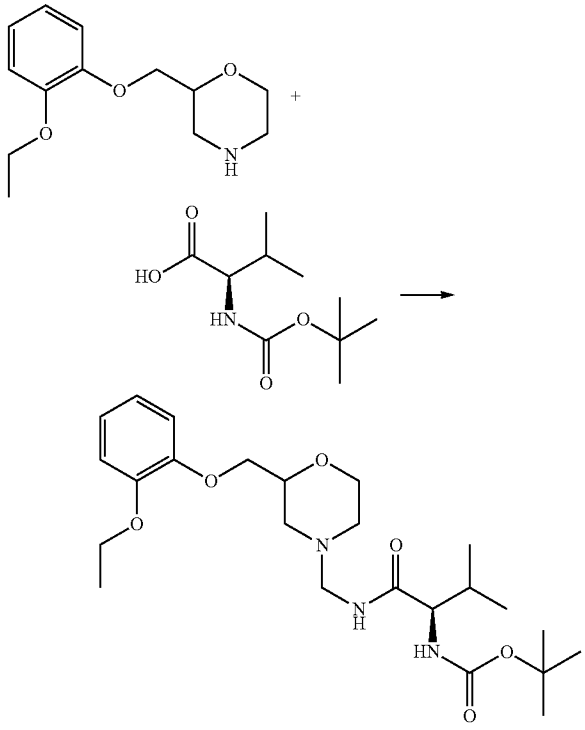

SP-18A

To a solution of 2-((2-ethoxyphenoxy)methyl)-morpholine hydrochloride (108 mg, 0.4 mmol) and polyformaldehyde (50 mg) in THE (2 ml) was added a slurry of sodium bicarbonate (92 mg, 1.1 mmol). The reaction mixture was stirred for 48 hours minutes. The reaction mass was filtered, and the filtrate was concentrated under vacuum. The residue was dissolved in chloroform and purified by column chromatography (hexane:EtOAc 8:1) to obtain 80 mg (43%) of semi-solid oil.

Step 2

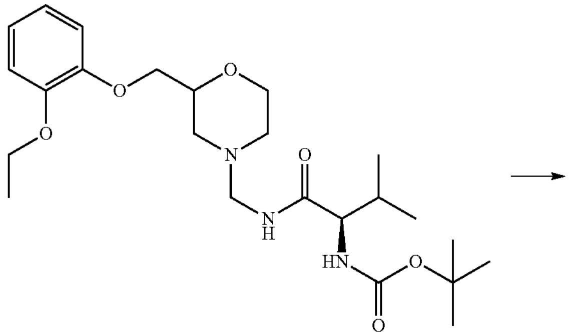

SP-18A

-continued

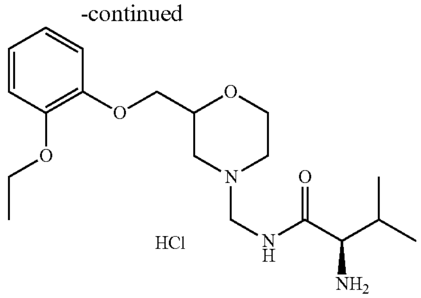

SP-18

Solution of SP-18A (70 mg, 0.15 mmol) and 2M HCl in dioxane was stirred at room temperature overnight. The solvent was evaporated and dried under vacuum to obtain 50 mg (76%) of pure desired product (SP-18) as a brown solid. LCMS: M+H=366.20. Purity 98.73% by ELS detector. $^{1}H$ NMR ($CDCl_3$, 400 MHz): δ ppm 9.8-10.5 (br m, 1H), 8.2-8.5 (br s, 2H), 6.75-7.1 (m, 4H), 4.2-5.0 (m, 4H), 3.9-4.2 (m, 6H), 3.70-3.87 (m, 2H), 3.0-3.5 (br s, 1H), 1.75-2.25 (m, 4H), 1.3-1.5 (m, 3H), 1.1 (br s, 6H).

SP-19: Pyridin-2-yl 2-((2-ethoxyphenoxy)methyl) morpholine-4-carboxylate

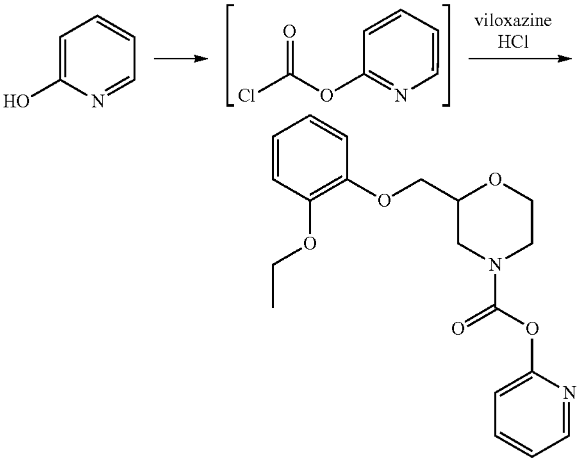

SP-19

A solution of triphosgene (163 mg, 0.55 mmol) in dichloromethane (DCM; 1 ml) was stirred in an ice bath at 0-5° C. temperature for 15 min and a solution of 2-hydroxypyridine (150 mg, 1.58 mmol), N,N-diisopropylethylamine (DIPEA; 208 mg, 1.61 mmol) in DCM (1 ml) was added dropwise. The reaction mixture allowed to attain room temperature. The completion of the reaction was monitored by TLC. After the reaction was completed, the reaction mixture was evaporated, reconstituted with DCM and evaporated (×3) to remove excess of triphosgene. Residue was reconstituted with DCM, and a solution of 2-((2-ethoxyphenoxy)methyl) morpholine hydrochloride (363 mg, 1.26 mmol) and TEA (13.6 mg, 1.34 mmol) in DCM added and stirred overnight at room temperature. The reaction mixture was absorbed on silica and was purified by column chromatography using hexane-ethyl acetate (2:1) to obtain the target compound (SP-19) as a semisolid 56 mg (12.3%). LCMS: M+H=359.08. Purity 100% by ELS detector. $^{1}H$ NMR (400

MHz, $CDCL_3$): δ 1.25-1.46 (m, 3H), 3.02-3.34 (m, 2H), 3.69-3.76 (m, 1H), 3.95-4.16 (m, 7H), 4.28-4.42 (d, 1H), 6.85-6.99 (m, 4H), 7.11 (dd, 1H), 7.21 (dd, 1H), 7.75-7.83 (m, 1H), 8.39 (dd, 1H).

SP-20: 2-Chloropyridin-4-yl 2-((2-ethoxyphenoxy)methyl)morpholine-4-carboxylate

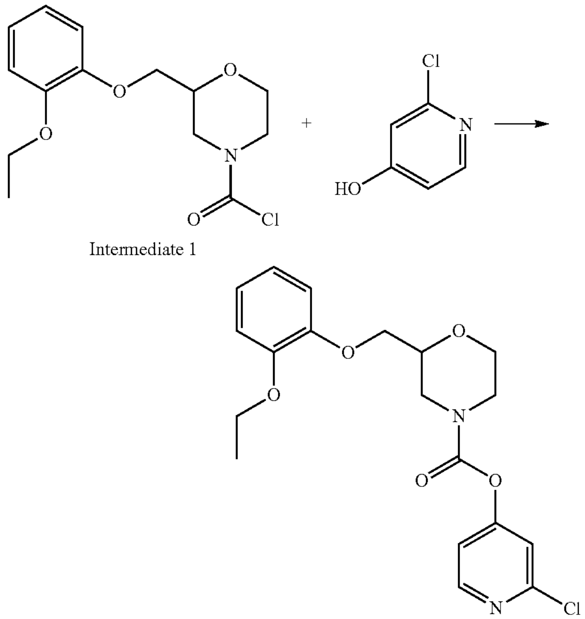

Intermediate 1

SP-20

To a stirred and ice-cooled solution of 2-chloro-4-hydroxy pyridine, (95 mg, 0.73 mmol) in anhydrous THF (10 mL) was added 2-((2-ethoxyphenoxy)methyl)morpholine-4-carbonyl chloride (Intermediate 1) (273 mg, 0.33 mmol), followed by a dropwise addition of NaH (60% in oil, 35 mg, 0.146 mmol). The reaction mixture was stirred for 14 hours at room temperature under argon. After evaporation of the solvent in vacuo, water (5 mL) was added and extracted with ether (3×10 mL). The organic phase was washed with dilute NaOH (pH 10-11), dried, and evaporated to dryness in vacuum. Purification by column chromatography (hexane:EtOAc 2:1) afforded 83 mg (29%) of a semisolid (SP-20). LCMS: Purity 100% by ELS detector. MS: M+H=393.08. $^1$H NMR ($CDCl_3$, 400 MHz): δ ppm 1.38-1.47 (m, 3H), 3.04-3.32 (m, 2H), 3.70 (t, 1H) 3.9-3.93 (m, 1H), 4.03-4.08 (m, 5H), 4.15-4.18 (m, 1H), 4.30-4.35 (m, 1H), 6.87-6.99 (m, 4H), 7.11-7.12 (m, 1H), 7.23 (d, 1H), 8.37 (d, 1H).

SP-21: Methylene bis(2-((2-ethoxyphenoxy)methyl)morpholine-4-carboxylate)

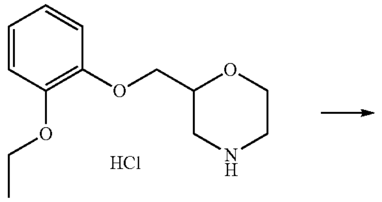

-continued

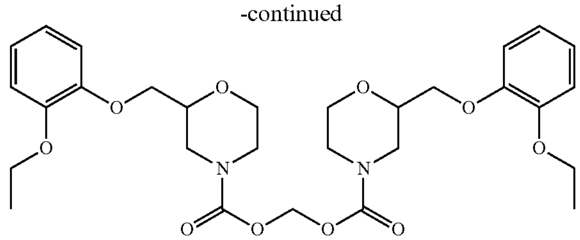

SP-21

A solution of 2-((2-ethoxyphenoxy)methyl)morpholine hydrochloride (108 mg, 0.4 mmol) and methylene dibromide (50 mg) in DMF (2 ml) was added a slurry of cesium carbonate (100 mg, 1.2 mmol). Carbon dioxide gas was passed into the reaction for 30 minutes and the mixture stirred at room temperature for 48 hours. The reaction mass was filtered and the filtrate was concentrated under vacuum. The residue was dissolved in chloroform and purified by column chromatography (hexane:EtOAc 4:1) to afford 52 mg (22.6%) of a solid. Purity 100% by ELS detector. MS: M+H=575.15. $^1$H NMR ($CDCl_3$, 400 MHz): δ ppm 6.7-7.00 (m, 8H), 5.83 (s, 2H), 3.8-4.2 (m, 16H), 3.5-3.6 (m, 2H), 2.8-3.0 (m, 4H), 1.43-1.47 (t, 6H).

SP-22: 1-((L-phenylalanyl)oxy)ethyl 2-((2-ethoxyphenoxy)methyl)morpholine-4-carboxylate Step 1

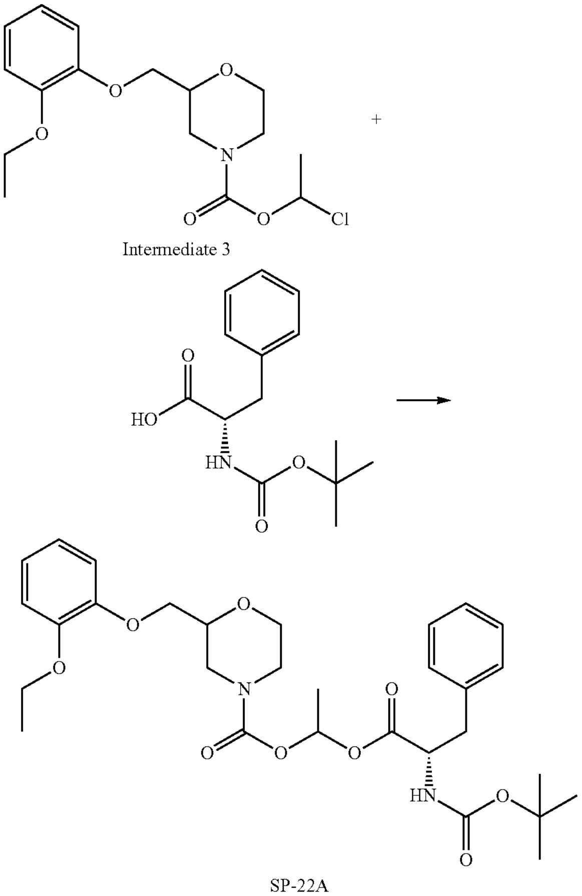

Intermediate 3

SP-22A

A reaction mixture of N-Boc-phenylalanine (175 mg, 0.66 mmol), cesium carbonate (107 mg, 0.33 mmol), in methanol (1.3 ml) were stirred at room temperature for 3 hours, then methanol was evaporated, residue reconstituted with DMF (1 ml). To the reaction mixture was added 1-chloroethyl 2-((2-ethoxyphenoxy)methyl)morpholine-4-carboxylate (Intermediate 3) (150 mg, 0.42 mmol). The resulting mixture was stirred at 80° C. for 20 hours. The DMF was then evaporated under vacuum, the residue dissolved in chloroform, and then purified by column chromatography (hexane: EtOAc 8:2) to afford 232 mg (61%) of semi-solid oil.

Step 2

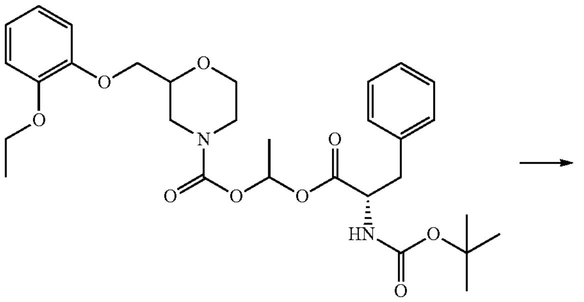

SP-22A

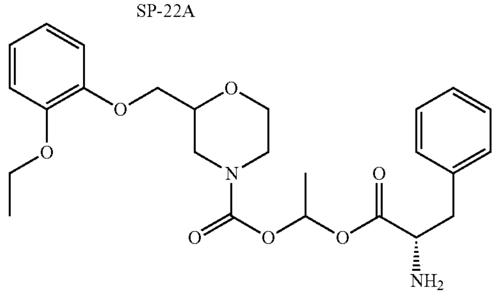

SP-22

Solution of SP-22A (140 mg, 0.238 mmol) and 2M HCl in dioxane was stirred at room temperature overnight. The solvent was evaporated and dried under vacuum to obtain 58 mg (52%) of pure desired product as a light brown solid. LCMS: Purity: 100% by ELS detector. MS: M+H=495.24. $^1$H NMR ($CDCl_3$, 400 MHz): δ ppm 1.25-1.50 (m, 6H), 2.95-3.06 (m, 2H), 3.35-3.71 (m, 4H) 3.76-4.13 (m, 8H) 4.34-4.40 (m, 2H) 6.85-6.92 (m, 5H), 7.25-7.36 (m, 5H), 8.70 (br. s., 1H), 8.79 (br. s., 1H).

SP-23 1-((dimethyl-L-valyl)oxy)ethyl 2-((2-ethoxyphenoxy)methyl)morpholine-4-carboxylate, hydrochloride

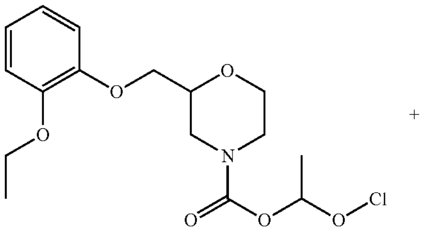

Intermediate 3

-continued

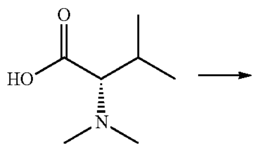

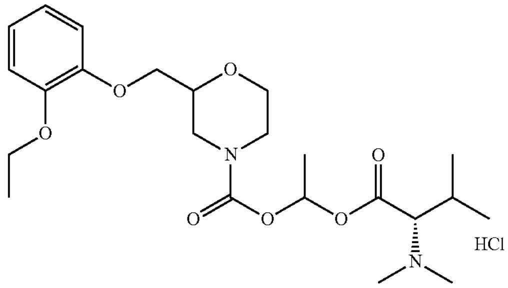

SP-23

A reaction mixture of L-Val-N,N-dimethyl (100 mg, 0.68 mmol), cesium carbonate (110 mg, 0.34 mmol), in methanol (0.75 ml) were stirred at room temperature for 3 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (160 mg, 0.44 mmol). The resulting mixture was stirred at 80° C. for 20 hours. The DMF was evaporated under vacuum, residue dissolved in chloroform and purified by column chromatography (hexane:EtOAc 3:2) to afford 91 mg (45.7%) of semisolid.

77 mg of the parent compound was dissolved in 2 ml of chloroform and 0.17 ml of 2M HCl in dioxane was added. The reaction mixture was stirred at room temperature for 2 hours. The solvent was then evaporated under Argon and then under vacuum to obtain 81 mg of an oil. LCMS: Purity: 99.61% by ELS detector. MS: M+H=453.30 M+Na=475.28. $^1$H NMR ($CDCl_3$, 400 MHz): δ ppm 0.89 (dd, 3H), 0.97 (d, 3H), 1.45 (t, 3H), 1.53 (d, 3H), 1.63 (s, 1H), 2.01 (dt, 6.54 Hz, 1H), 2.31 (s, 6H), 2.72 (m, 1H), 3.04 (br. s., 2H), 3.59 (d, 1H), 3.81-4.18 (m, 8H), 6.88-6.91 (m, 5H).

SP-24: 1-((Acetyl-L-valyl)oxy)ethyl 2-((2-ethoxyphenoxy)methyl)morpholine-4-carboxylate

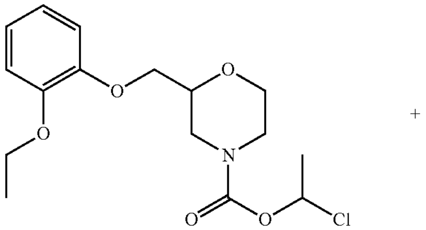

Intermediate 3

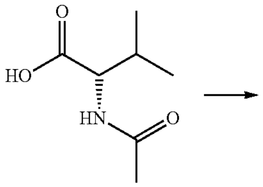

-continued

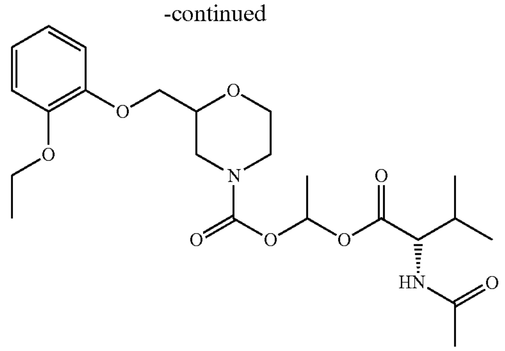

SP-24

A reaction mixture of N-acetylvaline (120 mg, 0.69 mmol), cesium carbonate (110 mg, 0.34 mmol), in methanol (0.9 ml) were stirred at room temperature for 3 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (160 mg, 0.44 mmol). The resulting mixture was stirred at 80° C. for 20 hours. The DMF was evaporated under vacuum, residue dissolved in chloroform and purified by column chromatography (hexane:EtOAc 3:2) to afford 75 mg (37%) of oil. LCMS: Purity: 100% by ELS detector. MS: M+H=473.26 M+Na=495.24. $^{1}H$ NMR ($CDCl_3$, 400 MHz): δ ppm 0.82-1.03 (m, 3H), 0.93 (d, 3H), 1.45 (br. s., 3H), 1.52-1.53 (m, 3H), 2.04 (d, 3H), 2.17 (m, 1H), 2.94-3.10 (m, 2H), 3.57-3.60 (m, 1H), 3.84-4.17 (m, 8H), 4.55-4.62 (m, 1H), 5.97 (br. s., 1H), 6.89-6.95 (m, 5H).

SP-25: 1-((methyl-D-valyl)oxy)ethyl 2-((2-ethoxyphenoxy)methyl)morpholine-4-carboxylate, trifluoroacetic acid salt Step 1

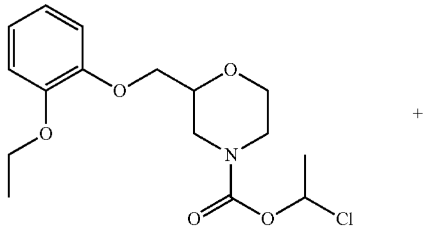

Intermediate 3

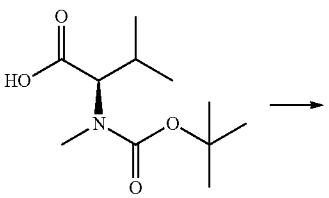

-continued

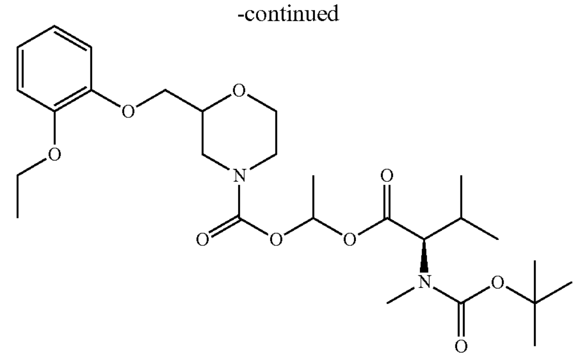

SP-25A

A reaction mixture of N-Boc-D-Valine (160 mg, 0.69 mmol), cesium carbonate (110 mg, 0.35 mmol), in methanol (1.2 ml) was stirred at room temperature for 3 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (160 mg, 0.44 mmol). The resulting mixture was stirred at 80° C. for 20 hours. DMF was evaporated under vacuum, residue dissolved in chloroform and purified by column chromatography (hexane:EtOAc 2:1) to afford 90 mg (36.1%) of semi-solid oil.

Step 2

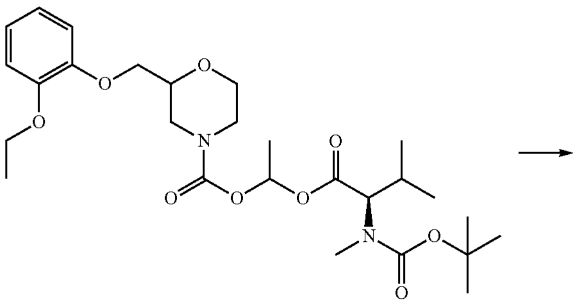

SP-25A

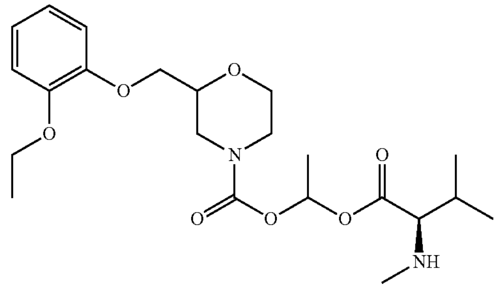

SP-25

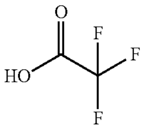

Solution of SP-25A (50 mg, 0.09 mmol) in DCM (1 ml) and TFA (0.1 ml) was stirred at room temperature overnight (18 hours). The solvent was then evaporated and dried under vacuum to obtain 35.8 mg (85.3%) of pure desired product as a yellow oil. LCMS: Purity: 100% by ELS detector. MS:

M+H=439.24. $^1$H NMR ($CDCl_3$, 400 MHz): δ 0.98-1.15 (m, 6H), 1.36-1.49 (m, 3H), 1.57 (d, 3H), 2.37 (br. s., 1H), 2.78 (s, 3H), 2.88-3.10 (m, 2H), 3.14 (d, 1H), 3.49-3.64 (m, 1H), 3.67 (br. s., 1H), 3.84 (br. s., 1H), 3.89 (br. s., 1H), 3.97 (br. s., 2H), 4.00-4.11 (m, 3H), 4.16 (d, 2H), 6.84-7.00 (m, 5H).

SP-26: 1-((D-valyl)oxy)-2-methylpropyl 2-((2-ethoxyphenoxy)methyl)-morpholine-4-carboxylate HCl salt Step 1

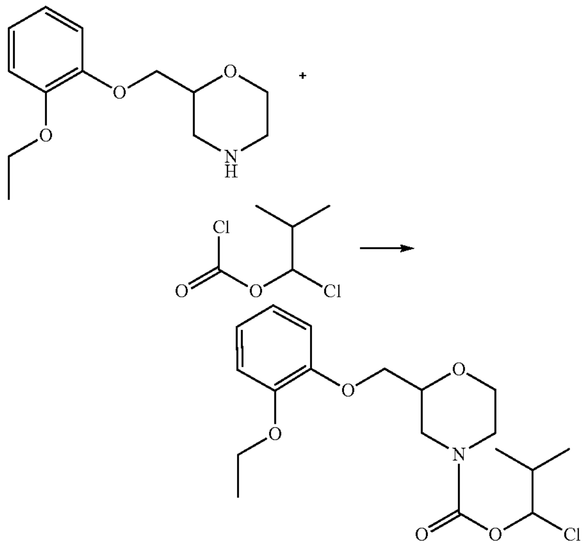

SP-26A

To a stirred ice cold mixture of 2-((2-ethoxyphenoxy)-methyl)morpholine hydrochloride (350 mg, 1.22 mmol), trimethylamine (271 mg, 2.68 mmol) dichloromethane was added dropwise 1-chloro-2-methylpropylchloroformate (210 mg, 1.46 mmol). The reaction mixture was stirred at 10-15° C. and allowed to attain room temperature and stirred for 2 hours. Precipitated solids were filtered, and the filtrate was concentrated. The crude product was purified by column chromatography (hexane:EtOAc 4:1) to afford 0.55 gm (59.3%) of oil. $^1$H NMR ($CDCl_3$, 400 MHz): δ ppm 1.06-1.09 (m, 6H), 1.43-1.46 (t, 3H), 2.18-2.22 (m, 1H), 2.95-3.20 (m, 2H), 3.55-3.69 (m, 1H), 3.86-4.27 (m, 8H), 6.36-6.37 (d, 1H), 6.86-6.97 (m, 4H).

Step 2

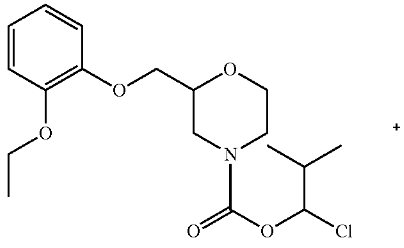

SP-26A

-continued

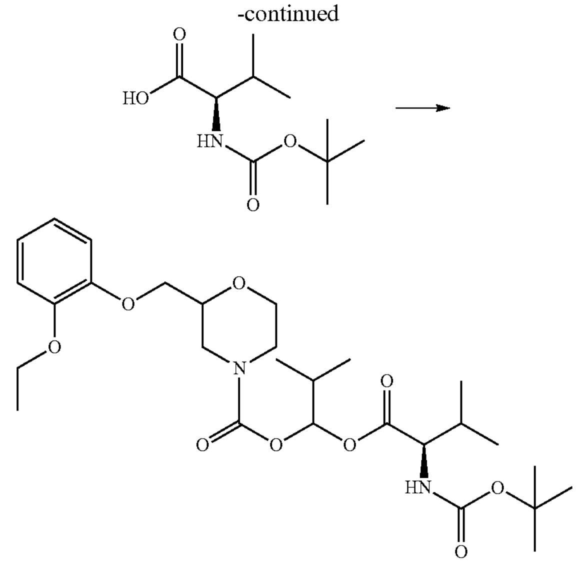

SP-26B

A reaction mixture of N-Boc-D-Valine (200 mg, 0.92 mmol), cesium carbonate (150 mg, 0.46 mmol), in methanol (1.5 ml) were stirred at room temperature for 2 hours, then methanol evaporated, residue reconstituted with DMF (1 ml). To the reaction mixture was added 1-chloro-2-methylpropyl 2-((2-ethoxyphenoxy)methyl)morpholine-4-carboxylate (SP-26A) (230 mg, 0.59 mmol). The resulting mixture was stirred at 80° C. for 20 hours. DMF was evaporated under vacuum, residue dissolved in chloroform and purified by column chromatography (hexane:EtOAc 4:1) to afford 170 mg (52.1%) of semisolid oil.

Step 3

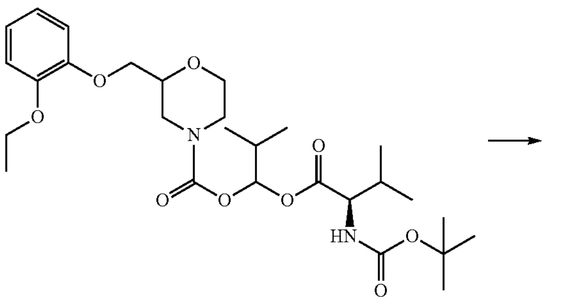

SP-26B

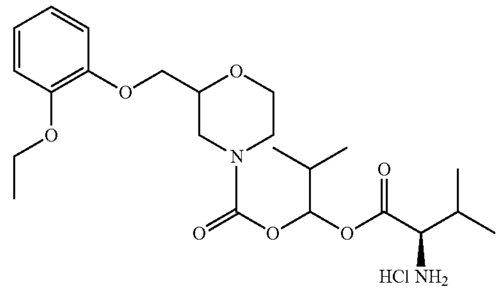

SP-26

Solution of SP-26B (110 mg, 0.2 mmol) in dioxane (1 ml) and 2M HCl in dioxane (0.4 ml) stirred at room temperature overnight (18 hours). The solvent was then evaporated and dried under vacuum to obtain 80 mg (88%) of pure desired product as an oil. LCMS: Purity: 100% by ELS detector. MS: M+H=453.22. $^1$H NMR ($CDCl_3$, 400 MHz): δ ppm 0.92-1.04 (m, 6H), 1.04-1.23 (m, 6H), 1.42 (t, 3H), 2.09 (br, 1H), 2.48 (br, 1H), 2.89-3.17 (m, 1H), 3.49-4.25 (m, 13H), 6.81-6.73 (m, 1H), 6.88-6.92 (m, 4H), 8.70-8.76 (d, 2H).

SP-27: 1-(((R)-2-(aminomethyl)-3-methylbutanoyl)oxy)ethyl 2-((2-ethoxyphenoxy)methyl)morpholine-4-carboxylate trifluoroacetic acid salt Step 1

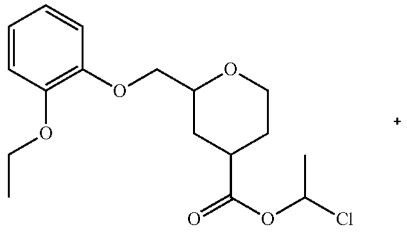

Intermediate 3

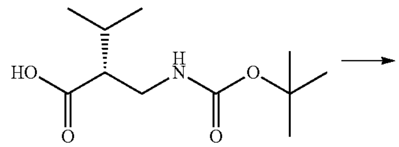

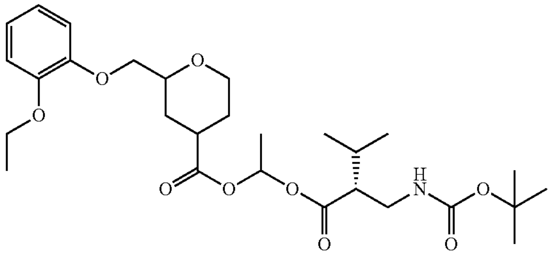

SPI-27A

A reaction mixture of N-Boc-3-amino-2-isopropionic acid (100 mg, 0.43 mmol), cesium carbonate (70 mg, 0.22 mmol), in methanol (0.75 ml) were stirred at room temperature for 2 hours ("h"), then methanol evaporated, residue reconstituted with DMF (0.75 ml). To the reaction mixture was added chloromethyl 2 1-chloroethyl 2-((2-ethoxyphenoxy)methyl)morpholine-4-carboxylate (Intermediate 3) (99 mg, 0.28 mmol). The resulting mixture was stirred at 80° C. for 20 hours. The DMF was evaporated under vacuum, the residue dissolved in chloroform and purified by column chromatography (hexane:EtOAc 4:1) to afforded 117 mg (77.6%) of semi-solid.

Step 2

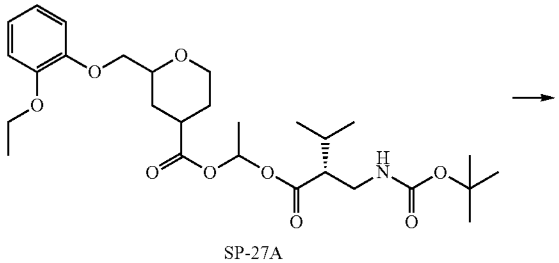

SP-27A

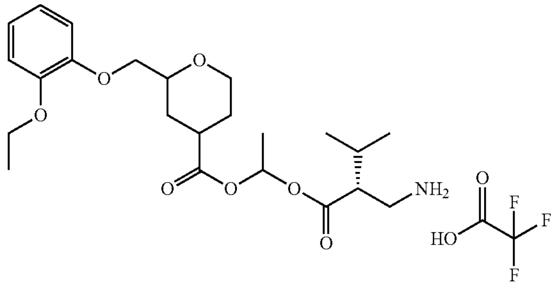

SP-27

A solution of SP-27A (58 mg, 0.012 mmol) in chloroform (1 ml) and TFA (0.2 ml) stirred at room temperature for 24 hours. The solvent was then evaporated and dried under vacuum to obtain 52 mg (90%) of pure desired product as oil. LCMS: Purity: 100% by ELS detector. MS: M+H=439.21. $^1$H NMR ($CDCl_3$, 400 MHz): δ ppm 0.86-1.04 (m, 6H), 1.35-1.49 (m, 3H), 1.53 (br. s., 3H), 2.96-3.09 (m, 1H), 3.10-3.31 (m, 2H), 3.79-3.91 (m, 2H), 3.92-4.16 (m, 6H), 6.85-7.01 (m, 4H), 7.65 (br. s., 3H).

SP-28: 1-(((R)-2-(aminomethyl)-3-methylbutanoyl)oxy)ethyl 2-((2-ethoxyphenoxy)methyl)morpholine-4-carboxylate trifluoroacetic acid salt Step 1

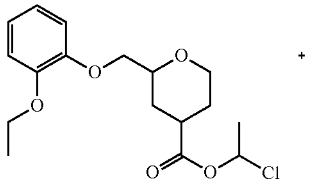

Intermediate 3

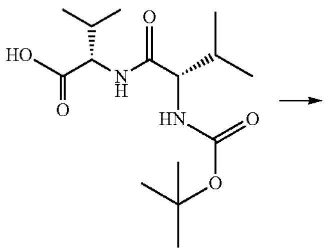

-continued

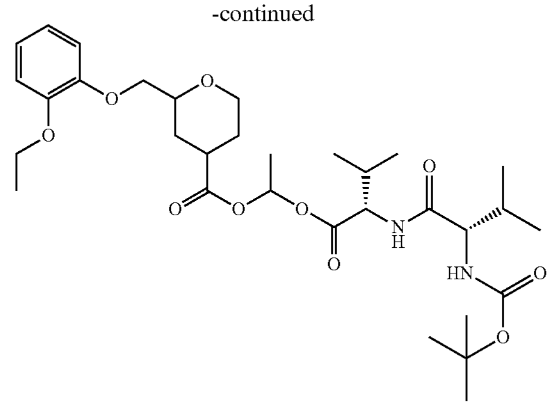

SP-28A

A reaction mixture of Boc-Val-Val (150 mg, 0.47 mmol), cesium carbonate (80 mg, 0.24 mmol), in methanol (1.13 ml) was stirred at room temperature for 2 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (110 mg, 0.3 mmol). The resulting mixture was stirred at 80° C. for 18 hours. The DMF was evaporated under vacuum, residue dissolved in DCM and purified by column chromatography (hexane:EtOAc 1:1) to afforded 35 mg (11.9%) of semi-solid.

Step 2

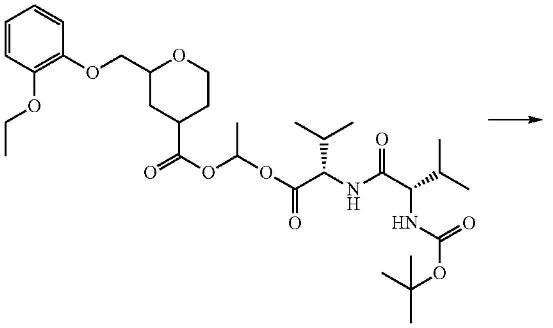

SP-28A

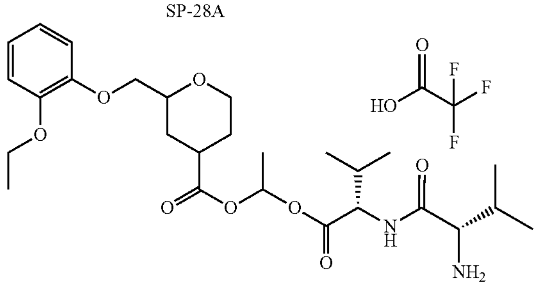

SP-28

Solution of SP-28A (32 mg, 0.005 mmol) in chloroform (1 ml) and TFA (0.085 ml) was stirred at room temperature for 6 hours. The solvent was then evaporated and dried under vacuum to obtain 33 mg (98%) of pure desired product as yellow semi-solid. LCMS: Purity: 100% by ELS detector. MS: M+H=524.27. $^1$H NMR ($CDCl_3$, 400 MHz): δ ppm 0.87-1.16 (m, 11H), 1.36-1.56 (m, 6H), 2.18 (br. s., 2H), 2.99-3.05 (m, 2H), 3.59-4.24 (m, 11H), 6.18 (br. s., 2H), 6.84-7.05 (m, 5H), 7.34-7.53 (m, 1H), 8.10 (br. s., 2H).

SP-29: (((R)-3-amino-4-methylpentanoyl)oxy) methyl 2-((2-ethoxyphenoxy)-methyl)morpholine-4-carboxylate, trifluoroacetic acid salt Step 1

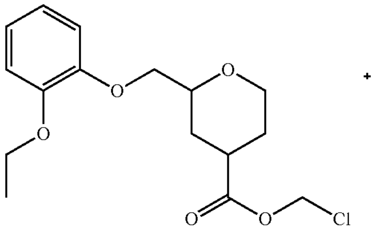

Intermediate 2

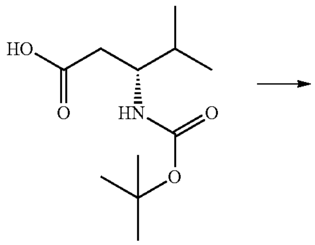

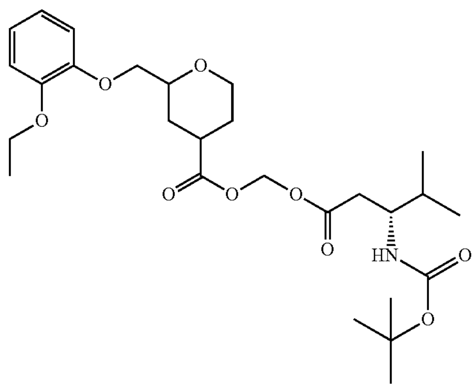

SP-29A

A reaction mixture of Boc-L-O-leucine (150 mg, 0.65 mmol), cesium carbonate (110 mg, 0.146 mmol), in methanol (1.13 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (140 mg, 0.42 mmol). The resulting mixture was stirred at 80° C. for 18 hours. The DMF was evaporated under vacuum, residue dissolved in DCM and purified by column chromatography (hexane:EtOAc 4:1) to afford 120 mg (54.5%) of semi-solid.

Step 2

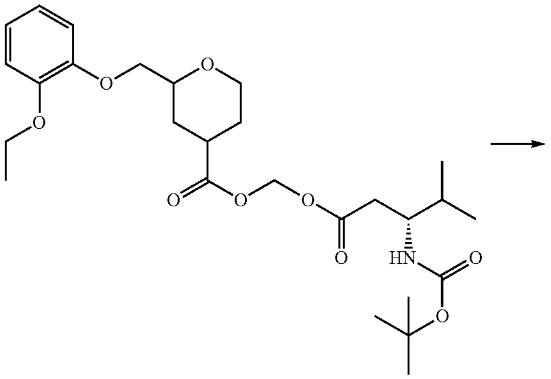

SP-29A

-continued

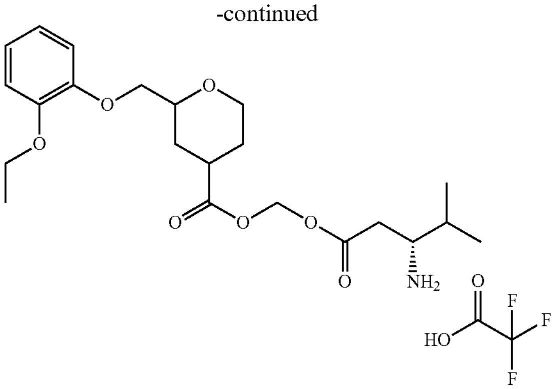

SP-29

Solution of SP-29A (58 mg, 0.11 mmol) in chloroform (1 ml) and TFA (0.55 ml) stirred at room temperature for 24 hours. The solvent was then evaporated and dried under vacuum to obtain 50 mg (90%) of pure desired product as oil. LCMS: Purity: 100% by ELS detector. MS: M+H=425.19. $^{1}$H NMR ($CDCl_3$, 400 MHz): δ ppm 1.03 (dd, 6H), 1.36-1.48 (m, 3H), 2.04 (m, 1H), 2.79 (d, 2H), 2.93-3.22 (m, 2H), 3.46 (br. s. 1H), 3.57-3.65 (m, 1H), 3.90-4.18 (m, 6H), 5.72-5.91 (m, 2H), 6.86-7.02 (m, 3H), 7.43-7.73 (m, 3H), 8.35 (br. s., 3H).

SP-30: Bis(((2-((2-ethoxyphenoxy)methyl)morpholine-4-carbonyl)oxy)methyl) pyridine-3,5-dicarboxylate

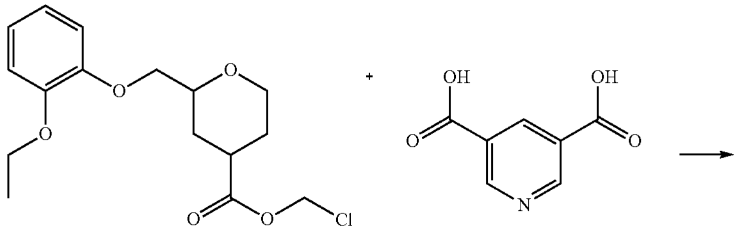

Intermediate 2

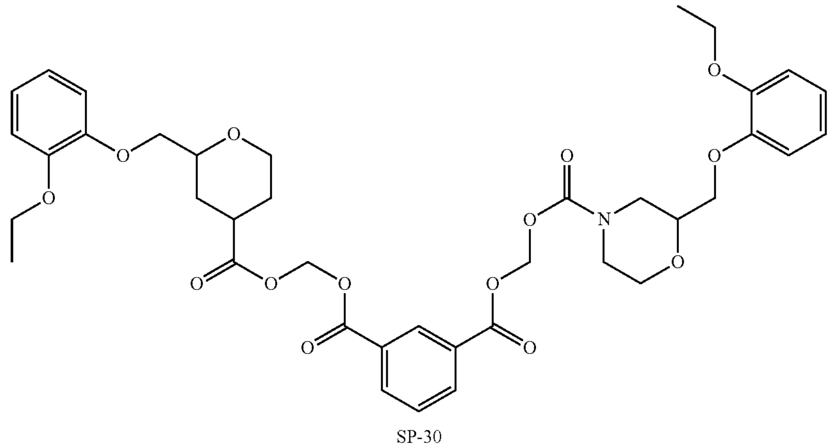

SP-30

A reaction mixture of 3,5-pyridinedicarboxylic acid (75 mg, 0.4 mmol), cesium carbonate (190 mg, 0.6 mmol), in methanol (0.6 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (370 mg, 1.1 mmol). The resulting mixture was stirred at 80° C. for 18 hours. DMF was evaporated under vacuum, residue dissolved in DCM and purified by column chromatography (hexane:EtOAc 1:1) to afford 56 mg (18.5%) of semi-solid oil. LCMS: Purity: 100% by ELS detector. MS: M+H=754.21. $^1$H NMR ($CDCl_3$, 400 MHz): δ ppm 1.44 (t, 6H), 2.92-3.21 (m, 4H), 3.57-3.67 (m, 2H), 3.84 (br. s, 2H) 3.93-4.12 (m, 12H), 4.18-4.27 (m, 2H), 6.07-6.11 (m, 4H), 6.82-7.04 (m, 8H), 8.93 (s, 1H), 9.43 (s, 2H).

SP-31: ((2,2'-(methylazanediyl)bis(acetyl))bis(oxy))bis(methylene)bis(2-((2-ethoxyphenoxy)methyl)morpholine-4-carboxylate)

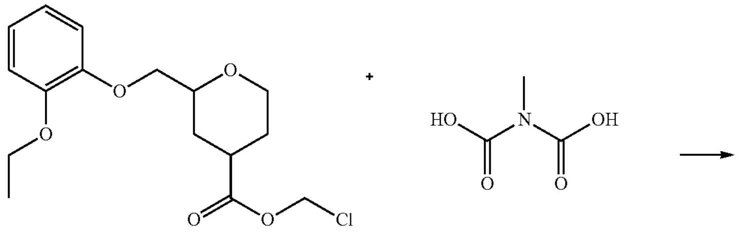

Intermediate 2

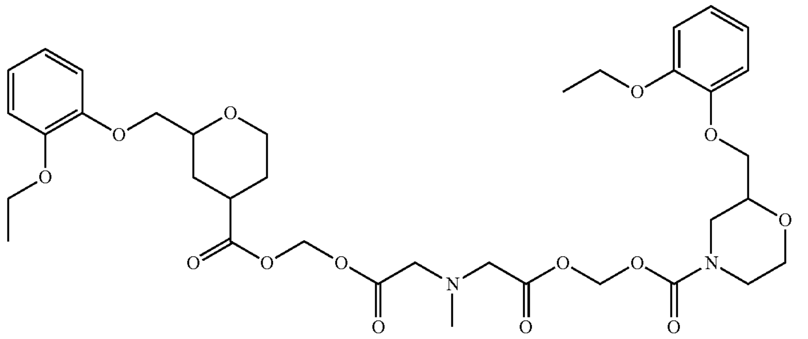

SP-31

A reaction mixture of methyliminodiacetic acid (50 mg, 0.3 mmol), cesium carbonate (144 mg, 0.4 mmol), in methanol (0.4 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (280 mg, 0.8 mmol). The resulting mixture was stirred at 80° C. for 18 hours. DMF was evaporated under vacuum, residue dissolved in DCM and purified by column chromatography (hexane:EtOAc 1:1). Resulting product re-purified by reverse phase C18 column using acetonitrile and water gradient mixture to obtain 30.5 mg (13.8%) of pure semisolid-oil product. LCMS: Purity: 100% by ELS detector. MS: M+H=734.23. $^1$H NMR ($CDCl_3$, 400 MHz): δ ppm 1.43-1.48 (t, 6H), 2.55 (s, 3H), 2.89-3.18 (m, 4H), 3.51-3.69 (m, 6H), 3.82-4.24 (m, 16H), 5.82 (s, 4H), 6.83-7.00 (m, 8H).

SP-32: (((R)-2-(aminomethyl)-3-methylbutanoyl)oxy)methyl 2-((2-ethoxyphenoxy)methyl)morpholine-4-carboxylate, trifluoroacetic acid salt Step 1

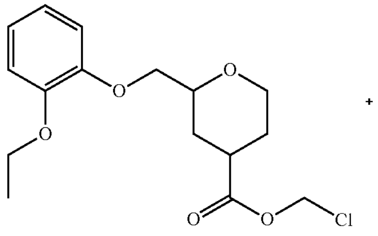

Intermediate 2

-continued

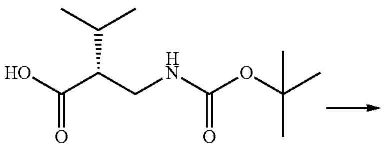

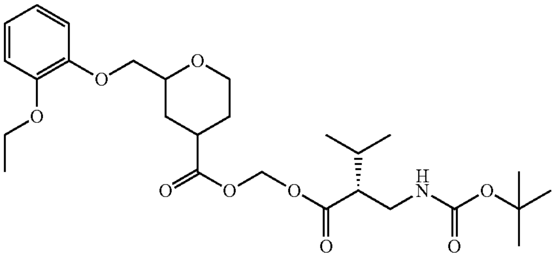

SP-32A

A reaction mixture of N-Boc-3-amino-2-isopropylpropionic acid (10 mg, 0.4 mmol), cesium carbonate (78 mg, 0.2 mmol), in methanol (0.85 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (95 mg, 0.3 mmol). The resulting mixture was stirred at 80° C. for 18 hours. The DMF was evaporated under vacuum, residue dissolved in DCM and purified by column chromatography (hexane:EtOAc 4:1) to afford 80 mg (50.8%) of semi-solid.

Step 2

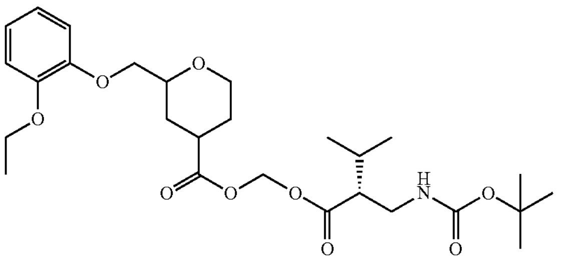

SP-32A

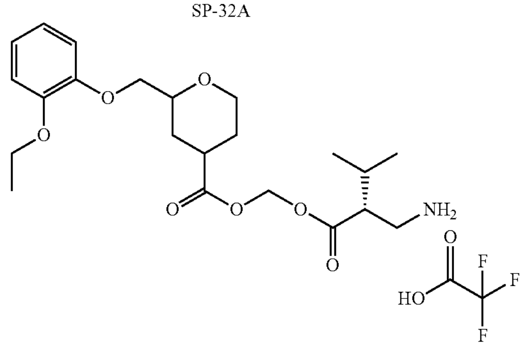

SP-32

Solution of SP-32A (65 mg, 0.124 mmol) in chloroform (1 ml) and TFA (0.23 ml) was stirred at room temperature for 24 hours. Solvent evaporated and dried under vacuum to obtain 49 mg (93%) of pure desired product as a semisolid-oil. LCMS: Purity: 100% by ELS detector. MS: M+H=425.18. $^1$H NMR ($CDCl_3$, 400 MHz): δ ppm 0.95 (d, 3H), 0.93 (d, 3H), 1.40-1.48 (m, 3H), 2.13 (br. s., 1H), 2.72-2.83 (m, 1H), 2.90-3.16 (m, 3H), 3.20-3.32 (m, 1H), 3.51-3.67 (m, 1H), 3.84 (d, 1H), 3.91-4.20 (m, 7H), 5.74-5.86 (m, 2H), 6.83-7.01 (m, 4H).

In Vitro Stability Studies

Example 2. In Vitro Stability of COMPOUND A, COMPOUND B and COMPOUND C in Human Plasma An in vitro study was conducted to assess the metabolic stability of COMPOUND A, COMPOUND B and COMPOUND C in human plasma by monitoring disappearance of prodrug and formation of metabolite.

The structure of COMPOUND A, COMPOUND B and COMPOUND C are shown below

COMPOUND A

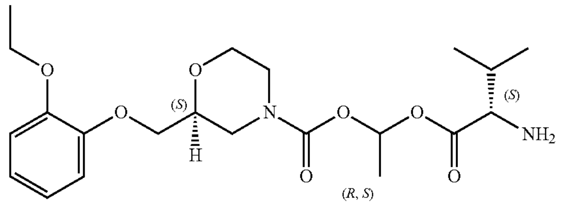

COMPOUND B

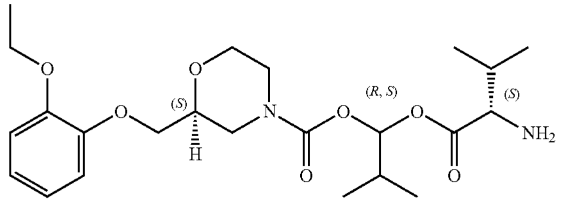

COMPOUND C

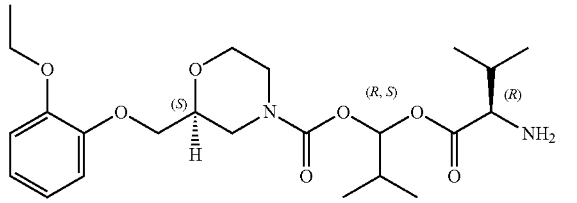

Preparation of Solutions

Test Article Solutions: COMPOUND A, COMPOUND B and COMPOUND C stock solutions at 10 mM were prepared in dimethyl sulfoxide (DMSO). Further dilution with DMSO was made to prepare 2.0 mM. The working solutions of 50 μM was prepared with 20% MeOH/water. Positive Control Stock and Working Solutions: the positive control stock solution, propantheline, was prepared in DMSO and stored at approximately −20° C. Prior to use, the stock solutions were brought to room temperature and thoroughly mixed and prepared same as described above. Internal Standard Solutions and Stop Solutions: the stock solutions of internal standards, tolbutamide (1 mg/mL) and labetalol (1 mg/mL), were prepared in DMSO and stored at approximately −20° C. The stop solution was prepared by spiking the stock solution to acetonitrile to achieve a 200 ng/mL final concentration.

Assay Procedures

Frozen plasma of all species was thawed in a water bath at approximately 37° C. and centrifuged at 3220×g for 5 minutes to remove any debris. Incubations were conducted in 96-well plate format. The time points defined for this study are 0, 5, 15, 30 and 60 minutes.

An appropriate volume of plasma from test species were added to a 96-deep well plate, and COMPOUND A, COMPOUND B and COMPOUND C working solution was spiked into the plasma in duplicate to achieve a final concentration of 2.0 μM. For positive controls, the rat plasma was spiked with enalapril, the dog plasma spiked with bisacodyl and the human plasma was spiked with propantheline. All spiked plasma sample plates were incubated in a water bath at 37° C. with shaking.

At the end of each time point, samples were immediately quenched with three volume of cold quenching solution. All sample plates were mixed thoroughly by shaking for approximately 10 minutes and centrifuged at 3220×g for 15 minutes. Subsequently, 100 μL of supernatant was removed from each well, mixed with 100 μL water in a new 96-well plate and subjected to LC-MS/MS analysis.

Results

Results of the in vitro stability of COMPOUND A, COMPOUND B and COMPOUND C and formation of viloxazine are summarized in Table 1 and illustrated in FIGS. 1*a*-3*c*. The percent remaining at 60 minutes were 680, 91.5%, 84.4 for COMPOUND A, COMPOUND B and COMPOUND C, respectively. Formation of metabolite viloxazine was found to increase over time for all three compounds

TABLE 1

Stability of COMPOUND A, COMPOUND B and COMPOUND C in Human Plasma after 60 Minutes Incubation.

| Compound ID | Time (min) | Analyte Peak area/ IS Peak area Mean (N = 2) | % Remaining | $t_{1/2}$ (min) | Viloxazine Formed (Analyte Peak area/IS Peak area) |
|---|---|---|---|---|---|
| COMPOUND A | 0 | 2.31 | 100 | 94.9 | 0.56 |
| | 5 | 2.46 | 107 | | 0.69 |
| | 15 | 2.15 | 93.1 | | 0.88 |
| | 30 | 1.86 | 80.8 | | 0.97 |
| | 60 | 1.57 | 68.0 | | 1.22 |
| COMPOUND B | 0 | 1.90 | 100 | >187 | 0.07 |
| | 5 | 1.72 | 90.6 | | 0.11 |
| | 15 | 1.79 | 94.5 | | 0.18 |
| | 30 | 1.65 | 87.1 | | 0.25 |
| | 60 | 1.73 | 91.5 | | 0.47 |
| COMPOUND C | 0 | 1.99 | 100 | >187 | 0.07 |
| | 5 | 1.84 | 92.3 | | 0.14 |
| | 15 | 1.76 | 88.3 | | 0.20 |
| | 30 | 1.71 | 86.1 | | 0.34 |
| | 60 | 1.68 | 84.4 | | 0.61 |

Accordingly, results showed that the metabolite viloxazine was formed, COMPOUND A, COMPOUND B and COMPOUND C were metabolized in human plasma.

Example 3. In Vitro Stability of COMPOUND A in Intestinal, Whole Blood, and Blood Components An in vitro study was conducted to assess the stability of COMPOUND A in intestinal, whole blood, and blood components.

Preparation of Solutions

Simulated Gastric Fluid (SGF) was prepared with 34.2 mM NaCl, 80 μM sodium taurocholate, 20 μM of L-alpha phosphatidylcholine/lecithin, and 0.1 mg/mL of Pepsin. 1 M HCl was added dropwise to adjust the pH to 1.96. Simulated Intestinal Fluid (SIF) was prepared with sodium phosphate monobasic, 105.9 mM NaCl, 3 pM sodium taurocholate, and 750 pM of L-alpha phosphatidylcholine/lecithin. 1 N NaOH was added dropwise to adjust the pH to 5.98. Phosphate buffered saline (PBS) at pH 6.0 was made by titrating PBS at pH 7.4 with 1 M HCl.

Stability of Test Articles at Different pH Values. 10 mM stock solutions of COMPOUND A were prepared in DMSO. From this stock solution, a single concentration in a 10 μL aliquot was added to three fluid matrices: SGF at pH 2.0 (gastric), SIF at pH 6.0 (upper intestine), and PBS at 7.4 (systemic). The final volume was 1 mL (0.1 mM). The preparations were then incubated at 37° C. and samples were collected at 0, 15, 30, 60, and 120 min for analysis of parent material by LC/MS/MS. The collected sample was quenched in acetonitrile/0.1% formic acid mixture. Red Blood Cell (RBC): Human and rat blood were centrifuged to separate out red blood cells at 117 4×g for 15 min. The upper plasma level was aspirated with a micropipette and placed in a bleach solution for disposal. The RBC pellet was resuspended in sterile isotonic saline. The pellet was gently resuspended by rocking the tube. The sample was then centrifuged again to collect the RBC pellet and then resuspended and washed one more time following the same procedure. A total of three was done. Following the last wash and centrifugation, the RBCs were resuspended with PBS; and mixed by inversion. Aliquots of the resuspended and washed RBCs were then placed into 4 reaction tubes. These tubes were centrifuged to collect the RBCs. The fluid level was marked on each tube, then the supernatant was aspirated off and the cells resuspended with room temperature PBS pH 7.4 to the original mark. An aliquot of the RBC suspension was added to four sterile tubes containing PBS pH 7.4 at room temperature.

Assay Procedures

Intestinal Permeability and Metabolic Stability. COMPOUND A (100 μL of 100 pM solution, or 4.25 pg) was applied to the apical surface of the EpiIntestinal model. Samples were collected from the basolateral compartment of the EpiIntestinal model at 0, 15, 30, 60, and 120 min. Metabolic stability was determined by loss of parent compound using LC/MS/MS. The collected sample was quenched in acetonitrile/0.1% formic acid mixture.

Stability in Human and Rat Red Blood cells and Hemolysis. Stability Experiments: the stability of COMPOUND A in whole blood, red blood cells only, and plasma was done to determine stability in each blood compartment. 50 μL of test article was placed in each blood matrix. The final volume was 1 mL (0.5 mM). Samples were taken at 0, 15, 30, 60, and 120 min. LC/MS/MS of parent compound was used to determine stability. The collected sample was quenched in acetonitrile/0.1% formic acid mixture. Hemolysis Studies: To a clear 96-well V-bottom polystyrene plate, COMPOUND A (10 μL) and the diluted RBCs (190 μL) from human or rat blood were mixed for final concentrations of 25, 50, and 100 μM. The reaction mixture was incubated at 37° C. for 60 min. Following the exposure period, the plates were centrifuged. After centrifugation, 70 μL of supernatant (without disturbing the pellet) was transferred to a clean and clear polystyrene flat bottomed 96-well plate and the absorbance of the sample at a single wavelength was measured using a Bio Tech Synergy Hl Plate Reader at a wavelength of 410 nm. The positive control for this assay was amphotericin B test at concentrations of 1, 10, 30, and 100 μM. Protease Inhibitor studies: Human whole blood (9 mL) was centrifuged at 117 4×g for 30 min. Aliquots (950 μL) were transferred to 1.5 mL centrifuge tubes. Inhibitor cocktail was then added to the tubes: 10 μL in the 1: 100 tube and 5 L in the 1:200 tube. The remaining plasma (about 3 mL) was transferred to a new 15 mL canonical bottom tube. The blood was then titrated with 1 N HCl to a final pH of 5.99. Aliquots of this matrix (950 μL) were transferred to 1.5 mL centrifuge tubes. All tubes were pre-warmed at 3 7° C. An aliquot of stock 10 mM COMPOUND A (50 μL) was added to the tubes. The tubes were then pulse vortexed for 15 s and 50 μL aliquots of sample were removed and quenched in 0.1% formic acid in acetonitrile and pulse vortexed for 3 s. The tubes were then incubated for 15 and 30 min and samples were taken using the same procedure. All samples were frozen at −80° C. until analysis. Stability was measured by measuring loss of parent compound using LC/MS/MS.

Stability in Rat and Human Gut Microbiota. Rat fecal material was obtained and weighed. One capsule of the raw probiotics was crushed and weighed prior to use. The weighed samples were then solubilized in PBS at pH 6.0 and 7.4 to extract microorganisms. The samples were centrifuged at 18,000×g for 10 min to remove particulates and the supernatant was used to evaluate test article stability. An aliquot (50 μL) of the COMPOUND A stock solution was added to the fecal extract (final concentration 0.5 mM) and allowed to incubate at 37° C. Aliquots were collected at 0, 15, 30, 60, and 120 min and analyzed by LC/MS/MS to determine stability of the parent molecule. The collected sample was quenched in acetonitrile/0.1% formic acid mixture.

Results

Figure 1A:
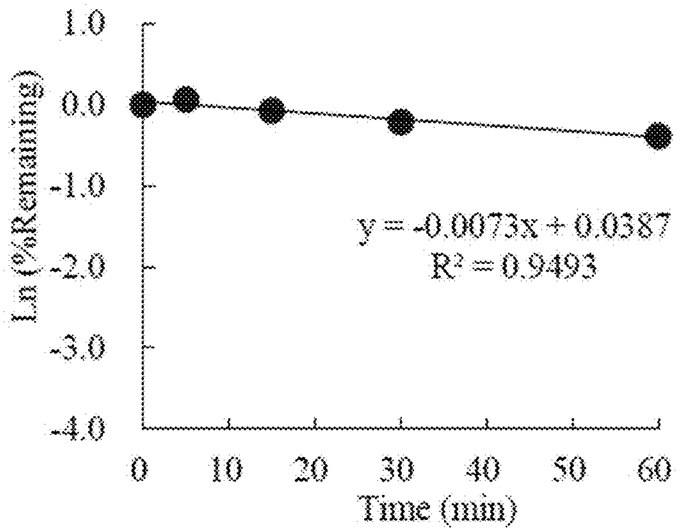
FIGS. 1*a*-1*c* illustrate in vitro stability of Compound A (FIG. 1*a*), COMPOUND B (FIG. 1*b*), and COMPOUND C (FIG. 1*c*) by showing their percent remaining in human plasma.
Figure 1B:
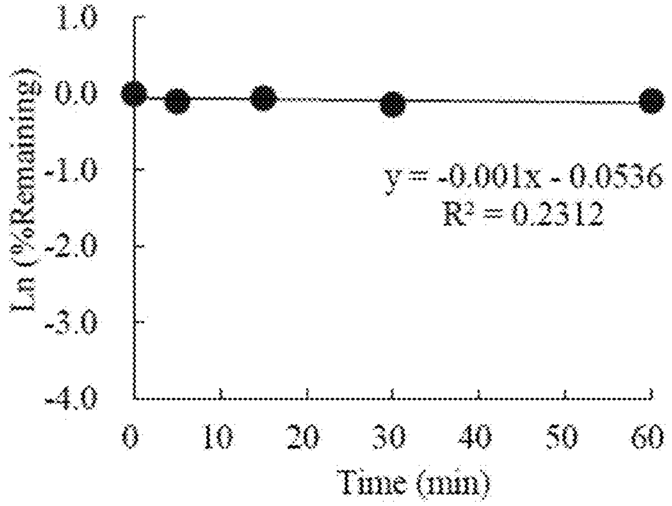
Figure 1C:
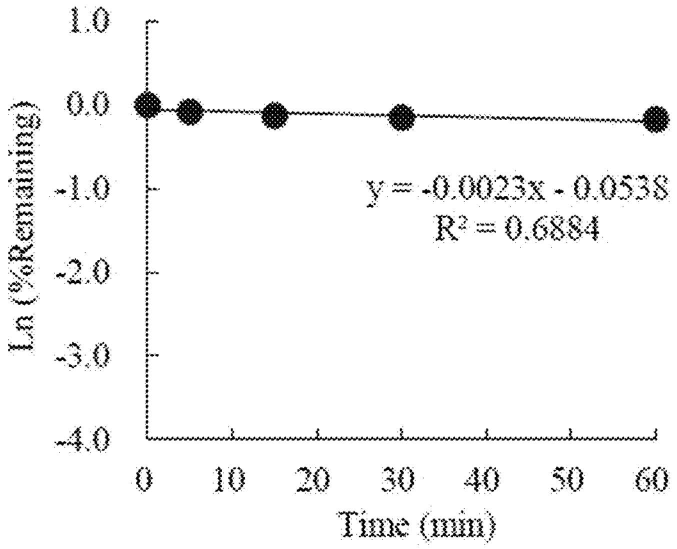
Figure 2:
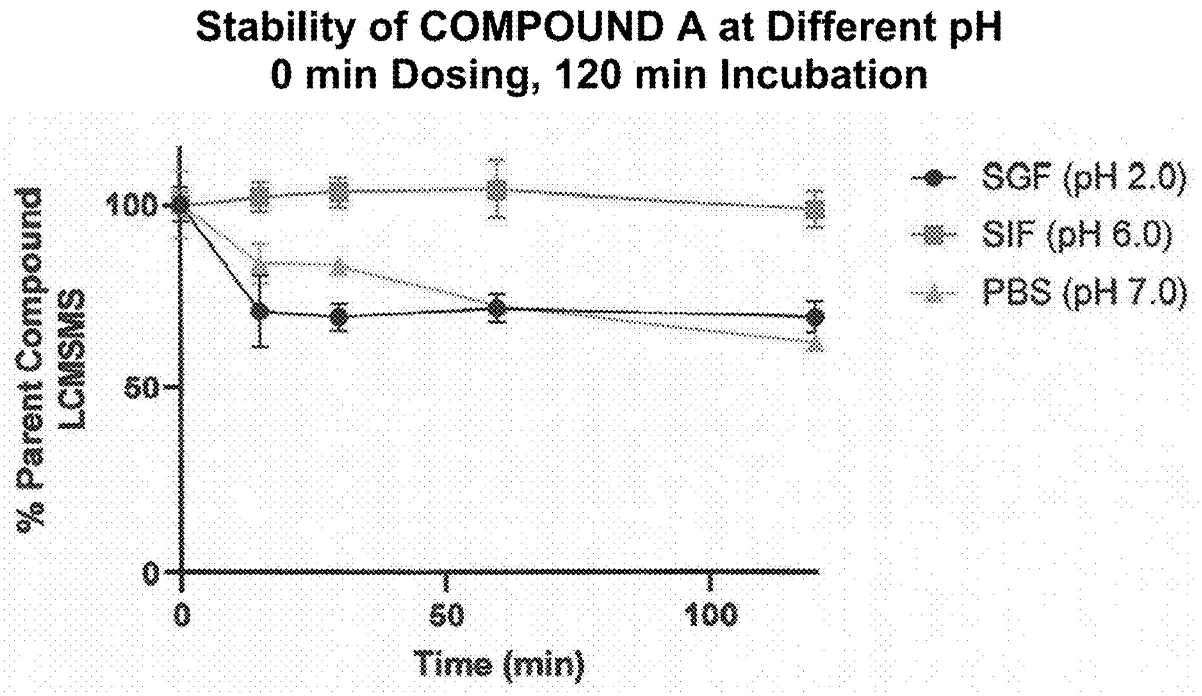
FIG. 2 shows stability of COMPOUND A in 3 different fluid matrices modeling 3 different body fluids: SGF (gastric, pH 2.0), SIF (upper intestinal, pH 6.0), and PBS (systemic, pH 7.4), respectively.

FIG. 2 shows stability of test articles in difference matrices representing different body fluids. After COMPOUND A was incubated in SGF (pl-I 2.0), there was a time-dependent decrease in the LC/MS/MS peak area until 20 min. After 20 min, COMPOUND A remained stable in SGF. After COMPOUND A was incubated in SIP (pH 6.0), the amount of parent compound remained at 100% for all time points. After COMPOUND A was incubated in PBS (pH 7.4), there was a time-dependent decrease in the amount of parent compound.

Figure 3:
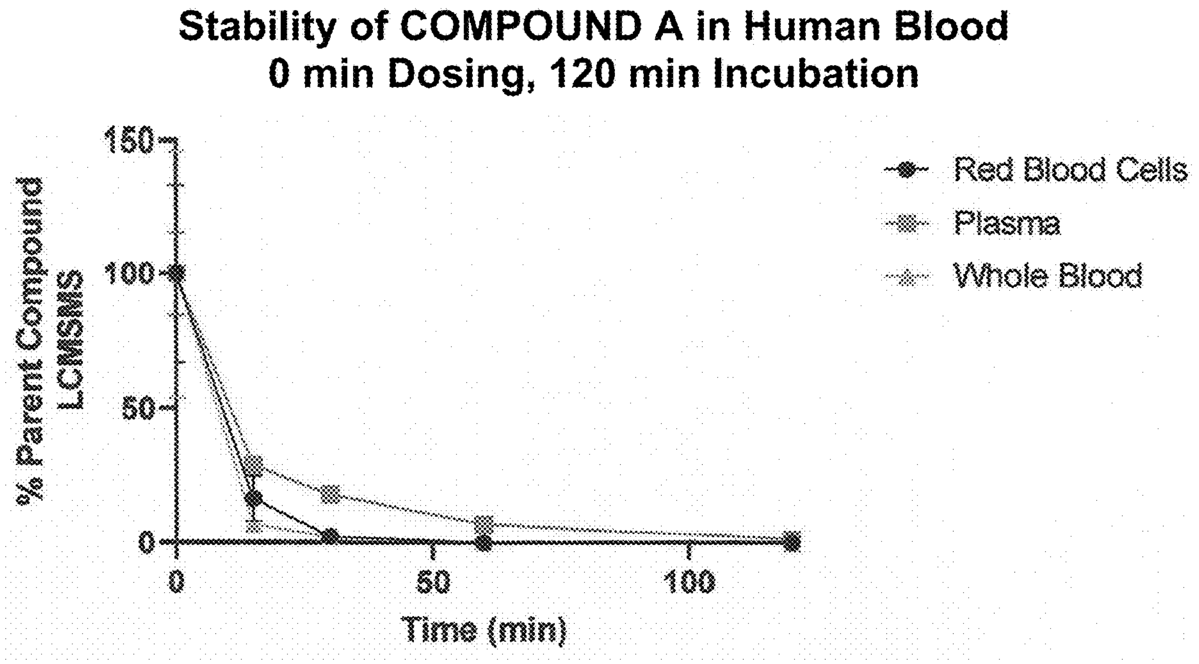
FIG. 3 shows stability of COMPOUND A in components of human blood (red blood cells, plasma, and whole blood, respectively).
Figure 4:
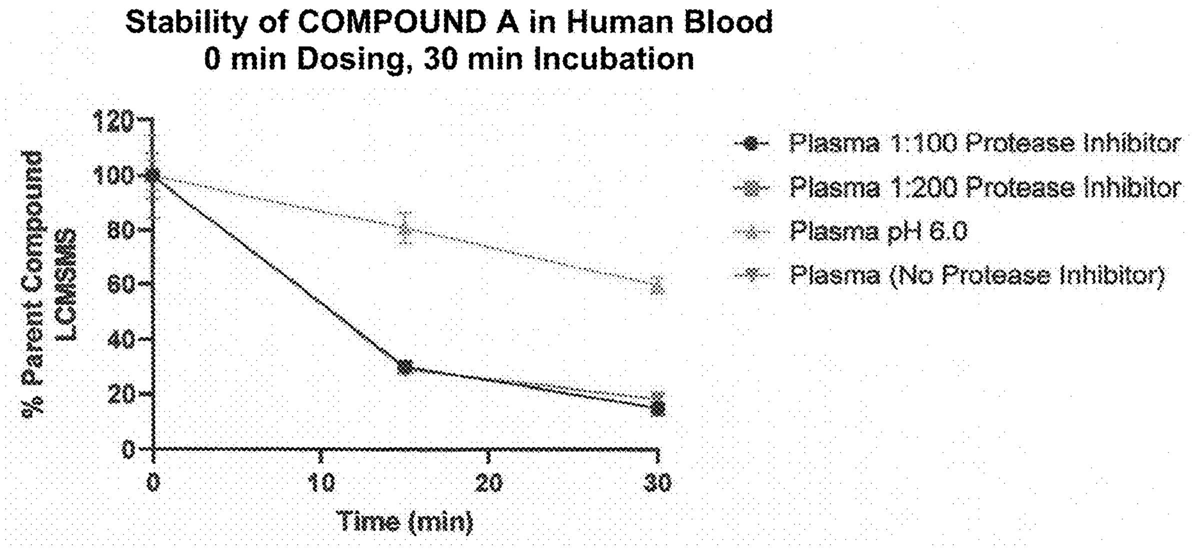
FIG. 4 shows stability of COMPOUND A in human blood with protease inhibitors, without protease inhibitors, and incubated at pH 6.0, respectively

FIG. 3 shows the stability of test article in human blood. After COMPOUND A was incubated in red blood cells and whole blood, there was a time-dependent decrease in the amount of parent compound present. FIG. 4 shows the stability of test article in human blood with protease inhibitors added. After COMPOUND A was incubated in plasma with protease inhibitor cocktail, there was a time-dependent decrease in the amount of parent compound present. When COMPOUND A was incubated with plasma at pH 6.0, there was a time-dependent increase with slower degradation compared to the other matrices.

Figure 5A:
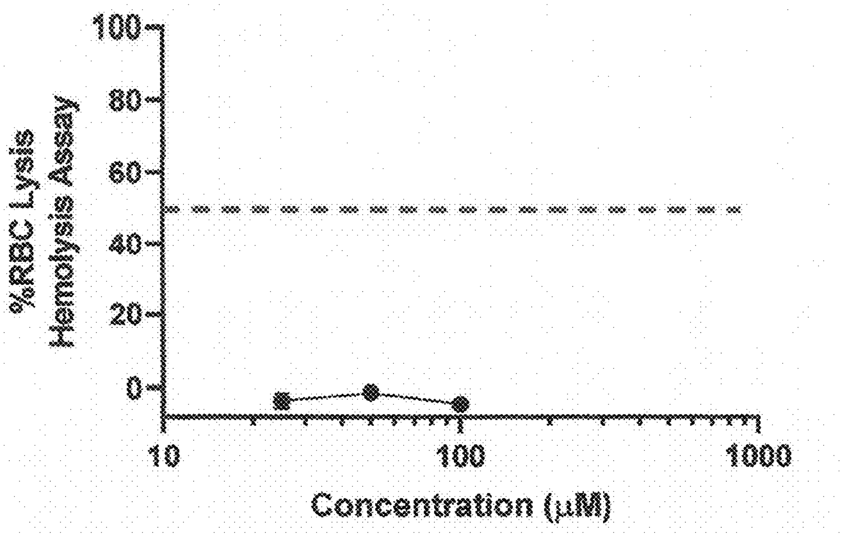
FIG. 5*a* shows hemolytic potential of COMPOUND A in human blood.
Figure 5B:
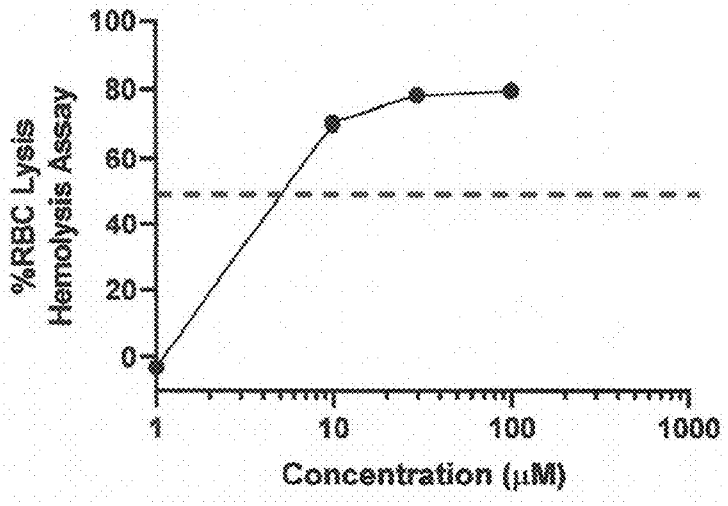
FIG. 5*b* shows hemolytic potential of Amphotericin B (positive assay control) in human blood.

FIGS. 5*a*-5*b* show the hemolytic potential of the test article in human blood. After exposure to COMPOUND A, for 1 hr, there was no dose-dependent response in % RBC lysis in human blood. There was no detectable hemolysis under the conditions used in this test. The EC50 for this sample is outside the concentration range tested. After exposure to amphotericin B (positive assay control) for 60 min, there was a dose-dependent increase in % RBC lysis. After 10 μg/mL of amphotericin B was dosed, there was a response above 50% and EC50 was calculated to be 7.06 pM.

Figure 6:
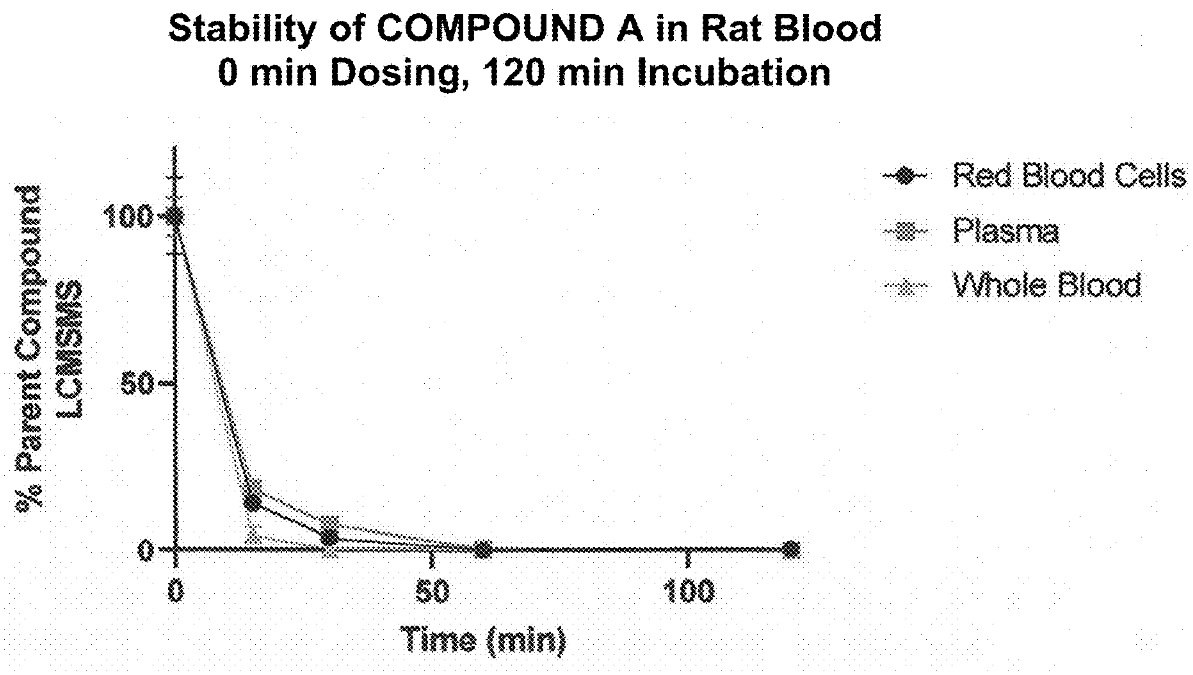
FIG. 6 shows stability of COMPOUND A in components of rat blood (red blood cells, plasma, and whole blood, respectively).

FIG. 6 shows the stability of the test article in rat blood. After COMPOUND A was incubated in all three matrices (red blood cells, plasma, and whole blood, respectively), there was a time-dependent decrease in the amount of parent compound present.

Figure 7A:
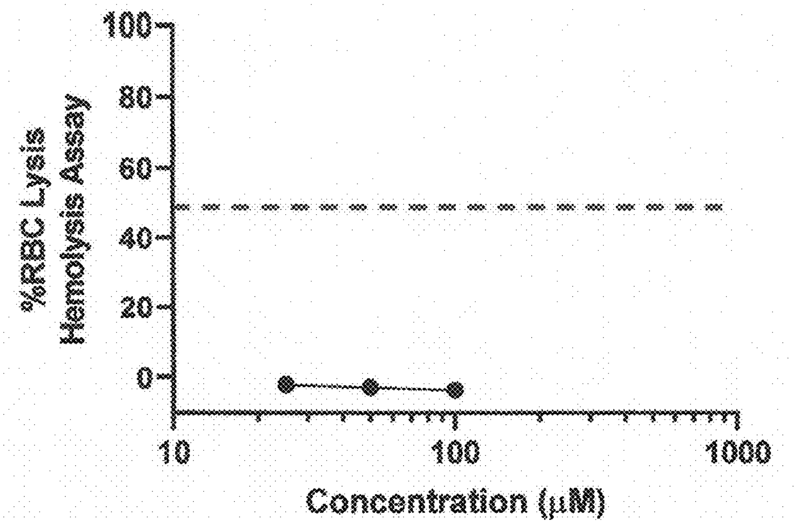
FIG. 7*a* shows hemolytic potential of COMPOUND A in rat blood.
Figure 7B:
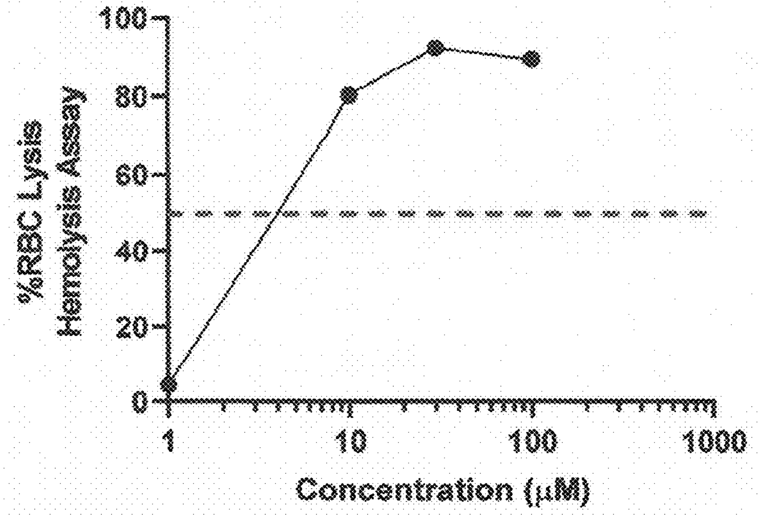
FIG. 7*b* shows hemolytic potential of Amphotericin B (positive assay control) in rat blood.

FIGS. 7*a*-7*b* show the hemolytic potential of the test article in rat blood. After exposure to COMPOUND A for 1 hr in rat blood, there was no dose-dependent response in % RBC lysis. There was no detectable hemolysis under the conditions used in this test. The EC50 for this sample is outside the concentration range tested. After exposure to amphotericin B (positive assay control) for 60 min, there was a dose-dependent increase in % RBC lysis. After 10 pg/mL of amphotericin B was dosed, there was a response above 50% and EC50 was calculated to be 4.73 μM.

Figure 8:
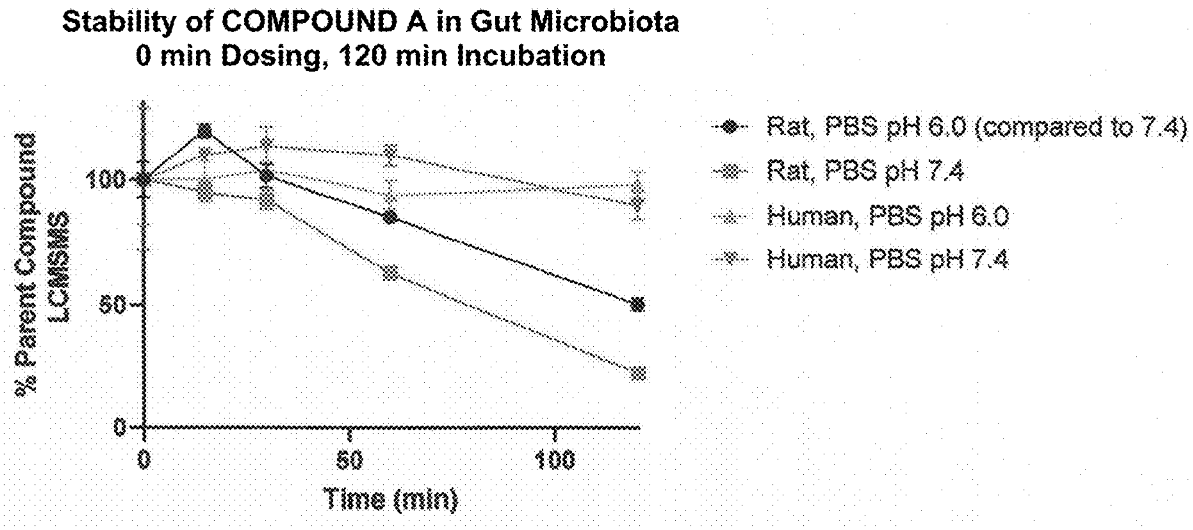
FIG. 8 shows stability of COMPOUND A in human and rat fecal matter at pH of 6.0 or 7.4.

FIG. 8 shows stability of the test article in human and rat gut microbiota. After exposure to COMPOUND A in rat fecal matter at pH 6 and pH 7.4, there was a time-dependent decrease in the amount of parent compound. After exposure to COMPOUND A in human fecal matter at pH 6 and 7.4, the amount of parent compound remained near 100% for all time points.

Accordingly, COMPOUND A was stable at all body fluid matrices. The drug was unstable in human and rat blood and rat gut microbiota. In addition, it did not permeate through the intestine. Finally, there was no hemolytic activity detected in human or rat blood under the conditions tested. In comparison, the positive control (amphotericin B) produced a clear dose related increase in hemolysis in human and rat blood.

Example 4. In Vitro Stability of COMPOUND A in Intestinal, Whole Blood, and Blood Components An in vitro study was conducted to assess the stability of COMPOUND A in the blood and intestine. This study was also aimed to identify the enzyme families responsible for degradation of COMPOUND A in human and rat plasma and intestine (bacteria) enzymes.

Plasma Preparation. Whole blood was centrifuged at 1174×g for 30 min. Aliquots of the supernatant were then transferred to 5 mL centrifuge tubes.

Stability of COMPOUND A in the Presence of Amidase in Pure System. To demonstrate amidase dependent degradation of the COMPOUND A, stability was measured in PBS in the presence of amidase. Test article (COMPOUND A) stock solution was prepared in 100% DMSO at a concentration of 10 mM. An aliquot (50 μL) of test article stock solution was added to 950 μL of PBS with and without amidase (50 units) in 1.5 mL tubes, and the mixture was vortexed and incubated at 37° C. with 5% $CO_2$ for 120 min. Samples (50 μL) were taken at 0, 15, 30, 60, and 120 min after being vortexed. Samples were quenched in 150 μL acetonitrile/0.1% formic acid solution and briefly vortexed then immediately frozen at −80° C. Stability was determined by measuring loss of parent compound using LC/MS/MS methods. Each exposure condition and time point were done in triplicate.

Stability of COMPOUND A in the Presence of Amidase and Amidase Inhibitors in a Phosphate-buffered Saline (PBS). To confirm inhibition of the amidase, individual inhibitors were added to PBS with amidase (50 units). A solution without amidase and without inhibitors was also tested as a control. The individual inhibitors tested were Chloroacetone at 200 μM and MAFP at 40 nM. Amidase solution was prepared as described above and inhibitors were added to the solutions to the intended concentrations. Then solutions were aliquoted into 1.5 mL tubes and preincubated for 15 min prior to the addition of test article stock solution. An aliquot of test article stock solution was added (50 μL) to PBS solutions and tubes were vortexed then incubated at 37° C. with $C_{02}$. Degradation began with the addition of test article. Samples (50 μL) were taken at 0, 15, 30, 60, and 120 min after being vortexed. Samples were quenched in 150 μL acetonitrile/0.1% formic acid solution and briefly vortexed then immediately frozen at −80° C. Stability was determined by measuring loss of parent compound using LC/MS/MS methods. Each exposure condition and time point were done in triplicate.

Stability of COMPOUND A in Human and Rat Plasma (circulating enzymes) in the Presence of Protease Inhibitor Cocktail. COMPOUND A was added to plasma with and without protease inhibitor cocktail and incubated to study inhibition of test article (COMPOUND A) degradation. Plasma was prepared as described above, protease inhibitor cocktail (from Sigma-Aldrich, cat. No. P8340, comprising 104 mM AEBSF, 80 μM Aprotinin, 4 mM Bestatin, 1.4 mM E-64, 2 mM Leupeptin, and 1.5 mM Pepstatin A) dilutions were prepared in plasma to final dilutions of 1:50, and 1:10.

Plasma with and without inhibitor cocktail was aliquoted into 1.5 mL tubes to a volume of 950 μL, then preincubated for 15 min. An aliquot (50 μL) of test article stock solution was added to plasma with and without inhibitor and tubes were vortexed then incubated at 37° C. Degradation began with the addition of test article. Aliquots (50 μL) were taken at 0, 15, 30, 60, and 120 min after being vortexed and were quenched in 150 μL acetonitrile/0.1% formic acid solution and briefly vortexed then immediately frozen at −80° C. Stability was determined by measuring loss of parent compound using LC/MS/MS methods. Each exposure condition and time point were done in triplicate.

Stability of COMPOUND A in Human and Rat Plasma (circulating enzymes) in the Presence of Individual Protease Inhibitors. In addition to using a cocktail of protease inhibitors, individual inhibitors were used in plasma. Chloroacetone (amidase inhibitor) was tested at 200 and 500 μM. MAFP (amidase inhibitor) was tested at 40 and 100 nM. Ebelactone A (esterase inhibitor) was tested at 0.15 μg/mL. A mix of all three individual inhibitors was also tested to a final concentration of 500 μM Chloracetone, 100 nM MAFP, and 0.15 μg/mL Ebelactone A. Plasma with and without inhibitors was prepared as described above. Plasma with and without inhibitors was aliquoted into 1.5 mL tubes and preincubated for 15 min at 37° C. prior to adding the test article (COMPOUND A). Degradation began with the addition of 50 μL of test article stock solution to the 950 μL aliquots of plasma with and without inhibitors. Aliquots (50 L) were taken at 0, 15, 30, 60, and 120 min after being vortexed. Samples were quenched in 150 μL acetonitrile/0.1% formic acid solution and briefly vortexed then immediately frozen at −80° C. Stability was determined by measuring loss of parent compound using LC/MS/MS methods. Each exposure condition and time point were done in triplicate.

Results

Figure 9A:
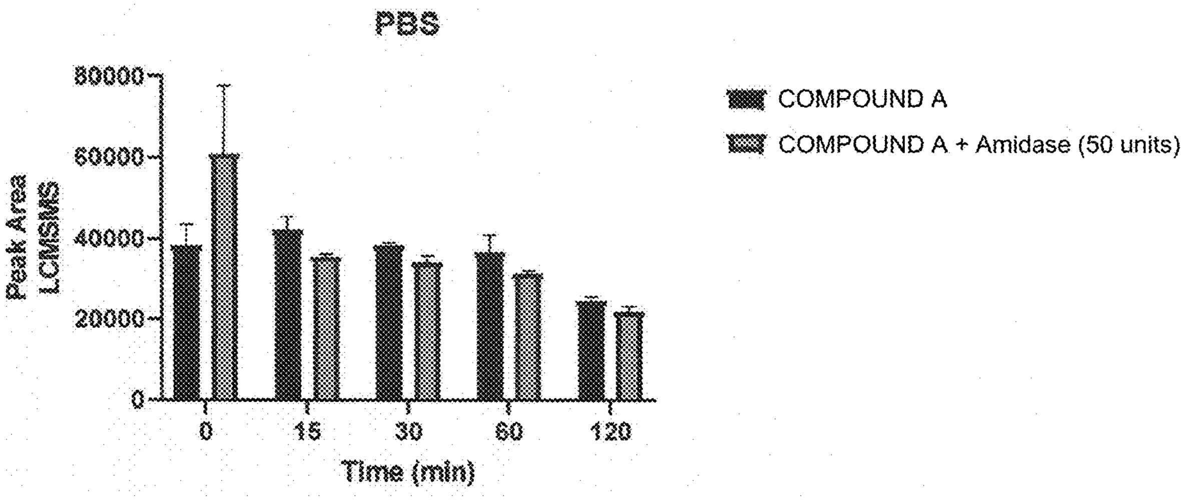
FIGS. 9*a*-9*b* show stability of COMPOUND A in the presence of amidase in phosphate-buffered saline (PBS).
Figure 9B:
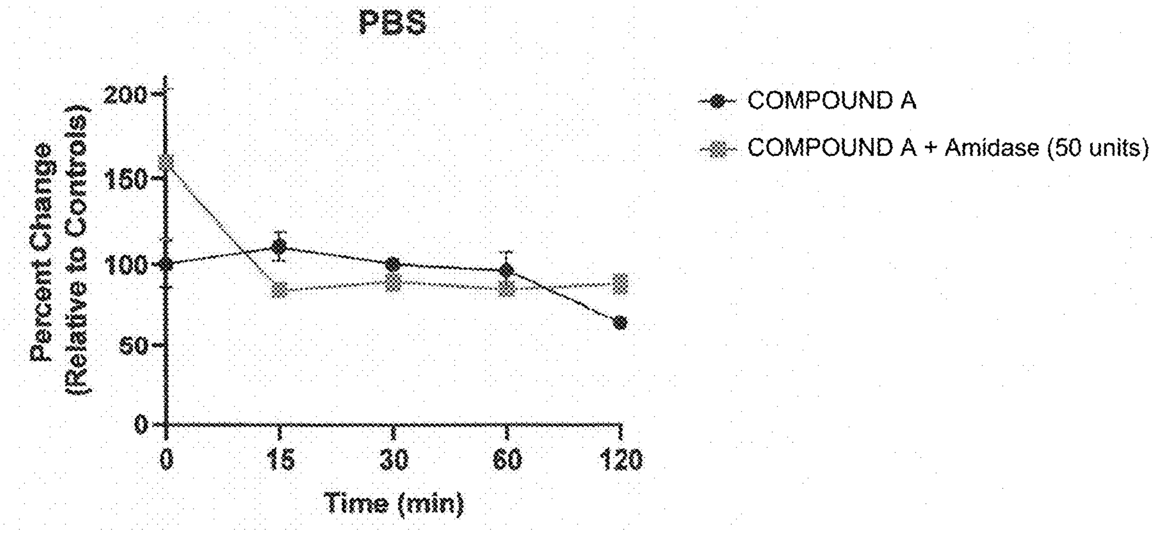
Figure 9C:
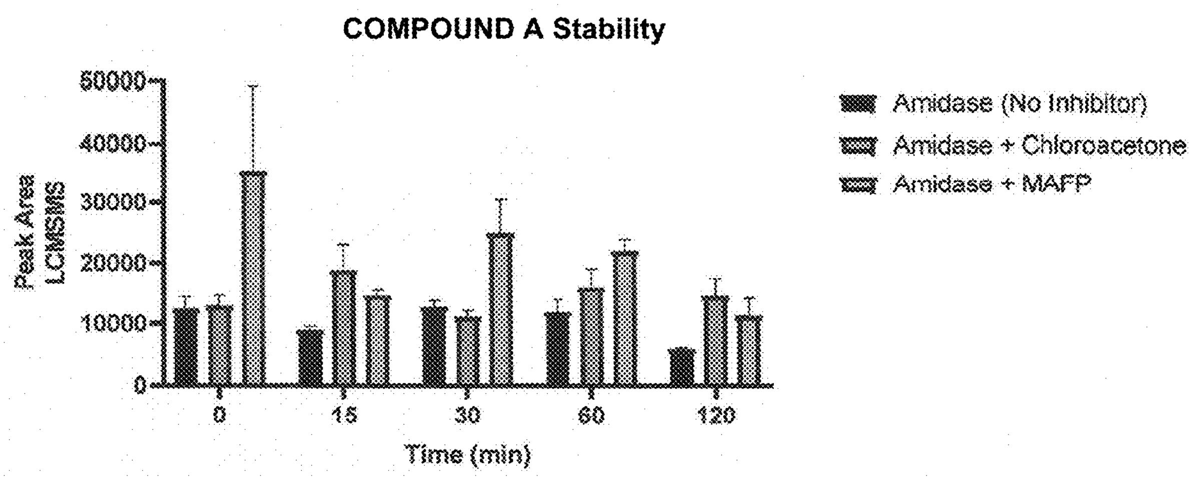
FIG. 9*c* shows stability of COMPOUND A in the presence of amidase and amidase inhibitors (Chloroacetone or MAFP) in phosphate-buffered saline.
Figure 10A:
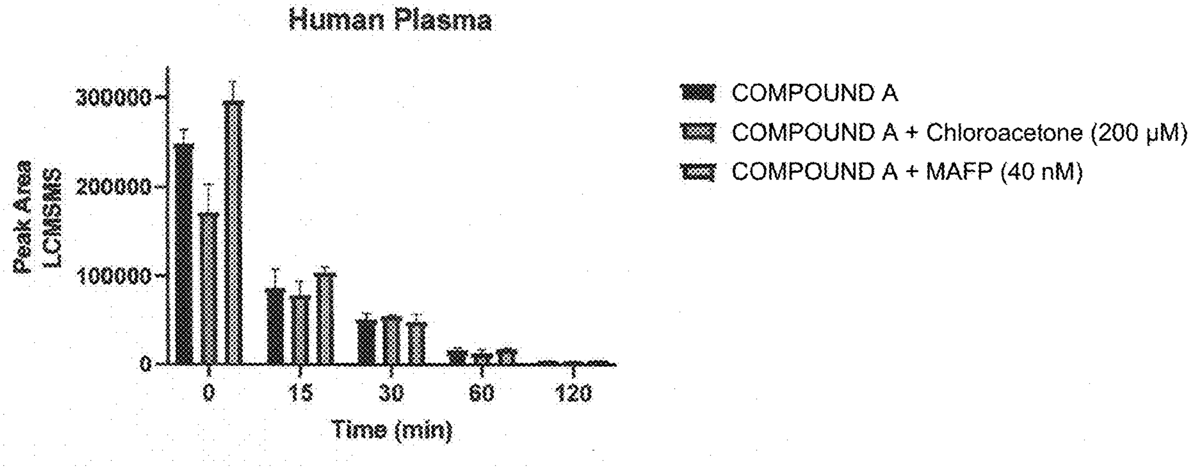
FIGS. 10*a*-10*b* show stability of COMPOUND A in the presence of amidase inhibitors (Chloroacetone or MAFP) in human plasma.
Figure 10B:
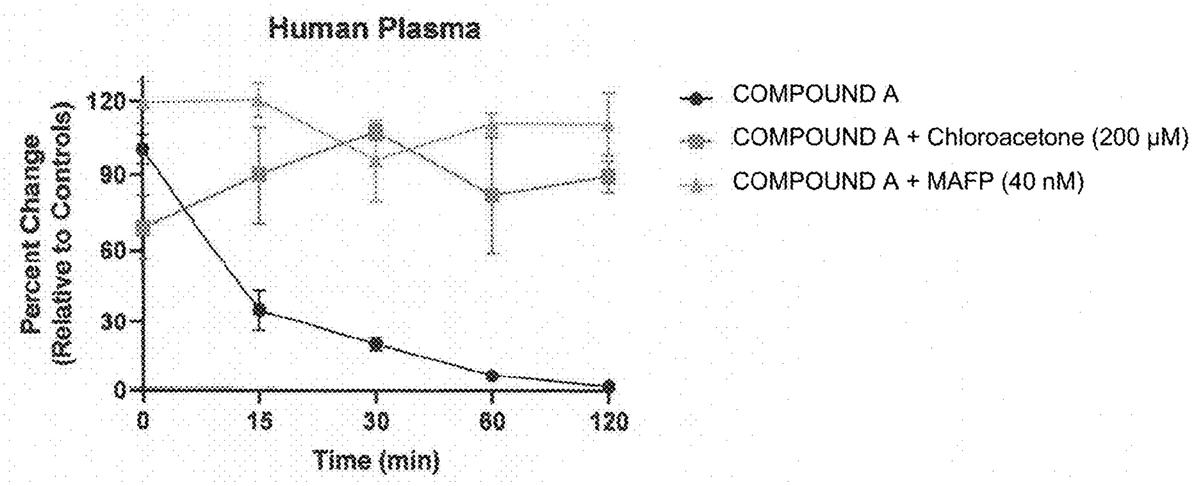
Figure 11A:
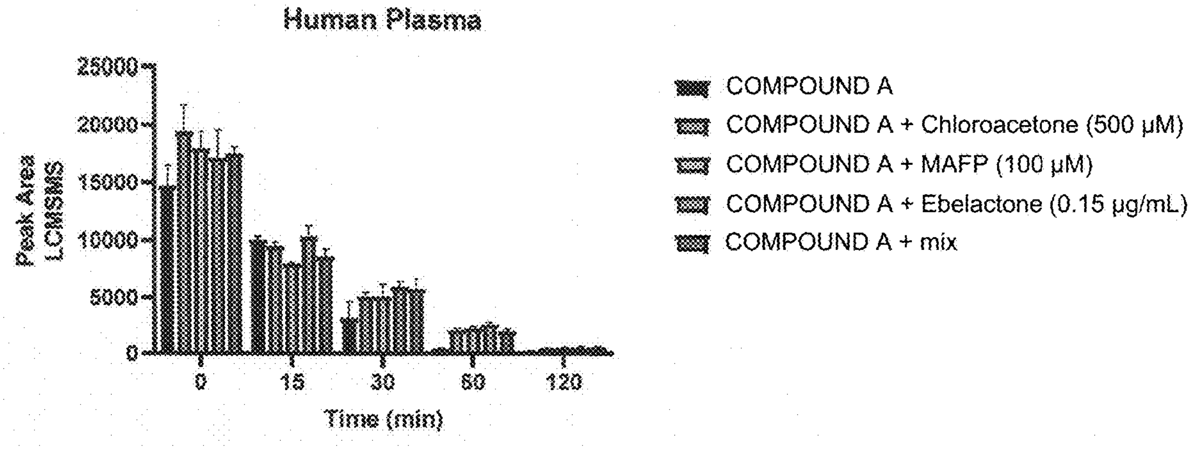
FIGS. 11*a*-11*b* show stability of COMPOUND A in the presence of amidase and/or esterase inhibitors in human plasma. Amidase inhibitors that were tested were Chloroacetone and MAFP. The Esterase inhibitor tested was Ebelactone.
Figure 11B:
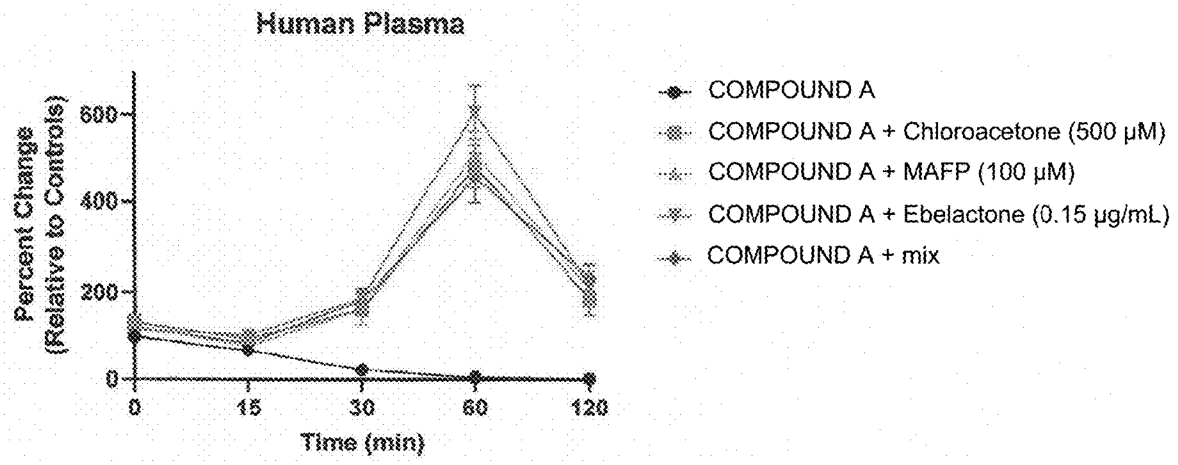
Figure 12A:
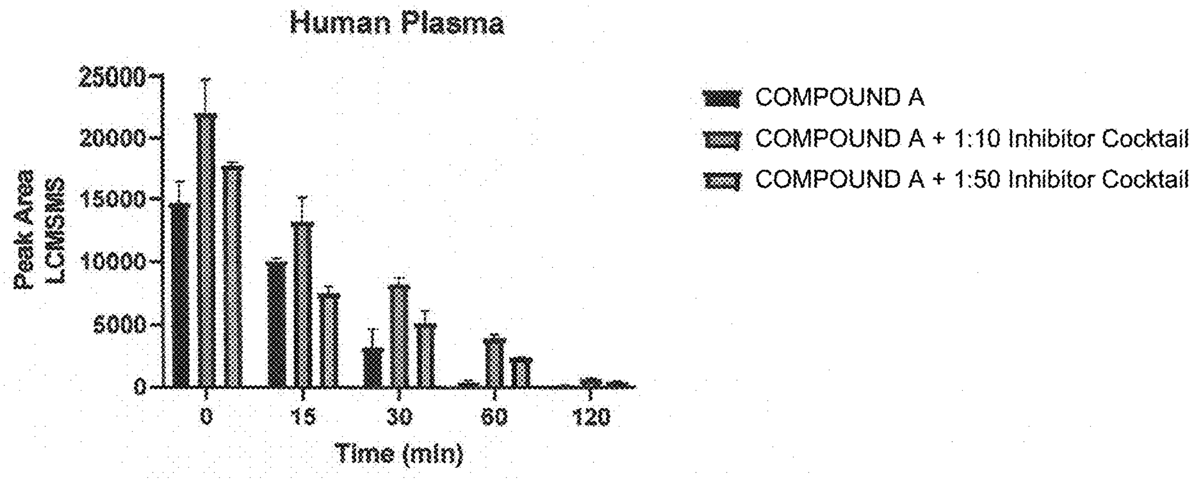
FIGS. 12*a*-12*b* show stability of COMPOUND A in the presence of protease inhibitor cocktail in human plasma. The cocktail included 104 mM AEBSF, 80 μM Aprotinin, 4 mM Bestatin, 1.4 mM E-64, 2 mM Leupeptin, and 1.5 mM Pepstatin A. Protease inhibitor cocktail dilutions were prepared in plasma to final dilutions of 1:50, and 1:10.
Figure 12B:
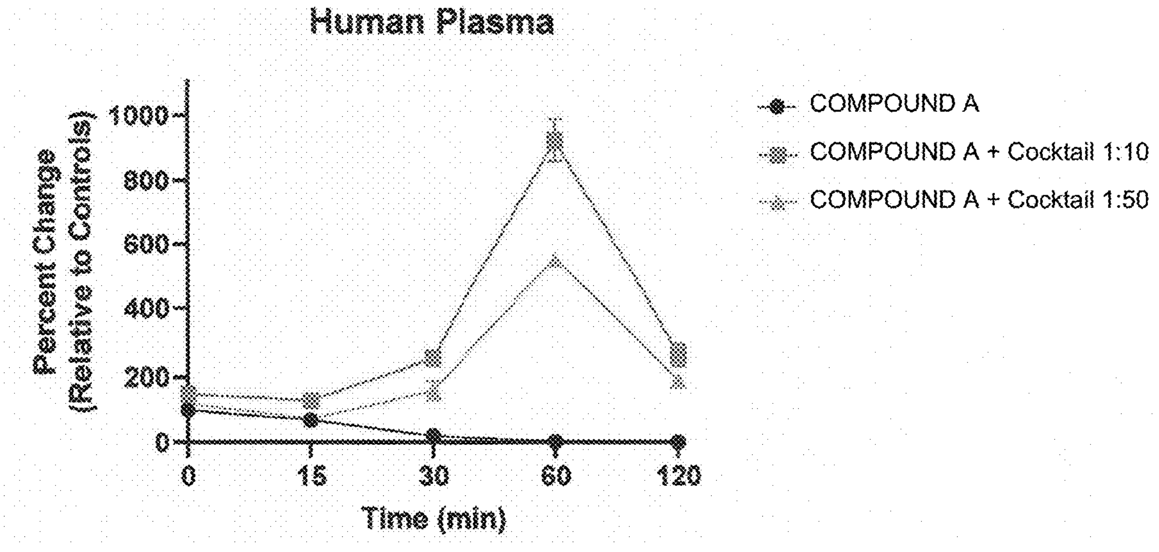
Figure 13A:
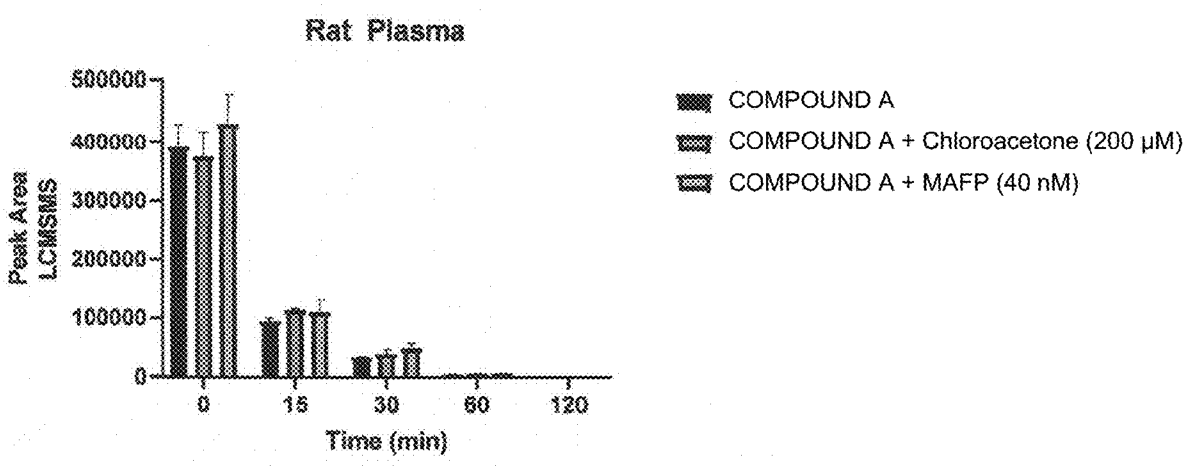
FIGS. 13*a*-13*b* show stability of COMPOUND A in the presence of amidase inhibitors (Chloroacetone or MAFP) in rat plasma.
Figure 13B:
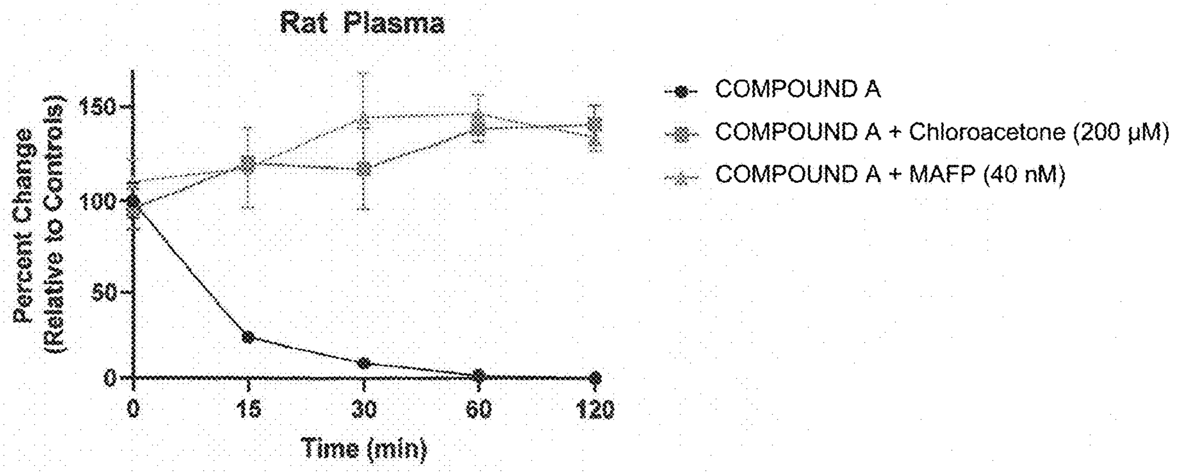
Figure 14A:
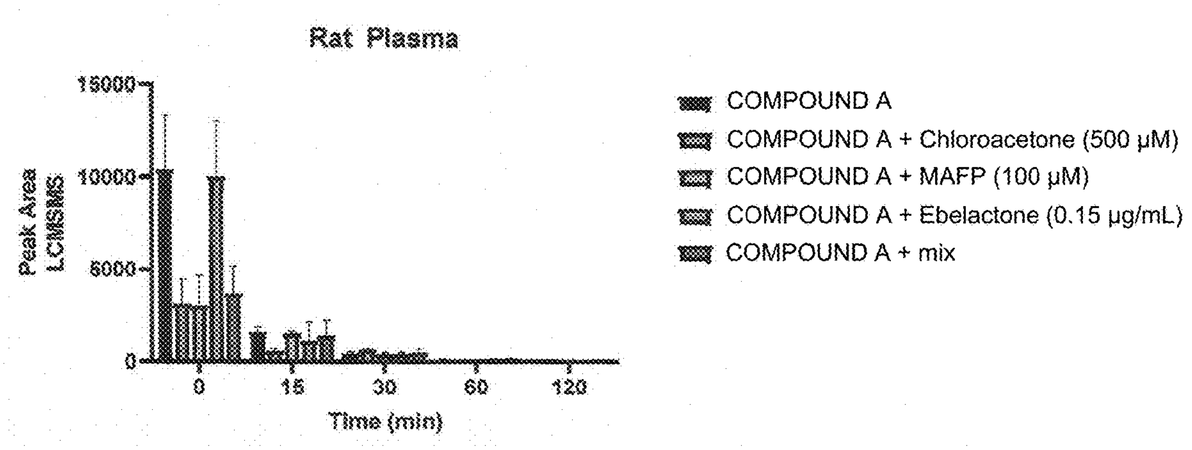
FIGS. 14*a*-14*b* show stability of COMPOUND A in the presence of amidase and/or esterase inhibitors in rat plasma. Amidase inhibitors that were tested were Chloroacetone and MAFP. The Esterase inhibitor tested was Ebelactone.
Figure 14B:
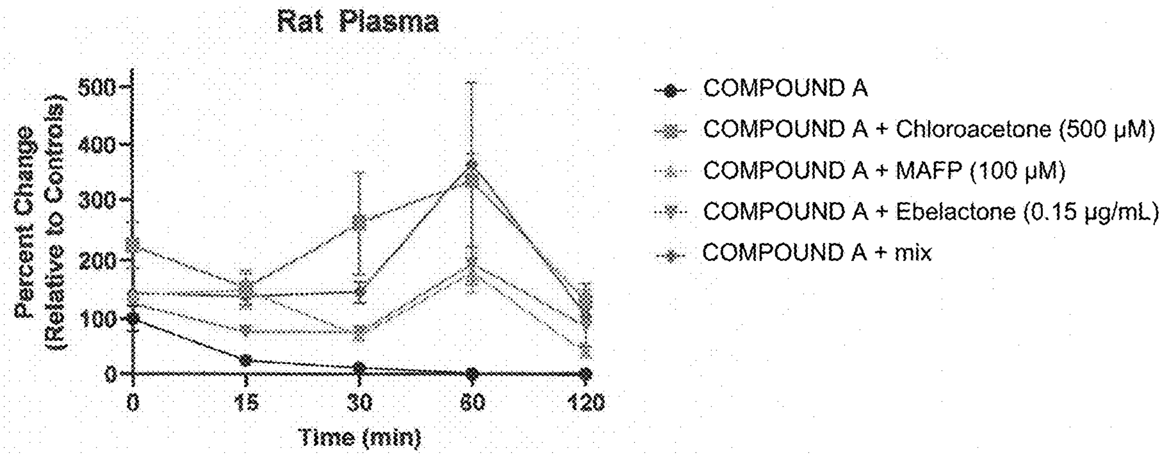
Figure 15A:
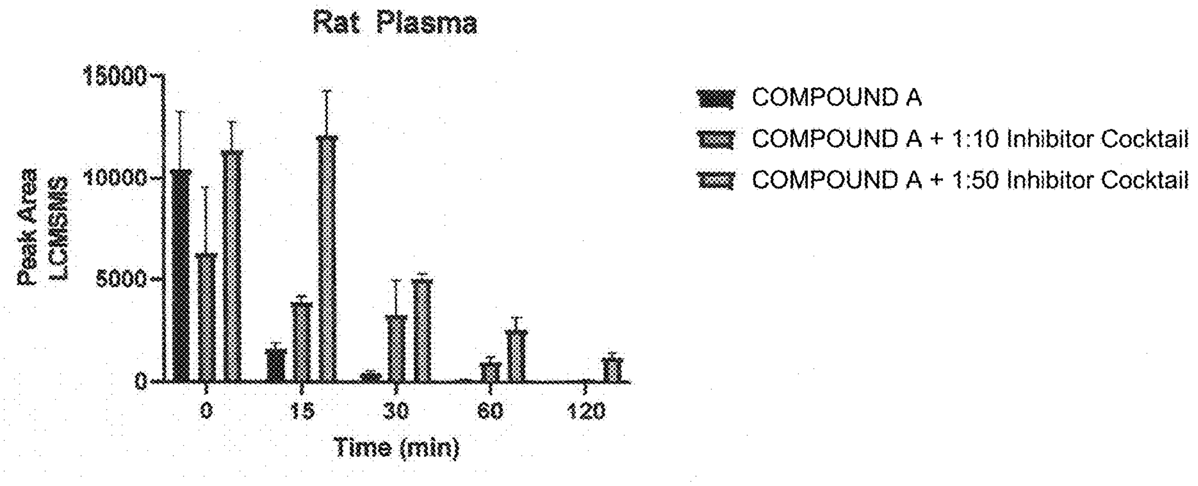
FIGS. 15*a*-15*b* show stability of COMPOUND A in rat plasma in the presence of protease inhibitor cocktail. Protease inhibitor cocktail dilutions were prepared in plasma to final dilutions of 1:50, and 1:10.
Figure 15B:
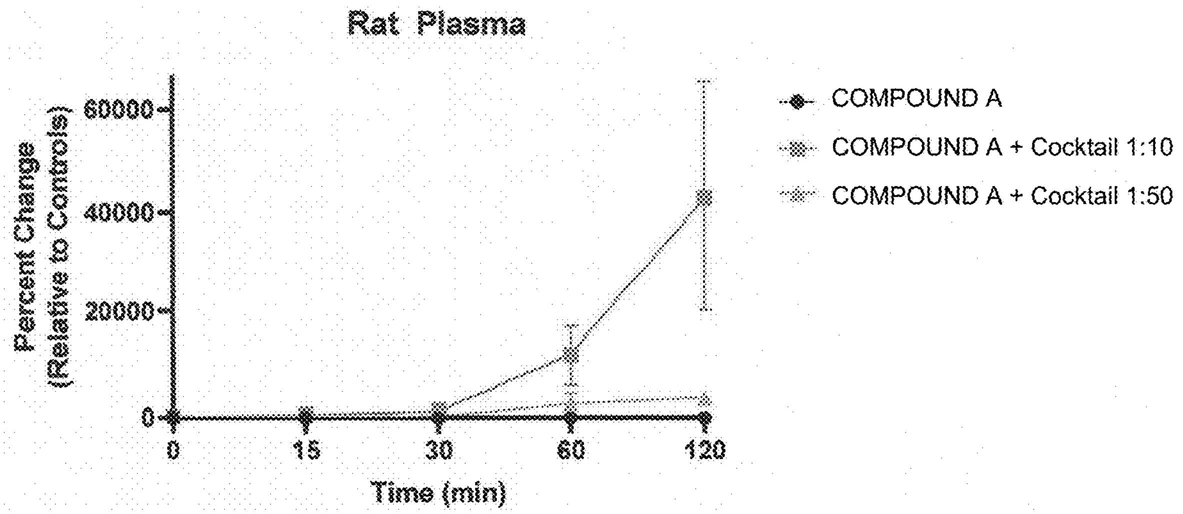
Figure 16:
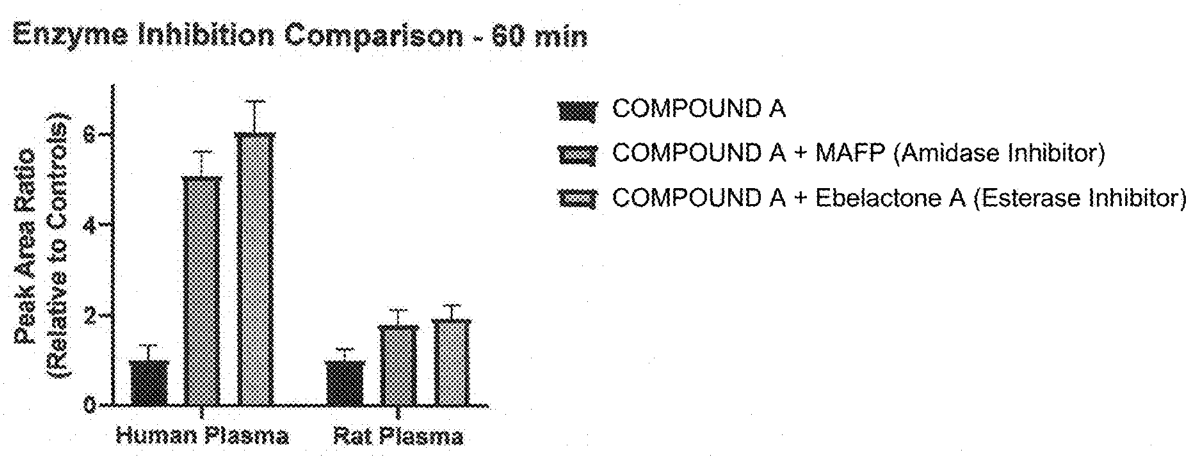
FIG. 16 shows enzyme inhibition comparison after 60 min of incubation. The following conditions were tested: without inhibitor, in the presence of MAFP, and in the presence of Ebelactone A, respectively.

Using phosphate-buffered saline (PBS) consisting of amidase enzyme in PBS with the test article (COMPOUND A) it was determined that amidase activity played an important role (FIGS. 9*a*-9*b*). By using fresh human and rat plasma in combination with amidase and esterase inhibitors it was possible to determine that nearly 100% of the test article (COMPOUND A) degradation could be accounted for by esterase and amidase enzymes (FIGS. 10-15). Human proteolytic activity was about 3-fold greater than rat proteolytic activity (FIG. 16). Both amidases and esterases contribute about equally to the degradation of test article under these in vitro conditions (FIG. 16).

The test article COMPOUND A was evaluated in both human and rat plasma. Both amidase and esterase proteases can degrade the test article. This was made clear by including amidase (chloroacetone and MAFP) and an esterase specific inhibitor (Ebelactone A) in the plasma incubations which resulted in complete inhibition of proteolytic degradation (and esterase-mediated degradation) when the incubations with inhibitor were compared to incubations without inhibitor. Both amidase and esterase enzymes showed similar degradation of the test article (COMPOUND A) and in the presence of sufficient quantity of the inhibitors there was complete inhibition after 1 hr. The protease inhibitor showed similar results in the in vitro conditions evaluated.

In Vitro Metabolic Stability Studies

Example 5. In Vitro Metabolic Stability of COMPOUND A, COMPOUND B and COMPOUND C in Human Intestinal Homogenate An in vitro study was conducted to assess the metabolic stability of COMPOUND A, COMPOUND B and COMPOUND C in human intestinal homogenate by monitoring both the disappearance of prodrug and formation of metabolite.

Preparation of Solutions

Incubation Buffer (PBK): 50 mM potassium phosphate buffer (PBK) was prepared from 1 M potassium phosphate buffer, pH 7.2. Test Article Solutions: COMPOUND A, COMPOUND B and COMPOUND C stock solutions at 10 mM were prepared in DMSO. The dilution of 1 mM intermediate was prepared from 10 mM stock with 90% methanol/water, then 10 pM working solutions were prepared by diluting the 1 mM intermediates with 50 mM PBK. All working solutions were freshly prepared on the day of experiment and disposed after use. Positive Control Stock and Working Solution: the positive control stock solutions, testosterone and 7-hydroxycoumarin were prepared at 10 mM in DMSO and stored at approximately −20° C. Prior to use, the stock solutions were brought to room temperature and thoroughly mixed. The working solutions were freshly prepared similarly as described for the test article working solution. Internal Standard Solutions and Stop Solutions: the stock solution of internal standards, tolbutamide and labetalol, were prepared in DMSO and stored at approximately −20° C. The stop solution was prepared by spiking the stock solution (1 mg/mL) into acetonitrile to achieve a 200 ng/mL final concentration. Test System: the human intestinal homogenate was diluted with 50 mM PBK buffer to make mixture solution of 0.625 mg/mL protein. Cofactors Solutions: the cofactor solution was made at 10 mM of NADPH (nicotinamide-adenine dinucleotide phosphate, reduced form) in 50 mM PBK buffer.

Assay Procedures

The incubation was carried out in 96-well plates. The intestinal homogenate mixture solution was added to 96-well plates (80 μL/well) in duplicate. The plates were pre-incubated for 10 min at 37° C. in a water bath and then spiked 10 μL each of 10 μM COMPOUND A, COMPOUND B and COMPOUND C or positive control working solutions into correspondence wells, separately. Reaction was initiated by adding cofactor solution at 10 L/well. The plates were incubated at 37° C. in a water bath with shaking. The final incubation mixture contained COMPOUND A, COMPOUND B and COMPOUND C, or positive control at 1 μM, and 0.5 mg/mL of human intestinal homogenate, and 1 mM NADPH. The final organic solvent content in the incubation was ≤1%.

At specified time points, i.e., 5, 10, 20, 30 and 60 minutes, NCF60 (no cofactor at 60 min, without adding NADPH replaced with 50 mM PBK buffer) reaction was stopped by adding three volumes of stop solution. The time zero (T0) samples were prepared by adding three volumes of stop solution to intestinal homogenate samples, followed by addition of test article or control, and cofactor solution 10 μL/well.

All sample plates were mixed well by shaking for approximately 10 minutes and centrifuged at 3220×g for 20 minutes. Subsequently, 100 μL of supernatant was removed from each well, diluted with 100 μL pure water and analyzed by LC/MS/MS.

Results

The results of metabolic stability of COMPOUND A, COMPOUND B and COMPOUND C in human intestinal homogenate, including percent remaining, $t_{1/2}$(min), and intrinsic clearance values ($CL_{int(HIH)}$) are summarized in Table 2a, formation of metabolite viloxazine is summarized in Table 2b TABLE 2a Metabolic Stability of COMPOUND A, COMPOUND B and COMPOUND C in Human Intestinal Homogenate at 60-Minute Incubation.

| Compound ID | Time (min) | Analyte Peak area/IS Peak area Mean (n = 2) | % Remaining | $t_{1/2}$ (min) | $CL_{int(HIH)}$ (μL/min/mg) |
|---|---|---|---|---|---|
| COMPOUND A | 0 | 0.269 | 100 | <2.5 | NA |
| | 5 | 0.000 | 0 | | |
| | 10 | 0.000 | 0 | | |
| | 20 | 0.000 | 0 | | |
| | 30 | 0.000 | 0 | | |
| | 60 | 0.000 | 0 | | |
| | NCF60 | 0.000 | 0 | | NA |
| COMPOUND B | 0 | 0.275 | 100 | 10.3 | 135 |
| | 5 | 0.020 | 7.3 | | |
| | 10 | 0.020 | 7.1 | | |
| | 20 | 0.017 | 6.1 | | |
| | 30 | 0.007 | 2.7 | | |
| | 60 | 0.002 | 0.57 | | |
| | NCF60 | 0.002 | 0.8 | | NA |
| COMPOUND C | 0 | 0.286 | 100 | 7.20 | 192 |
| | 5 | 0.013 | 4.4 | | |
| | 10 | 0.009 | 3.0 | | |
| | 20 | 0.004 | 1.3 | | |
| | 30 | 0.002 | 0.67 | | |
| | 60 | 0.000 | 0.08 | | |
| | NCF60 | 0.000 | 0.12 | | NA |

TABLE 2b

Formation of Viloxazine in Human Intestinal Homogenate at 60-Minute Incubation

| Species | Time (min) | Viloxazine Formed (Analyte Peak area/IS Peak area) From COMPOUND A | from COMPOUND B | from COMPOUND C |
|---|---|---|---|---|
| Human | 0 | 0.50 | 0.17 | 0.18 |
| | 5 | 1.17 | 1.00 | 1.11 |
| | 10 | 1.22 | 1.00 | 1.10 |
| | 20 | 1.21 | 0.99 | 1.19 |
| | 30 | 1.21 | 1.04 | 1.01 |
| | 60 | 1.19 | 0.97 | 1.10 |
| | NCF60 | 1.22 | 1.06 | 1.17 |

COMPOUND A, COMPOUND B and COMPOUND C were rapidly metabolized in human intestinal homogenate, formation of metabolite viloxazine at 5 minutes was significantly higher than that of time zero but did not increase further with incubation time.

Example 6. In Vitro Metabolic Stability of COMPOUND A, COMPOUND B and COMPOUND C in Sprague Dawley Rat, Beagle Dog and Human Liver S9

An in vitro study was conducted to assess the metabolic stability of COMPOUND A, COMPOUND B and COMPOUND C in rat, dog and human liver S9 by monitoring both the disappearance of prodrug and formation of metabolite.

Preparation of Solutions

Incubation Buffer (PBK): 50 mM potassium phosphate buffer was prepared from 1 M potassium phosphate buffer, pH 7.2. Test Article Solutions: COMPOUND A, COMPOUND B and COMPOUND C stock solutions at 10 mM were prepared in DMSO. The dilution of 1 mM intermediate was prepared by 90% methanol/10% DMSO, then 10 μM working solutions were prepared by diluting the 0.1 mM intermediates with 50 mM PBK. All working solutions were freshly prepared on the day of experiment and disposed after use. Positive Control Stock and Working Solutions: the positive control stock solutions, 7-ethoxycumarin and 7-hydroxycoumarin were prepared at 10 mM in DMSO and stored at approximately −20° C. Prior to use, the stock solutions were brought to room temperature and thoroughly mixed. The working solutions were freshly prepared similarly as described for the test article working solution. Internal Standard Solutions and Stop Solution: the stock solution of internal standards, tolbutamide and labetalol, were prepared in DMSO and stored at approximately −20° C. The stop solution was prepared by spiking the stock solution (1 mg/mL) into acetonitrile to achieve a 200 ng/mL final concentration. S9 Working Solution: the liver S9 from tested species were diluted with PBK buffer to make working solutions of 0.625 mg/mL. Cofactors Solutions: the mixture of cofactors solution was made at 10 mM of NADPH and 10 mM of UDPGA in PBK buffer.

Assay Procedures

The incubation was carried out in 96-well plates. The liver S9 working solutions were added to 96-well plates (80 μL/well) in duplicate. The plates were pre-incubated for 10-min at 37° C. in a water bath and then spiked 10 μL each of 10 μM COMPOUND A, COMPOUND B and COMPOUND C or positive control working solution into correspondence wells, separately. Reaction was initiated by adding cofactor mixture 10 μL/well. The plates were incubated at 37° C. in a water bath with shaking. The final incubation mixture contained COMPOUND A, COMPOUND B and COMPOUND C, or positive control at 1 μM, and 0.5 mg/mL of liver S9, and 1 mM NADPH, 1 mM of UDPGA. The final organic solvent content in the incubation was ≤1%.

At specified time points, i.e., 5, 10, 20, 30 and 60 minutes, NCF60 (without adding NADPH (Nicotinamide-adenine dinucleotide phosphate, reduced form) and UDPGA (Uridine 5'-diphosphoglucuronic acid trisodium salt) replaced with PBK buffer reaction was stopped by adding three volumes of stop solution. The time zero (T0) samples were prepared by adding three volumes of stop solution to liver S9 samples, followed by addition of test article or control, and cofactor mixture solution 10 μL/well.

All sample plates were mixed well by shaking for approximately 10 minutes and centrifuged at 3220×g for 20 minutes. Subsequently, 100 μL of supernatant.

Results

The results of metabolic stability of COMPOUND A, COMPOUND B and COMPOUND C in liver S9 of the tested species, including percent remaining, $t_{1/2}$ (min) and intrinsic clearance ($CL_{int(LS9)}$) values are summarized in Table 3a-3d. Formation of metabolite viloxazine are summarized in Table 3e TABLE 3a

| Summary of Metabolic Stability in SD Rat, Dog and Human Liver S9. | | | | | | |
|---|---|---|---|---|---|---|
| | | Stability at 1 μM | | | | |
| | | | $CL_{int(LS9)}$ (μL/min/mg) | | Viloxazine formed (Mean of Ratio) | |
| Compound ID | Species | $t_{1/2}$ (min) | Mean (n = 2) | % Remaining at 60 min | At 0 min | At 60 min |
| COMPOUND A | SD Rat | 8.61 | 161 | 0.25 | 0.28 | 0.76 |
| | Dog | 11.0 | 126 | 0.80 | 0.32 | 0.90 |
| | Human | 5.76 | 241 | 0.01 | 0.35 | 0.94 |
| COMPOUND B | SD Rat | 4.09 | 339 | 0.08 | 0.10 | 0.64 |
| | Dog | 7.30 | 190 | 0.09 | 0.10 | 0.70 |
| | Human | 7.74 | 179 | 0.24 | 0.11 | 0.72 |
| COMPOUND C | SD Rat | 8.53 | 163 | 0.39 | 0.11 | 0.65 |
| | Dog | 12.0 | 115 | 1.41 | 0.11 | 0.70 |
| | Human | 8.12 | 171 | 0.19 | 0.11 | 0.76 |

TABLE 3b

Metabolic Stability of COMPOUND A in Liver S9 at 60-Minute Incubation

| Compound ID | Species | Time (min) | Analyte Peak area/IS Peak area Mean × 100 (n = 2) | % Remaining | $t_{1/2}$ (min) | $CL_{int(LS9)}$ (μL/min/mg) |
|---|---|---|---|---|---|---|
| COMPOUND A | Rat | 0 | 10.7 | 100 | 8.61 | 161 |
| | | 5 | 0.669 | 6.3 | | |
| | | 10 | 0.574 | 5.4 | | |
| | | 20 | 0.362 | 3.4 | | |
| | | 30 | 0.171 | 1.6 | | |
| | | 60 | 0.026 | 0.25 | | |
| | | NCF60 | 0.237 | 2.2 | NA | |
| | Dog | 0 | 12.2 | 100 | 11.0 | 126 |
| | | 5 | 0.98 | 8.0 | | |
| | | 10 | 1.078 | 8.8 | | |
| | | 20 | 0.635 | 5.2 | | |
| | | 30 | 0.381 | 3.1 | | |
| | | 60 | 0.097 | 0.8 | | |
| | | NCF60 | 0.248 | 2.0 | | |
| | Human | 0 | 11.7 | 100 | 5.76 | 241 |
| | | 5 | 0.164 | 1.4 | | |
| | | 10 | 0.143 | 1.2 | | |
| | | 20 | 0.039 | 0.3 | | |
| | | 30 | 0.021 | 0.2 | | |
| | | 60 | 0.001 | 0.0 | | |
| | | NCF60 | 0.008 | 0.1 | NA | |

TABLE 3c

Metabolic Stability of COMPOUND B in Liver S9 at 60-Minute Incubation

| Compound ID | Species | Time (min) | Analyte Peak area/IS Peak area Mean × 100 (n = 2) | % Remaining | $t_{1/2}$ (min) | $CL_{int(LS9)}$ (μL/min/mg) |
|---|---|---|---|---|---|---|
| COMPOUND B | Rat | 0 | 7.71 | 100 | 4.09 | 339 |
| | | 5 | 0.524 | 6.8 | | |
| | | 10 | 0.351 | 4.6 | | |
| | | 20 | 0.174 | 2.3 | | |
| | | 30 | 0.019 | 0.2 | | |
| | | 60 | 0.006 | 0.1 | | |
| | | NCF60 | 0.029 | 0.4 | NA | |
| | Dog | 0 | 7.78 | 100 | 7.30 | 190 |
| | | 5 | 0.226 | 2.9 | | |
| | | 10 | 0.309 | 4.0 | | |
| | | 20 | 0.166 | 2.1 | | |

TABLE 3c-continued

Metabolic Stability of COMPOUND B in Liver S9 at 60-Minute Incubation

| Compound ID | Species | Time (min) | Analyte Peak area/IS Peak area Mean × 100 (n = 2) | % Remaining | $t_{1/2}$ (min) | $CL_{int(LS9)}$ (μL/min/mg) |
|---|---|---|---|---|---|---|
| | | 30 | 0.035 | 0.5 | | |
| | | 60 | 0.007 | 0.1 | | |
| | | NCF60 | 0.000 | 0.0 | | |
| | Human | 0 | 8.22 | 100 | 7.74 | 179 |
| | | 5 | 1.12 | 14 | | |
| | | 10 | 0.973 | 12 | | |
| | | 20 | 0.342 | 4.2 | | |
| | | 30 | 0.131 | 1.6 | | |
| | | 60 | 0.020 | 0.2 | | |
| | | NCF60 | 0.099 | 1.2 | | NA |

TABLE 3d

Metabolic Stability of COMPOUND C in Liver S9 at 60-Minute Incubation

| Compound ID | Species | Time (min) | Analyte Peak area/IS Peak area Mean × 100 (n = 2) | % Remaining | $t_{1/2}$ (min) | $CL_{int(LS9)}$ (μL/min/mg) |
|---|---|---|---|---|---|---|
| COMPOUND C | Rat | 0 | 6.55 | 100 | 8.53 | 163 |
| | | 5 | 1.24 | 19 | | |
| | | 10 | 0.834 | 13 | | |
| | | 20 | 0.365 | 5.6 | | |
| | | 30 | 0.228 | 3.5 | | |
| | | 60 | 0.026 | 0.4 | | |
| | | NCF60 | 0.228 | 3.5 | | NA |
| | Dog | 0 | 8.27 | 100 | 12.0 | 115 |
| | | 5 | 1.44 | 17 | | |
| | | 10 | 0.962 | 12 | | |
| | | 20 | 0.720 | 8.7 | | |
| | | 30 | 0.501 | 6.1 | | |
| | | 60 | 0.116 | 1.4 | | |
| | | NCF60 | 0.418 | 5.1 | | |
| | Human | 0 | 10.6 | 100 | 8.12 | 171 |
| | | 5 | 0.808 | 7.7 | | |
| | | 10 | 0.446 | 4.2 | | |
| | | 20 | 0.297 | 2.8 | | |
| | | 30 | 0.160 | 1.5 | | |
| | | 60 | 0.020 | 0.2 | | |
| | | NCF60 | 0.061 | 0.6 | | NA |

TABLE 3e

Formation of Viloxazine in Liver S9 at 60-Minute Incubation

| Species | Time (min) | Viloxazine formed (Analyte Peak area/IS Peak area) from COMPOUND A | from COMPOUND B | from COMPOUND C |
|---|---|---|---|---|
| Rat | 0 | 0.28 | 0.10 | 0.11 |
| | 5 | 0.87 | 0.82 | 0.66 |
| | 10 | 0.84 | 0.79 | 0.66 |
| | 20 | 0.88 | 0.76 | 0.67 |
| | 30 | 0.88 | 0.78 | 0.71 |
| | 60 | 0.76 | 0.64 | 0.65 |
| | NCF60 | 0.93 | 0.86 | 0.84 |
| Dog | 0 | 0.32 | 0.10 | 0.11 |
| | 5 | 0.90 | 0.84 | 0.66 |
| | 10 | 0.86 | 0.84 | 0.68 |
| | 20 | 0.88 | 0.83 | 0.68 |
| | 30 | 0.90 | 0.86 | 0.72 |
| | 60 | 0.90 | 0.70 | 0.70 |
| | NCF60 | 0.99 | 0.86 | 0.79 |

TABLE 3e-continued

Formation of Viloxazine in Liver S9 at 60-Minute Incubation

| Species | Time (min) | Viloxazine formed (Analyte Peak area/IS Peak area) from COMPOUND A | from COMPOUND B | from COMPOUND C |
|---|---|---|---|---|
| Human | 0 | 0.35 | 0.11 | 0.11 |
| | 5 | 0.93 | 0.74 | 0.81 |
| | 10 | 0.94 | 0.74 | 0.79 |
| | 20 | 0.88 | 0.71 | 0.76 |
| | 30 | 0.94 | 0.75 | 0.81 |
| | 60 | 0.94 | 0.72 | 0.76 |
| | NCF60 | 0.94 | 0.82 | 0.85 |

COMPOUND A, COMPOUND B and COMPOUND C were metabolized rapidly with half-lives of 4-12 minutes in rat, dog and human liver S9 incubations. The degradation appeared to be cofactor independent since the samples at 60 minutes in the presence and absence of cofactors all displayed ≤5% of remaining test compound. The amount of viloxazine in samples from 5-minute incubation was substantially more than that of time zero samples but stayed at similar level with longer incubation time.

In Vitro Binding Studies

Example 7. In Vitro Tissue Binding of COMPOUND A, COMPOUND B and COMPOUND C in CD-1 Mouse Brain Homogenate An in vitro study was conducted to determine tissue binding of COMPOUND A, COMPOUND B and COMPOUND C in CD-1 mouse brain homogenate and monitor the metabolite viloxazine formation.

Preparation of Solutions

Test Article Solutions: test articles of COMPOUND A, COMPOUND B and COMPOUND C at 10 mM and viloxazine at 3.6 mM stock solutions were prepared with DMSO. Working solution in DMSO at 0.4 mM for each compound was prepared from the stock solutions. All working solutions were freshly prepared on the day of experiment and disposed of after use. Positive Control Stock and Working Solution: propranolol stock solution (10 mM) was prepared in DMSO and stored at approximately −20° C. A working solution at 0.4 mM concentration was freshly prepared similarly as described for the test article working solution. Internal Standard Solutions and Stop Solutions: the stock solutions of internal standards for positive controls, tolbutamide (1 mg/mL) and labetalol (1 mg/mL), were prepared in DMSO and stored at approximately −20° C. Stop solution was prepared by spiking the stock solution (2 mg/mL) into acetonitrile to achieve a 200 ng/mL final concentration. Dialysis Buffer: Phosphate buffered saline (PBS), pH 7.4 was used in the study. Test System: frozen mouse and human brain homogenate were thawed in a water bath at 37° C. and centrifuged at 3220×g for 5 minutes to remove any debris.

Assay Procedures

The blank mouse brain homogenate (995 μL) was spiked with 5 μL of COMPOUND A, COMPOUND B and COMPOUND C and viloxazine working solutions (0.4 mM) or propranolol working solution (0.4 mM) separately. The final concentration of COMPOUND A, COMPOUND B and COMPOUND C; viloxazine and propranolol in the assay mixtures were 2 μM. The concentration of organic solvent (DMSO) in the assay mixtures was 0.5%.

After mixing thoroughly, the time zero samples ($C_0$) were prepared by transferring 50 μL aliquots of spiked brain homogenate in triplicate to sample collection plates, and immediately matched with 50 μL of dialysis buffer, followed by addition of 300 μL of stop solution. The samples were thoroughly mixed and stored at 2~8° C. until being further processed together with other post-dialysis samples.

The rest remaining of the spiked brain homogenate (150 μL) was loaded to the donor side chambers, and 150 μL of dialysis buffer were added to the receiver side chambers in triplicate in the dialysis device. The dialysis device was then sealed with a breathable sealer and incubated at 37° C. in a humidified incubator with 5% $CO_2$ for 4 hours on 3-D Analog Waving Platform Shaker with constant rotation. (COMPOUND A was incubated for 1 hr). At the end of dialysis, 50 μL aliquots were removed separately from both chambers, and transferred into a new 96-well plate. Each sample was matched with equal volume of blank buffer or blank brain homogenate as appropriate to obtain a final volume of 100 μL, followed by addition of 300 μL of stop solution.

All samples (including time zero) were thoroughly mixed and centrifuged at 3220×g for 20 minutes. Aliquots of 100 μL were removed from the supernatant of each well, mixed with 100 μL ultrapure water in a new 96-well plate, and subjected to LC-MS/MS analysis.

Results

The results of binding of COMPOUND A, COMPOUND B and COMPOUND C at 2 μM in mouse brain homogenate are shown in Table 4a, formation of viloxazine is shown in Table 4b. It was noted that COMPOUND A, COMPOUND B and COMPOUND C were unstable in mouse brain homogenate, therefore, the % binding values under the experiment conditions may be biased. The results of binding of viloxazine in mouse and human brain homogenate are summarized in Table 4c. The viloxazine tissue binding was 80.5 and 74.0% and recovery was 91.4 and 94.8% in mouse and human brain homogenate TABLE 4a Tissue Binding of COMPOUND A, COMPOUND B and COMPOUND C in CD-1 Mouse Brain Homogenate

| Conc. | Analyte Peak area/IS Peak area | | | $C_0$ | % Unbound[a] | $f_{u,\ brain}$[b] | % Recovery[e] |
|---|---|---|---|---|---|---|---|
| (μM) | $C_R$ | $C_D$ | $C_o$ | Mean | Experimental | Mean (SD) | Mean (SD) |
| COMPOUND A[c] | 0.0003 | 0.0001 | 0.010 | 0.011 | ND[d] | ND | 2.39 |
| | 0.0002 | 0.0000 | 0.012 | | | | (0.568) |
| | 0.0002 | 0.0000 | 0.012 | | | | |
| COMPOUND B | 0.001 | 0.009 | 0.057 | 0.06 | 15.5 | 4.39 | 18.4 |
| | 0.001 | 0.010 | 0.059 | | | (0.51) | (1.7) |
| | 0.002 | 0.010 | 0.064 | | | | |
| COMPOUND C | 0.000 | 0.002 | 0.036 | 0.04 | 20.9 | 6.20 | 7.79 |
| | 0.001 | 0.003 | 0.037 | | | (0.71) | (1.0) |
| | 0.001 | 0.002 | 0.041 | | | | |

[a]Determined using brain homogenates from 4 hr incubation except where noted. % Unbound = 100 * ($[C_R]/[C_D]$).

[b]Calculated from % unbound. $f_{u,\ brain} = 1/D/((1/(C_R/C_D) - 1) + 1/D)$, where D is dilution factor that is 4.

[c]Incubated for 1 hr due to concern of instability.

[d]Can't be determined due to instability of test article, which has 1.3% remaining after 1 hr (data not shown).

[e]% Recovery = 100 * {($[C_R] + [C_D])/[C_o]$}.

[f] $[C_R]$ is the analyte concentration on the buffer side of the chamber at 4 hours; $[C_D]$ is the concentration on brain homogenate side of the chamber collected at 4 hours; $[C_0]$ is the analyte concentration in the brain homogenate sample at time zero.

TABLE 4b

Formation of Viloxazine from Samples of COMPOUND A, COMPOUND B and COMPOUND C in CD-1 Mouse Brain Homogenate

| | Analyte Peak area/IS Peak area of Viloxazine (mean) | | |
|---|---|---|---|
| Test Compound | $C_R$ | $C_D$ | $C_o$ |
| COMPOUND A | 0.322 | 0.702 | 0.720 |
| COMPOUND B | 0.243 | 0.625 | 0.223 |
| COMPOUND C | 0.252 | 0.609 | 0.399 |

TABLE 4c

Tissue Binding of Viloxazine in CD-1 Mouse and Human Brain Homogenate

| | Analyte Peak area/IS Peak area | | | $C_0$ | % Unbound[a] | fu, brain[b] | % Recovery |
|---|---|---|---|---|---|---|---|
| Species | $C_R$ | $C_D$ | $C_o$ | Mean | Experimental | Mean (SD) | Mean (SD) |
| Mouse | 0.540 | 1.26 | 2.17 | 2.06 | 49.0 | 19.9 | 91.4 |
| | 0.632 | 1.23 | 1.98 | | | (3.2) | (5.0) |
| | 0.687 | 1.31 | 2.03 | | | | |
| Human | 0.751 | 1.27 | 2.10 | 2.02 | 58.1 | 26.0 | 94.8 |
| | 0.729 | 1.15 | 1.99 | | | (4.7) | (4.5) |
| | 0.632 | 1.22 | 1.98 | | | | |

[a]Determined using brain homogenates from 4 hr incubation except where noted.
[b]Calculated from % unbound using dilution factor of 4.

Example 8. In Vitro Protein Binding of COMPOUND A, COMPOUND B and COMPOUND C in CD-1 Mouse and Human Plasma An in vitro study was conducted to determine the protein binding of COMPOUND A, COMPOUND B and COMPOUND C in CD-1 mouse and human plasma.

Preparation of Solutions

Test Article Solutions: test articles of COMPOUND A, COMPOUND B and COMPOUND C at 10 mM and viloxazine (metabolite) at 3.6 mM stock solutions were prepared with DMSO. Working solution in DMSO at 0.4 mM for each compound was prepared from the stock solutions. All working solutions were freshly prepared on the day of experiment and disposed of after use. Positive Control Stock and Working Solution: warfarin stock solution (10 mM) was prepared in DMSO and stored at approximately −20° C. A working solution at 0.4 mM concentration was freshly prepared similarly as described for the test article working solution. Internal Standard Solutions and Stop Solutions: the stock solutions of internal standards for positive controls, tolbutamide and labetalol, were prepared in DMSO and stored at approximately −20° C. Stop solution was prepared by spiking the stock solution (2 mg/mL) into CAN (acetonitrile) to achieve a 200 ng/mL final concentration. Dialysis Buffer: Phosphate buffered saline (PBS), pH 7.4 was used in the study. Test System: frozen plasma was thawed in a water bath at 37° C. and centrifuged at 3220×g for 5 minutes to remove any debris.

Assay Procedures

The mouse and human plasma samples (995 μL/well) were spiked with 5 μL of 0.4 mM COMPOUND A, COMPOUND B and COMPOUND C and viloxazine working solutions separately, or warfarin working solution (0.4 mM). The final concentrations of COMPOUND A, COMPOUND B and COMPOUND C, and viloxazine or warfarin in the samples were 2 μM. The concentration of organic solvent (DMSO) was 0.5% in the final incubation.

After mixing thoroughly, the time zero samples ($C_0$) were prepared by transferring 50 μL aliquots of spiked plasma in triplicate to sample collection plates, and matched with 50 μL of dialysis buffer, immediately followed by addition of 300 μL of stop solution. The samples were thoroughly mixed and stored at 2~ 8° C. until being further processed together with other post-dialysis samples.

Spiked plasma (150 μL) in triplicate was loaded into the donor side chamber, and 150 μL of dialysis buffer was loaded into the receiver side chamber of the dialysis device. The dialysis device was then sealed with a breathable sealer and incubated at 37° C. in a humidified incubator with 5% $CO_2$ for 4 hours on a 3-D Analog Waving Platform Shaker with constant rotation. (COMPOUND A was incubated for 1 hr). At the end of dialysis, 50 μL aliquots were removed separately from both chambers, and transferred into a new 96-well plate. Each sample was matched with an equal volume of blank buffer or plasma as appropriate to obtain a final volume of 100 μL, immediately followed by addition of 300 μL of stop solution.

All samples (including time zero) were thoroughly mixed for approximately for 30 minutes and centrifuged at 3220×g for 15 minutes. Aliquots of 100 μL supernatant were removed from each well and mixed with 100 μL ultrapure water in a new 96-well plate for analysis by LC/MS/MS.

Results

Plasma Protein Binding of COMPOUND A, COMPOUND B and COMPOUND C. Due to instability of these three compounds in the mouse plasma, no plasma binding and recoveries were reported.

Plasma Protein Binding of Viloxazine (Metabolite). The percentage of protein binding of viloxazine were 80.5% and 74.0% in mouse and human plasma, respectively. The range of recoveries of viloxazine from all dialysis wells was from 101% to 105%, indicating that the compound was stable during the dialysis process in this study. Results are summarized in Table 5 below

TABLE 5

Protein Binding of Viloxazine in CD-1 Mouse and Human Plasma after 4 Hours Incubation

| | Analyte/IS ratio | | | % Unbound | | % | % Recovery | |
|---|---|---|---|---|---|---|---|---|
| Species | $C_R$ | $C_D$ | $C_0$ | Mean | S.D. | Bound | Mean | S.D. |
| Mouse | 0.896 | 1.25 | 1.92 | 73.0 | 2.63 | 27.0 | 101 | 7.21 |
| Plasma | 0.776 | 1.09 | 2.12 | | | | | |
| | 0.873 | 1.15 | 1.95 | | | | | |
| Human | 0.659 | 1.44 | 1.80 | 1.92 | 0.107 | 52.8 | 105 | 2.75 |
| Plasma | 0.643 | 1.36 | 2.01 | | | | | |
| | 0.653 | 1.35 | 2.03 | | | | | |

$C_R$: concentration of the sample in the receiver side of the chamber.
$C_D$: concentration of the sample in the donor side of the chamber.
$C_0$: concentration of the plasma sample at time zero
S.D.: Standard deviation
% Recovery: percentage of compound recovery from the dialysis wells after 4-hr of incubation.

In Vivo Studies

Example 9. Evaluation of Brain Penetration of Viloxazine Following Single Intravenous Administration of Analog (S) to Male CD-1 Mice A study was conducted to determine the pharmacokinetic (PK) profiles of viloxazine in the plasma and brain following a single intravenous (IV) administration of three analogs, COMPOUND A, COMPOUND B, and COMPOUND C, to male CD-1 mice.

Study Design. Forty-five male CD-1 mice were divided into three treatment groups, n=15 per group. The animals were not fasted prior to dosing; food and water were freely accessible during the entire study. COMPOUND A, COMPOUND B and COMPOUND C, the analogs of viloxazine, each was given to one of the three groups of mice at 9.911, 10.439 and 10.557 mg/kg, respectively. The doses of the three viloxazine analogs were equivalent to 5 mg/kg of free base viloxazine. Following the treatments, 3 mice at each time were euthanized at 0.083, 0.25, 0.5, 1 and 4 hours respectively to collect plasma and brains. The concentrations of viloxazine in the plasma and brain homogenates were measured by LC-MS/MS. The average concentration-time data of viloxazine in the plasma and brain were used to evaluate the PK properties and the brain plasma ratios.

Test Article Formulation. The dose solutions were prepared on the day of study prior to dosing. The vehicles used for the dose preparations were the same for all three analogs and consisted of DMSO, PEG400 and 30% HP-β-CD in $H_2O$ at the ratio of 4, 30 and 64 (v/v/v). The target concentrations of the dose solutions for COMPOUND A, COMPOUND B and COMPOUND C were 1.982, 2.088 and 2.111 mg/mL, respectively. The final formulations all appeared as a clear solution, and each was dosed at 5 mL/kg to achieve the target dose of 9.991, 10.439 and 10.557 mg/kg, respectively. The analog doses were equivalent to 5 mg/kg of free base viloxazine.

Results

Clinical Observation. All animals appeared lethargic and exhibited slower and shallow breathing pattern immediately post dosing. The adverse effects lasted for about 2 minutes and all the animals recovered afterwards. Compound administrations were slowed down to ~30 seconds to alleviate the adverse effects.

Figure 17A:
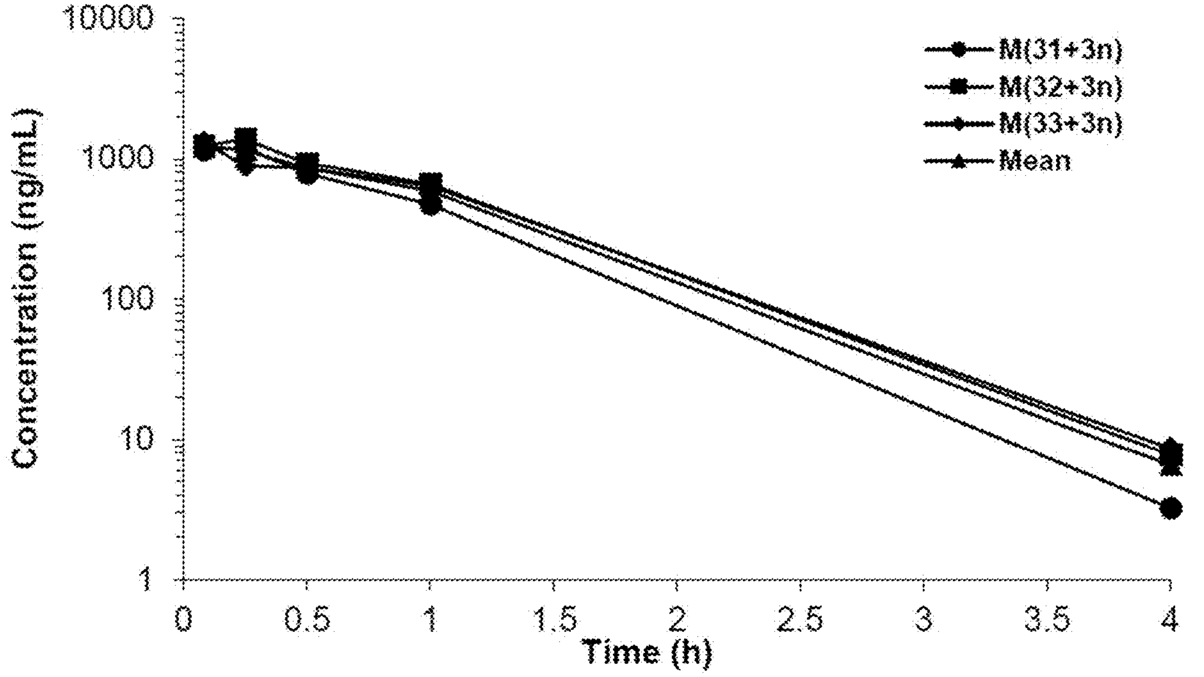
FIGS. 17*a*-17*b* shows individual and mean concentration-time profiles of viloxazine in the plasma (FIG. 17*a*) and brain (FIG. 17*b*) following IV administration of COMPOUND A at 9.911 mg/kg to male CD-1 mice.
Figure 17B:
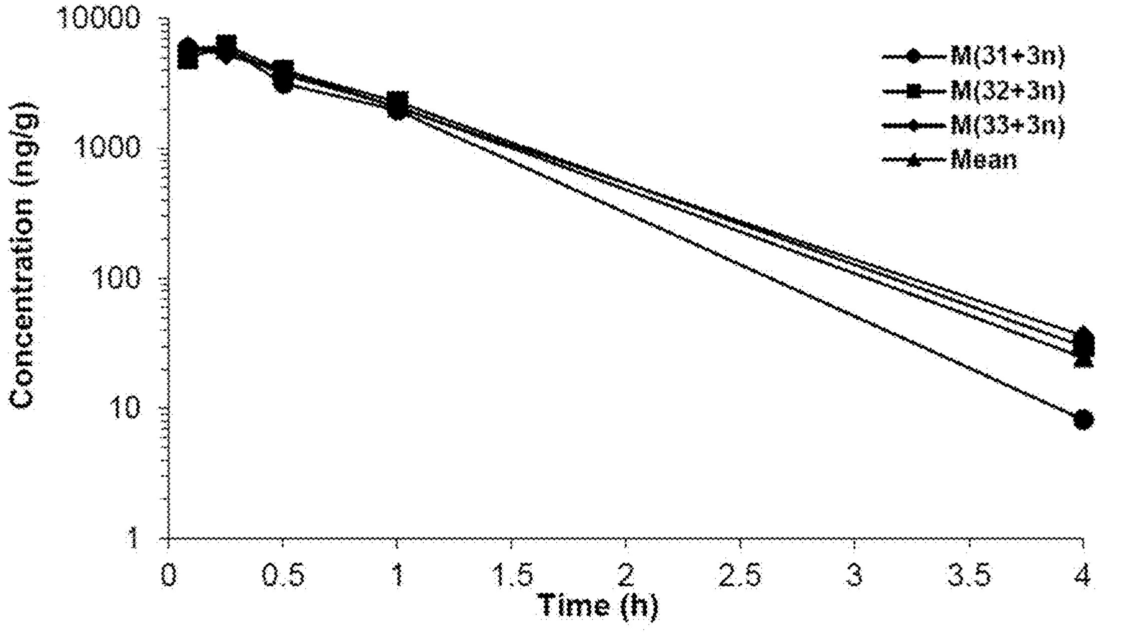
Figure 18A:
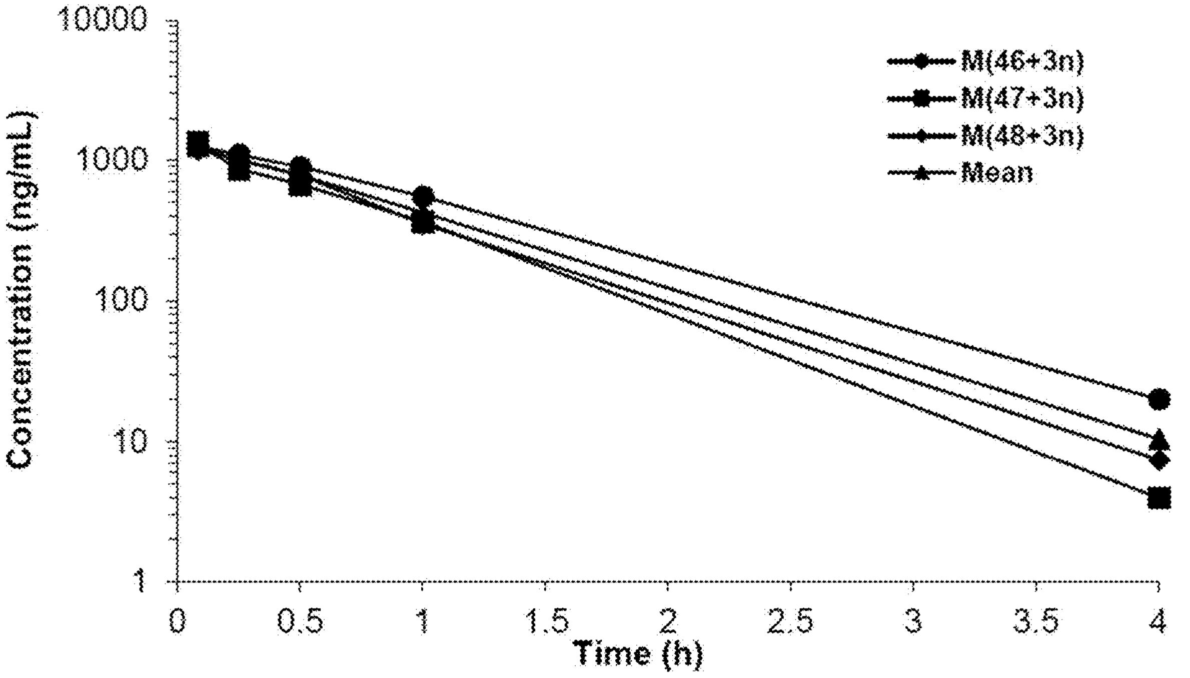
FIGS. 18*a*-18*b* shows individual and mean concentration-time profiles of viloxazine in the plasma (FIG. 18*a*) and brain (FIG. 18*b*) following IV administration of COMPOUND B at 10.439 mg/kg to male CD-1 mice.
Figure 18B:
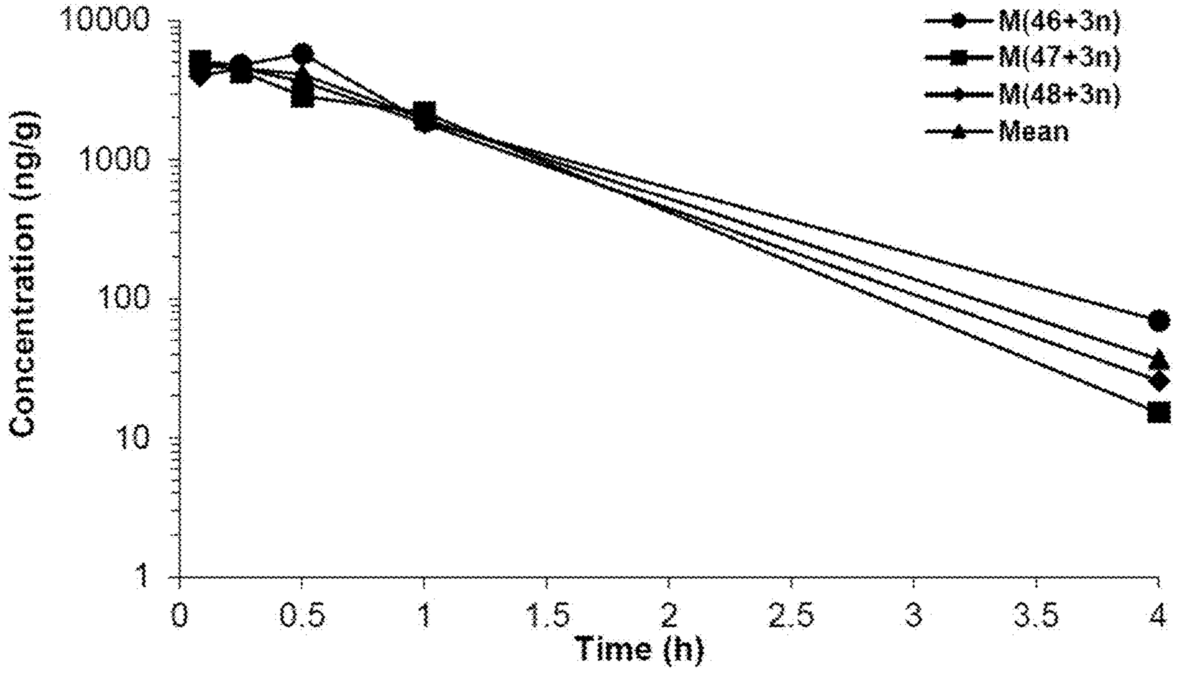
Figure 19A:
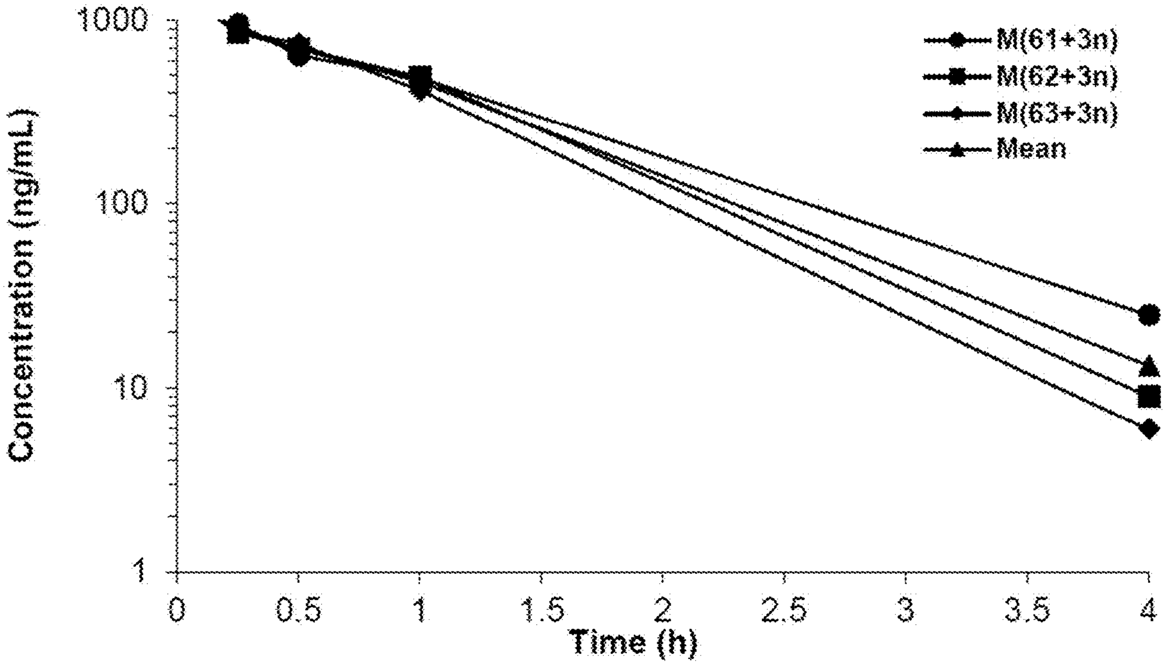
FIGS. 19*a*-19*b* show individual and mean concentration-time profiles of viloxazine in the plasma (FIG. 19*a*) and brain (FIG. 19*b*) following IV administration of COMPOUND C at 10.557 mg/kg to male CD-1 mice.
Figure 19B:
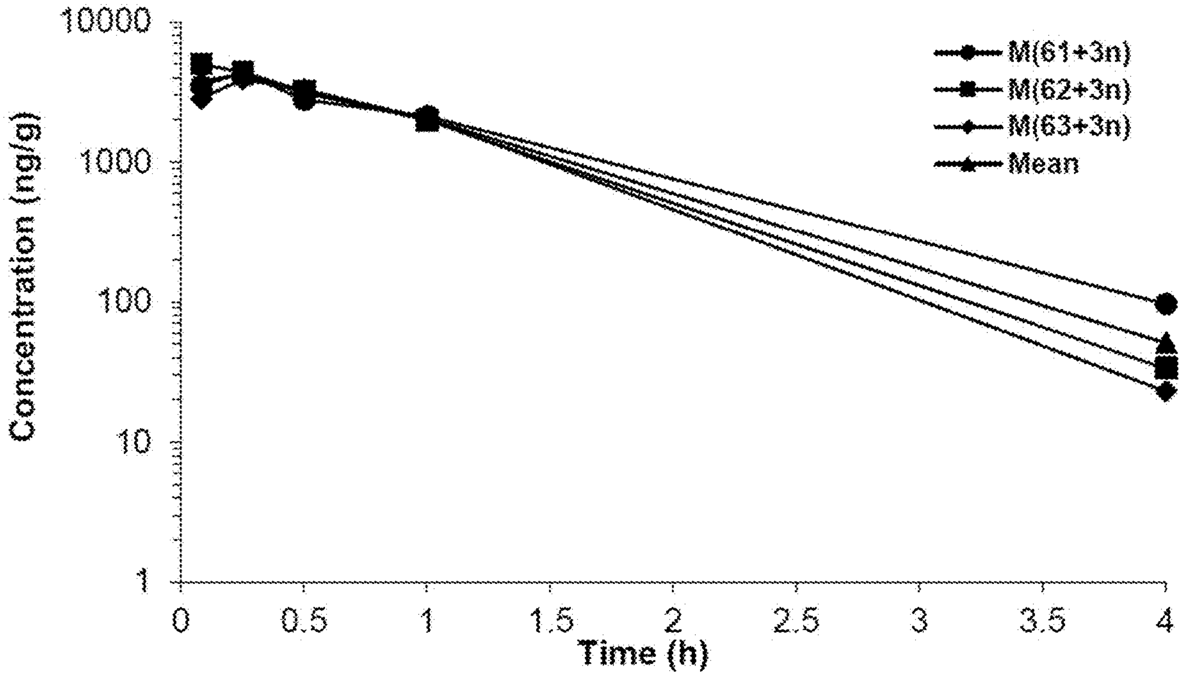
Figure 20A:
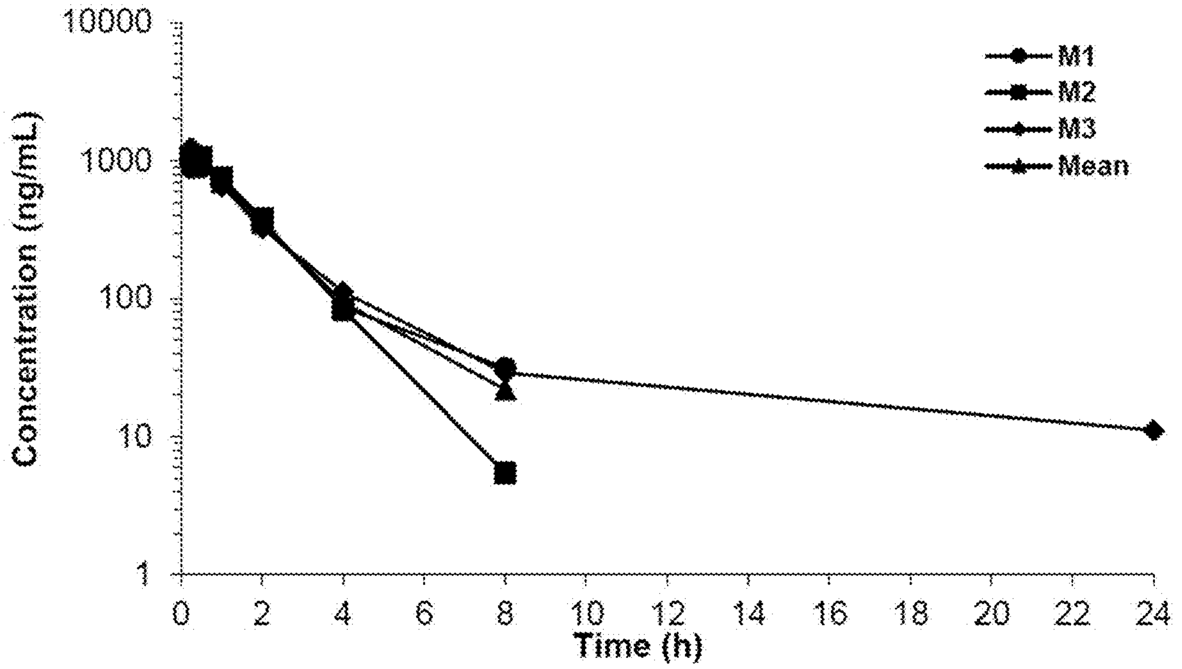
FIGS. 20*a*-20*h* show individual and mean plasma concentration-time profiles of S(−)- and R(+)-viloxazine following single PO administration to male CD-1 mice.
Figure 20B:
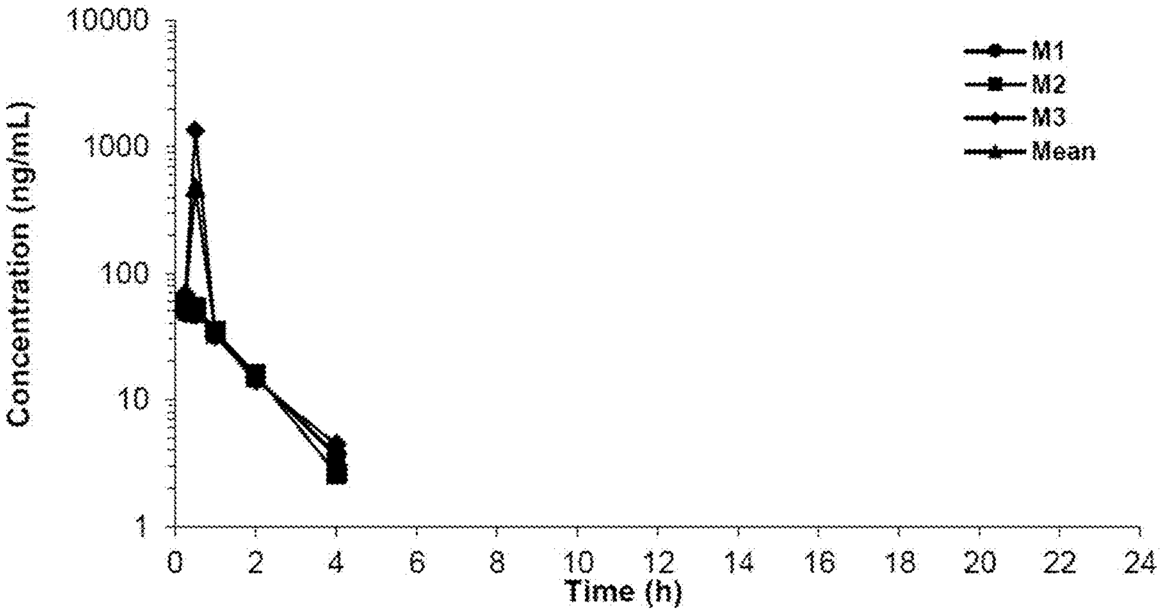
Figure 20C:
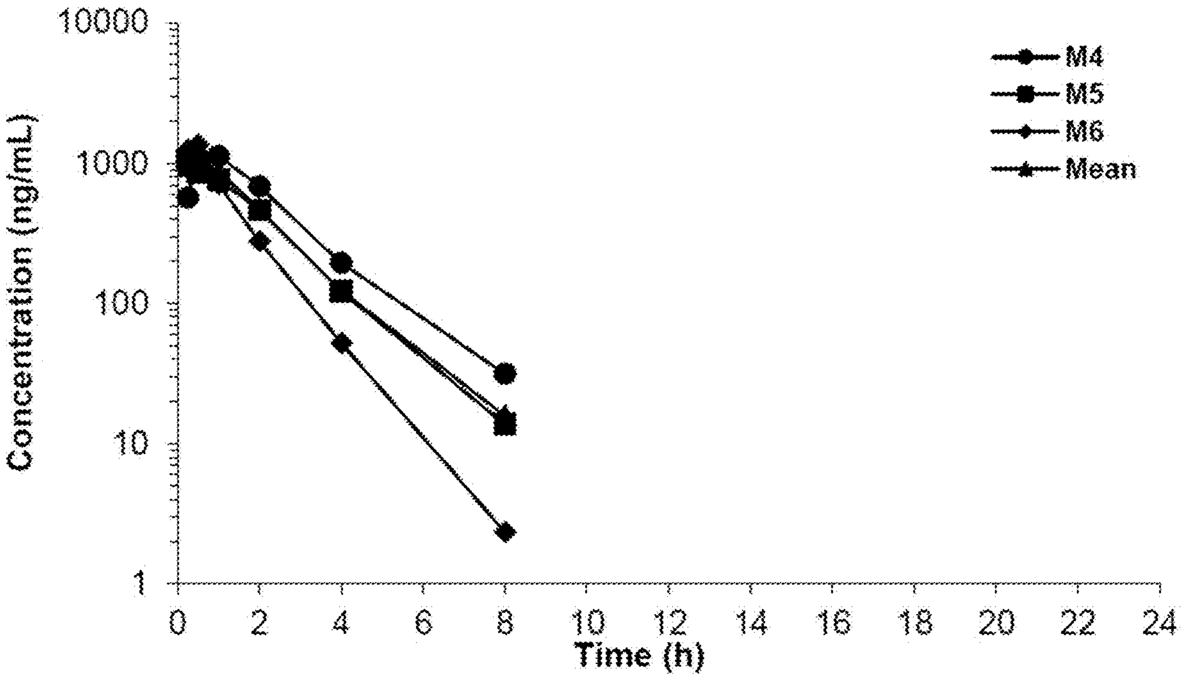
Figure 20D:
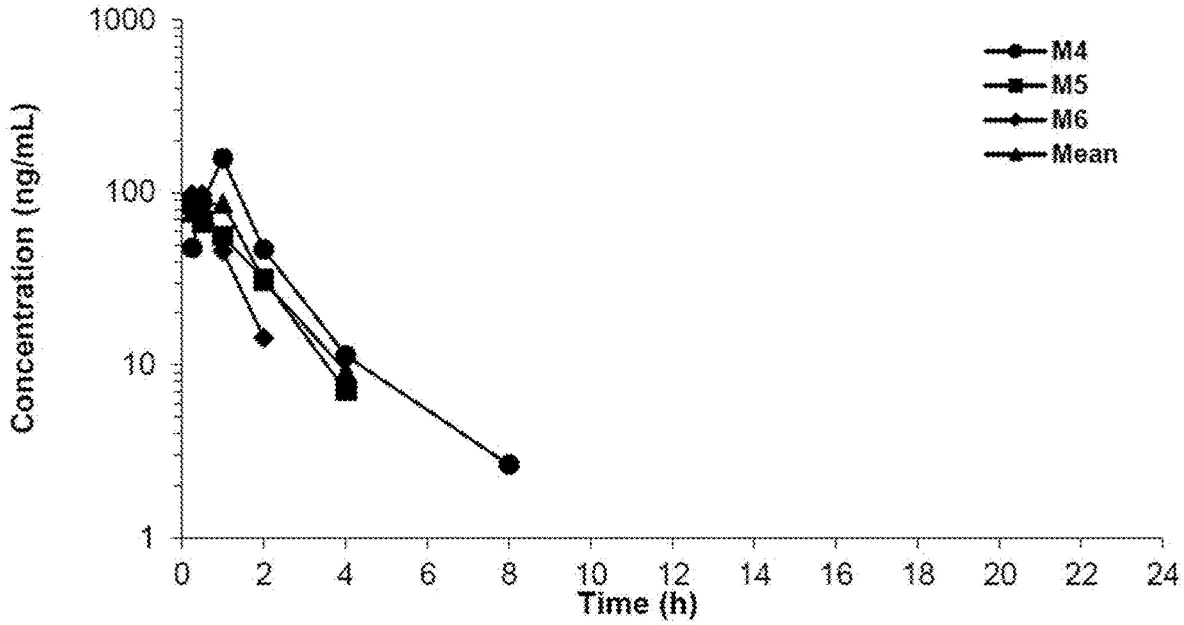
Figure 20E:
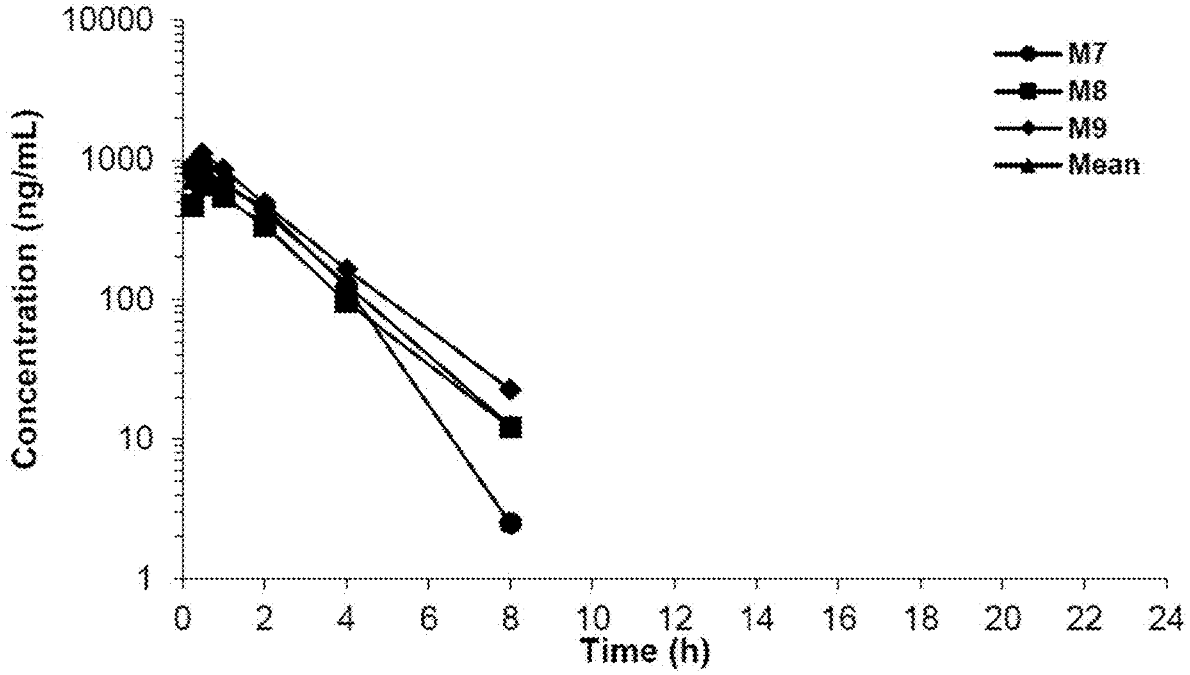
Figure 20F:
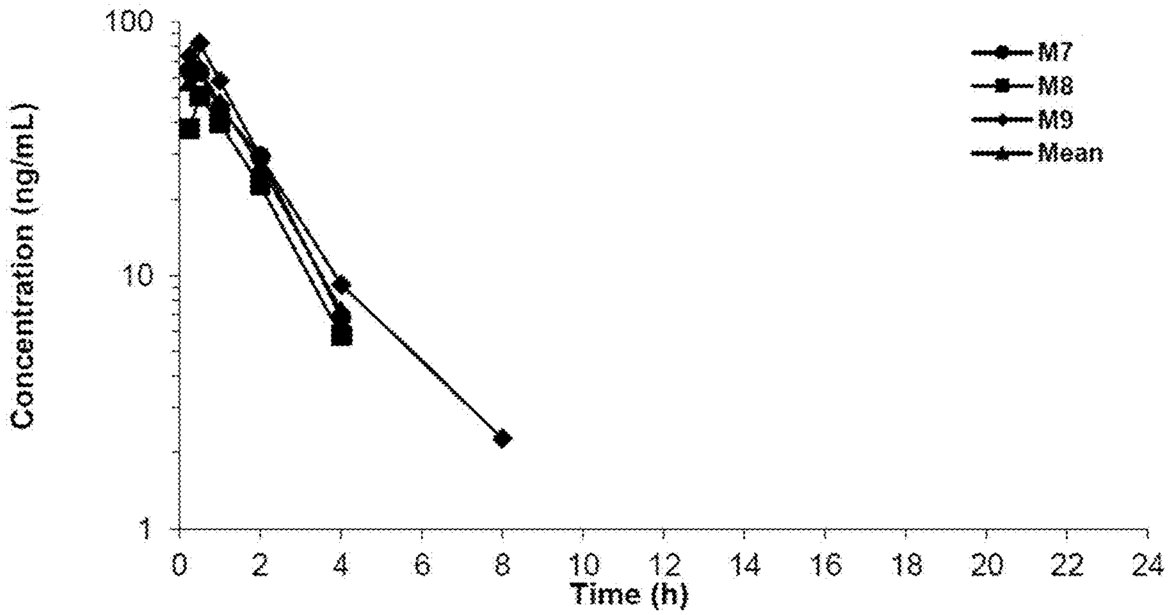
Figure 20G:
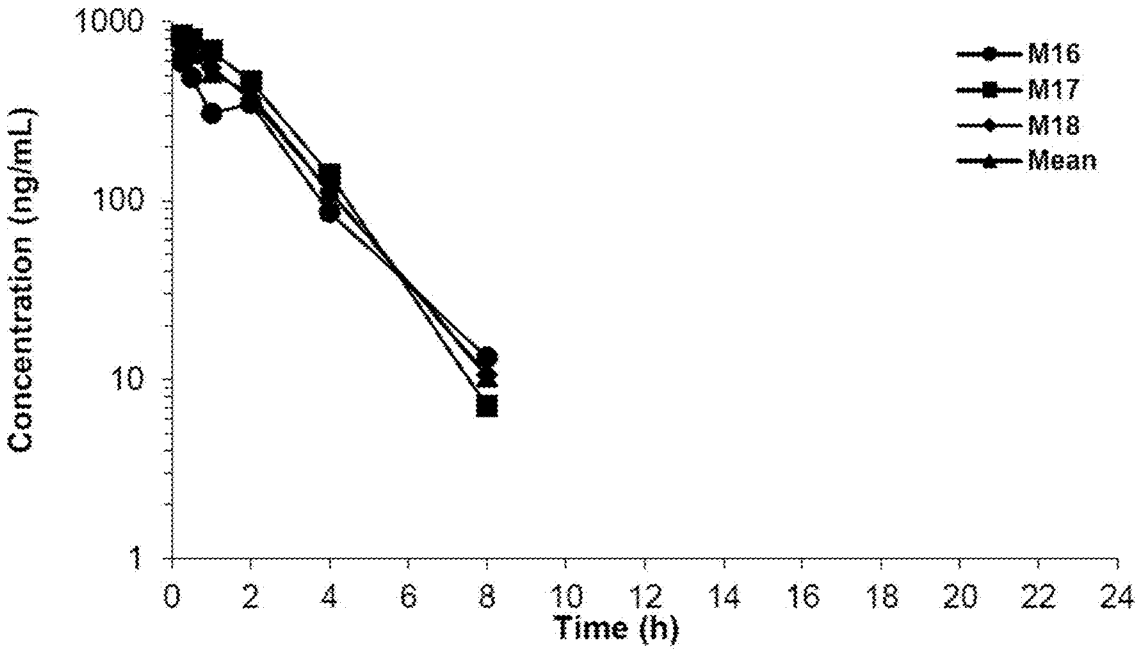
Figure 20H:
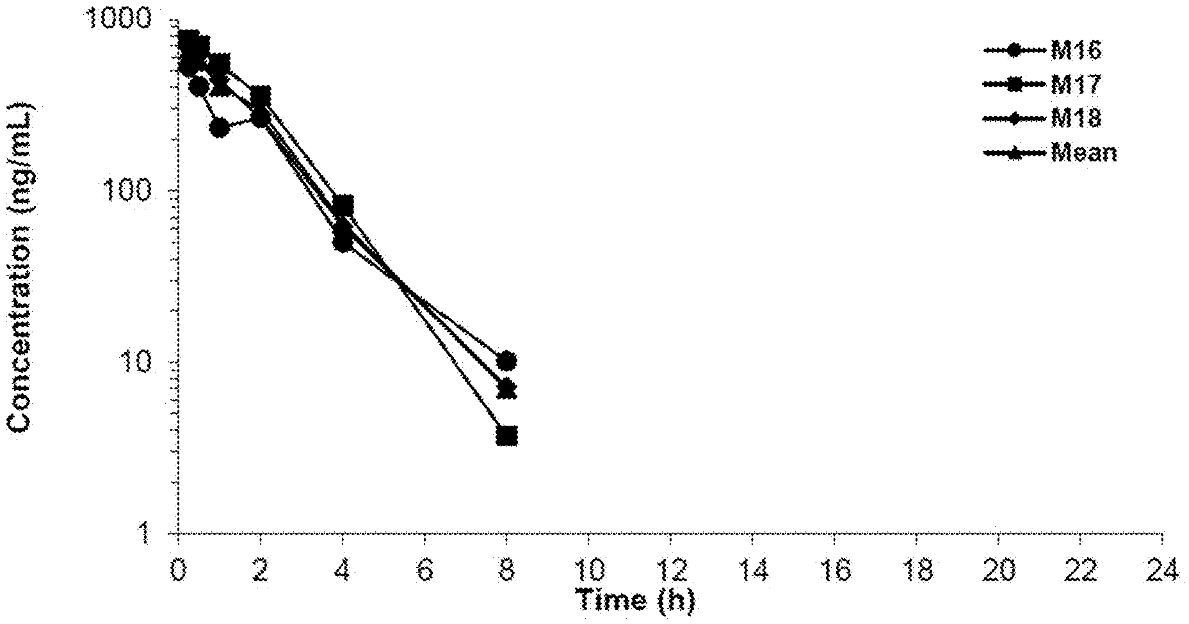

The PK parameters of viloxazine in the plasma and brain are summarized in Table 6. The concentration-time profiles of viloxazine in the plasma and brain following IV administration of COMPOUND A, COMPOUND B and COMPOUND C are presented in FIG. 17, FIG. 18, and FIG. 19, respectively

TABLE 6

Pharmacokinetics of viloxazine in the plasma and brain following IV administration of COMPOUND A, COMPOUND B and COMPOUND C to male CD-1 mice

| Plasma | | | | Brain | | | |
|---|---|---|---|---|---|---|---|
| Analogs | Compd. A | Compd. B | Compd. C | Analogs | Compd. A | Compd. B | Compd. C |
| Rsq_adj | 0.993 | 1.00 | 0.997 | Rsq_adj | 0.998 | 1.00 | 0.997 |
| $C_{max}$ (ng/mL) | 1247 | 1270 | 1223 | $C_{max}$ (ng/mL) | 5847 | 4737 | 4228 |
| $T_{max}$ (h) | 0.0830 | 0.0830 | 0.0830 | $T_{max}$ (h) | 0.250 | 0.0830 | 0.250 |
| $T_{1/2}$ (h) | 0.494 | 0.562 | 0.611 | $T_{1/2}$ (h) | 0.479 | 0.518 | 0.581 |
| $T_{last}$ (h) | 4.00 | 4.00 | 4.00 | $T_{last}$ (h) | 4.00 | 4.00 | 4.00 |
| $AUC_{0\text{-}last}$ (ng · h/mL) | 1248 | 1092 | 1088 | $AUC_{0\text{-}last}$ (ng · h/mL) | 5198 | 4965 | 4624 |
| $AUC_{0\text{-}inf}$ (ng · h/mL) | 1253 | 1101 | 1099 | $AUC_{0\text{-}inf}$ (ng · h/mL) | 5215 | 4993 | 4666 |
| $MRT_{0\text{-}last}$ (h) | 0.822 | 0.835 | 0.902 | $MRT_{0\text{-}last}$ (h) | 0.761 | 0.819 | 0.910 |
| $MRT_{0\text{-}inf}$ (h) | 0.836 | 0.866 | 0.945 | $MRT_{0\text{-}inf}$ (h) | 0.774 | 0.841 | 0.946 |

The data showed that IV administration of the three viloxazine analogs, COMPOUND A, COMPOUND B and COMPOUND C, at the doses equivalent to 5 mg/kg of free base viloxazine yielded similar viloxazine pharmacokinetic profiles in both the plasma and brain. The brain to plasma ratios of viloxazine measured by either the concentrations or the AUC were also comparable following IV administration among the three analogs (brain/plasma ratio is about 4-5). The higher brain concentrations or AUC of viloxazine indicated that the compound can efficiently penetrate the blood-brain barrier (BBB), seemingly by active uptake transport. These data indicate that the three viloxazine analogs were not differentiable in terms of converting to viloxazine as measured by the PK profiles or brain penetration properties of viloxazine.

Example 10. Evaluation of Pharmacokinetics of S(−)- and R(+)-Viloxazine Following Single Oral Administration of Prodrugs and Racemic Viloxazine to Male CD-1 Mice A study was carried out to evaluate the pharmacokinetic (PK) properties of S(−)- and R(+)-viloxazine following single oral (PO) administration of three prodrugs, COMPOUND A, COMPOUND B, COMPOUND C, and racemic viloxazine to male CD-1 mice.

Study Design. Twelve male CD-1 mice were divided into 4 treatment groups, n=3 per group. The animals were fasted overnight prior to dosing. Food was returned 2 hours post-dose. Animals had access to water freely the entire time throughout the study. The three prodrugs, COMPOUND A, COMPOUND B, COMPOUND C, and the racemic viloxazine each was given to one group of mice by oral gavage at 19.82, 21.03, 21.11 and 11.64 mg/kg, respectively. The dosages of the prodrugs and the racemic viloxazine were equivalent to 10 mg/kg free base viloxazine. Blood samples were collected from each animal at 0.25, 0.5, 1, 2, 4, 8 and 24 hours post-dose, and then centrifuged to extract plasma for the determination of the concentrations of S(−)- and R(+)-viloxazine. The concentrations of the two isomers in the plasma were quantified by liquid chromatography tandem mass spectrometry (LC-MS/MS). The bioanalytical assay provided a lower limit of quantification (LLOQ) of 1.5 ng/mL and a linear range up to 1500 ng/mL for both isomers. The data of plasma concentration vs. time were analyzed using Phoenix WinNonlin 6.3 to determine the PK properties of S(−)- and R(+)-viloxazine. The non-compartmental analysis model and the linear log trapezoidal method were applied to the PK calculation.

Test Article Formulation. Dose solutions were prepared freshly on the day of study prior to dosing. The formulations of the three prodrugs and the racemic viloxazine were prepared the same way using 4% DMSO, 30% PEG 400, and 66% HPβCD (30% in $H_2O$, w/v) as vehicle. The target concentrations of COMPOUND A, COMPOUND B, COMPOUND C and the racemic viloxazine were 19.82, 21.03, 21.11 and 11.64 mg/kg respectively, all were equivalent to 10 mg/mL free base viloxazine. The nominal dose volume was 10 mL/kg for all four administered compounds. All formulations appeared as clear solution at the time of dosing.

Results

Clinical Observation. COMPOUND A, COMPOUND B, COMPOUND C and the racemic viloxazine at the administered dosages was well tolerated by all animals. No adverse effects were observed throughout the study.

The corresponding PK parameters are summarized in Tables 7a-7d. The plasma concentration-time profiles of S(−)- and R(+)-viloxazine following PO administrations are shown in FIGS. 20*a*-20*h*, respectively TABLE 7a Mean PK parameters of S(−)-viloxazine and R(+)-viloxazine following single PO administration of COMPOUND A to male CD-1 mice at 19.82 mg/kg

| | S(−)-viloxazine | | | R(+)-viloxazine | | |
|---|---|---|---|---|---|---|
| Time (h) | Mean | SD | CV (%) | Mean | SD | CV (%) |
| Rsq_adj | 0.957 | 0.0494 | 5.16 | 0.993 | 0.00800 | 0.805 |
| $C_{max}$ (ng/mL) | 1064 | 169 | 15.9 | 482 | 743 | 154 |

TABLE 7a-continued

Mean PK parameters of S(−)-viloxazine and R(+)-viloxazine following single PO administration of COMPOUND A to male CD-1 mice at 19.82 mg/kg

| | S(−)-viloxazine | | | R(+)-viloxazine | | |
|---|---|---|---|---|---|---|
| Time (h) | Mean | SD | CV (%) | Mean | SD | CV (%) |
| $T_{max}$ (h) | 0.333 | 0.144 | 43.3 | 0.333 | 0.144 | 43.3 |
| $T_{1/2}$ (h) | 1.45 | 0.410 | 28.4 | 0.939 | 0.139 | 14.8 |
| $T_{last}$ (h) | 13.3 | 9.24 | 69.3 | 4.00 | 0 | 0 |
| $AUC_{0-last}$ (ng · h/mL) | 1990 | 222 | 11.2 | 186 | 184 | 99.0 |
| $AUC_{0-inf}$ (ng · h/mL) | 2026 | 213 | 10.5 | 191 | 185 | 97.4 |
| $MRT_{0-last}$ (h) | 2.32 | 1.08 | 46.7 | 1.05 | 0.316 | 30.0 |
| $MRT_{0-inf}$ (h) | 2.53 | 1.18 | 46.4 | 1.21 | 0.389 | 32.2 |

TABLE 7b

Mean PK parameters of S(−)-viloxazine and R(+)-viloxazine following single PO administration of COMPOUND B to male CD-1 mice at 21.03 mg/kg

| | S(−)-viloxazine | | | R(+)-viloxazine | | |
|---|---|---|---|---|---|---|
| Time (h) | Mean | SD | CV (%) | Mean | SD | CV (%) |
| Rsq_adj | 0.993 | 0.00707 | 0.712 | 0.973 | 0.0341 | 3.51 |
| $C_{max}$ (ng/mL) | 1177 | 155 | 13.2 | 113 | 39.0 | 34.4 |
| $T_{max}$ (h) | 0.583 | 0.382 | 65.5 | 0.500 | 0.433 | 86.6 |
| $T_{1/2}$ (h) | 1.15 | 0.253 | 22.0 | 1.01 | 0.475 | 46.9 |
| $T_{last}$ (h) | 8.00 | 0 | 0 | 4.67 | 3.06 | 65.5 |
| $AUC_{0-last}$ (ng · h/mL) | 2243 | 559 | 24.9 | 161 | 79.0 | 49.1 |
| $AUC_{0-inf}$ (ng · h/mL) | 2273 | 589 | 25.9 | 170 | 76.0 | 44.7 |
| $MRT_{0-last}$ (h) | 1.71 | 0.412 | 24.0 | 1.32 | 0.534 | 40.5 |
| $MRT_{0-inf}$ (h) | 1.81 | 0.488 | 27.1 | 1.54 | 0.527 | 34.1 |

TABLE 7c

Mean PK parameters of S(−)-viloxazine and R(+)-viloxazine following single PO administration of COMPOUND C to male CD-1 mice at 21.11 mg/kg

| | S(−)-viloxazine | | | R(+)-viloxazine | | |
|---|---|---|---|---|---|---|
| Time (h) | Mean | SD | CV (%) | Mean | SD | CV (%) |
| Rsq_adj | 0.993 | 0.00711 | 0.716 | 0.978 | 0.0163 | 1.67 |
| $C_{max}$ (ng/mL) | 876 | 224 | 25.6 | 65.7 | 15.7 | 23.8 |
| $T_{max}$ (h) | 0.500 | 0 | 0 | 0.417 | 0.144 | 34.6 |
| $T_{1/2}$ (h) | 1.14 | 0.311 | 27.3 | 1.27 | 0.344 | 27.1 |
| $T_{last}$ (h) | 8.00 | 0 | 0 | 5.33 | 2.31 | 43.3 |
| $AUC_{0-last}$ (ng · h/mL) | 1918 | 453 | 23.6 | 124 | 33.7 | 27.2 |
| $AUC_{0-inf}$ (ng · h/mL) | 1942 | 466 | 24.0 | 132 | 31.8 | 24.0 |
| $MRT_{0-last}$ (h) | 1.87 | 0.123 | 6.57 | 1.58 | 0.272 | 17.2 |
| $MRT_{0-inf}$ (h) | 1.96 | 0.193 | 9.87 | 1.91 | 0.234 | 12.2 |

TABLE 7d

Individual and mean PK parameters of S(−)-viloxazine and R(+)-viloxazine following single PO administration of racemic viloxazine to male CD-1 mice at 11.64 mg/kg

| | S(−)-viloxazine | | | R(+)-viloxazine | | |
|---|---|---|---|---|---|---|
| Time (h) | Mean | SD | CV (%) | Mean | SD | CV (%) |
| Rsq_adj | 0.990 | 0.0122 | 1.23 | 0.975 | 0.0334 | 3.43 |
| $C_{max}$ (ng/mL) | 733 | 124 | 16.9 | 667 | 123 | 18.5 |
| $T_{max}$ (h) | 0.250 | 0 | 0 | 0.250 | 0 | 0 |
| $T_{1/2}$ (h) | 1.15 | 0.157 | 13.7 | 1.17 | 0.260 | 22.2 |
| $T_{last}$ (h) | 8.00 | 0 | 0 | 8.00 | 0 | 0 |
| $AUC_{0\text{-}last}$ (ng · h/mL) | 1627 | 351 | 21.6 | 1231 | 280 | 22.8 |
| $AUC_{0\text{-}inf}$ (ng · h/mL) | 1645 | 344 | 20.9 | 1243 | 272 | 21.9 |
| $MRT_{0\text{-}last}$ (h) | 1.93 | 0.107 | 5.55 | 1.76 | 0.132 | 7.51 |
| $MRT_{0\text{-}inf}$ (h) | 2.02 | 0.162 | 8.04 | 1.85 | 0.206 | 11.2 |

The data showed that the $C_{max}$ and $AUC_{0\text{-}last}$ of the S(−)-viloxazine were consistently higher (about 10×) than those of the R(+)-viloxazine following PO administration of the three prodrugs. For either isomer, the yield was higher numerically for COMPOUND A and COMPOUND B relative to COMPOUND C. The $C_{max}$ and $AUC_{0\text{-}last}$ of the two isomers following administration of the racemic viloxazine were comparable. The $T_{1/2}$ and the $MRT_{0\text{-}last}$ were similar between the two isomers independent of the prodrugs.

Example 11. Evaluation of Pharmacokinetics of S-Viloxazine in Male Sprague-Dawley Rats A study was carried out to evaluate the pharmacokinetic (PK) properties of S-viloxazine, following single oral (PO) administration to male Sprague-Dawley rats.

Study Design. A single dose of S-viloxazine was administered to 3 male Sprague-Dawley rats by oral gavage at 40 mg/kg, which was equivalent to 40 mg/kg of the free base VLX (viloxazine). The animals were fasted overnight prior to dosing. Food was returned 2 hours post-dose. Animals had access to water freely the entire time throughout the study. Blood samples were collected from each animal at 0.25, 0.5, 1, 2, 4, 6, 8, and 24 hours post-dose for the determination of plasma concentrations of R(+)- and S(−)-VLX. The plasma concentrations of the 2 analytes were quantified by liquid chromatography tandem mass spectrometry (LC-MS/MS). The bioanalytical assay provided a lower limit of quantification (LLOQ) of 1.5 ng/mL and an upper limit of quantification (ULOQ) of 1500 ng/mL for both R(+)- and S(−)-VLX. The plasma concentration-time data were analyzed using Phoenix WinNonlin (version 8.3) to characterize the PK properties of the analytes. The non-compartmental analysis model and the linear/log trapezoidal method were applied to the calculation of the PK parameters.

Test Article Formulation. The dose solution was prepared freshly on the day of study prior to dosing. The formulation appeared as a clear solution with a final concentration of 40 mg/mL in 0.9% Saline.

Results

Clinical Observation. S-Viloxazine at the administered dosage was well tolerated by all animals. No adverse effects were observed throughout the study.

Figure 21:
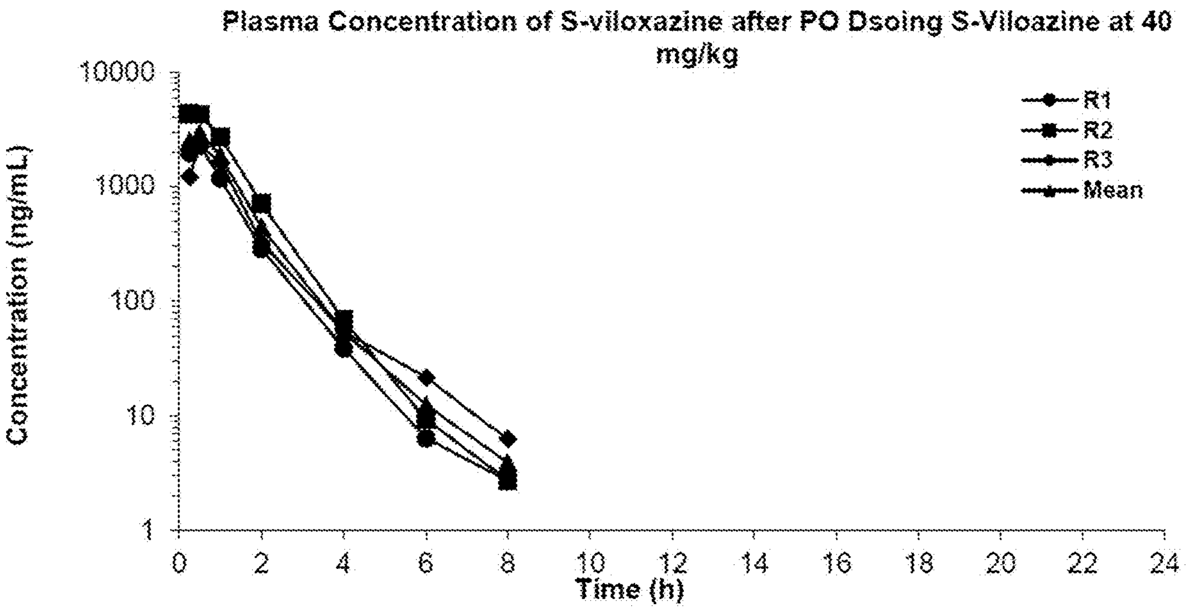
FIG. 21 shows individual and mean plasma concentrations-time profiles of S(−)-viloxazine following a single oral administration of S(−)-viloxazine at 40 mg/kg to fasted male Sprague-Dawley rats

The PK parameters of S(−)-VLX are summarized in Table 8. The plasma concentration-time profiles of S(−)-VLX are presented in FIG. 21

TABLE 8

Mean Pharmacokinetic Parameters Following a Single Oral Administration of S(−)-VLX at 40 mg/kg to Fasted Male Sprague-Dawley Rats

| PK Parameters | Mean | SD | CV (%) |
|---|---|---|---|
| Rsq_adj | 0.975 | 0.0145 | 1.49 |
| No. points used for $T_{1/2}$ | 3.33 | 0.577 | 17.3 |
| $C_{max}$ (ng/mL) | 2973 | 1201 | 40.4 |
| $T_{max}$ (h) | 0.417 | 0.144 | 34.6 |
| $T_{1/2}$ (h) | 0.97 | 0.271 | 27.8 |
| $T_{last}$ (h) | 8.00 | 0.00 | 0.0 |
| $AUC_{0\text{-}last}$ (ng · h/mL) | 3594 | 1641 | 45.7 |
| $AUC_{0\text{-}inf}$ (ng · h/mL) | 3600 | 1638 | 45.5 |
| $MRT_{0\text{-}last}$ (h) | 1.10 | 0.106 | 9.7 |
| $MRT_{0\text{-}inf}$ (h) | 1.12 | 0.123 | 11.0 |
| $AUC_{Extra}$ (%) | 0.20 | 0.19 | 93.6 |
| $AUMC_{Extra}$ (%) | 1.64 | 1.43 | 87.5 |

Following the single oral administration of S-Viloxazine at 40 mg/kg, the enantiomer R(+) VLX was not detectable at any time points and so all PK parameters were not determined. The peak plasma concentrations ($C_{max}$) of S(−)-VLX was 2973±1201 ng/mL, respectively. The $C_{max}$ was achieved at 0.417±0.144 hour ($T_{max}$) post-dose. The area under the plasma concentration-time curve from time 0 to the last quantifiable time ($AUC_{0\text{-}last}$) of S(−)-VLX were 3594±1641 ng h/mL. The S(−)-VLX had a terminal elimination half-life ($T_{1/2}$) of 0.97±0.271 hours and a mean residence time from time 0 to the last quantifiable time ($MRT_{0\text{-}last}$) of 1.10±0.106 hours.

The S-Viloxazine was detected in plasma with a typical PK, with no detectable conversion into R-Viloxazine which was below the lower limit of quantitation.

Example 12. Evaluation of Pharmacokinetics of COMPOUND A in Male Sprague-Dawley Rats A study was carried out to evaluate the pharmacokinetic (PK) properties of COMPOUND A (also known as COMPOUND A), a viloxazine (VLX) derivative, following single oral (PO) administration to male Sprague-Dawley rats.

Study Design. The animals were fasted overnight prior to dosing. Food was returned 2 hours post-dose. Animals had access to water freely the entire time throughout the study. For group 1, a single dose of COMPOUND A was administered to 3 male Sprague-Dawley rats by oral gavage at 60 mg/kg, which was equivalent to 36 mg/kg of the free base VLX. For group 2, a single dose of COMPOUND A was administered to 3 male Sprague-Dawley rats by oral gavage at 120 mg/kg, which was equivalent to 72 mg/kg of the free base VLX. Blood samples were collected from each animal at 0.25, 0.5, 1, 2, 4, 6, 8, and 24 hours post-dose for the determination of plasma concentrations of COMPOUND A, and R(+)- and S(−)-VLX. The plasma concentrations of the 3 analytes were quantified by liquid chromatography tandem mass spectrometry (LC-MS/MS). The bioanalytical assay provided a lower limit of quantification (LLOQ) of 1.5 ng/mL and an upper limit of quantification (ULOQ) of 1500 ng/mL for both R(+)- and S(−)-VLX. The LLOQ and ULOQ for the analysis of COMPOUND A were 3 ng/mL and 3000 ng/mL, respectively. The plasma concentration-time data were analyzed using Phoenix WinNonlin (version 8.3) to characterize the PK properties of the analytes. The non-compartmental analysis model and the linear/log trapezoidal method were applied to the calculation of the PK parameters.

Test Article Formulation. The dose solution was prepared freshly on the day of study prior to dosing. The formulation appeared as a clear solution with a final concentration of 60 mg/mL (Group1) and 120 mg/mL (Group2) in 0.9% Saline.

Results

Clinical Observation. COMPOUND A at the administered dosage was well tolerated by all animals. No adverse effects were observed throughout the study.

Figure 22A:
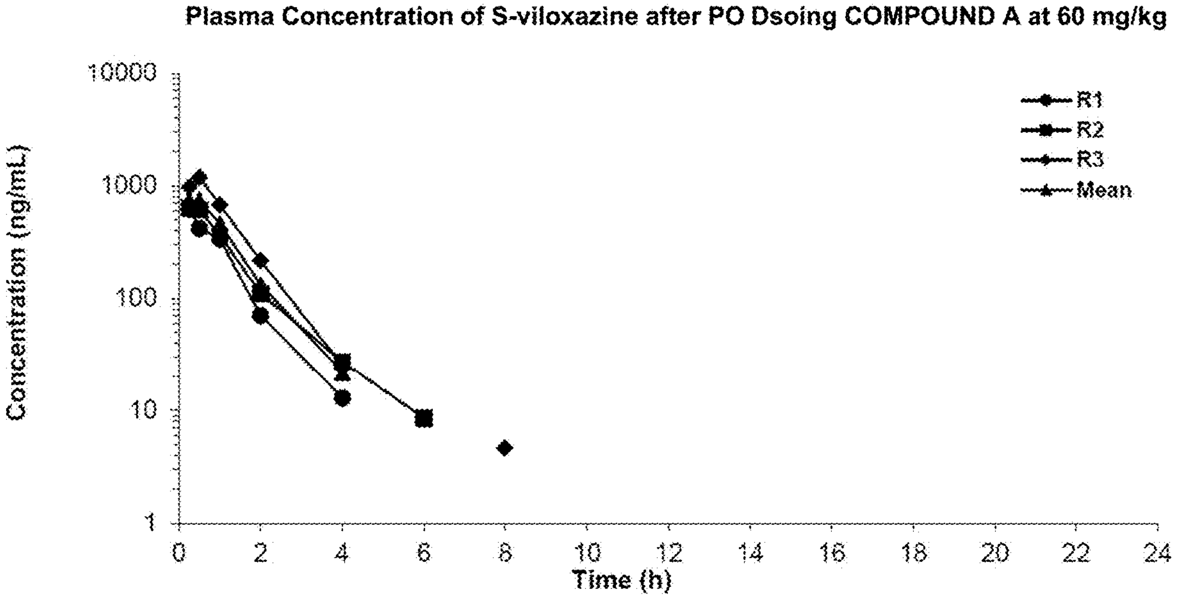
FIGS. 22*a*-22*b* show individual and mean plasma concentrations-time profiles of S(−)-viloxazine following a single oral administration of COMPOUND A at 60 mg/kg (FIG. 22*a*) or 120 mg/kg (FIG. 22*b*) to fasted male Sprague-Dawley Rats.
Figure 22B:
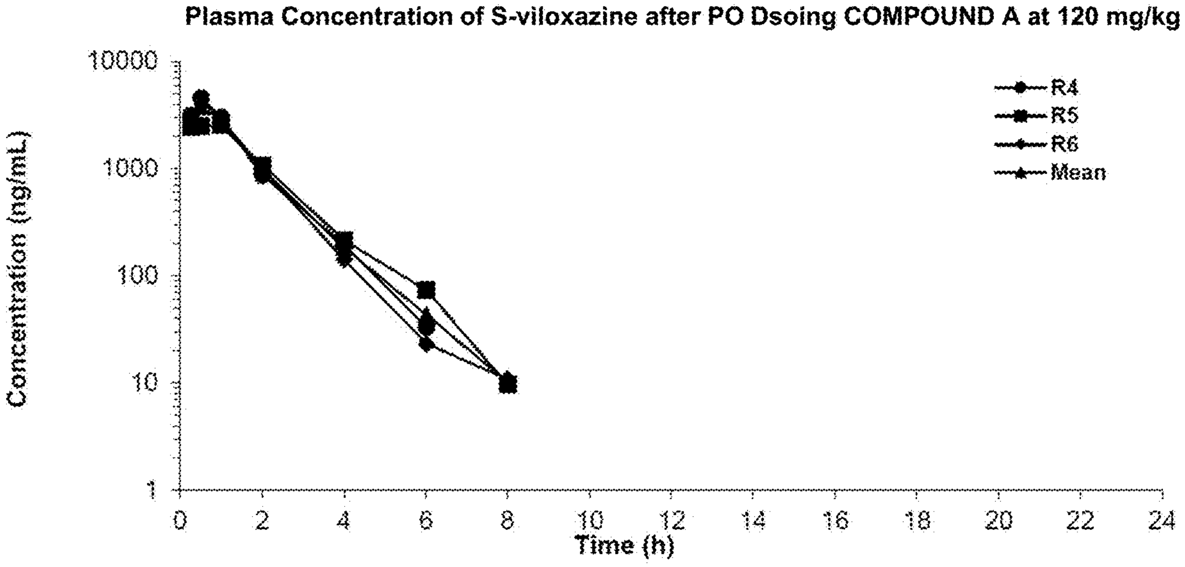
Figure 23:
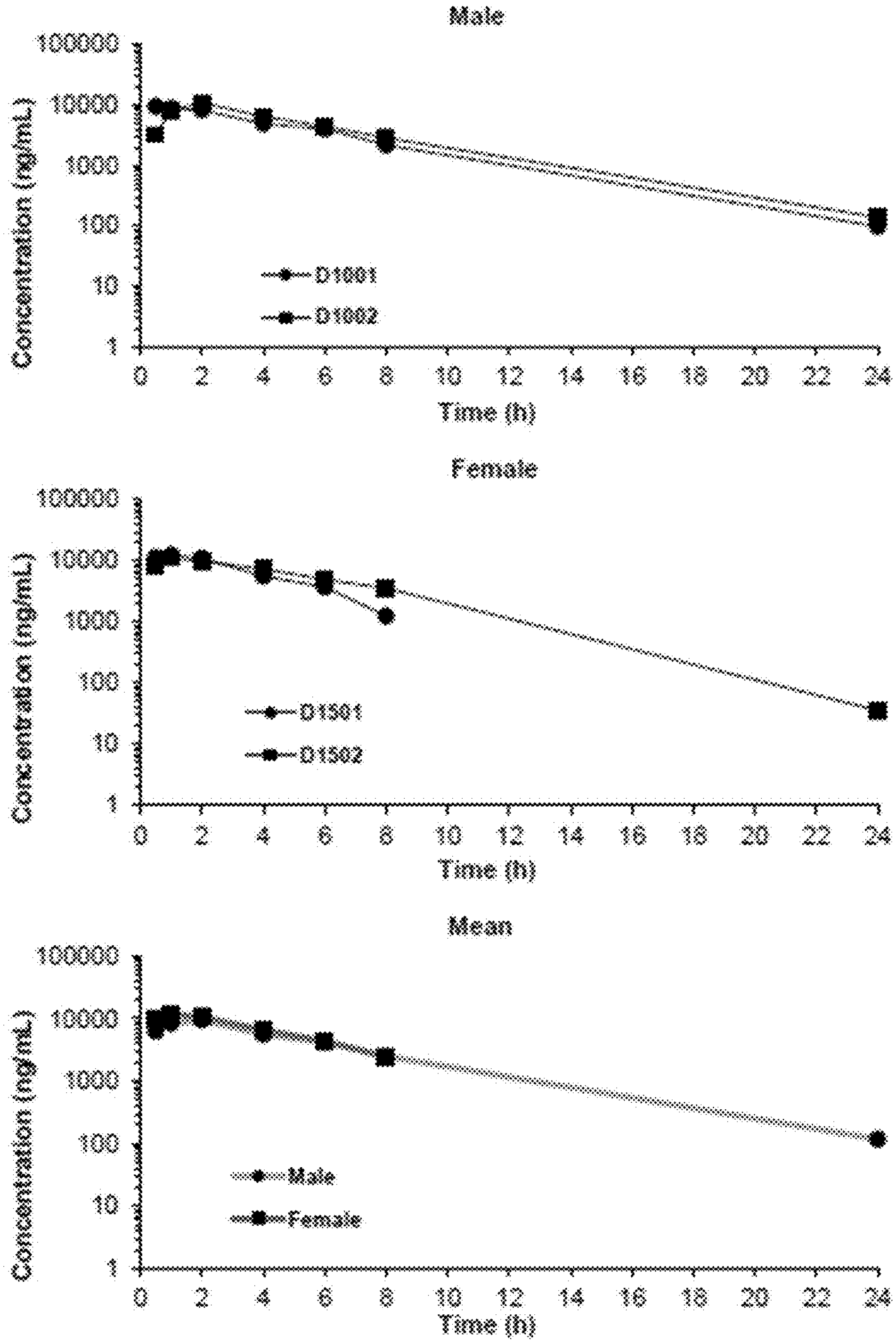
FIG. 23 shows plasma concentration-time profiles of S(−)-viloxazine following single PO administration of COMPOUND A to male (top) and female (middle) beagle dogs at 80 mg/kg, as well as the corresponding mean (bottom) plasma concentration-time profiles.
Figure 24:
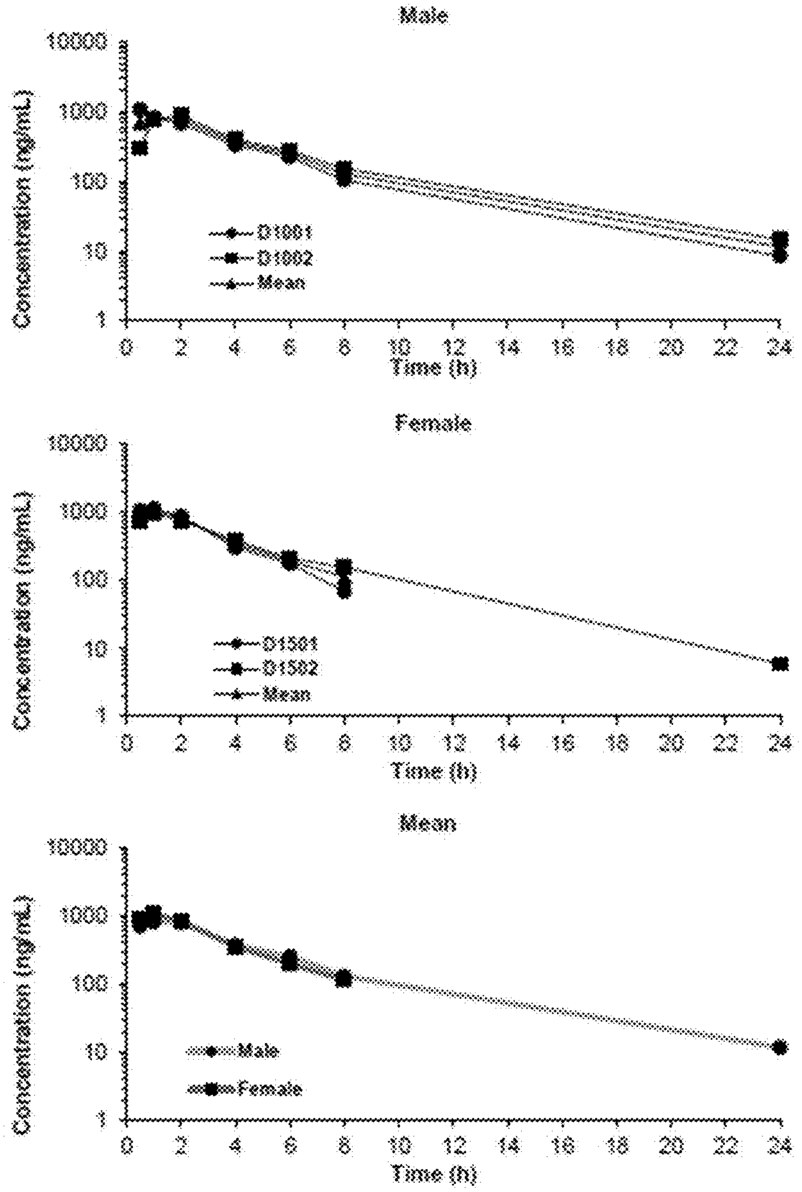
FIG. 24 shows plasma concentration-time profiles of R(+)-viloxazine following single PO administration of COMPOUND A to male (top) and female (middle) beagle dogs at 80 mg/kg, as well as the corresponding mean (bottom) plasma concentration-time profiles.
Figure 25:
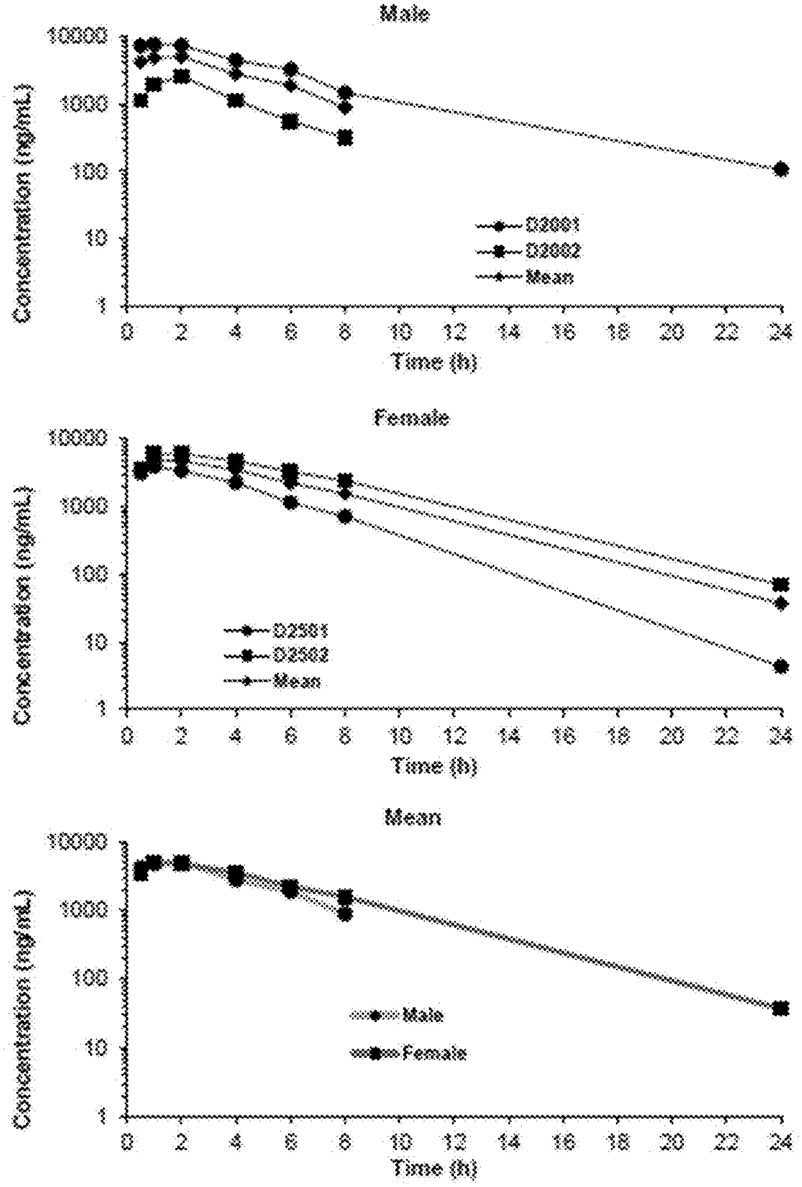
FIG. 25 shows plasma concentration-time profiles of S(−)-viloxazine following single PO administration of COMPOUND B to male (top) and female (middle) beagle dogs at 80 mg/kg, as well as the corresponding mean (bottom) plasma concentration-time profiles.
Figure 26:
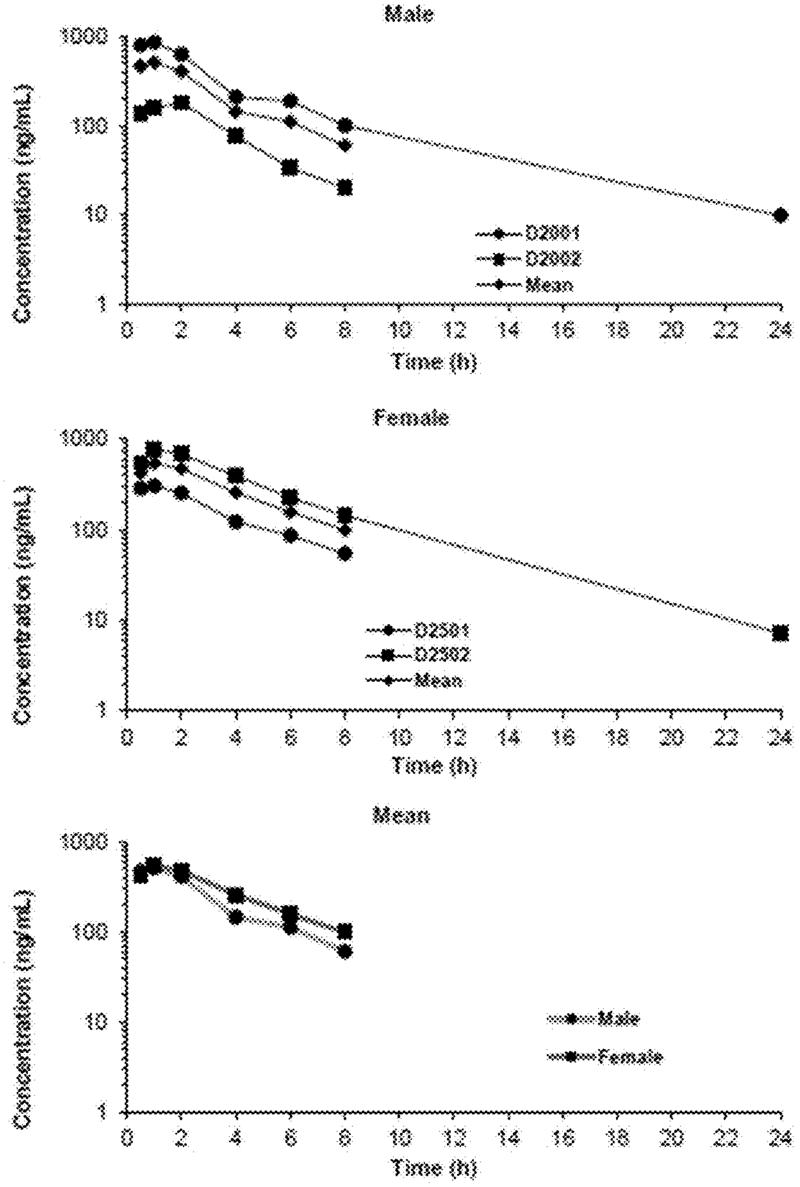
FIG. 26 shows plasma concentration-time profiles of R(+)-viloxazine following single PO administration of COMPOUND B to male (top) and female (middle) beagle dogs at 80 mg/kg, as well as the corresponding mean (bottom) plasma concentration-time profiles.
Figure 27:
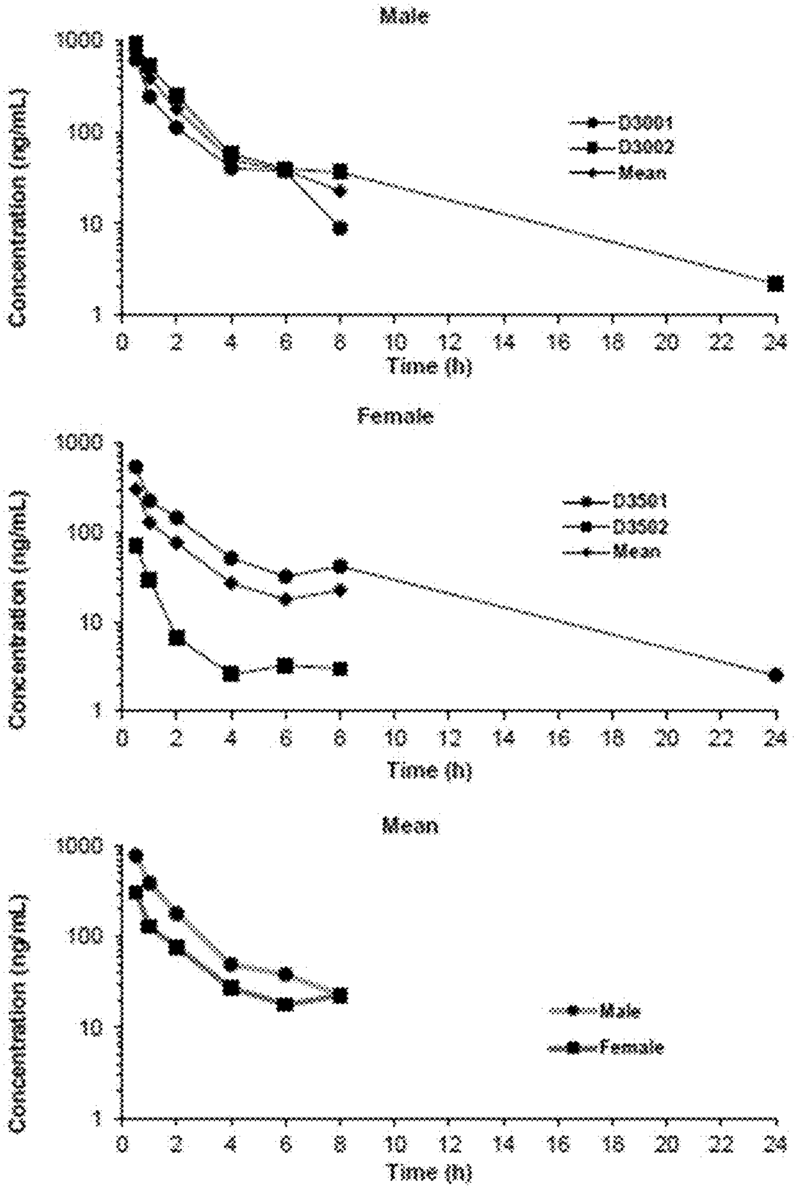
FIG. 27 shows plasma concentration-time profiles of COMPOUND C following single PO administration to male (top) and female (middle) beagle dogs at 80 mg/kg, as well as the corresponding mean (bottom) plasma concentration-time profiles.
Figure 28:
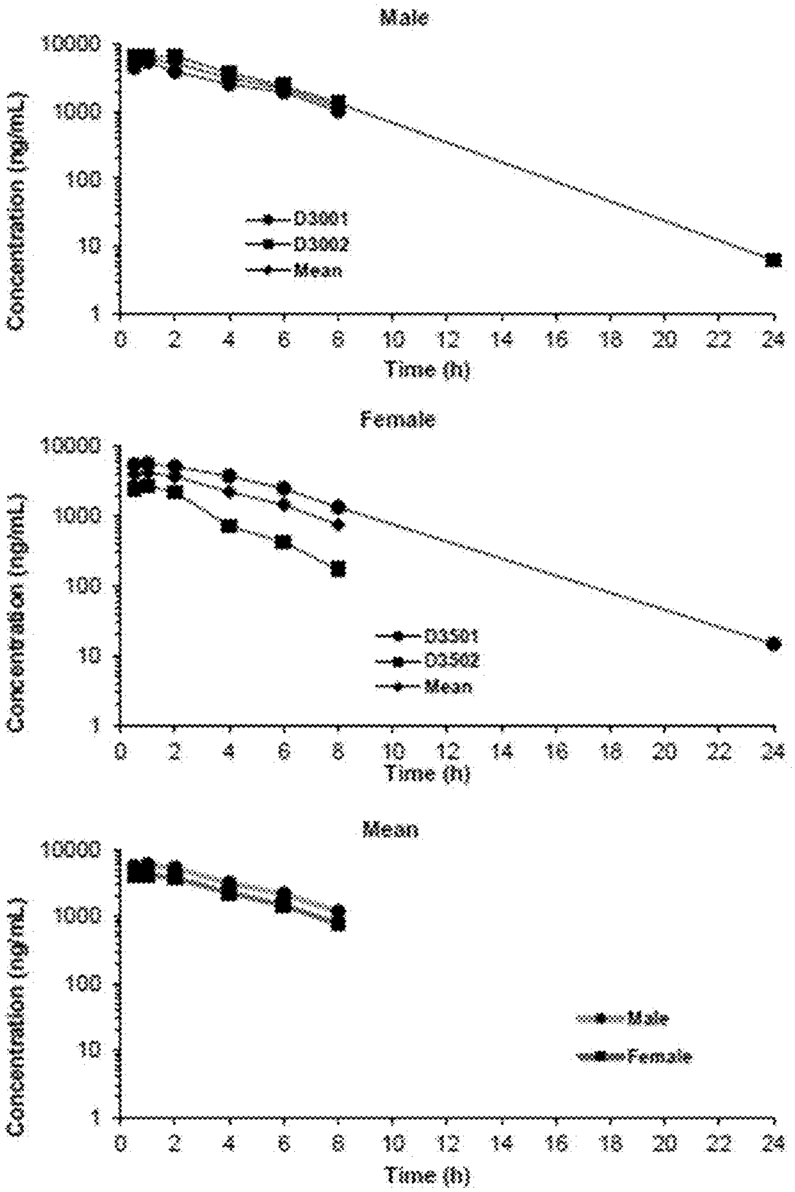
FIG. 28 shows plasma concentration-time profiles of S(−)-viloxazine following single PO administration of COMPOUND C to male (top) and female (middle) beagle dogs at 80 mg/kg, as well as the corresponding mean (bottom) plasma concentration-time profiles.
Figure 29:
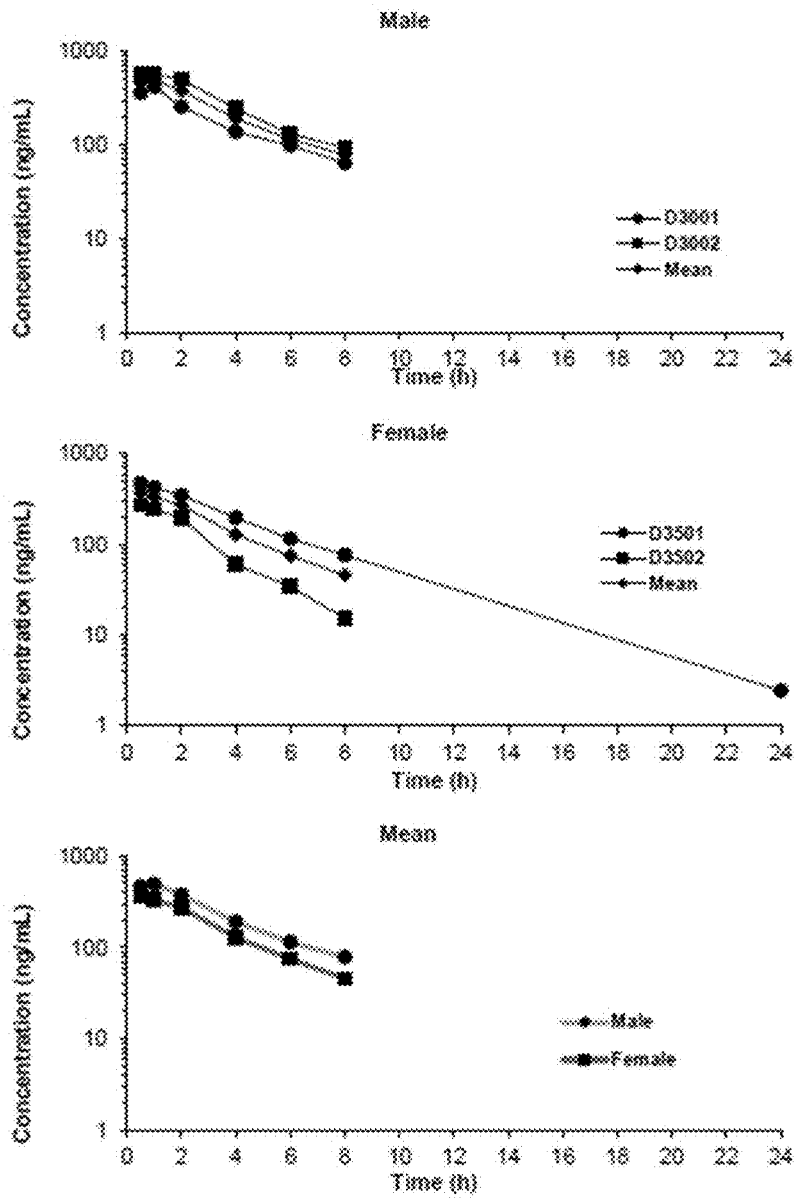
FIG. 29 shows plasma concentration-time profiles of R(+)-viloxazine following single PO administration of COMPOUND C to male (top) and female (middle) beagle dogs at 80 mg/kg, as well as the corresponding mean (bottom) plasma concentration-time profiles.

Following the single oral administration of COMPOUND A, the derivative itself was not detectable, therefore there was no data to report. The enantiomer R(+)-VLX was not detectable at most time points, with only a few concentration values that were not enough for PK calculations. The PK parameters of S(−)-VLX are summarized in Table 9. The plasma concentration-time profiles of R(+)- and S(−)-VLX are presented in FIGS. 22*a* and 22*b*, respectively TABLE 9a Mean Pharmacokinetic Parameters of S(−)-VLX Following a Single Oral Administration of COMPOUND A at 60 mg/kg to Fasted Male Sprague-Dawley Rats

| PK Parameters | Mean | SD | CV (%) |
|---|---|---|---|
| Rsq_adj | 0.983 | 0.0119 | 1.21 |
| No. points used for $T_{1/2}$ | 3.33 | 0.577 | 17.3 |
| $C_{max}$ (ng/mL) | 815 | 325 | 39.9 |
| $T_{max}$ (h) | 0.333 | 0.144 | 43.3 |
| $T_{1/2}$ (h) | 0.922 | 0.221 | 23.9 |
| $T_{last}$ (h) | 6 | 2 | 33.3 |
| $AUC_{0-last}$ (ng · h/mL) | 981 | 442 | 45.1 |
| $AUC_{0-inf}$ (ng · h/mL) | 992 | 439 | 44.2 |
| $MRT_{0-last}$ (h) | 1.14 | 0.133 | 11.7 |
| $MRT_{0-inf}$ (h) | 1.21 | 0.136 | 11.2 |
| $AUC_{Extra}$ (%) | 1.33 | 0.776 | 58.5 |
| $AUMC_{Extra}$ (%) | 7.17 | 3.19 | 44.5 |

TABLE 9b

Mean Pharmacokinetic Parameters of S(−)-VLX Following a Single Oral Administration of COMPOUND A at 120 mg/kg to Fasted Male Sprague-Dawley Rats

| PK Parameters | Mean | SD | CV (%) |
|---|---|---|---|
| Rsq_adj | 0.976 | 0.0222 | 2.27 |
| No. points used for $T_{1/2}$ | 3.67 | 0.577 | 15.7 |
| $C_{max}$ (ng/mL) | 3807 | 1104 | 29.0 |
| $T_{max}$ (h) | 0.667 | 0.289 | 43.3 |
| $T_{1/2}$ (h) | 0.890 | 0.0327 | 3.68 |
| $T_{last}$ (h) | 7.33 | 1.15 | 15.7 |
| $AUC_{0-last}$ (ng · h/mL) | 5753 | 402 | 7.00 |
| $AUC_{0-inf}$ (ng · h/mL) | 5776 | 413 | 7.15 |
| $MRT_{0-last}$ (h) | 1.36 | 0.179 | 13.1 |
| $MRT_{0-inf}$ (h) | 1.39 | 0.173 | 12.4 |
| $AUC_{Extra}$ (%) | 0.385 | 0.249 | 64.7 |
| $AUMC_{Extra}$ (%) | 2.30 | 1.26 | 54.8 |

The peak plasma concentrations ($C_{max}$) of S(−)-VLX in Group 1 and Group 2 were 815±325 and 3806.7±1103.5 ng/mL, respectively. The $C_{max}$ was achieved at 0.333±0.144 hour ($T_{max}$) post-dose for Group 1 and 0.667±0.289 hour ($T_{max}$) post-dose for Group 2. The area under the plasma concentration-time curve from time 0 to the last quantifiable time ($AUC_{0-last}$) of S(−)-VLX were 981±442 ng h/mL for Group 1 and 5753±402 ng h/mL for Group 2. The S(−)-VLX had a terminal elimination half-life ($T_{1/2}$) of 0.92±0.22 hours and a mean residence time from time 0 to the last quantifiable time ($MRT_{0-last}$) of 1.14±0.133 hours for Group 1, and half-life ($T_{1/2}$) of 0.89±0.0327 hours and $MRT_{0-last}$ of 1.36±0.18 hours for Group 2.

The data indicated that COMPOUND A was rapidly metabolized once absorbed since it was below LLOQ in all the samples collected. The breakdown of COMPOUND A yielded more S(−)-VLX than the R(+)-VLX as manifested by the significantly higher values of $C_{max}$ and $AUC_{0-last}$ of the S-enantiomer. The $T_{max}$ were the same and the $MRT_{0-last}$ were comparable between the two dose groups.

Example 13. Evaluation of Pharmacokinetics of Viloxazine Analogs and S(−)- and R(+)-Viloxazine Following Single Oral Administration of the Analogs to Male and Female Beagle Dogs A study was carried out to evaluate the pharmacokinetic (PK) properties of three viloxazine analogs, COMPOUND A, COMPOUND B, COMPOUND C, and S(−)- and R(+)-viloxazine following single oral (PO) administration of the analogs to male and female beagle dogs.

Study Design. The three viloxazine analogs, COMPOUND A, COMPOUND B, COMPOUND C, each was given to two male and two female beagle dogs at 80 mg/kg by oral gavage. The animals were fasted overnight prior to dosing. Food was returned 4 hours post-dose. Animals had access to water freely the entire time throughout the study. Blood samples were collected from each animal at 0.5, 1, 2, 4, 6, 8 and 24 hours post-dose, and then centrifuged to extract plasma for the determination of the concentrations of the analogs and the two viloxazine isomers, S(−)- and R(+)-viloxazine. The concentrations of the analytes in the plasma were quantified by liquid chromatography tandem mass spectrometry (LC-MS/MS). The bioanalytical assay provided a lower limit of quantification (LLOQ) of 1.5 ng/mL and an upper limit of quantification (ULOQ) of 1500 ng/mL for the two viloxazine isomers, and a LLOQ of 3.0 ng/mL and an ULOQ of 3000 ng/mL for the three analogs. The data of plasma concentration vs. time were analyzed using Phoenix WinNonlin 8.3 to determine the PK properties of the analytes. The non-compartmental analysis model and the linear log trapezoidal method were applied to the PK calculation.

Test Article Formulation. Dose solutions were prepared freshly on the day of study prior to dosing. The formulations of the three analogs were prepared the same way using HPLC water as vehicle. The target concentration of COMPOUND A, COMPOUND B, COMPOUND C was 16 mg/mL; when administered at the nominal dose volume of 5 mL/kg, it yielded a target dosage of 80 mg/kg of each prodrug.

Results

Clinical Observation. COMPOUND A, COMPOUND B and COMPOUND C at the administered dosages was well tolerated by all animals. No adverse effects were observed throughout the study.

With respect to COMPOUND A and COMPOUND B group, following oral administration at 80 mg/kg, their concentration in the plasma was mostly below the LLOQ in both the male and female beagle dogs. Therefore, the PK properties of COMPOUND A and COMPOUND B were not determined. The corresponding PK parameters are summarized in Tables 10a-10c. The plasma concentration-time profiles of PV-0448 and S(−)- and R(+)-viloxazine are shown in FIGS. 23-28

TABLE 10a

Mean PK parameters of S(−)-viloxazine and R(+)-viloxazine following single PO administration of COMPOUND A to male and female beagle dogs at 80 mg/kg

| | S(−)-viloxazine | | R(+)-viloxazine | |
|---|---|---|---|---|
| Time (h) | Male | Female | Male | Female |
| Rsq_adj | 0.998 | 0.970 | 0.982 | 0.989 |
| $C_{max}$ (ng/mL) | 10032 | 11922 | 983 | 1064 |
| $T_{max}$ (h) | 1.25 | 1.00 | 1.25 | 1.00 |
| $T_{1/2}$ (h) | 3.56 | 2.24 | 4.08 | 2.58 |
| $T_{last}$ (h) | 24.0 | 16.0 | 24.0 | 16.0 |
| $AUC_{0\text{-}last}$ (ng · h/mL) | 57582 | 59434 | 4185 | 3976 |
| $AUC_{0\text{-}inf}$ (ng · h/mL) | 58192 | 61297 | 4254 | 4076 |
| $MRT_{0\text{-}last}$ (h) | 5.34 | 3.89 | 4.85 | 3.50 |
| $MRT_{0\text{-}inf}$ (h) | 5.59 | 4.17 | 5.25 | 3.77 |

TABLE 10b

Mean PK parameters of S(−)-viloxazine and R(+)-viloxazine following single PO administration of COMPOUND B to male and female beagle dogs at 80 mg/kg

| | S(−)-viloxazine | | R(+)-viloxazine | |
|---|---|---|---|---|
| Time (h) | Male | Female | Male | Female |
| Rsq_adj | 0.986 | 0.999 | 0.978 | 0.993 |
| $C_{max}$ (ng/mL) | 5112 | 5039 | 524 | 542 |
| $T_{max}$ (h) | 1.50 | 1.50 | 1.50 | 1.00 |
| $T_{1/2}$ (h) | 2.98 | 2.70 | 3.26 | 3.54 |
| $T_{last}$ (h) | 16.0 | 24.0 | 16.0 | 16.0 |
| $AUC_{0\text{-}last}$ (ng · h/mL) | 27111 | 32021 | 2061 | 2581 |
| $AUC_{0\text{-}inf}$ (ng · h/mL) | 27898 | 32188 | 2123 | 2736 |
| $MRT_{0\text{-}last}$ (h) | 4.00 | 4.82 | 3.71 | 3.90 |
| $MRT_{0\text{-}inf}$ (h) | 4.55 | 4.91 | 4.27 | 4.94 |

TABLE 10c

Mean PK parameters of COMPOUND C, S(−)-viloxazine and R(+)-viloxazine following single PO administration to male and female beagle dogs at 80 mg/kg

| | COMPOUND C | | S(−)-viloxazine | | R(+)-viloxazine | |
|---|---|---|---|---|---|---|
| Time (h) | Male | Female | Male | Female | Male | Female |
| Rsq_adj | 0.991 | 0.924 | 0.979 | 0.987 | 0.977 | 0.984 |
| $C_{max}$ (ng/mL) | 775 | 308 | 6059 | 4247 | 495 | 371 |
| $T_{max}$ (h) | 0.500 | 0.500 | 0.750 | 1.00 | 0.750 | 0.500 |
| $T_{1/2}$ (h) | 2.94 | 4.73 | 2.65 | 2.06 | 3.03 | 2.46 |
| $T_{last}$ (h) | 16.0 | 16.0 | 16.0 | 16.0 | 8.00 | 16.0 |
| $AUC_{0\text{-}last}$ (ng · h/mL) | 1186 | 572 | 28629 | 21120 | 1824 | 1441 |
| $AUC_{0\text{-}inf}$ (ng · h/mL) | 1203 | 591 | 31005 | 21354 | 2154 | 1466 |
| $MRT_{0\text{-}last}$ (h) | 2.58 | 3.16 | 3.59 | 3.47 | 2.88 | 3.42 |
| $MRT_{0\text{-}inf}$ (h) | 2.80 | 4.78 | 4.43 | 3.67 | 4.44 | 3.67 |

The data showed that the $C_{max}$ and $AUC_{0\text{-}last}$ of the S(−)-viloxazine were consistently higher (about 10×) than those of the R(+)-viloxazine following PO administration of the three analogs, indicating a better yield of the S(−)-isomer than the R(+)-isomer for all three analogs. The PK properties of either isomer were comparable among the three analogs. The only difference between the three analogs was that the plasma concentrations of COMPOUND C were well above LLOQ, while the plasma concentrations of the other two analogs were mostly below the LLOQ. The study did not find significant differences in any measured PK parameters between the male and female dogs.

Example 14. Dose-Response Evaluation of S-Viloxazine Prodrug COMPOUND C in Mice Using Tail Suspension Test (TST)

The tail suspension test is an experimental method used in scientific research to measure a state of being helpless in rodents, especially in mice. It is based on the observation that if a mouse is subjected to short term inescapable stress then the mouse will stop struggling. Immobility is quantified by measuring the amount of time lacking whole body activity. Less immobilized time (sec) following a treatment indicates that the drug might have antidepressant effects.

A study was conducted to evaluate the behavioral effects of acute treatment of the S-viloxazine prodrug COMPOUND C on the tail suspension test. Adult C57Bl/6 mice were administered one of four doses (PO) of COMPOUND C and underwent TST 30 min later. The immobilized time in the last 4 min of the TST, which indicated depression-like behavior, was quantified using offline video manual scoring in a blinded manner.

Methods and Materials

Animals. Adult (7 to 8 weeks) male mice (C57Bl/6, Charles River Laboratories) were used in the study. Upon arrival, animals were group-housed (5/cage) with access to food and water ad libitum. Animals were maintained on a 12/12-hour light/dark cycle in a temperature—(22±2° C.) and humidity—(approx. 50%) controlled room. Animals were numbered consecutively by tail marks. Each cage was identified by a card indicating the study number, sex, animal numbers and date of birth.

Substances & Formulation. The test article was formulated according to below table

| Substance | MW | F.W | Dose (mg/kg) | Concentration (mg/mL) | Volume (mL/kg) | Route | Formulation |
|---|---|---|---|---|---|---|---|
| Vehicle | N/A | | N/A | N/A | 10 | PO | 0.8% DMSO, |
| COMPOUND | 452.54 | 489.95 | 10 | 1 | 10 | PO | 6% PEG 400, |
| C | | | 30 | 3 | 10 | PO | 93.2% |
| | | | 60 | 6 | 10 | PO | HPβCD (6% |
| | | | 90 | 9 | 10 | PO | in $H_2O$) |

Test article formulations were prepared fresh based on weight-to-volume in the vehicle on each dosing day. Vehicle formulation: 0.8% DMSO, 6% PEG 400, 93.2% HPβCD (6% in $H_2O$) which was diluted in water (1 vol stock solution+4 vol $H_2O$) from a five-time concentrated (5×) stock solution in 4% DMSO+30% PEG400±66% HβCD (30%). The appearance of the formulations was clear, with no precipitations. The solution of COMPOUND C was slightly pink. Compounds were protected from light and kept on ice until dosing. Animals (10-11/group) were gavaged (10 mL/kg, p.o.) 30 min prior to the TST. The doses of COMPOUND C included 10, 30, 60 and 90 mg/kg. A vehicle group was included for comparison.

Monitoring. A piezoelectric sensor operated by the SmartCage system was utilized and video recording was conducted for scoring. After animals acclimated to the testing room, an individual mouse's tail was placed onto the piezoelectric sensor-board and the mouse was hung upside down, which signaled the immediate start of the recording of struggle activity, and it lasted for 6 min. The mouse was then taken off and returned to the home cage. The immobilized time, indicating depression-like behavior, was quantified using manual scoring of the video recordings for the period from 120 seconds to 360 seconds during TST. The percent immobility time was calculated: (immobility time/240 seconds)*100.

Results

Figure 30:
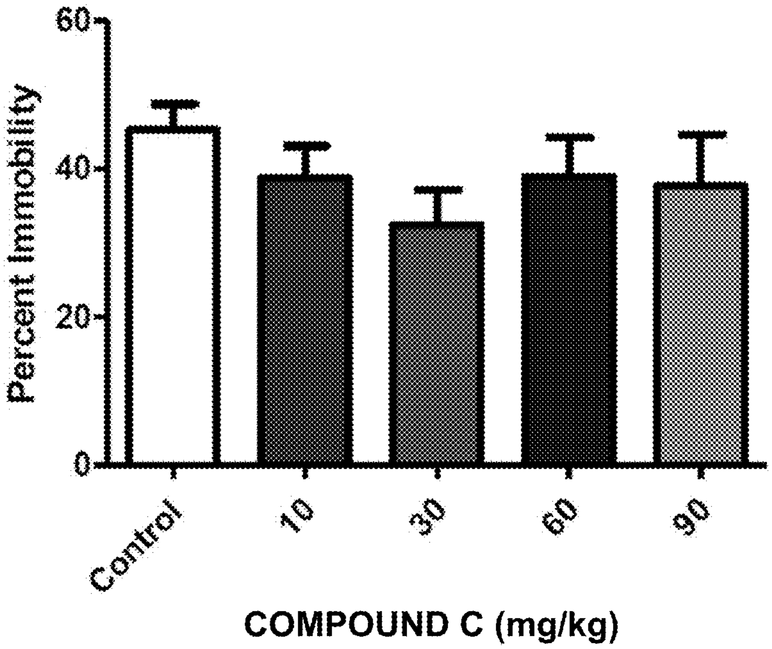
FIG. 30 shows COMPOUND C effects on the percent of immobility time during 240 min tail suspension. Bars are means±SEM. Groups included male C57Bl/6 mice (N=10-11/group) treated with COMPOUND C (po) 30 min prior to testing.

Across all doses, COMPOUND C resulted in no significant reduction in immobility by ANOVA (F4.47=0.8366, p=0.5089). The groups of mice treated with COMPOUND C (30 mg/kg, PO) showed a tendency in decreasing immobility compared to the vehicle-treated group (FIG. 30).

Example 15. Follow-Up Assessment of COMPOUND C in Mice Using Tail Suspension Test (TST)

A study was conducted to evaluate the behavioral effects of acute treatment of the S-viloxazine prodrug COMPOUND C on the tail suspension test. This was a follow-up study to Example 14, which was a dose-response selection study for COMPOUND C in the TST. Due to the low immobility levels of the negative control group and a lack of positive control group to support the reliability of the task in the previous study, this follow-up study was conducted to evaluate the promising dose of COMPOUND C (30 mg/kg) along with a positive and negative control group to clarify the data from the previous study. To do so, adult C57Bl/6 mice were administered one of three treatments, 30 mg/kg dose (PO) of COMPOUND C, vehicle (negative control), or imipramine (positive control) and underwent TST 30 min later. The immobilized time in the last 4 min of the TST, which indicates depression-like behavior, was quantified using offline video manual scoring in a blinded manner.

Methods and Materials

Animals. Adult (8 weeks, approximately 20-25 g) male mice (C57Bl/6, Vendor: Charles River Laboratories) were used in the study. Upon arrival, animals were group-housed (5/cage) with access to food and water ad libitum. Animals were maintained on a 12/12-hour light/dark cycle in a temperature—(22±2° C.) and humidity—(35-50%) controlled room. Animals were numbered consecutively by tail ID. Each cage was identified by a colored card indicating the study number, sex, animal numbers and date of birth.

Substances & Formulation. The test article was formulated according to below table

| Substance | MW | F.W | Dose (mg/kg) | Concentration (mg/mL) | Volume (mL/kg) | Route | Formulation |
|---|---|---|---|---|---|---|---|
| Vehicle | N/A | | N/A | N/A | 10 | PO | 0.8% DMSO, |
| Compd. C | 452.54 | 489.95 | 30 | 3 | 10 | PO | 6% PEG 400, |
| Imipramine | | | 15 | | | IP | 93.2% HPBCD |
| | | | | | | | (6% in $H_2O$) |

Test article formulations were prepared fresh based on weight-to-volume in the vehicle on dosing day. Vehicle formulation: 0.8% DMSO, 6% PEG 400, 93.2% HPβCD (6% in H2O) which was diluted in water (1 vol stock solution+4 vol H2O) from a five-time concentrated (5×) stock solution in 4% DMSO+30% PEG400±66% HβCD (30%). The appearance of the formulations was clear, with no precipitations. The solution of COMPOUND C was slightly pink. Compounds were protected from light and kept on ice until dosing. Animals (10/group) were gavaged (10 mL/kg, p.o.) 30 min prior to the TST. A 30 mg/kg dose of COMPOUND C was tested along with a vehicle negative control group and imipramine (15 mg/kg) positive control group included for comparison.

Monitoring. A piezoelectric sensor operated by the SmartCage system was utilized and video recording was conducted for scoring. After animals acclimated to the testing room, an individual mouse's tail was placed onto the piezoelectric sensor-board and the mouse was hung upside down, which signaled the immediate start of the recording of struggle activity, and it lasted for 6 min. The mouse was then taken off and returned to the home cage. The immobilized time, indicating depression-like behavior, was quantified using manual scoring of the video recordings for the period from 120 seconds to 360 seconds during TST. The percent immobility time was calculated: (immobility time/240 seconds)*100.

Results

Figure 31:
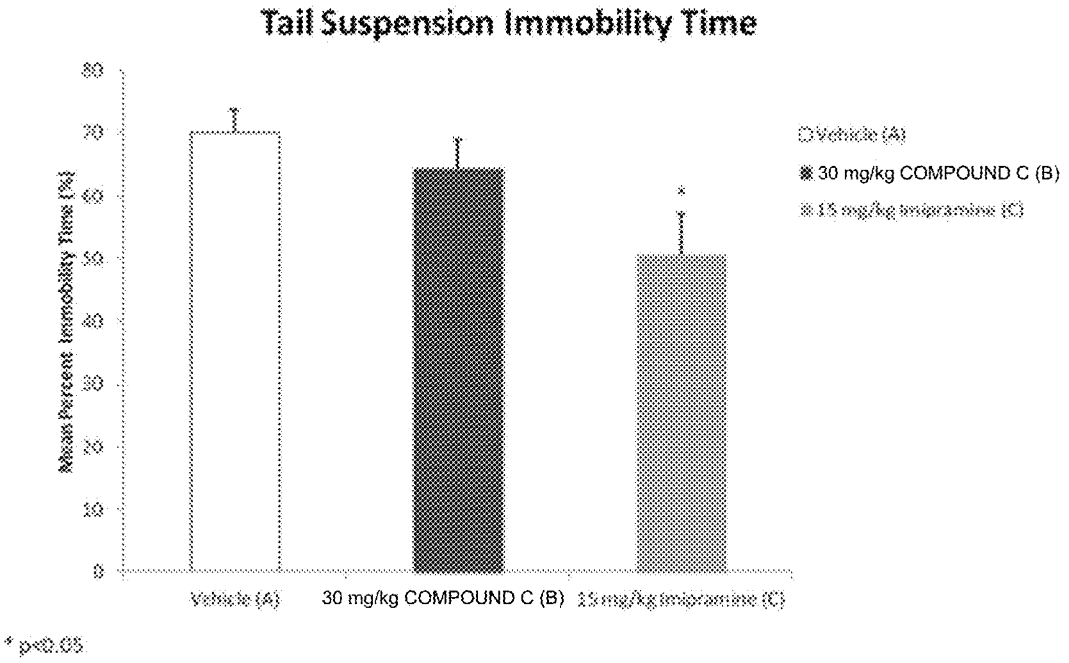
FIG. 31 shows COMPOUND C effects on the percent of immobility time during 240s of tail suspension. Bars are means±SEM. Groups included male C57Bl/6 mice (N=10-group) treated with COMPOUND C (PO), vehicle (PO), or imipramine (IP) 30 min prior to testing. * indicates p<0.05, compared to vehicle.

With all treatment groups included, one-way ANOVA demonstrated a significant effect of treatment on immobility time. A post-hoc test demonstrated that this effect was predominantly driven by the effect of the positive control, imipramine, which significantly reduced immobility time compared to vehicle ($p=0.01$; FIG. 31). A 30 mg/kg dose of COMPOUND C, however, resulted in no significant reduction in immobility compared to vehicle ($p=0.43$).

Example 16. Dose-Response Evaluation of S-Viloxazine Prodrug COMPOUND C in Mice Using SmartCage for Locomotor Activity A study was conducted to evaluate the behavioral effects of acute treatment with the S-viloxazine prodrug COMPOUND C on locomotor activity over 24 hr using the SmartCage™.

Methods and Materials

Animals. A cohort of 39 adult male mice (C57BL/6, 7-8 weeks old; body weights 20-25 g, Vendor: Charles River Laboratories) was used for this study. Upon arrival at the facility, animals were group-housed (5/cage) with access to food and water ad libitum. Animals were maintained on a 12/12-hour light/dark cycle in a temperature—(22±2° C.) and humidity-(approx. 35-50%) controlled room. Animals were numbered consecutively by tail ID marker in each home cage. Each home cage was identified by a colored ID card indicating the study number, sex, animal numbers, and dates of birth. The animals used in this study were previously used in a TST evaluation (Example 14).

Substances & Formulation. The test article was formulated according to below table

| Substance | MW | F.W | Dose (mg/kg) | Concentration (mg/mL) | Volume (mL/kg) | Route | Formulation |
|---|---|---|---|---|---|---|---|
| Vehicle | N/A | | N/A | N/A | 10 | PO | 0.8% DMSO, |
| COMPOUND | 452.54 | 489.95 | 10 | 1 | 10 | PO | 6% PEG 400, |
| C | | | 30 | 3 | 10 | PO | 93.2% HPβCD |
| | | | 60 | 6 | 10 | PO | (6% in $H_2O$) |
| | | | 90 | 9 | 10 | PO | |

Test article formulations were prepared fresh based on weight-to-volume ratio in the vehicle on each dosing day. Vehicle formulation included 0.8% DMSO, 6% PEG400, 93.2% HPβCD (6% in $H_2O$), which was diluted in water (1 vol stock solution+4 vol $H_2O$) from a five-times concentrated (5×) stock solution in 4% DMSO+30% PEG400+66% HPβCD (30%).

Stock solution preparation. The compounds were prepared at 5× (mg/ml) the final concentration in 4% DMSO+30% PEG400+66% HPβCD (30%) in a stepwise sequence. Then the PEG400 was added, followed by HPβCD (30%). The appearance of the formulations was clear, with no precipitations. Compounds were protected from light and kept on ice until dosing.

Animals (7-8/group) were gavaged (10 mL/kg, p.o.; around 12-1 pm) after a full 24 hr period of recordings for baseline activity. For locomotor activity recordings, COMPOUND C doses included 10, 30, 60 and 90 mg/kg.

Behavioral Methods

Figure 32:
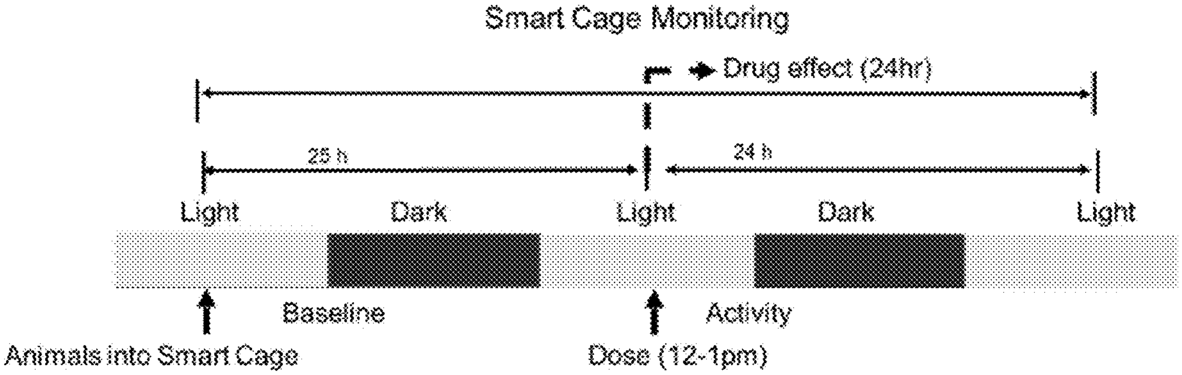
FIG. 32 shows the experimental schematic. Activity levels of mice were assessed for 24 hr prior to and 24 hr following oral treatment with COMPOUND C.
Figure 33A:
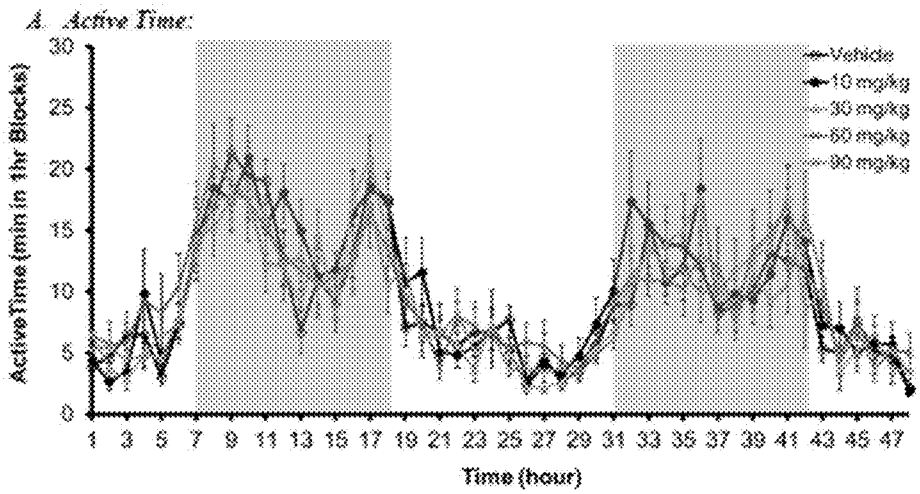
FIGS. 33*a*-33*d* show effects of COMPOUND C on active time (FIG. 33*a*), locomotion travel distance (FIG. 33*b*), velocity (FIG. 33*c*), and rearing activity (FIG. 33*d*) using SmartCage™ recordings. The gray bars indicate dark phase 6 pm-6 am.
Figure 33B:
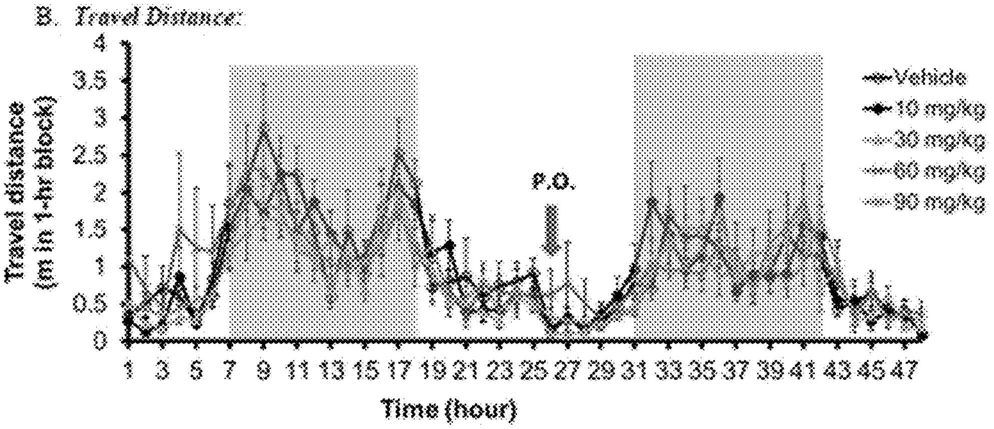
Figure 33C:
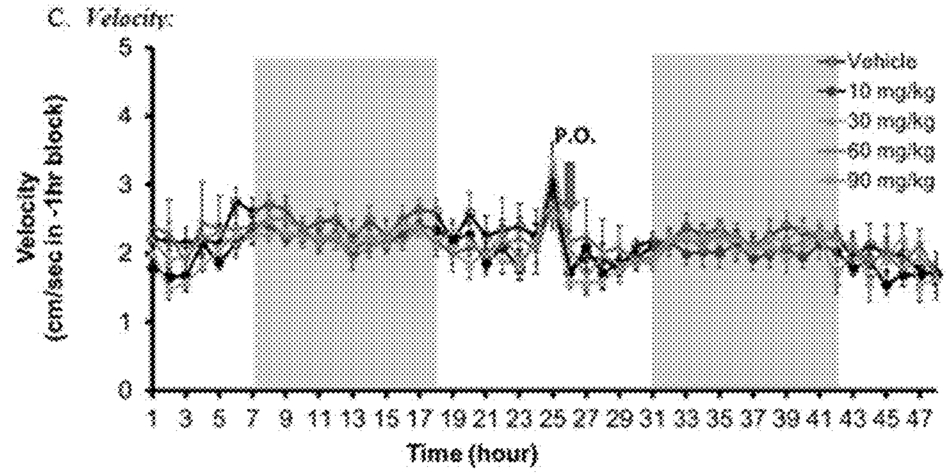
Figure 33D:
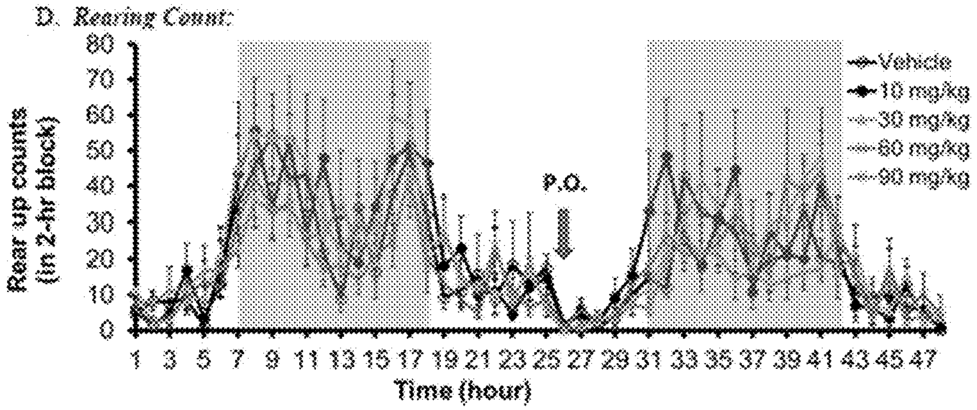
Figure 34A:
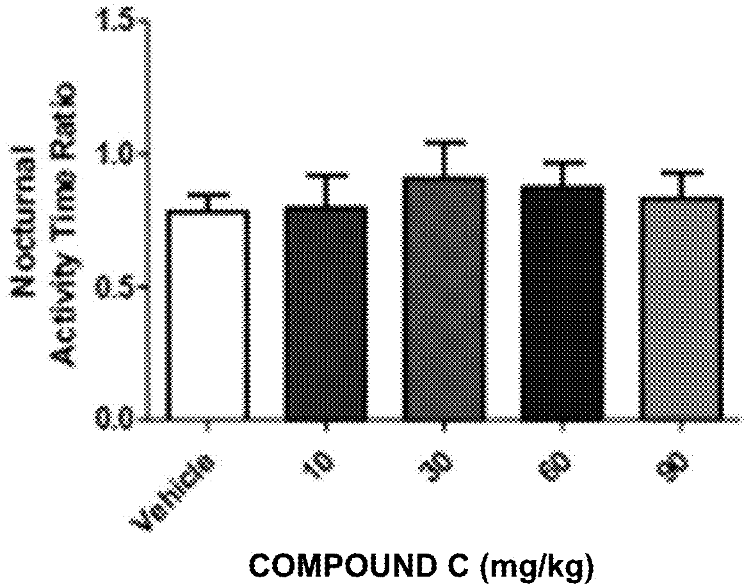
FIGS. 34*a*-34*d* show effects of COMPOUND C on nocturnal activity ratios (nocturnal activity time ratio, nocturnal rearing counts ratio, nocturnal distance traveled ratio, and nocturnal travel velocity ratio, respectively) for pre/post drug administration. Data are displayed as means±SEM.
Figure 34B:
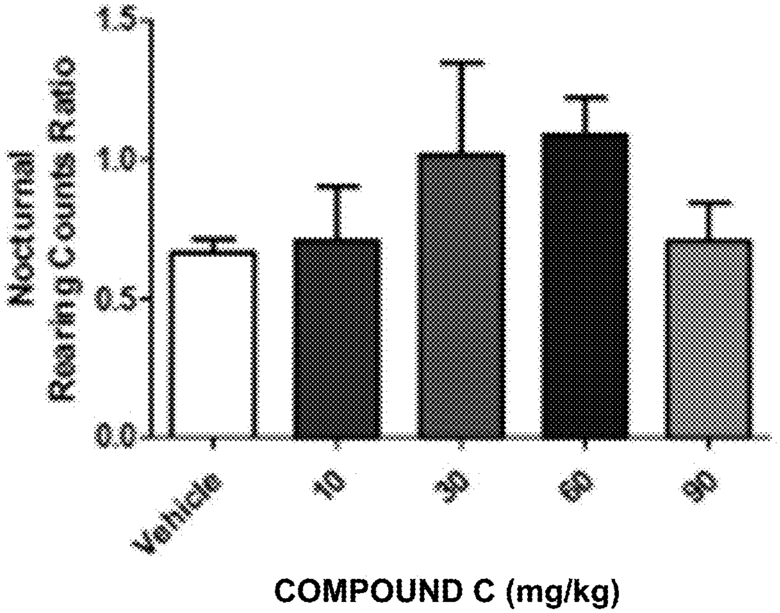
Figure 34C:
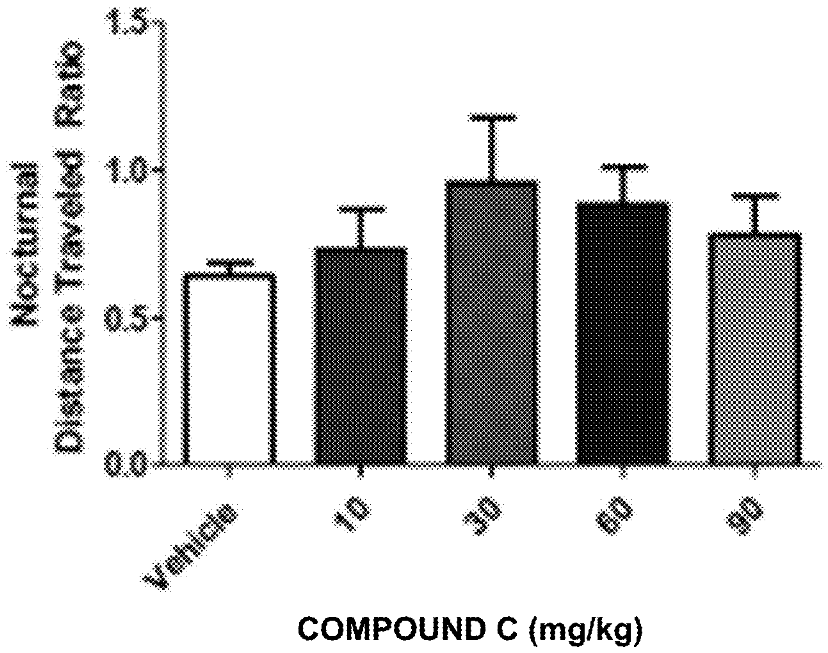
Figure 34D:
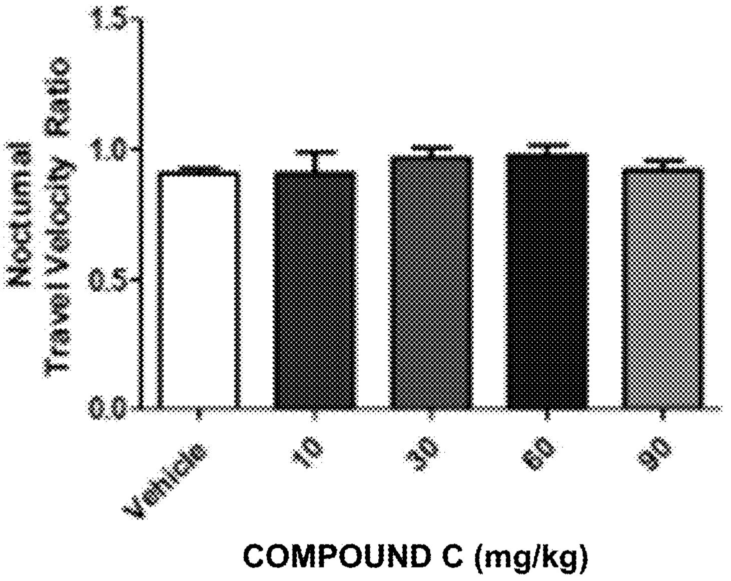
Figure 35A:
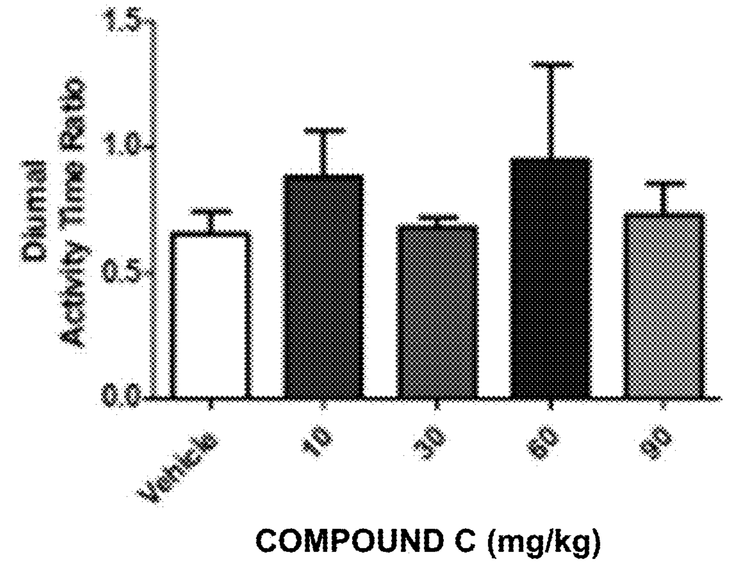
FIGS. 35*a*-35*d* show effects of COMPOUND C on diurnal activity ratios (diurnal activity time ratio, diurnal rearing counts ratio, diurnal distance traveled ratio, and diurnal travel velocity ratio, respectively) for pre/post drug administration. Data are displayed as means SEM.
Figure 35B:
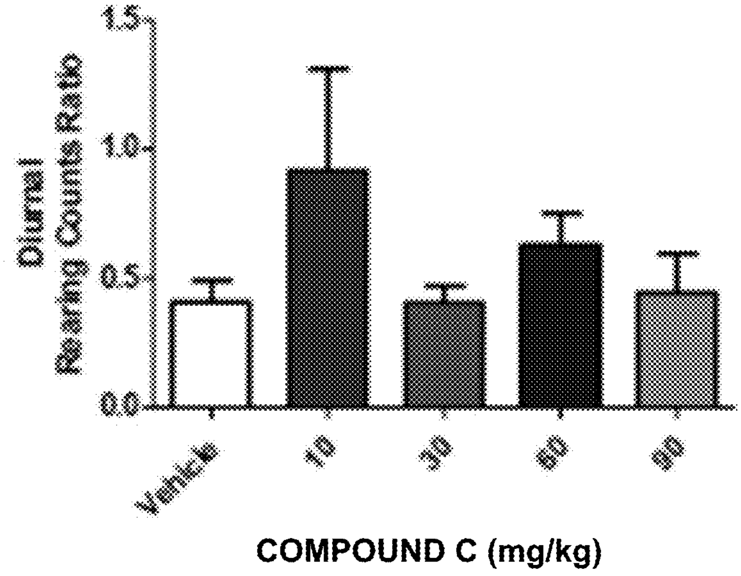
Figure 35C:
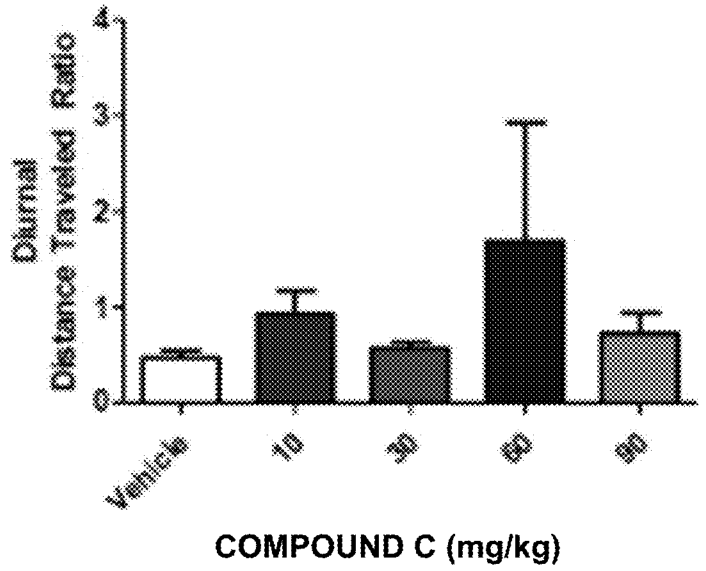
Figure 35D:
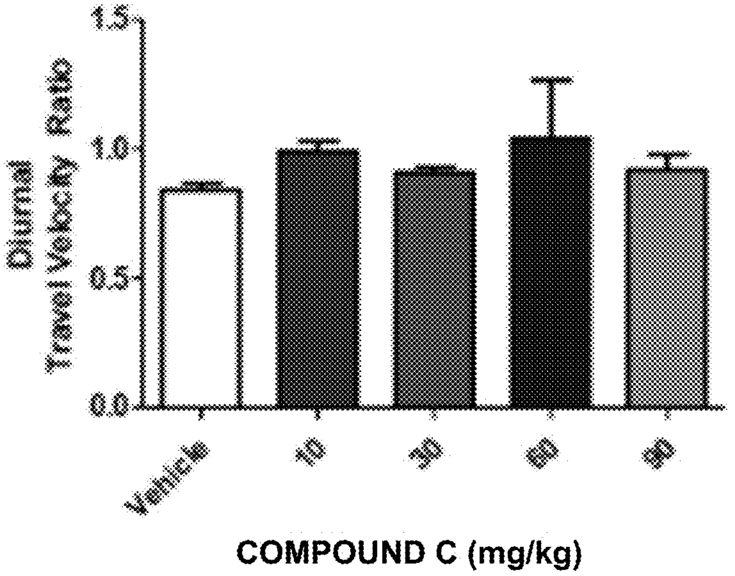

Locomotor Activity Monitoring. Mice underwent Smart Cage monitoring for 48 h (Experimental schematic, FIG. 32). Baseline activities were measured during the first 24 h. After the first day, animals were administered one of four doses (PO) of test article and monitored for the next 24 hours. The animal's activity during the monitored hours was quantified using the parameters of distance travelled, time active, and rearing activity.

SmartCage. After a washout period of at least 24 hours following a TST evaluation during which the animals were group-housed (5/cage), individual mice were placed into a freshly prepared home cage and their activity recorded simultaneously using the SmartCage™ system and a video camera placed above the SmartCage™ system. The activity over defined time blocks (1-hr blocks) was automatically calculated using CageScore™ (Program associated with the SmartCage™ system; AfaSci, Inc).

Active wakefulness was defined as actively moving, rearing, and exploratory behaviors. Home cage activity variables included activity counts (i.e., the photocell beam breaks), locomotion (distance traveled and speed) and rearing counts. Activity counts were obtained from the lower horizontal infrared (IR) sensors (along the X and Y axis). Likewise, distance traveled in centimeters was obtained from the lower horizontal IR and calculated taking into account the animal's path. Locomotion was defined as moving a distance longer than the body-length of the test animal. The calculated distance traveled (at any given time period, called 'block', or 'total measuring period') and speed were the two main parameters for locomotor activity. The Z-axis photocell beam break counts reflected the number of beam interruptions in the upper row of IR sensors and indicated rearing or climbing activity, which was considered to be part of the exploratory behavior parameters. All IR data (beam break activity counts, locomotion, rearing, and rotations) were continuously recorded at a 4 Hz sampling rate. Absolute and percent time in a chosen block (or 'time bin') spent in this arousal state were also collected. Mice were most active within the first 1 hour when transferred to a fresh or new cage, after which their activity levels gradually decreased. Once their activity was stable, treatment with the test article was started.

Endpoints/parameters. SmartCage behavioral evaluation for a 48-hour period, measured in 1-hr blocks:

Activity Time

Distance traveled (and travel velocity)

Rearing

Scoring method. The SmartCage system uses an automatic scoring algorithm to calculate traveling distance and speed by integrating X and Y coordinates and time elapsed. The upper row of IR sensors detects the Z photobeam break account to indicate rearing activity. Data analysis included calculating light (diurnal) and dark (nocturnal) time ratios. The nocturnal time ratio was calculated using the full 12 h of dark period (T31-42) following drug administration, which occurred at T26, and compared IR data with the identical time before drug treatment (i.e., T7-T18). The diurnal time ratio was calculated using a 5 h post-drug period (T26-30) and comparing it with the identical time prior to drug treatment (T2-6). At the end of the experiment, mice were euthanized using $CO_2$ followed by a secondary method. No tissue was collected.

Results

Locomotor Activity. There were no obvious increases in active time, nor enhancement in the locomotion parameters of travel distance, velocity, or rearing counts after dosing of COMPOUND C (FIGS. 33*a*-33*d*). By averaging and comparing the nocturnal (FIGS. 34*a*-34*d*) and diurnal (FIGS. 35*a*-35*d*) activity data, there was no difference between pre- and post-treatment with COMPOUND C in any of the activity parameters measured. Accordingly, home cage activity exhibited a typical circadian rhythm regardless of COMPOUND C administration (10, 30, 60 and 90 mg/kg, PO). COMPOUND C had no significant effect on daytime or nighttime activity measurements, including activity, rearing, distance, or velocity.

Example 17. Evaluation of COMPOUND C on Prepulse Inhibition in Rats

A study was conducted to evaluate COMPOUND C for effects on prepulse inhibition of the acoustic startle response in an experimental animal model. Prepulse inhibition, which is a preattentional component of information processing (i.e., sensorimotor gating), is characterized by the suppression of a startle reflex when it is preceded by a weak prepulse stimulus. This process is impaired in schizophrenia, as well as other psychiatric disorders (e.g., obsessive-compulsive disorder). The dopamine agonist, apomorphine, decreases prepulse inhibition and serves as a model for screening antipsychotic treatments in the prepulse inhibition task. COMPOUND C was evaluated for its ability to attenuate the impairing effects of apomorphine on prepulse inhibition, which would lend support to its potential in improving cognitive capacities in schizophrenia. During the evaluation process of each COMPOUND C dose, a single dose of the typical antipsychotic, haloperidol, was included as a positive control. The principal readout parameters for this study were % prepulse inhibition and the mean startle amplitude (in arbitrary units-AU).

Experimental Design

Study subjects. Sixty adult (approx. 3 months old) male Wistar rats (Envigo, Inc, Indianapolis, IN) were used in the study. Subjects were double housed in polycarbonate cages (45×30×18 cm) with corncob bedding in a vivarium of constant temperature (21-23° C.) and humidity (40-50%). Lighting was maintained on a 12-hr light-dark cycle (7:00 a.m.-7:00 p.m.) and the subjects had free access to water and food throughout the study. All behavioral testing was performed during the light portion (9 a.m.-5 p.m.) of the light/dark cycle (Monday thru Friday).

Prepulse Inhibition (PPI) of the Auditory Startle Response-Procedures. Four standard startle chambers (San Diego Instruments, San Diego, CA) were used. These startle chambers consist of a Plexiglas tube (diameter 8.2 cm, length 25 cm), placed in a sound-attenuated chamber, in which the rats are individually placed. The tube is mounted on a plastic frame, under which a piezoelectric accelerometer is mounted, which records and transduces the motion of the tube. Three days before drug testing the experimental subjects were each placed in one of the startle test chambers for a period of 10 minutes (without any startle stimuli) as an initial period of acclimation to the apparatus. Two days before drug testing the animals were again placed in the test chamber and then exposed to 12 startle stimuli and to each prepulse level 3 times (see below). This procedure was done to reduce the highly variable responses to the initial exposures to the startle stimuli as well as to ensure that the prepulse stimuli (alone) had no significant effect on the startle response. One day before drug testing, a full 60 trial PPI test session (as subsequently described for the drug testing experiments, see below) was conducted for all experimental subjects. The drug testing groups (N=8-10) were then created and balanced so that the mean startle amplitudes were similar.

On the day of drug testing the rats were transported to the startle chamber room and left undisturbed for at least 30 min. Afterwards, the rats were placed in the chamber and then present. After this period, the rats received 12 startle trials, 12 no-stimulus trials, and 12 trials of each of the prepulse/startle trials (see below) for a total of 60 trials. The intertrial interval ranged from 10 to 30 s, and the total session lasted about 25-30 min. The startle trials consisted of single 120 dB white noise bursts lasting 20 ms.

The prepulse inhibition trials consisted of a prepulse (20 ms burst of white noise with intensities of 75, 80, or 85 dB) followed, 100 ms later, by a startle stimulus (120 dB, 20 ms white noise). During the no-stimulus trial, no startle noise was presented, but the movement of the rat was recorded. This represented a control trial for detecting differences in overall activity. The 60 different trials were presented pseudo-randomly, ensuring that each trial was presented 12 times and that no two consecutive trials were identical. The resulting movement of the rat in the startle chamber was measured during 100 ms after startle stimulus onset (sampling frequency 1 kHz), rectified, amplified, and fed into a computer that determined the maximal response that occurred during the 100-ms period. Basal startle amplitude was determined as the mean amplitude of the 12 startle trials. Prepulse inhibition was calculated according to the formula 100−100%×(PPx/P120), in which PPx is the mean of the 12 prepulse inhibition trials (i.e., for each individual prepulse level), and p120 is the basal startle amplitude. The average level of PPI was also calculated (average of the responses to pp75, pp80, or pp85) and analyzed separately.

Drug Preparation and Administration. The doses of all compounds were calculated based on the free base of each compound. The dose of apomorphine (0.5 mg/kg, s.c.) and the positive control compound haloperidol (0.3 mg/kg) are based on previously published studies. Based on phenotypic screening in mice, COMPOUND C demonstrated a pro-cognitive signature at 120 and 150 mg/kg (p.o.) and an antipsychotic signature at 150 mg/kg. To include similar plasma concentrations of COMPOUND C in rats, 60, 90, and 120 mg/kg doses of COMPOUND C were utilized in this study and administered at 2.0 mL/kg (po).

Test article formulations were prepared fresh based on weight-to-volume in the vehicle. Compounds were weighed and then vehicle added. Notes were made on the physical characteristics of the formulation including appearance (solution vs. suspension), color, precipitations, etc. When prepared, all compounds in this study were completely dissolved (i.e., solution with no particles) and clear.

After preparation all compound solutions were protected from light and kept on ice until dosing. Dosing was completed within 8 hr of formulation. The vehicle for COMPOUND C had a final consistency of 0.8% DMSO, 6% PEG400, 93.2% HPβCD (6% in H2O), which was diluted in water (1 vol stock solution+4 vol H2O) from five times concentrated (5×) stock solution in 4% DMSO+30% PEG400+66% HPβCD (30%), prepared in a stepwise sequence. Low heat (37° C. water bath) was used to dissolve drug. Then PEG400 was added, followed by HPβCD (30%)

| Compound | Free MW | F.W | Dose (mg/kg) | Route | Formulation |
|---|---|---|---|---|---|
| COMPOUND C | 452.55 | 489.01 | 60<br>90<br>120 | PO | 0.8% DMSO,<br>6% PEG 400,<br>93.2% HPβCD (6% in $H_2O$) |

Results

Figure 36:
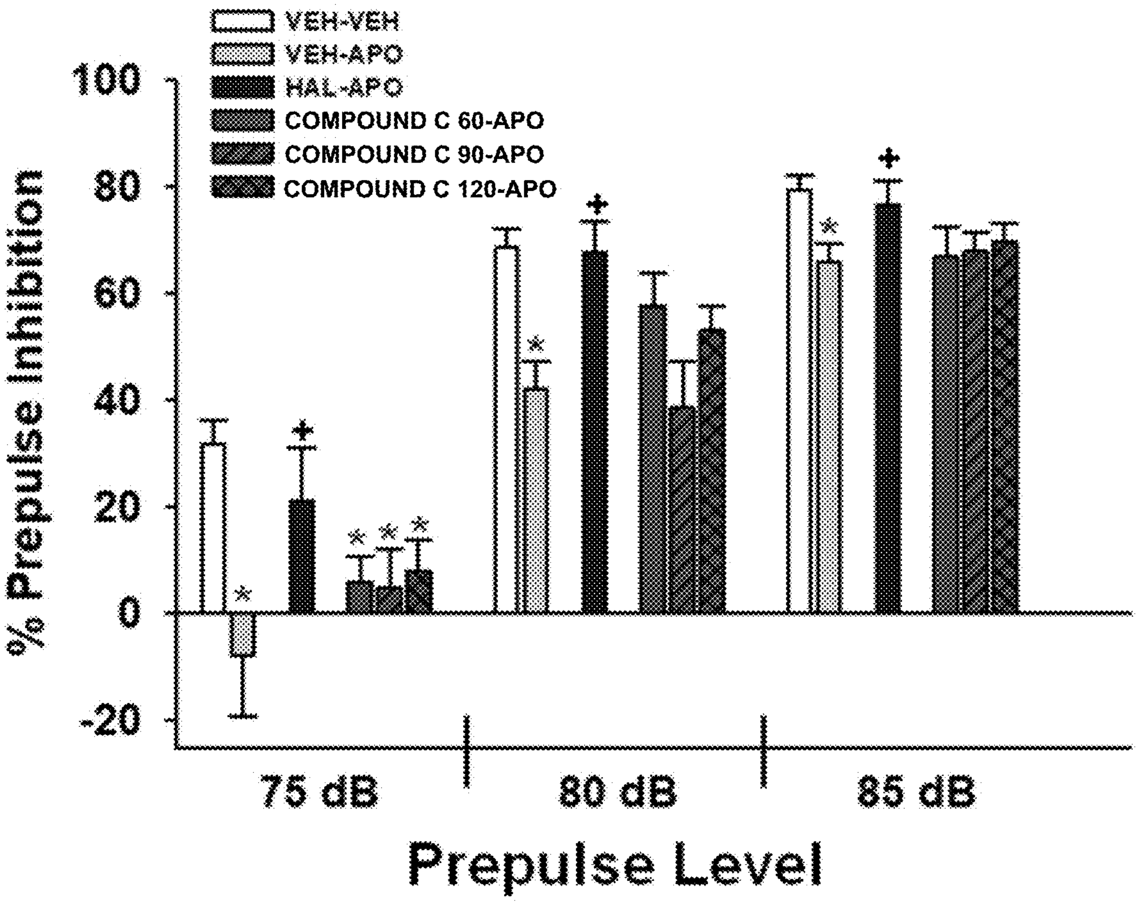
FIG. 36 shows effects of COMPOUND C on prepulse inhibition (PPI) of the auditory startle response in the apomorphine-impairment model in rats. The effects of apomorphine (0.5 mg/kg), a reference dose of haloperidol, or 3 doses of COMPOUND C on apomorphine-induced deficits in PPI associated with three prepulse intensities (75, 80, and 85 dB) are illustrated. Bars represent mean±S.E.M. for each treatment (N=10). VEH=vehicle; APO=apomorphine. HAL=haloperidol. *=significantly different (p<0.05) from the VEH-VEH associated response. +=significantly different (p<10.05) from the VEH-APO-associated response.
Figure 37:
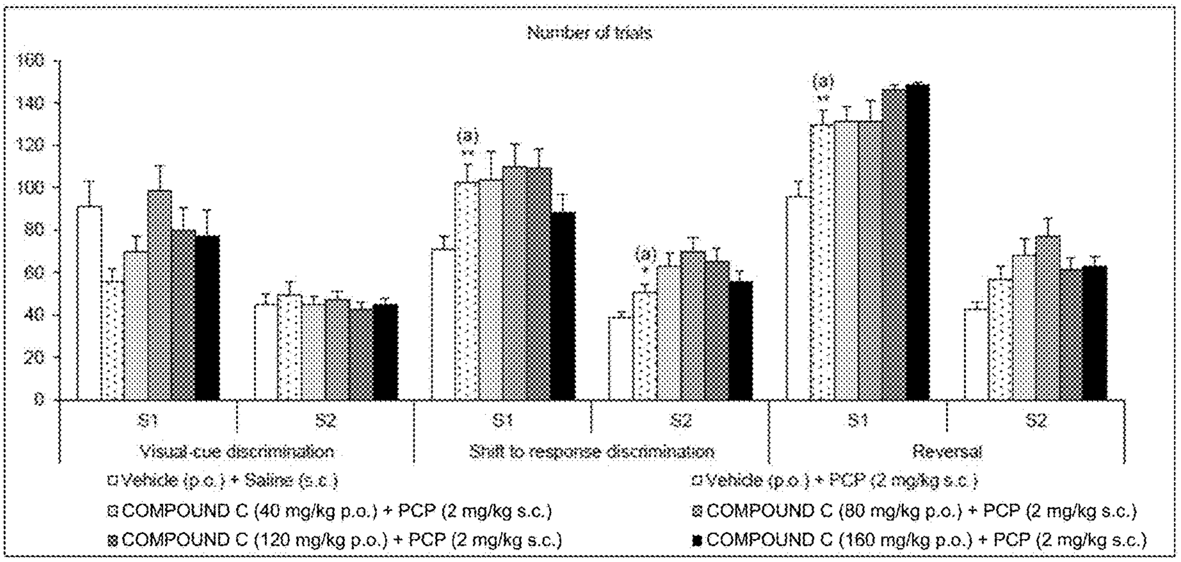
FIG. 37 shows number of trials to criterion, representative of learning, with respect to measures of cognitive flexibility, including visual-cue discrimination, shift to response discrimination, and reversal upon administration of vehicle+saline, vehicle+PCP, COMPOUND C (40 mg/kg)+PCP, COMPOUND C (80 mg/kg)+PCP, COMPOUND C (120 mg/kg)+PCP, and COMPOUND C (160 mg/kg)+PCP, respectively. PCP impaired learning and COMPOUND C was unable to reverse these effects. *p<0.05;  p<0.01 compared to vehicle+Saline
Figure 38:
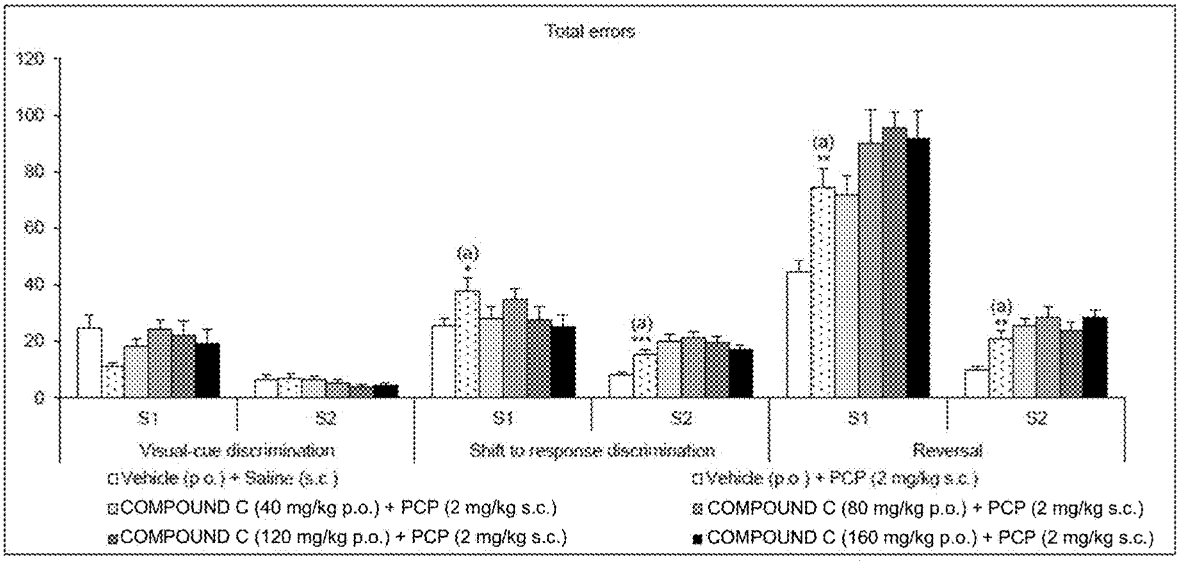
FIG. 38** shows total errors with respect to measures of cognitive flexibility, including visual-cue discrimination, shift to response discrimination, and reversal upon administration of vehicle+saline, vehicle+PCP, COMPOUND C (40 mg/kg)+PCP, COMPOUND C (80 mg/kg)+PCP, COMPOUND C (120 mg/kg)+PCP, and COMPOUND C (160 mg/kg)+PCP, respectively. PCP increased errors and COMPOUND C was unable to reverse these effects. *p<0.05;  p<0.01, *p<0.001 compared to vehicle+Saline
Figure 39:
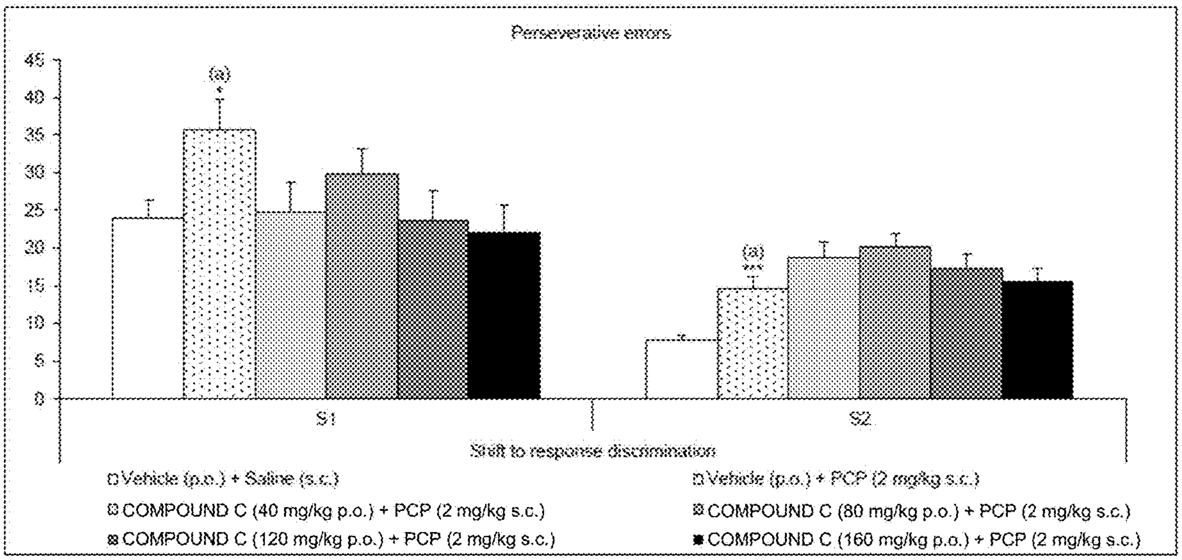
FIG. 39 shows perseverative errors, which are indicative of performance reverting to the previous task contingency, with respect to visual-cue discrimination, shift to response discrimination, and reversal upon administration of vehicle+saline, vehicle+PCP, COMPOUND C (40 mg/kg)+PCP, COMPOUND C (80 mg/kg)+PCP, COMPOUND C (120 mg/kg)+PCP, and COMPOUND C (160 mg/kg)+PCP, respectively. *p<0.05; *p<0.001 compared to vehicle+Saline
Figure 40:
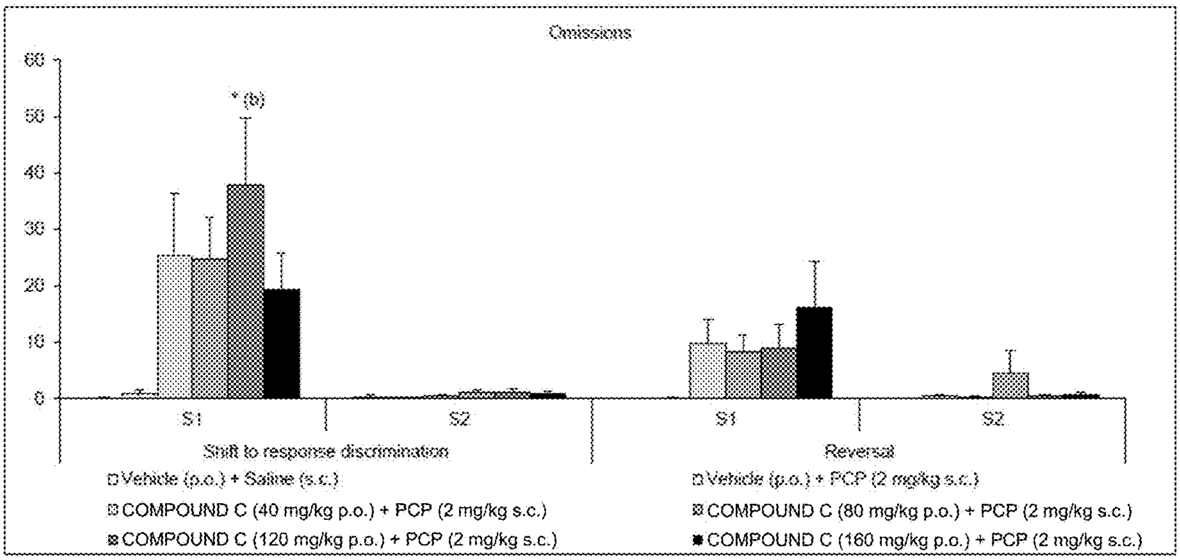
FIG. 40** shows omissions with respect to visual-cue discrimination, shift to response discrimination, and reversal upon administration of vehicle+saline, vehicle+PCP, COMPOUND C (40 mg/kg)+PCP, COMPOUND C (80 mg/kg)+PCP, COMPOUND C (120 mg/kg)+PCP, and COMPOUND C (160 mg/kg)+PCP, respectively. COMPOUND C increased omissions compared to PCP-treated rats. *p<0.05, compared to vehicle+PCP

The effects of COMPOUND C and the positive control, antipsychotic haloperidol, on PPI at the different prepulse levels are illustrated in FIG. 36, and the mean PPI responses (averaged across prepulse level) are provided in Table 11. There were statistically significant differences in responses to the various drug treatments [F(5,54)=4.2, p=0.003] and to the different prepulse levels [F(2,108)=343.1, p<0.001], and the treatment x prepulse intensity interaction was significant [F(10,108)=2.0, p=0.044]. Post hoc analyses indicated that apomorphine significantly (p<0.05) diminished PPI at all three prepulse levels compared to vehicle. Haloperidol (0.3 mg/kg) significantly antagonized the effects of apomorphine on PPI at all three prepulse levels (75, 80 and 85 dB; p<0.05). The effect of Haloperidol on the apomorphine-associated response was also significant (p<0.05) when the data were averaged across prepulse intensity (see Table 1). None of the doses of COMPOUND C were associated with a statistically significant attenuation of the effects apomorphine on PPI. There were also no statistically significant treatment-related effects on the mean startle amplitude in this study (Table 11)

TABLE 11

Effects of COMPOUND C and the Reference Antipsychotic Haloperidol on Mean PPI and Acoustic Startle in Rats

| Treatment | N | % PPI (mean ± SEM) | Acoustic Startle (AU) (mean ± SEM) |
|---|---|---|---|
| VEH-VEH | 10 | 59.9 ± 3.3 | 1558.9 ± 165.7 |
| VEH-APO | 10 | 33.4 ± 5.5 * | 1546.1 ± 260.5 |
| HAL-APO | 10 | 55.2 ± 6.3 + | 1774.3 ± 770.6 |
| COMPOUND C 60-APO | 10 | 43.6 ± 5.0 | 1719.1 ± 211.2 |
| COMPOUND C 90-APO | 10 | 37.2 ± 5.6 | 1579.9 ± 171.1 |
| COMPOUND C 120-APO | 10 | 43.7 ± 3.7 | 1856.8 ± 245.8 |

VEH = vehicle; APO = apomorphine; HAL = haloperidol.

* = sig different (p < 0.05) from the VEH-VEH associated response.

+ = sig different (p < 0.05) from the VEH-APO associated response.

In sum, under vehicle (control) conditions, the prepulse stimuli utilized (75, 80 and 85 dB) clearly inhibited the startle response to a 120 dB auditory stimulus in a fashion that was dependent on the decibel level (i.e., the greater the decibel level of the prepulse, the greater the inhibition of the startle response). Apomorphine clearly diminished the effects of the prepulse stimuli on the acoustic startle response. The single dose of the positive control antipsychotic haloperidol was effective in attenuating the impairing effects of apomorphine at all three of the prepulse levels. COMPOUND C did not significantly attenuate the effects of apomorphine at any of the prepulse levels. Thus, from the current study, which was based on the dopamine hypothesis of schizophrenia, COMPOUND C (at least at the 3 doses evaluated) did not appear to exhibit a significant pro-cognitive capacity to normalize preattentional processing functions following dopaminergic disruption (i.e., apomorphine-induced deficits).

Example 18. Evaluation of COMPOUND C Against PCP in the Operant Set-Shifting Test in the Rat PCP has been shown to induce deficits on cognitive flexibility (i.e., the ability to modify/adapt behavior according to the change of the rule) using the Operant Set-Shifting Test in the rat. This assay serves as a model of impaired executive function associated with neuropsychiatric disorders like schizophrenia. The aim of this study was to evaluate COMPOUND C to reverse deficits observed with PCP on cognitive flexibility using the operant set-shifting test in the rat.

Methods and Materials

Substances & Formulation. COMPOUND C, white powder, was first dissolved in 5×(mg/mL) of the final concentration in 4% dimethylsulfoxide (DMSO), then 30% polyethylene glycol (PEG) 400, then 66% of 30% 2-hydroxypropyl-β cyclodextrin (HPβCD) in a stepwise sequence and finally diluted in water (1 vol stock solution+4 vol H20).

Doses were prepared by separate weighing (W/V). COMPOUND C formulations were prepared fresh on each dosing day and dosing was completed within 8 hours of formulation. Phencyclidine (PCP) hydrochloride, white powder, was dissolved in physiological saline by magnetic stirring, fresh each day of dosing. Vehicle (20% of 4% DMSO, 30% PEG 400, 66% of 30% HPβCD in distilled water and 80% distilled water) was used as control substance.

Test System. 78 male Wistar rats were supplied for this study.

- 72 rats, 8-9 weeks old, weighing 218-299 g at the beginning of the visual discrimination were submitted to the entire behavioral testing and assigned to match groups based on their performance during the second visual discrimination session.
- 6 spare rats were submitted to lever pressing, side bias and visual discrimination but were discarded for the testing period (set-shift and reversal)

Animals were delivered to the laboratory at least 5 days before the beginning of the experiment (lever pressing) during which time they were acclimatized to laboratory conditions. They were housed in group of 2 in macrolon cages on wood litter (SAFE, 89290 Augy, France) with free access to water but restricted access to food (Code A04-SAFE, 89290 Augy, France). Environmental enrichment (gnawing and nesting material) was provided. The animal house was maintained under artificial lighting (12 hours)

between 7:00 and 19:00 in a controlled ambient temperature of 22±2° C., and relative humidity between 30-70%.

No mortality or any abnormal behavioral signs were observed during the experiment. The animals were sacrificed by exposure to $CO_2$. Animals were not submitted to necropsy.

Operant Set-Shifting Test in the Rat (Reference CNS 6.3R System)

The experimental protocol which detects effects on behavioral flexibility follows that described by Floresco et al. (Behav. Brain Res., 190, 85-96 (2008)).

Apparatus. The apparatus consists of standard Med Associates ENV-008 Skinner boxes (30×25×30 cm) fitted with a house light, two retractable levers and a food pellet dispenser. The levers are located on either side of the food receptacle connected to the pellet dispenser. A light emitting diode stimulus light is positioned centrally above each lever and served as a stimulus for visual-cue discrimination learning.

The Skinner boxes are housed within standard Med Associates sound-attenuating enclosures ENV-022MD and are connected to MED-PC programming system which controls the experiments and collets the data automatically.

Feeding Schedule. From arrival animals were submitted to restricted access to food (15 g per day) to habituate them to the food deprivation schedule used during the experiment. This food deprivation schedule continued throughout the experiment and was necessary to motivate the animals for the task. On testing days, animals received the 15 g food ration in their home cages after the last animal was tested.

During the day preceding the beginning of the lever-pressing, animals were also given several 45 mg food pellets in their home cage to habituate them to this novel food.

Acquisition of lever-pressing (training). The aim of this phase was to train animals to lever-press to receive a food pellet reward.

The animals were submitted to several acquisition sessions in the experimental chambers according to a fixed ratio (FR1) schedule of reinforcement. Reinforcement consists of a food pellet (45 mg) delivered after each lever-press.

Rats are first submitted to 2 to 6 daily lever-pressing acquisition sessions where a response on either the left or the right lever results in the delivery of a food pellet. The levers were inserted in the chamber at the beginning of the session and were withdrawn at the end of the session. The house light came on at the beginning of the session and was extinguished at the end of the session. Sessions terminated after 30 minutes or after the animals make 50 lever responses, whichever comes first.

Animals which will quickly learn the lever pressing were left to rest until the remaining animals learnt the lever pressing. Then, all animals were tested together in a final lever pressing session before moving to the next stage.

Afterwards, rats were subjected to sessions in which the left or the right lever was pseudo-randomly presented every 20 seconds. A session consisted of 90 lever-presentations (i.e. 1 trial=1 lever-presentation) and began with the levers retracted and the chamber in darkness. Every 20 seconds, a trial began with illumination of the house light and the insertion of one of the two levers into the chamber. If the rat failed to respond on the lever within 10 seconds, the lever was retracted, the chamber darkened and the trial was scored as an omission. If the rat responded within 10 seconds, the lever retracted, a single pellet was delivered and the house light remained illuminated for another 4 seconds. Importantly, the stimulus lights above each of the levers were never illuminated during these training sessions.

Rats received daily sessions until they achieved the criterion of less than 5 omissions over the 90 lever-presentations in a final single session before proceeding to the next stage (3 or 4 sessions in the present study).

Side bias. On the last day of training, the side bias for the rat was determined. The session was similar to the lever pressing session except that both levers were inserted into the chamber together (i.e. 90 levers presentations every 20 seconds). Again, the stimulus lights above each of the levers were not illuminated during this training session. On the first levers presentation, a food pellet was delivered after responding on either lever. Upon subsequent insertion of the levers, food was delivered only if the rat responded on the lever opposite to the one chosen initially. If the rat chose the same lever to the initial choice, no food was delivered. This continued until the rat chose the lever opposite to the one chosen initially. After choosing both levers, a new trial commenced. Thus, one trial for the side bias procedure consisted of responded on both levers. The sessions terminated after 90 levers presentations or after completion of 21 trials.

The lever (right or left) that a rat responded to during the initial choice of a trial was recorded and counted toward its side bias. The lever that a rat chose initially more times over the 21 trials was considered its side bias. However, if a rat made a disproportionate number of responses on one lever over the entire session (i.e., greater than a 2:1 ratio), that lever was considered its side bias.

Visual-cue discrimination learning. After determining the side bias, animals were submitted to visual-cue discrimination learning.

For this discrimination, the rat was required to respond to the lever (left or right randomly presented) that had a visual-cue stimulus light illuminated above it. A session began with both levers retracted and the chamber in darkness (the inter-trial state). Every 20 seconds, a trial began with illumination of one of the stimulus lights above one of the levers. 3 seconds later, the house light was illuminated, and both levers were inserted into the chamber. A response on the lever with the stimulus light illuminated above it (a correct response) resulted in levers retraction, stimulus light extinguishing and delivery of a food pellet. After food delivery, the house light remained on for another 4 seconds, after which the chamber returned to the inter-trial state. If the rat responded on the other lever (incorrect response), both levers retracted immediately without food delivery and the chamber reverted to the inter-trial state. Failure to respond on either lever within 10 s resulted in retraction of both levers, extinguishing of the house light, and the trial was recorded as an omission. In every pair of trails, the left or right stimulus light was illuminated once, and the order within the pairs of trials was random. For each trial, the lever that the animal chose and the location of the stimulus light was recorded. Trials continued until either a rat had received a minimum of 30 trials with achieving the criterion performance of 10 consecutive correct responses or after 150 trials, whichever came first. Omission trials were not included in the trials to criterion measure.

On the following day, a second visual-cue discrimination session was performed using the same criterion performance in order to verify that rats have learnt the visual-cue discrimination.

Shift to response discrimination. The acquisition of this discrimination required the animal to cease the use of a visual-cue discrimination strategy and instead use an egocentric spatial response strategy to obtain food reward. Here, a correct response entailed responding on the lever opposite of its side bias (left or right), previously defined, regardless of the location of the stimulus light illuminated above one of the levers. As with the initial visual-cue discrimination, in every pair of trials, the left or right stimulus light was illuminated once, and the order within the pair of trials was random. Trials were given in a manner identical to the visual-cue discrimination, and again, for each trial, the level that the animal chose and the location of the stimulus light was recorded. Trials continued until either the rat had received a minimum of 30 trials with achieving the criterion performance of 10 consecutive correct responses or after 150 trials, whichever came first. Omission trials were not included in the trials to criterion measure.

Again, on the following day a second shift to response discrimination session was performed (drug-free) in order to verify that rats have shifted to response discrimination.

Reversal learning. Finally, rats were moved to reversal as described for response discrimination except that here, a correct response entailed responding on the same lever of its side bias (left or right), regardless of the location of the stimulus light illuminated above one of the levers.

Again, on the following day this reversal session was performed (drug-free) in order to verify that rats have learnt the rule.

Behavioral Measures Recorded:

- The number of trials to achieve criterion of 10 consecutive correct responses, the number of omissions, and the number of errors for each session (visual-cue learning, set-shift to response discrimination and reversal learning)
- In addition, for the set-shift to response discrimination, the number of errors is reported as the total number of errors as well as the number of perseverative errors. The number of errors was thus broken down into 2 types:
  - Perseverative Errors: when a rat responds on a lever with the stimulus light illuminated (as in visual cue learning) above it on trials that required the rat to press the opposite lever.
  - Never-Reinforced Errors: when a rat presses the incorrect lever on trials where the visual-cue light is illuminated above the correct lever (i.e.; the choice was not reinforced during initial visual cue discrimination or the shift to response discrimination).

Drug testing procedure. 12 rats were studied per group. The test was performed blind and divided into 2 sub-experiments with the same number of animals per group in such sub-experiment. PCP (2 mg/kg s.c.), administered 30 minutes before the first shift to response discrimination and again before the first reversal session, was used as reagent substance. COMPOUND C was evaluated at 40, 80, 120, and 160 mg/kg, administered p.o. 10 minutes after PCP (i.e. 20 minutes prior to the testing sessions), and compared with a vehicle control group.

Results

Operant Set-shifting Test in the rat. Almost all rats achieved the criterion performance of 10 consecutive correct responses in fewer than 150 trials (78 trials as a mean score during the single visual-cue discrimination session). The acquisition of the visual cue discrimination was confirmed during their second session. They were assigned to treatment groups of n=12 animals based on their performance during the second visual cue discrimination session, so that there were no differences between groups on this measure before drug testing:

| Groups to be treated | Mean | | s.e.m. |
|---|---|---|---|
| Vehicle Controls | 45.1 | ± | 5.0 |
| PCP Controls | 49.8 | ± | 6.2 |
| COMPOUND C 40 mg/kg | 44.8 | ± | 4.3 |
| COMPOUND C 80 mg/kg | 47.2 | ± | 4.0 |
| COMPOUND C 120 mg/kg | 42.7 | ± | 3.6 |
| COMPOUND C 160 mg/kg | 44.9 | ± | 3.0 |

Saline-treated animals achieved the criterion performance of 10 consecutive correct responses within 70.8 trials mean score during the first set-shift to response discrimination session. Analysis of the errors indicated that they essentially made perseverative errors during the set-shift, confirming the impact of visual-cue discrimination learning (24.0±2.3 perseverative errors over 25.7±2.3 total errors). Subsequently, they achieved the criterion performance of 10 consecutive correct responses within 95.9 trials mean score during the first reversal session, suggesting adaptation to a new rule.

PCP (2 mg/kg), administered s.c. 30 minutes before the first set-shift to response discrimination session and the first reversal session, significantly increased the number of trials to reach the criterion as compared with saline controls (+45% and +35%, $t(22)=3.09$, $p<0.01$) during the first set-shift to response discrimination session and $t(22)=3.26$, $p<0.01$ for first reversal session). Consequently, it significantly increased the number of errors (+47% and +66%, $t(22)=2.42$, $p<0.05$ and $t(22)=3.65$, $p<0.01$), during the first set-shift to response discrimination and first reversal sessions, respectively), mainly perseverative errors during the first set-shift to response discrimination (average of 35.8 perseverative versus average of 37.8 total errors). However, acquisition of the rule was confirmed during the second session (drug-free treatment) as indicated by a clear decrease in the number of trials as compared to the first session. There was nevertheless a slight but significant increase as compared to saline controls (+31%, $t(22)=2.55$, $p<0.05$).

COMPOUND C (40, 80, 120 and 160 mg/kg), administered p.o. 20 minutes before the first set-shift to response discrimination session and the first reversal session (i.e. 10 minutes after PCP), did not significantly affect the number of trials to reach the criterion (One-way Anova: $F(4,55)=0.729$, NS and 2.009, NS, respectively) or the number of perseverative errors (One-way Anova: $F(4,55)=2.198$, NS and 1.197, NS, respectively) over the dose range tested as compared with PCP controls.

However, it increased the number of omissions at all doses tested particularly during the first set-shift to response discrimination session (One-way Anova: $F(4,55)=2.593$, $p<0.05$ and 1.438, NS, for the first set-shift session and the first reversal session, respectively). Post-hoc Dunnett's t tests indicate significant effects at the dose of 120 mg/kg ($p<0.05$).

These results indicate that PCP induced deficits on cognitive flexibility (i.e. ability to modify/adapt behavior according to the change of the rule) using the Operant Set-Shifting Test in the rat. These findings support the relevance of this assay as a model of impaired executive function associated with neuropsychiatric disorders like schizophrenia.

Example 19. SMARTCUBE® Phenotypic Screening

A study was conducted to evaluate the CNS-like efficacy of novel test compounds using the SmartCube® System.

Methods and Materials

Animals. Male C57/B16 mice from Taconic Laboratories (Germantown, NY) were used. Upon receipt, mice were group-housed in OPTIMice® ventilated cages with 4 mice per cage. Mice were acclimated to the colony room for at least one week prior to test, and subsequently tested at approximately 8-9 weeks of age. All animals were examined, handled, and weighed prior to initiation of the study to assure adequate health and suitability and to minimize nonspecific stress associated with manipulation. During the course of the study, 12/12 light/dark cycles were maintained. The room temperature was 20-23° C. with a relative humidity maintained between 30-70%. Chow and water were provided ad libitum for the duration of the study.

Test compounds. All compounds were administered orally at a dose volume of 10 mL/kg, 20 minutes prior to testing. Formulations were prepared fresh on day of testing and dosing was completed within one hour of formulation. Compounds were prepared according to the table below. Twelve mice were used in each treatment group:

| Compound | Dose (mg/kg) | Formulation |
|---|---|---|
| Viloxazine | 15, 30, 60, 90 | 4% DMSO, 30% |
| COMPOUND D | 40, 80 | PEG400, 66% |
| COMPOUND E | 40, 80 | HPβCD (30% in $H_2O$) |
| COMPOUND A | 30, 60, 90, 120 | |
| COMPOUND B | 90, 120 | |
| COMPOUND C | 60, 90, 120, 150 | |

The structure of COMPOUND D and COMPOUND E are shown below:

COMPOUND D

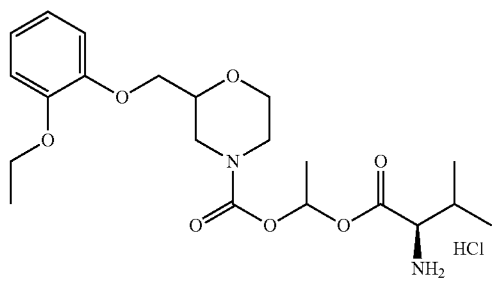

(HCl salt)

-continued

COMPOUND E

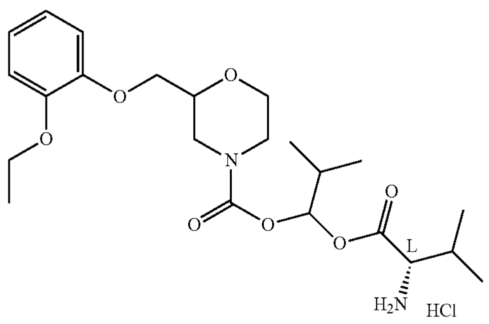

(HCl salt)

SmartCube®. The SmartCube® system is designed to and can successfully measure numerous spontaneous behaviors and response to challenges in the same testing environment. The hardware includes force sensors and a number of aversive stimuli to elicit behavior. Three high-resolution video cameras provide constant 3D view of the mouse in the SmartCube® apparatus (SC) throughout the entire testing period. During the 45-minute test session the mice are exposed to a sequence of challenges. The cubes are cleaned between each run.

To build the reference data set, drugs were injected 15 min before the test and multiple challenges were presented over the course of the test session. Digital videos of the subjects were processed through computer segmentation algorithms to fit geometrical models to each mouse frame image. The resulting fitted parameters were then analyzed using behavioral classifier algorithms to extract behavioral states, such as rearing, locomotion, and immobility. The data obtained in this way was used to define a drug signature for PGI's known reference compounds and establish a therapeutic class signature against which a test sample can be compared.

The data mining effort utilizes several analytical methods including Bayesian probabilistic density models and Decision trees. The algorithms consider ~2,600 measures including frequency and duration of behavioral states such as grooming, rearing, etc., and many other features obtained during the test session.

Two major types of analyses are routinely conducted: Class and subclass.

For class and subclass analysis, a reference data set has been built from hundreds of drug doses in multiple drug classes plus a control group. Each reference drug was tested at multiple doses appropriate for that drug in mice. The best performing classifiers were chosen from our evaluation tests and two separate types of classifiers were built that make independent predictions at drug class and subclass levels. The Class consists of drugs that are currently in the market or have been clinically validated for that specific indication. The sub-class consists of both marketed drugs and other compounds that have been mechanistically validated and is a larger set than the Class.

Data from the screening was processed using proprietary computer vision and data mining algorithms and the results were compared to signatures of the reference compounds in our database. Multiple analyses of the data were performed to quantitatively produce independent predictions of drug class, and drug subclass. The behavioral signatures of the test drugs were evaluated using these classifiers to predict potential therapeutic utility.

The results for the class and subclass analyses are presented as standardized bar charts with percentages that sum to 100 for each dose. The results of the classification at the drug level are presented as individual similarities.

Similarity Analysis Using "Clouds Framework". The outcome from SmartCube® is a large set of features (behavioral parameters) that can be used for various analyses. Many of these features are correlated. Therefore, we formed statistically independent combinations of the original features (further referred to as de-correlated features). Each de-correlated feature extracted information from the whole cluster of the original features, so the new feature space would have lower dimensionality. Next, we applied a proprietary feature ranking algorithm to score each feature for its discrimination power (ability to separate the two groups, e.g. vehicle from treatment). Ranking is an important part of our analyses because it weighs each feature change by its relevance. We applied a feature ranking algorithm, derived from support vector in the support vector machine learning method, to rank each feature. If there was a significant change in some irrelevant features measured for a particular phenotype, the low rank of these features would automatically reduce the effect of such change in our analyses, so we would not have to resort to the conventional "feature selection" approach and discard information buried in the less informative features.

Figure 41:
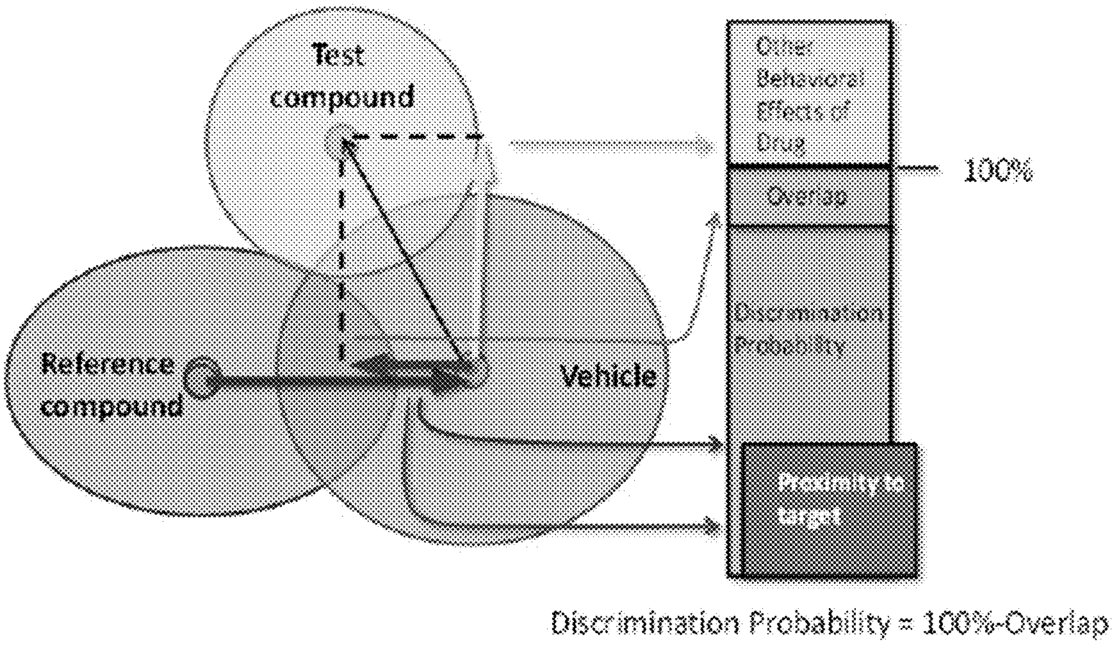
FIG. 41 shows visualization of binary discrimination in the ranked de-correlated feature space. The measure derived from the cloud overlap is discrimination probability=1−overlap, which measures how reliably a classifier can be trained to discriminate between two groups the chance level, zero corresponding to 100% overlap and no ability to distinguish the two groups above the chance level, whereas 100% meaning the error free discrimination.

We then examined the de-correlated ranked features as "clouds" (Gaussian distributions approximating the groups of mice (e.g reference compound and vehicle) in the ranked de-correlated features space) and calculated a quantitative measure of separability ("distinguishability") between the two groups (FIG. 41). The two highest ranked de-correlated features were chosen to form the 2D coordinate plane for visualization purposes. For visualization purposes, we plotted each cloud with its semi-axes equal to the one standard deviation along the corresponding dimensions. Proximity of test compound to the reference compound(s) was then calculated. A proximity over 80% would suggest a strong proximity.

Results

Figure 42A:
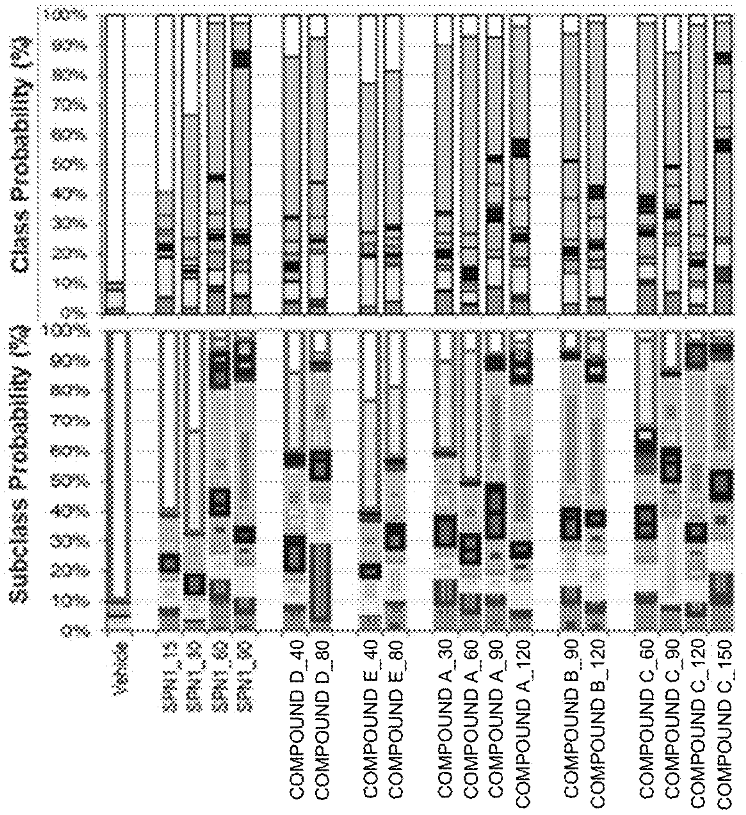
FIG. 42*a* shows Class and Subclass analysis of test compounds, the corresponding legend is provided in FIG. 42*b*.
Figure 42B:
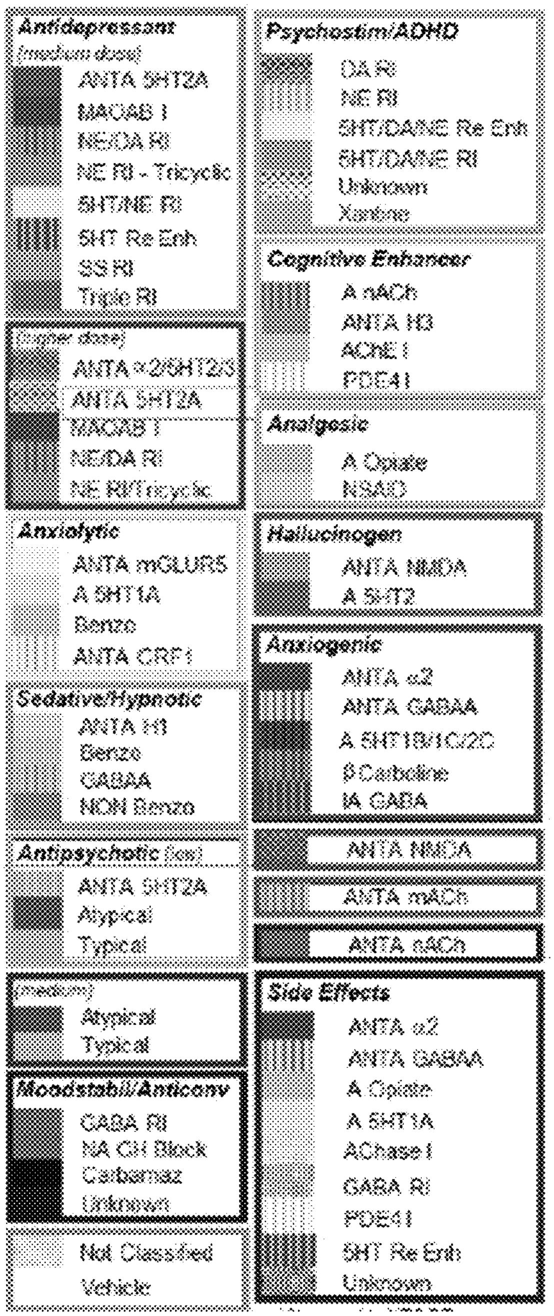

The class and subclass analyses for all compounds tested can be seen in FIGS. 42*a*-42*b*.

VILOXAZINE (15 mg/kg) showed low behavioral activity and a predominant vehicle-like signature as seen with the white bar. At 30 mg/kg, the compound showed moderate activity and high activity at 60 and 90 mg/kg. All doses showed a mixed signature with a predominant "unknown" signature in the class and mixed signature in the subclass. The unknown part of the signature indicated that the compound was active, but the classification system could not reliably assign certain features or patterns (which may be either novel or just insufficiently strong changes exhibited at lower doses) to any CNS class, although it detected the difference from vehicle COMPOUND E (40 and 80 mg/kg) showed moderate activity and a mixed signature in both class and subclass with a predominant "unknown" signature.

COMPOUND D (40 and 80 mg/kg) showed a dose dependent increase in activity and a mixed signature in both class and subclass. The predominant class signature was "unknown" and the subclass showed a mixed signature COMPOUND A (30-120 mg/kg) and COMPOUND B (90 and 120 mg/kg) showed high behavioral activity and a mixed signature with a predominant "unknown" signature in the class. Subclass analysis also showed a mixed signature which was predominantly cognitive enhancer-like for COMPOUND A, COMPOUND B.

COMPOUND C(60-150 mg/kg) showed high behavioral activity and a mixed signature in class and subclass. The 60, 90 and 120 mg/kg showed a predominant "unknown" signature in the class while the highest dose tested showed a predominant antipsychotic-like signature.

Interestingly for all active compounds, the Subclass signatures showed a mixture. The predominant signatures seen were cognitive enhancer and analgesic.

Subsequent data analyses consisted of running similarity analyses (DRFA) using the clouds framework to evaluate active doses against various reference compounds are summarized in FIGS. 43-54. The discrimination values were in relation to the vehicle cloud and the reference compound cloud, with the proximity value indicated the relative distance between the test compound and reference compound clouds. Unique features were those features present in the test cloud that were not similar to either the reference cloud or the vehicle cloud that could be non specific effects.

Figure 43:
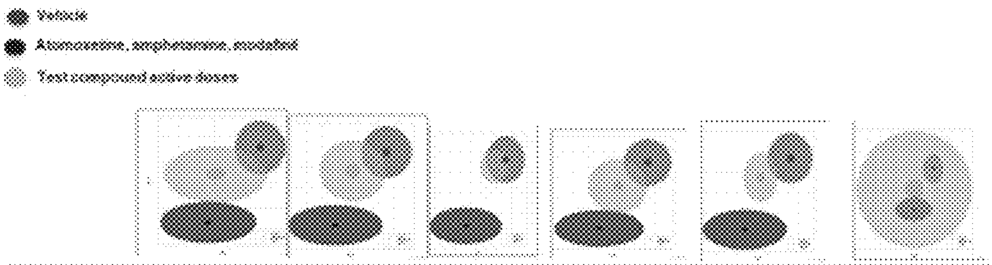
FIG. 43 shows DRFA Analysis of active doses of test compounds, in comparison to vehicle cloud and Atomoxetine, Amphetamine, and Modafinil cloud.
Figure 44:
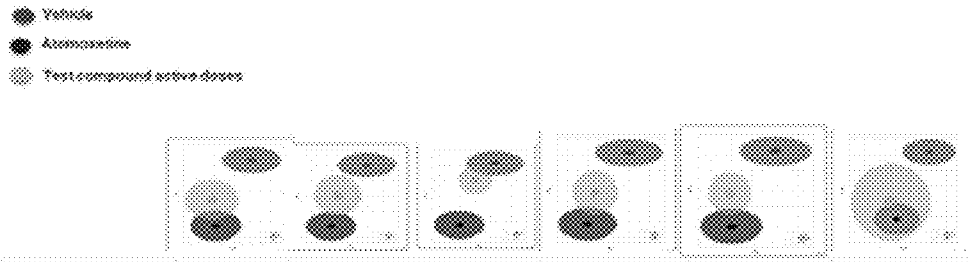
FIG. 44 shows DRFA Analysis of active doses of test compounds, in comparison to vehicle cloud and Atomoxetine cloud.
Figure 45:
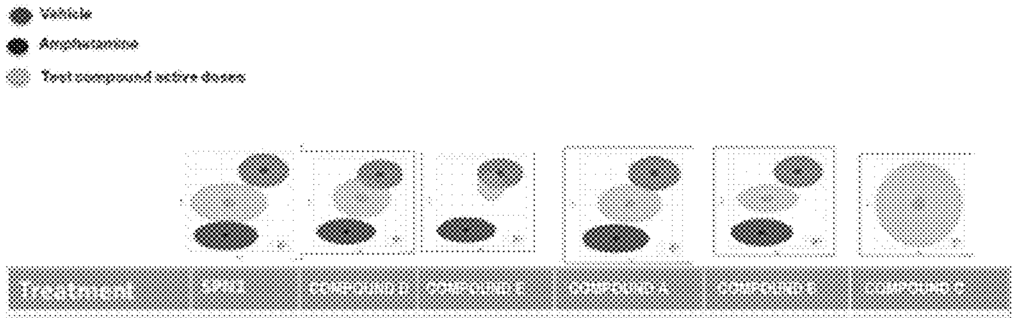
FIG. 45 shows DRFA Analysis of active doses of test compounds, in comparison to vehicle cloud and Amphetamine cloud.
Figure 46:
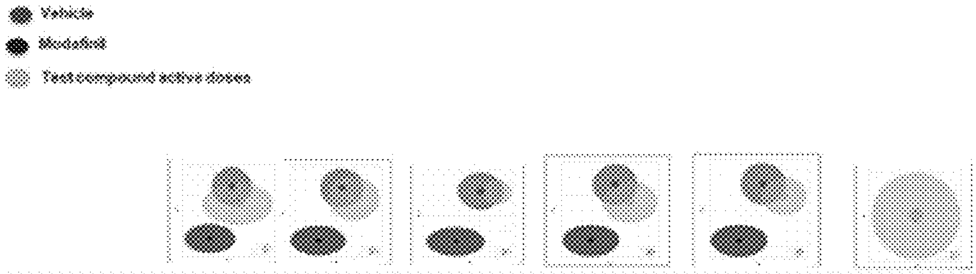
FIG. 46 shows DRFA Analysis of active doses of test compounds, in comparison to vehicle cloud and Modafinil cloud.
Figure 47:
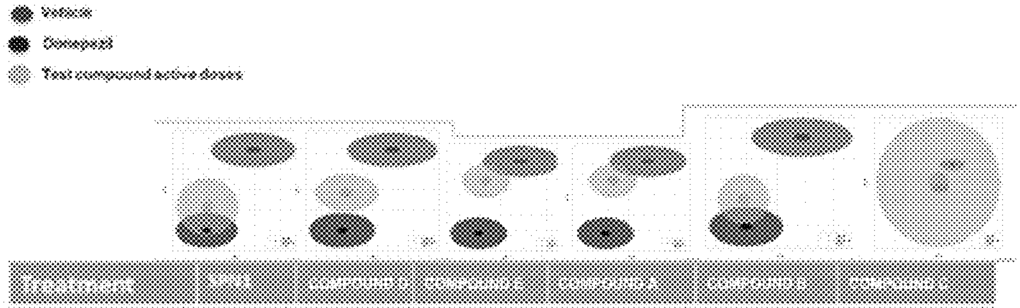
FIG. 47 shows DRFA Analysis of active doses of test compounds, in comparison to vehicle cloud and Donepezil cloud.
Figure 48:
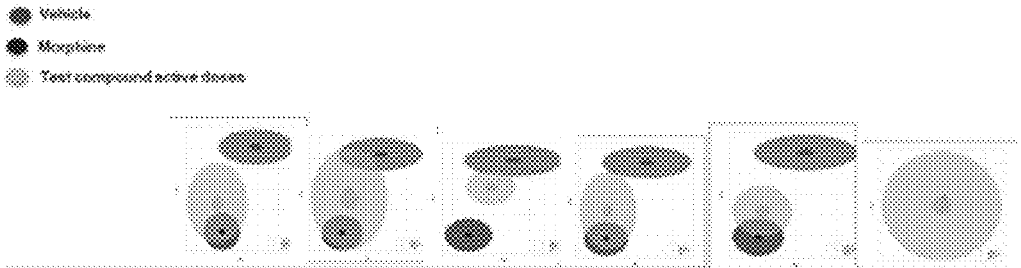
FIG. 48 shows DRFA Analysis of active doses of test compounds, in comparison to vehicle cloud and Morphine cloud.
Figure 49:
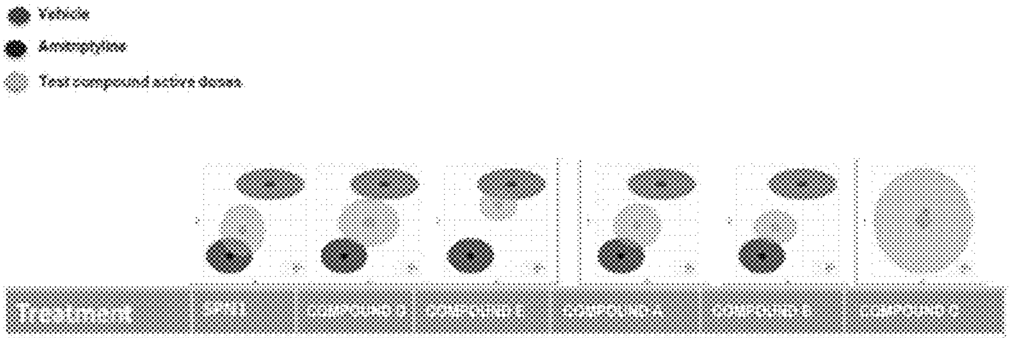
FIG. 49 shows DRFA Analysis of active doses of test compounds, in comparison to vehicle cloud and Amitriptyline cloud.
Figure 50:
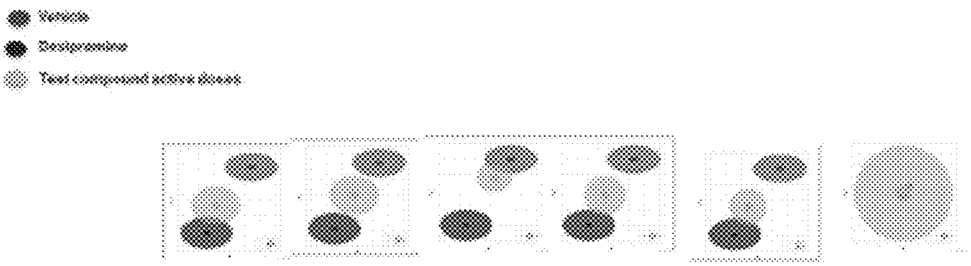
FIG. 50 shows DRFA Analysis of active doses of test compounds, in comparison to vehicle cloud and Desipramine cloud.
Figure 51:
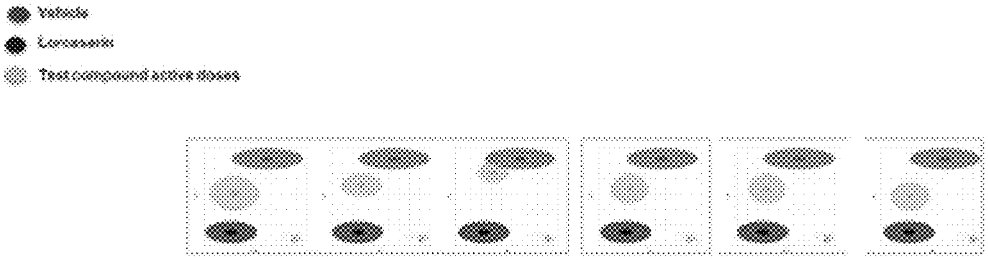
FIG. 51 shows DRFA Analysis of active doses of test compounds, in comparison to vehicle cloud and Lorcaserin cloud.
Figure 52:
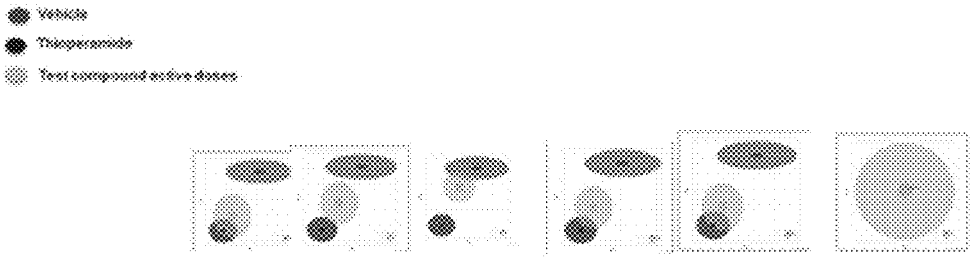
FIG. 52 shows DRFA Analysis of active doses of test compounds, in comparison to vehicle cloud and Thioperamide cloud.
Figure 53:
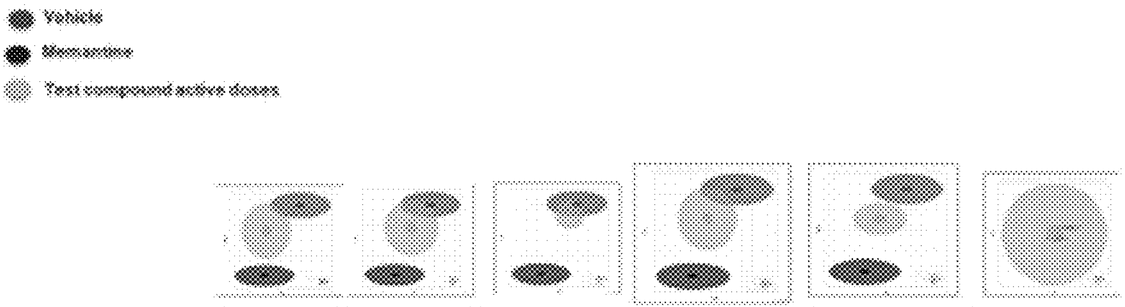
FIG. 53 shows DRFA Analysis of active doses of test compounds, in comparison to vehicle cloud and Memantine cloud.
Figure 54:
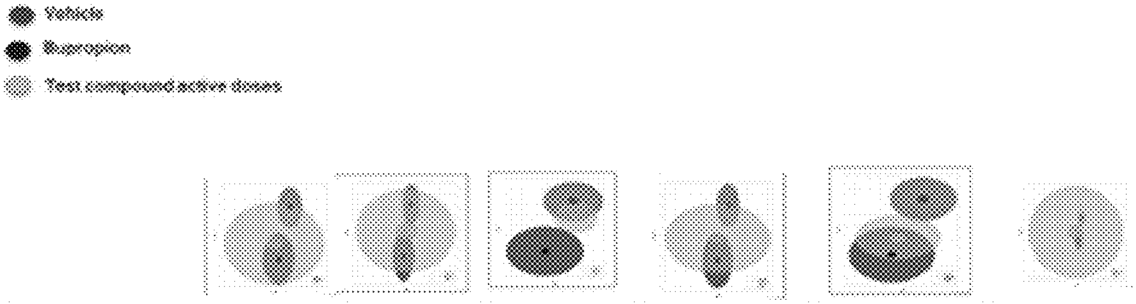
FIG. 54 shows DRFA Analysis of active doses of test compounds, in comparison to vehicle cloud and Bupropion cloud.
Figure 55:
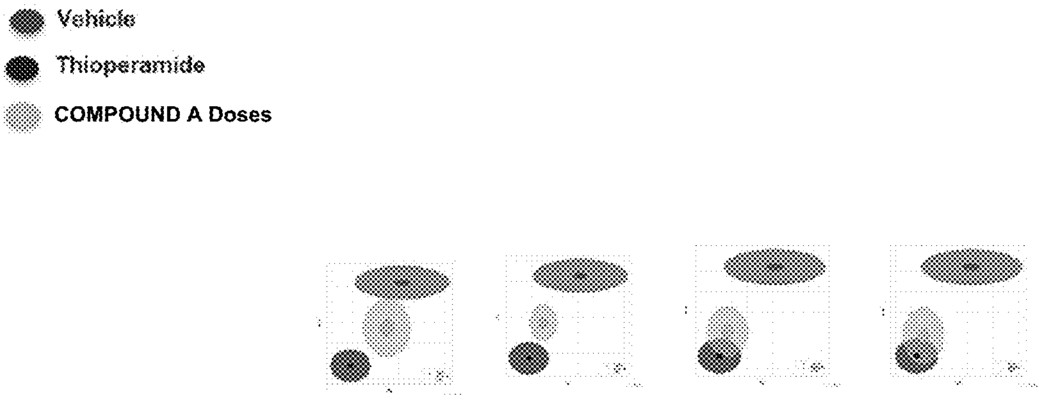
FIG. 55 shows DRFA Analysis of active doses of COMPOUND A, in comparison to vehicle cloud and Thioperamide cloud.
Figure 56:
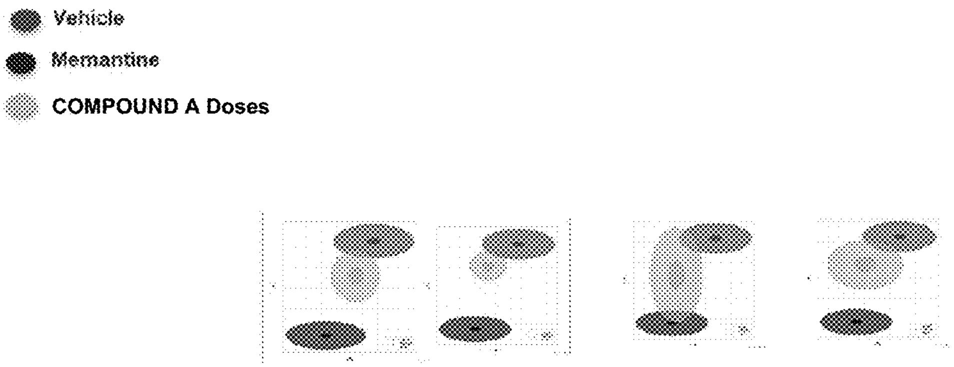
FIG. 56 shows DRFA Analysis of active doses of COMPOUND A, in comparison to vehicle cloud and Memantine cloud.
Figure 57:
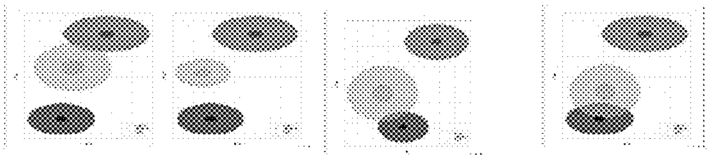
FIG. 57 shows DRFA Analysis of active doses of COMPOUND A, in comparison to vehicle cloud and Donepezil cloud.
Figure 58:
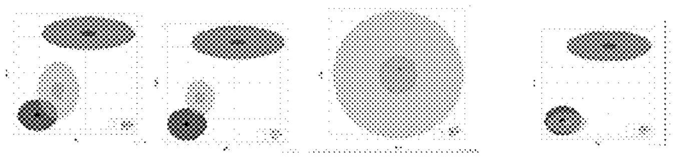
FIG. 58 shows DRFA Analysis of active doses of COMPOUND C, in comparison to vehicle cloud and Thioperamide cloud.
Figure 59:
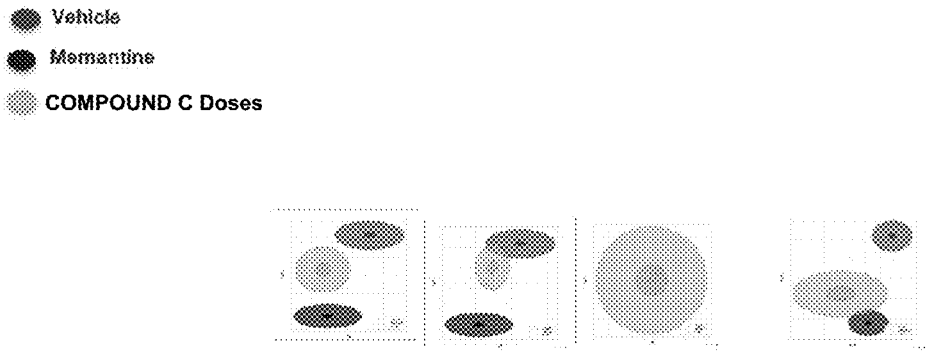
FIG. 59 shows DRFA Analysis of active doses of COMPOUND C, in comparison to vehicle cloud and Memantine cloud.
Figure 60:
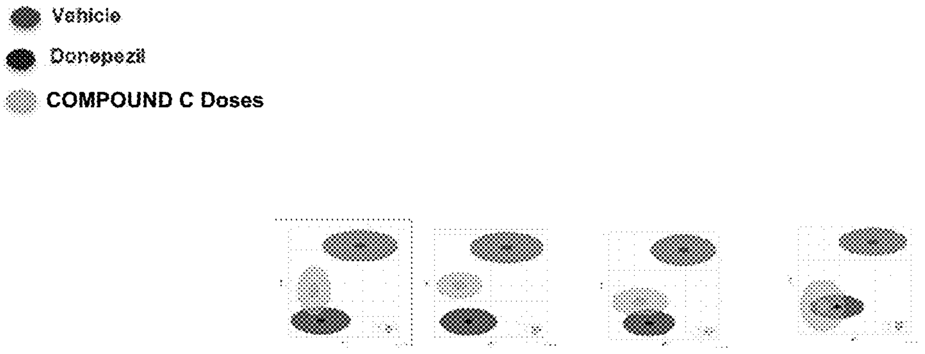
FIG. 60 shows DRFA Analysis of active doses of COMPOUND C, in comparison to vehicle cloud and Donepezil cloud.
Figure 61:
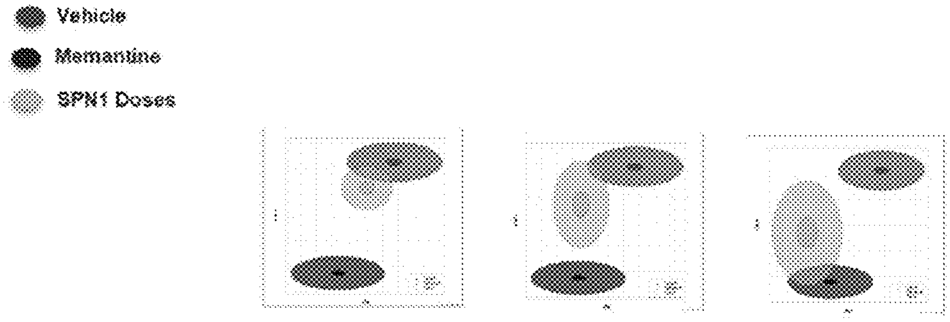
FIG. 61 shows DRFA Analysis of active doses of VILOXAZINE, in comparison to vehicle cloud and Memantine cloud.
Figure 62:
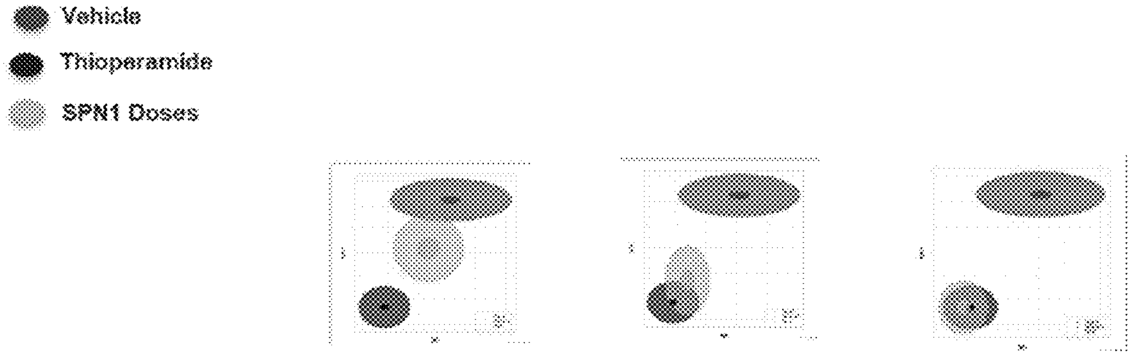
FIG. 62 shows DRFA Analysis of active doses of VILOXAZINE, in comparison to vehicle cloud and Thioperamide cloud.
Figure 63:
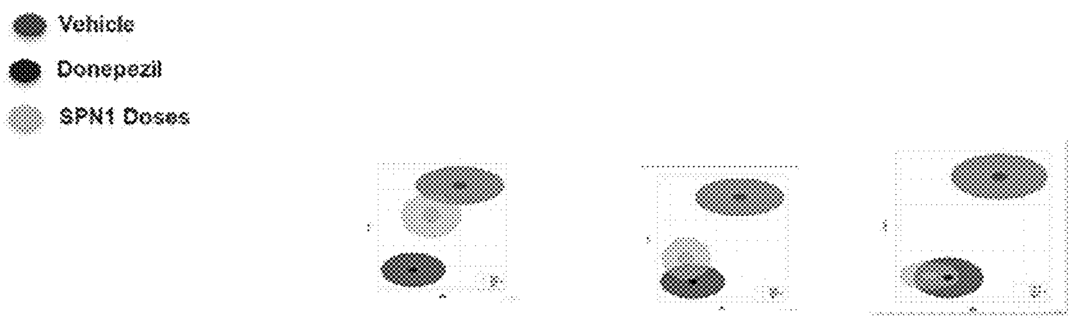
FIG. 63 shows DRFA Analysis of active doses of VILOXAZINE, in comparison to vehicle cloud and Donepezil cloud.

None of the compounds showed proximity to the Attention Deficit Hyperactivity Disorder (ADHD) compound combined cloud that was used for the analysis in FIG. 43. However, when the reference compounds were individually compared in FIGS. 44-46, there were varying levels of proximity amongst the active doses, although similarity to amphetamine and modafinil remained relatively moderate to low. Notably, COMPOUND C showed >75% proximity to atomoxetine and amphetamine.

Interestingly, when compared to donepezil, viloxazine, COMPOUND B and COMPOUND C showed >70% proximity, with viloxazine and COMPOUND B showing similar proximities to thioperamide. COMPOUND B and COMPOUND C also showed >70% proximity to morphine. COMPOUND C showed proximity to the antidepressants desipramine and amitriptyline. VILOXAZINE and COMPOUND B also showed proximity to these two antidepressants but to lesser extent at >60%. VILOXAZINE comparison to bupropion showed proximity >70%, with COMPOUND B and COMPOUND C at 69%.

VILOXAZINE, COMPOUND A and COMPOUND C were subsequently analyzed dose by dose and compared against some of the same reference compounds (see FIGS. 55-63). COMPOUND A showed increasing proximity to both thioperamide and donepezil as the dose increased. At the two highest doses (90 and 120 mg/kg), proximity maxed out at >75% and >65%, respectively. Overall, COMPOUND C and VILOXAZINE demonstrated similar patterns, but maxed out at around 100% proximity for both compound comparisons. In addition, VILOXAZINE demonstrated dose-dependent proximity increases for memantine, although it only reached 57%.

In sum, several compounds were tested in SmartCube® after being orally dosed, with a 20-minute pretreatment time. Most doses were highly active and showed mixed class and subclass signatures, almost always showing Subclass analysis. Viloxazine, COMPOUND A, COMPOUND B, and COMPOUND C also tended to show additional cognitive enhancer signatures at the higher doses tested, similar to that of H3 antagonists. Notably, VILOXAZINE at 90 mg/kg class analysis showed a significant analgesic class signature that was not seen in the other compounds tested. COMPOUND C at 120 and 150 mg/kg also showed additional analgesic subclass features and antipsychotic class features, respectively. Subsequent proximity analysis to selective reference compound(s) found that VILOXAZINE, COMPOUND B and COMPOUND C showed proximity to donepezil, desipramine, thioperamide, and amitriptyline. COMPOUND B and COMPOUND C showed >70% proximity to morphine. Proximity to bupropion was around 70% for VILOXAZINE, COMPOUND B, and COMPOUND C. COMPOUND C also showed >70% proximity to atomoxetine and amphetamine, when analyzed separately from another ADHD compound, modafinil. Dose by dose analysis of VILOXAZINE, COMPOUND A and COMPOUND C generally showed increasing proximities that were dose dependent for thioperamide and donepezil.

Example 20. Dose-Response Evaluation of S-Viloxazine Prodrug COMPOUND A in Mice Using SmartCage for Locomotor Activity and Tail Suspension Test The Locomotor Activity assessment is a simple means of establishing spontaneous locomotor activity, arousal, and willingness to explore in rodents. It is one of the most common rodent tests, which can be used to test the effects of various medications on animal behavior in both wild type and genetically modified animals. This study used a SmartCage™ system which is an automated non-invasive rodent behavioral monitoring system enabling biomedical researchers to conduct a variety of neurobehavioral assays through consistent and accurate monitoring of rodent home cage activity and behavior.

The Tail Suspension Test is a mouse behavioral test useful in the screening of potential antidepressant drugs and assessing of other manipulations that are expected to affect depression related behaviors. The tail suspension test is an experimental method used in scientific research to measure a state of being helpless in rodents, especially in mice. It is based on the observation that if a mouse is subjected to short term inescapable stress then the mice will give up struggling. "Immobility" is quantified by measuring the amount of time during which the animal has no whole-body activity. A shorter "immobile" time (sec) following a treatment indicates that the drug might have antidepressant effects.

A study was conducted to evaluate the behavioral effects of acute treatment of the S-viloxazine prodrug COMPOUND A on locomotor activity over 24 hr using the Smart Cage and evaluate potential anti-depressant effects through the Tail Suspension Test (TST). Results can be used for the selection of the dose range in a follow-up EEG sleep/wake study.

Methods and Materials

Animals. A cohort of 32 adult male mice (C57BL/6, 7-8 weeks old; body weights 18-25 g, Vendor: Charles River Laboratories) was utilized for locomotor activity, and a separate cohort of 40 male mice was used for the TST study. Upon arrival at the facility, animals were group-housed (5/cage) with access to food and water ad libitum. Animals were maintained on a 12/12-hour light/dark cycle in a temperature—(22±2° C.) and humidity—(approx. 50%) controlled room. Animals were numbered consecutively by tail ID marker in each home cage. Each home cage was identified by a colored ID card indicating the study number, sex, animal numbers and date of birth.

Substances & Formulation. The test articles were formulated according to the instructions reported in below Table

| Substance | Dose (mg/kg) | Concentration (mg/mL) | Volume (mL/kg) | Route | Formulation |
|---|---|---|---|---|---|
| Vehicle-A (TST) | N/A | N/A | 10 | PO | 4% DMSO, |
| COMPOUND A | 4 | 0.4 | 10 | PO | 30% PEG 400, 66% HPβCD, |
| COMPOUND A | 8 | 0.8 | 10 | PO | (30% in $H_20$) |
| COMPOUND A | 16 | 1.6 | 10 | PO | |
| COMPOUND A | 32 | 3.2 | 10 | PO | |
| Vehicle-B (LMA) | N/A | N/A | 10 | PO | |
| COMPOUND A | 10 | 1.0 | 10 | PO | |
| COMPOUND A | 30 | 3.0 | 10 | PO | |
| COMPOUND A | 90 | 9.0 | 10 | PO | |

Test article formulations were prepared freshly based on weight-to-volume in the vehicle on each dosing day. (Vehicle formulation: 4% DMSO, 30% PEG400, 66% HPβCD (30% in $H_2O$)). Compounds were weighed and then vehicle was added. The appearance of the formulations was clear, with no precipitations. Compounds were protected from light and kept on ice until dosing.

Animas (8/group) were gavaged (10 mL/kg, p.o.) 30 min prior to the TST. For locomotor activity monitoring, mice were gavaged (10 mL/kg, p.o.; around 12-1 pm) after a full 24 hr period of recordings were collected for baseline activity. For locomotor activity recordings, COMPOUND A doses included 10, 30, and 90 mg/kg. For TST, COMPOUND A doses included 4, 8, 16, and 32 mg/kg.

Dose selection: The dose range for SmartCage monitoring was based on a previous behavioral study. In the SmartCube phenotypic screening at 90 mg/kg (p.o.), COMPOUND A resulted in biological activity with no evidence of side effects.

Behavioral Methods

Figure 64:
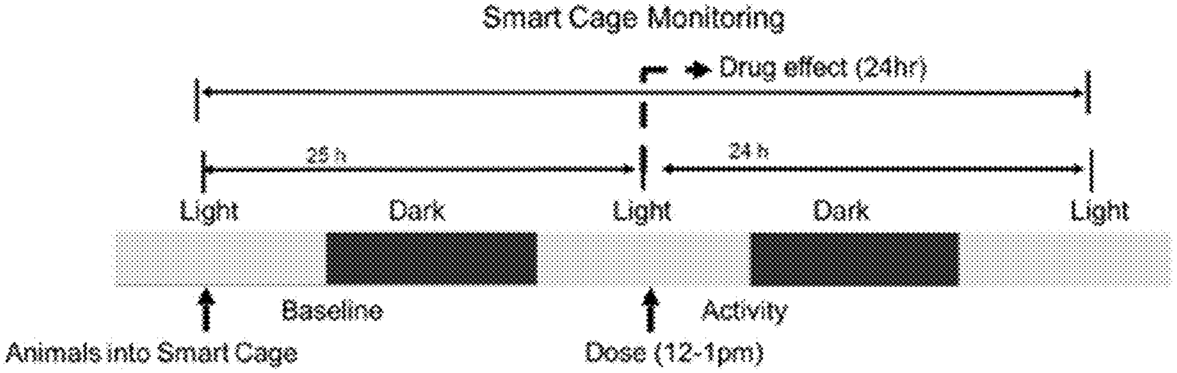
FIG. 64 shows the experimental schematic for Example 20. Activity levels of mice were assessed for 24 hr prior to and 24 hr following oral treatment with COMPOUND A.
Figure 65A:
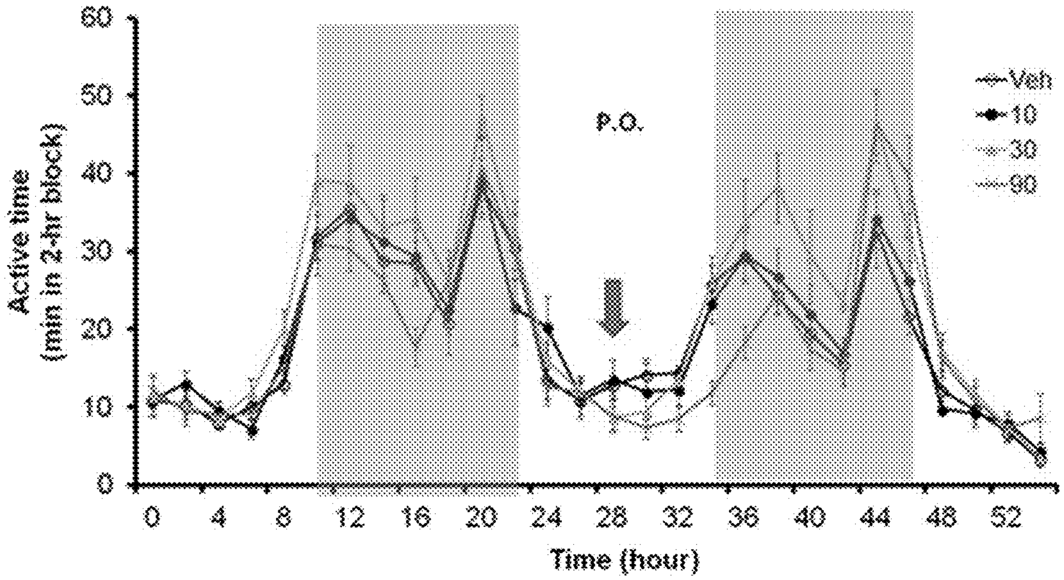
FIGS. 65*a*-65*d* show effects of COMPOUND A on active time (FIG. 65*a*), locomotion travel distance (FIG. 65*b*), velocity (FIG. 65*c*), and rearing activity (FIG. 65*d*) using SmartCage™ recordings. The gray bars indicate dark phase 6 pm-6 am.
Figure 65B:
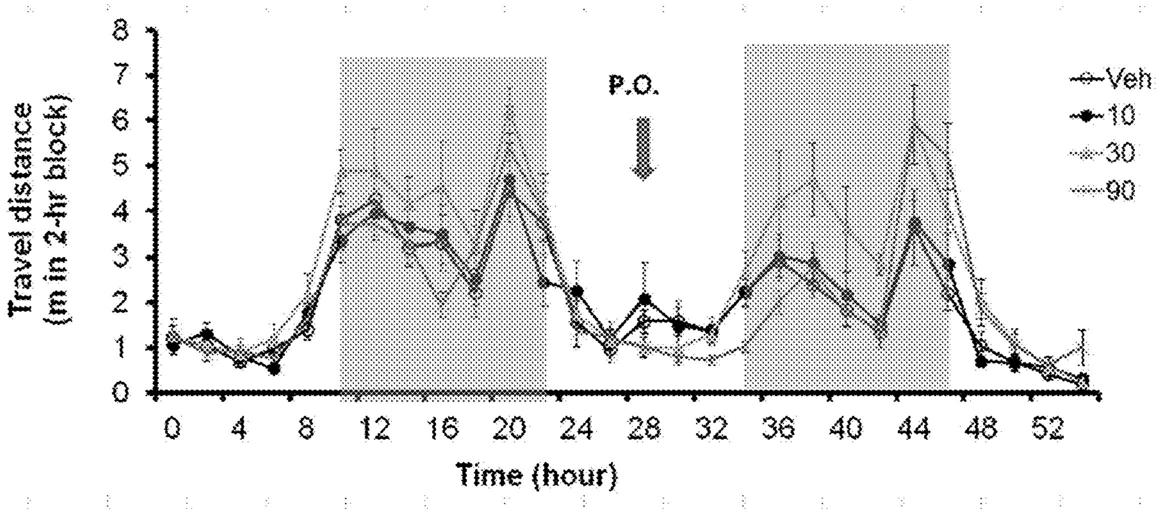
Figure 65C:
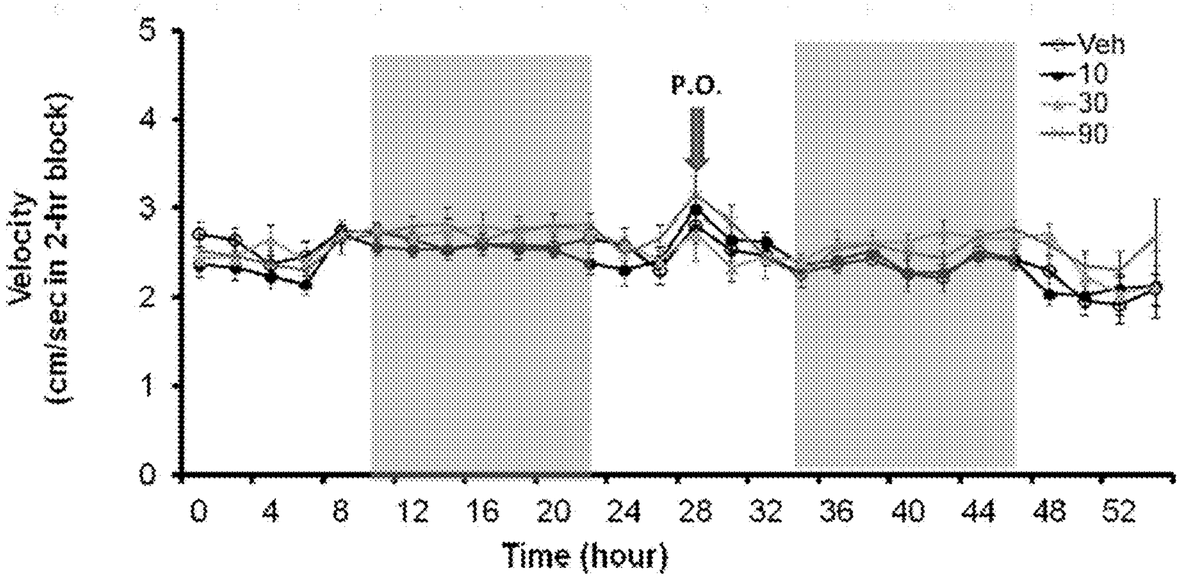
Figure 65D:
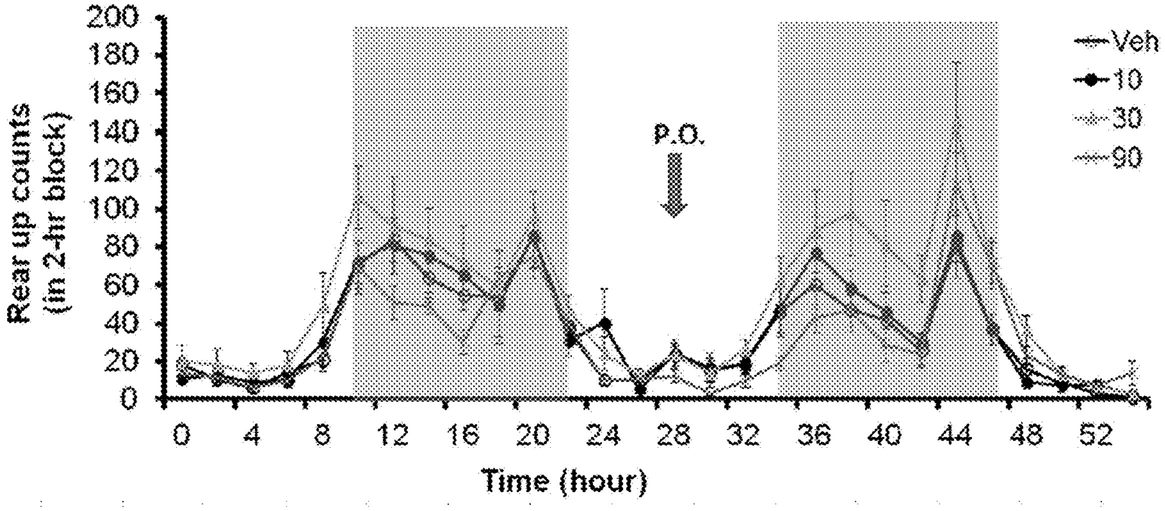

Locomotor Activity Monitoring. Mice underwent Smart Cage monitoring for 48 h (Experimental schematic, FIG. 64). Baseline activities were measured during the first 24 h. After the first day, animals were administered one of three doses (PO) of test article and monitored for the next 24 hours. The animal's activity during the monitored hours was quantified using the parameters of distance travelled, time active, and rearing activity.

SmartCage. Individual mice were placed into a freshly prepared home cage and recorded simultaneously using the SmartCage™ system and a video camera placed above the SmartCage™ system. The activity over a defined time block was automatically calculated by the CageScore™ program, which is the program associated with the SmartCage™ system (AfaSci, Inc).

Active wakefulness is defined as actively moving, rearing, and exploratory behaviors. Home cage activity variables include activity counts (ie., the photocell beam breaks), locomotion (distance traveled and speed) and rearing counts. Activity counts are obtained from the lower horizontal infrared (IR) sensors (along the X and Y axis). Likewise, distance traveled in centimeters is obtained from the lower horizontal IR and calculated taking into account the animal's path. Locomotion is defined as the moving distance longer than the body-length of the test animal. The calculated distance traveled (at any given time period, called 'block', or 'total measuring period'), and speed are two main parameters for locomotor activity. The z-axis photocell beam break counts reflect the number of beam interruptions in the upper row of R sensors and indicate rearing or climbing activity, which is considered to be part of exploratory behavior parameters. All IR data (beam break activity counts, locomotion, rearing, and rotations) were continuously recorded at a 4 Hz sampling rate. Absolute and percent time in a chosen block (or 'time bin') spent in this arousal state were also collected. Mice are most active within the first 1 hour when transferred to a fresh or new cage, after which their activity levels gradually decrease. Once their activity was stable, treatment with the test article was started.

Endpoints/parameters. SmartCage behavioral evaluation for a 48-hour period, measured in 2-hr blocks:

Activity Time

Distance traveled (and travel velocity)

Rearing

Scoring method. The SmartCage system uses an automatic scoring algorithm to calculate traveling distance and speed by integrating X and Y coordinates and time elapsed. The upper row of IR sensors detects the Z photobeam break account to indicate rearing activity.

Data analysis included calculating light (diurnal) and dark (nocturnal) time ratios. The nocturnal time ratio was calculated using the full 12 h of dark period (T34-46) following drug administration, which occurred at T28, and compared IR data with the identical time before drug treatment (i.e., T10-T22). The diurnal time ratio was calculated using a 2 h post-drug period (T30-32) and comparing it with the identical time prior to drug treatment (T6-8).

At the end of the experiment, mice were euthanized using $CO_2$ followed by a secondary method. No tissues were collected.

Tail Suspension Test (TST). A piezoelectric sensor operated by the SmartCage system was utilized and video recording was conducted for scoring. Once animals were acclimated to the testing room, the TST was initiated by placing the tail of the test mouse onto the piezoelectric sensor-board and hanging the mouse upside down. The recording period was initiated once the mouse was upside down and lasted for 6 min. After the recording period, the mouse was removed from the recording device and returned to its home cage. The immobilized time, indicating depression-like behavior, was quantified using manual scoring of the video recording from 120 seconds to 360 seconds during the TST. The percent immobility time was calculated as (immobility time (seconds)/240 seconds)*100.

Results

Basic statistical analysis was performed using GraphPad Prism and presented as mean±standard error of mean (SEM). The data were evaluated for normal distribution and homogeneous variances. Data that were not normally distributed were analyzed using alternative non-parametric tests. Group differences found to have normal distribution were evaluated using a 1-way ANOVA followed by a Dunnett's Multiple Comparison Test to compare all treatment groups to the vehicle control. Statistical significance was set at $p \leq 0.05$.

Figure 66:
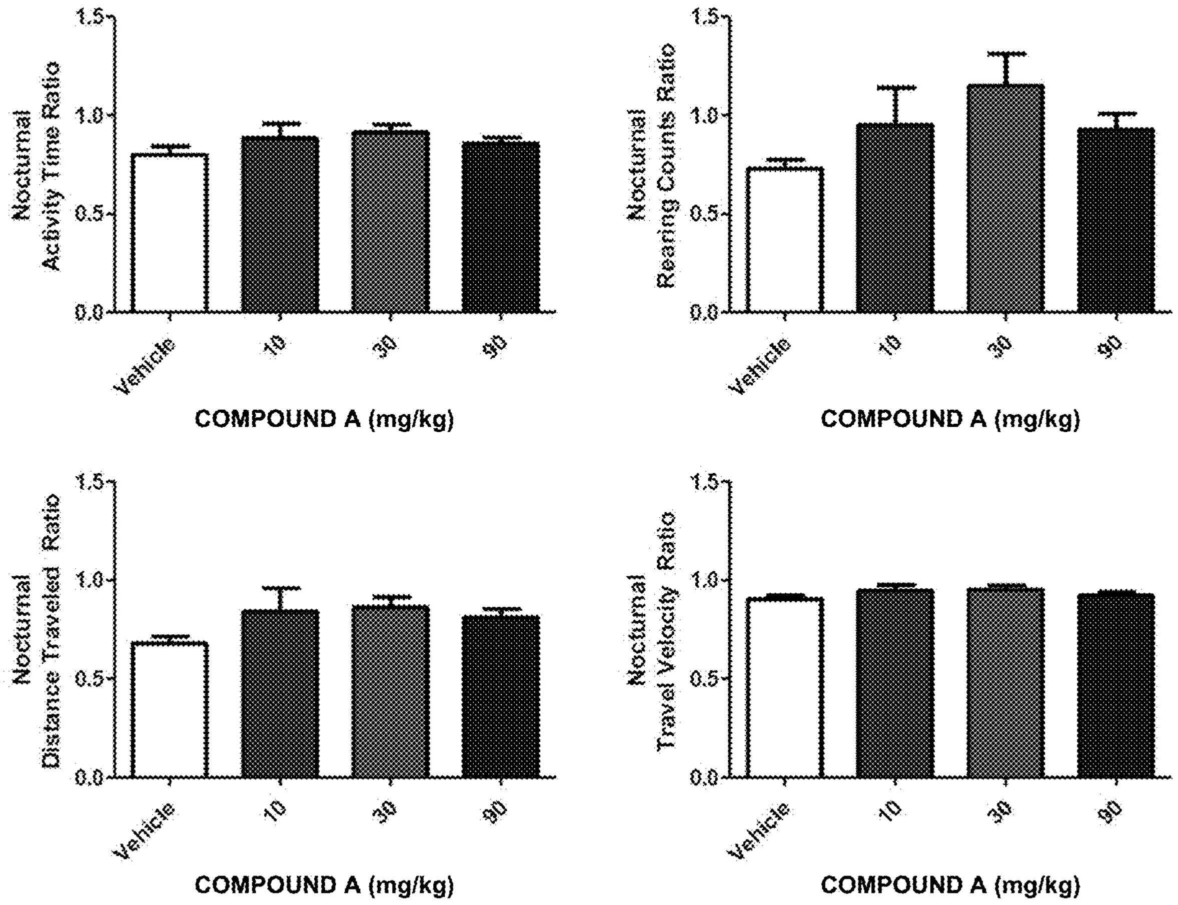
FIG. 66 shows effects of COMPOUND A on nocturnal activity ratios for pre/post drug administration. Data are displayed as means±SEM.
Figure 67:
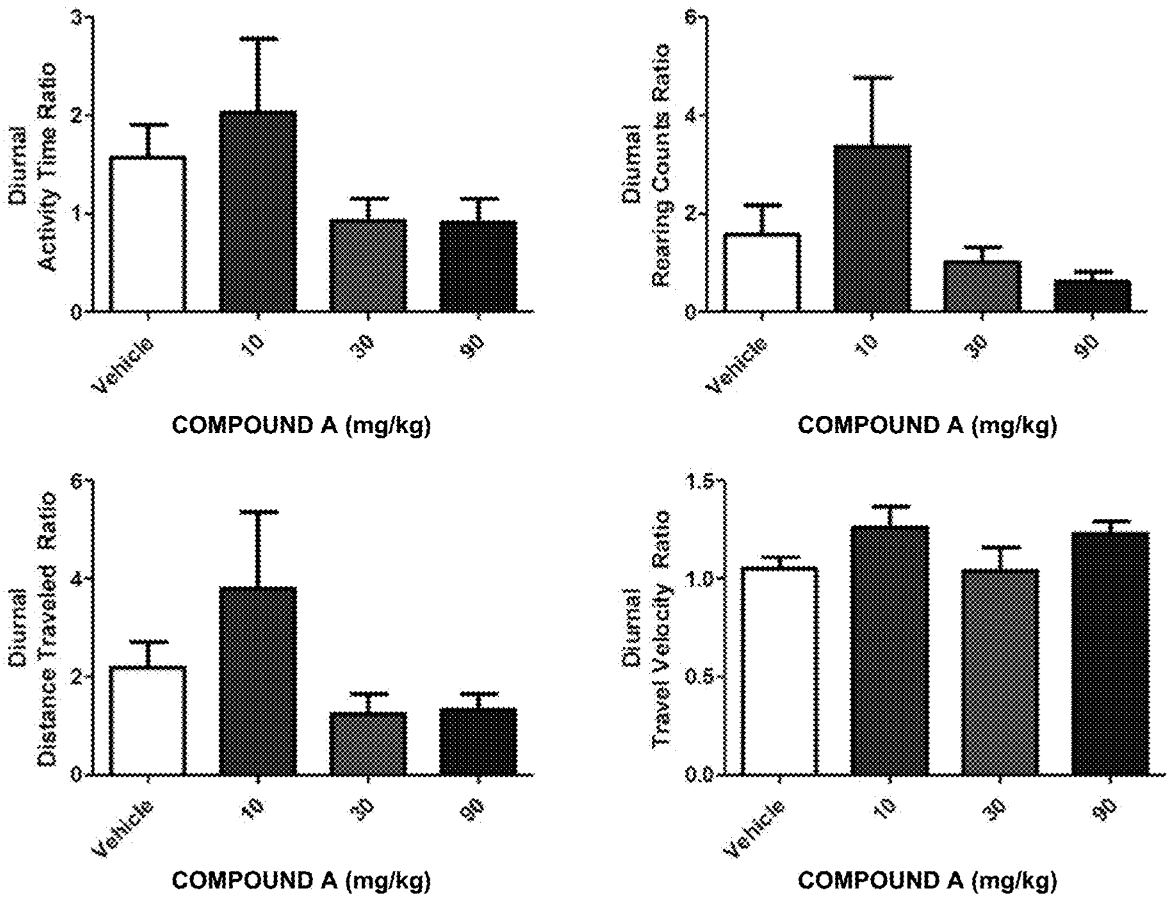
FIG. 67 shows effects of COMPOUND A on diurnal activity ratios for pre/post drug administration. Data are displayed as means±SEM.

Locomotor Activity. There were no obvious increases in active time, nor enhancement in locomotion parameters of travel distance, velocity and rearing counts after dosing of COMPOUND A (FIGS. 65*a*-65*d*). By averaging and comparing the nocturnal (FIG. 66) and diurnal (FIG. 67) activity data, there was no difference between pre- and post-treatment with COMPOUND A in any of the activity parameters measured.

Figure 68:
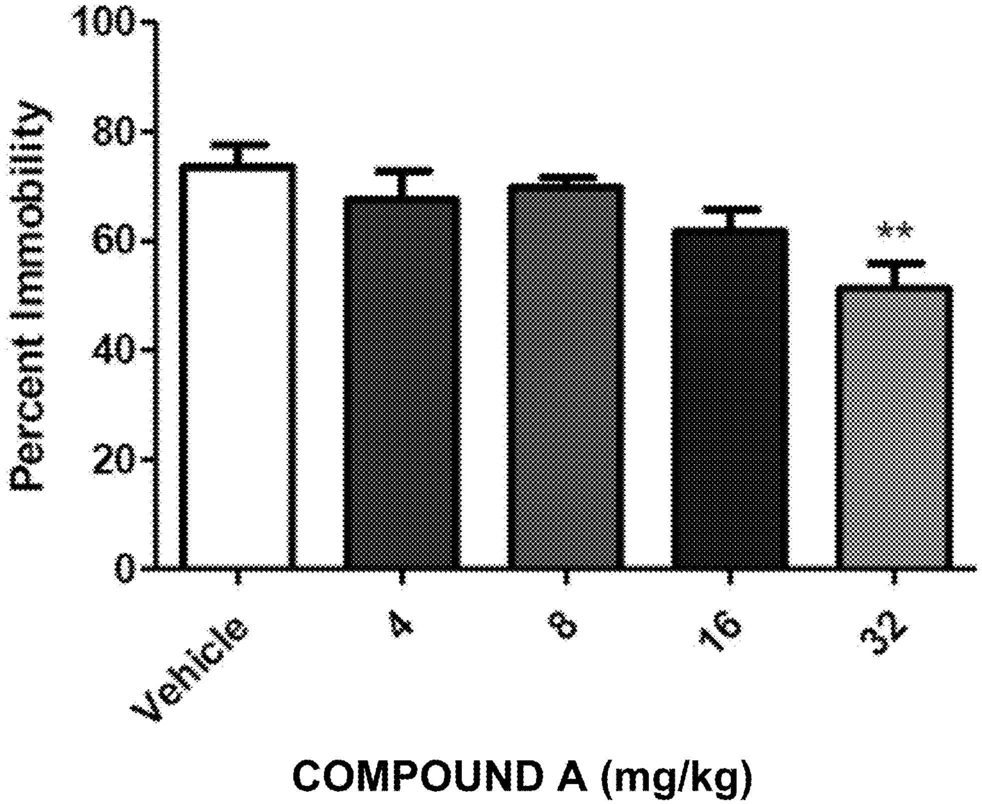
FIG. 68 shows effect of COMPOUND A on percent immobility during tail suspension test. Data are displayed as means±SEM. ** p<0.01 compared to vehicle.

Tail Suspension Test. COMPOUND A resulted in a significant reduction in immobility ($F4.35=4.398$, $p=0.006$). A post-hoc test revealed that mice were significantly more mobile at doses of 32 ($p \leq 0.01$) mg/kg when compared to the vehicle-treated group (FIG. 68).

In sum, home cage activity exhibited a typical circadian rhythm regardless of COMPOUND A administration (10, 30 and 90 mg/kg, PO). COMPOUND A had no significant effect on daytime or nighttime activity measurements, including activity, rearing, distance, or velocity. In contrast, the highest dose of COMPOUND A (32 mg/kg, PO) significantly decreased immobility in mice in the TST by 30% when compared to vehicle, suggesting an anti-depressive effect.

Example 21. Effects of COMPOUND A and S-Viloxazine on the Elevated Plus Maze in Rats A study was conducted to evaluate two compounds: COMPOUND A and S-Viloxazine for anti-anxiety-related behavioral effects in the elevated plus maze (EPM) task in rats. The EPM is a widely used behavioral assay for rodents that has been validated to assess the anti-anxiety effects of pharmacological agents. The EPM typically consists of two open arms and two closed (wall sheltered) arms elevated above the testing room floor and arranged to form a plus shape. The EPM relies on the innate, unconditioned fear rodents have for open spaces and heights. Anxious animals will spend more time in the closed arms, whereas an increase in open arm activity (duration and/or entries) reflects anti-anxiety (anxiolytic) behavior.

In this study, during the evaluation process of each compound, a single dose of the benzodiazepine anxiolytic, midazolam, was evaluated as a positive control/reference compound. The principal readout parameters for this study were open arm entries, % of time spent in the open arms, and total distance travelled, although a range of additional anxiety-related behaviors were also analyzed.

Methods and Materials

Study subjects. Ninety-seven (97) adult (approx. 3 months old) male Wistar rats (Envigo, Inc, Indianapolis, IN) were used in the study. Subjects were double housed in polycarbonate cages (45×30×18 cm) with corncob bedding in a vivarium of constant temperature (21-23° C.) and humidity (40-50%). Lighting was maintained on a 12-hr light-dark cycle (7:00 a.m.-7:00 p.m.) and the subjects had free access to water and food throughout the study. All behavioral testing was performed during the light portion (9 a.m.-5 p.m.) of the light/dark cycle (Monday thru Friday).

Method. Test subjects were allowed to habituate to the new housing environment for a minimum of one week after delivery to the test facility. At the beginning of the drug testing week, each subject was handled for approximately 5 min per day for two days. Subsequently, on day three test subjects were placed in an open field locomotor activity chamber (43.2×43.2 cm, Med Associates, St. Albans, VT) for 30 min. The handling and open field procedures were conducted to reduce the initial anxiety and variability associated with handling, transport, and exposure to novel environments. The EPM (Habitest® Modular Systems, Coulbourn Instruments, Allentown PA) used in these studies was made of black acrylic and consists of two open arms (44.5 cm×10 cm) and two enclosed arms of the same size, each with 29.5 cm high walls. The maze was configured such that arms of the same type are opposite each other and the apparatus was elevated 53 cm from the floor. The arms were connected by a central square measuring 10 cm×10 cm. All arms and the central square were equally illuminated at approximately 200 lux. For a test trial, each animal was placed at the center of the maze facing an open arm and observed for 5 min. Over the 5 min testing period, the number of entries and the time spent in each of the open and enclosed arms as well as the total distance travelled was recorded. The percent time in the open arms [(time spent in open arms/(time spent in open+enclosed arms))×100] and the total number of entries (entries in open+enclosed arms) was also calculated. An arm entry was recorded when all four paws were located in an arm. Additional anxiety-related behaviors were also assessed: head dipping (exploratory movement of head/shoulders over the sides of an open arm), stretch-attend postures (an exploratory posture in which the rodent stretches forward and retracts to the original position without locomoting forward), and closed arm returns (exiting a closed arm with only the forepaws, and returning/doubling back into the same arm; see Rogers and Johnson, 1995). All trials were video tracked and the outcome measures described above were determined via the use of EthoVision XT 14 software. Eight (8) to nine (9) animals per treatment group were used.

Drug Preparation and Administration. COMPOUND A was prepared in 0.8% DMSO, 6% PEG 400, 93.2% HPβCD (6% in H2O). COMPOUND A's vehicle formulation: 0.8% DMSO, 6% PEG 400, 93.2% HPβCD (6% in H2O), which was diluted in water (1 vol stock solution+4 vol $H_2O$) from a five-time concentrated (5×) stock solution in 4% DMSO+30% PEG400+66% HβCD (30%). The stock solution was dissolved in 0.8% DMSO, 6% PEG 400, and then diluted with water containing 6% HPβCD to a desired final concentration. Dosing was completed within 1 hour of formulation/re-mixing on each dosing day. Notes were made on the appearance of both formulations, including appearance (solution vs. suspension), color, precipitations, etc. The final preparation of COMPOUND A for administration was a light-yellow solution without any precipitation. Compounds were protected from light and kept on ice until dosing. The vehicle for S-VLX was purified water and the vehicle for COMPOUND A was 0.8% DMSO, 6% PEG 400, 93.2% HPβCD (6% in $H_2O$) (see formulation table below)

| Compound | Dose (mg/kg) | Route | Formulation |
|---|---|---|---|
| COMPOUND A | 30, 60, 120 | PO | 0.8% DMSO, 6% PEG400, and 93.2% HPβCD (6% in $H_2O$) |
| S-Viloxazine | 15, 30, 60 | | Milli-Q water |

The required quantity of S-VLX was weighed in an amber colored beaker (or beakers wrapped with aluminum foil), mixed with a small volume of the vehicle to wet the test article, stirred with magnetic stirrer, and transferred into the measuring cylinder/volumetric flask. The remaining volume of the vehicle was added to achieve the required concentrations. S-VLX was prepared at the highest concentration based on weight-to-volume in water (Milli-Q). The final preparation of S-VLX for administration was a colorless solution without any precipitation. The required quantity of midazolam was dissolved in 0.9% saline and diluted further with 0.9% saline to achieve the required concentration for injection.

Rationale for doses. The compounds were administered by oral gavage. The doses were calculated based on the free base of each compound. Based on previous in vivo pharmacology studies, it was found that COMPOUND A exhibited antidepressant-like effects on the tail suspension test at 32 mg/kg (po) in mice. In addition, immediate release viloxazine (racemate), given at 100 mg (for antidepressant effects), produced similar plasma levels as a 400 mg dose of extended release viloxazine, which translated to 34 mg/kg of VLX in a rat using allometric scaling or approximately 21 mg/kg of S-VLX in a rat.

As confirmation, when dosed at 40 mg/kg, racemic VLX produced approximately half the S-VLX $C_{max}$ level as when S-VLX was dosed on its own at 40 mg/kg in rats (po). Conversely, COMPOUND A required higher doses to obtain a similar plasma concentration of S-VLX, compared to when S-VLX was dosed on its own. Thus, based on these data, the doses for COMPOUND A in rats, delivered orally, for this study would be 30, 60, and 120 mg/kg, while the doses for S-VLX in rats would be the molar equivalent of COMPOUND A at 15, 30, and 60 mg/kg.

Based on PK data, COMPOUND A when dosed at 60 mg/kg and S-VLX (40 mg/kg) had a $t_{max}$ of 0.33 and 0.42, respectively. A higher dose of COMPOUND A (120 mg/kg), though, exhibited a $t_{max}$ of 0.67. Thus, due to the quick nature of the EPM task (5 min to complete) the lower two doses of COMPOUND A (30 and 60 mg/kg) and all doses of S-VLX were orally administered 20 min prior to the EPM task. The higher dose of COMPOUND A (120 mg/kg) was administered 40 min prior to the task.

For the positive control/reference anxiolytic midazolam, the dose and route of administration (0.5 mg/kg i.p. 30 min before testing) was based on published literature. (Gazarini, et al., Neuroscience. 2011; 179:179-187).

Results

The data were imported into SigmaPlot® 11.0 for statistical analyses. Unpaired t-tests and one factor analysis of variance (ANOVA) was used (when appropriate) followed by Dunnett's multiple comparisons post-hoc tests. All results were expressed as the mean (±S.E.M.). Differences between means from experimental groups were considered significant at the $p<0.05$ level.

Figures 69A, 69B, 69C:
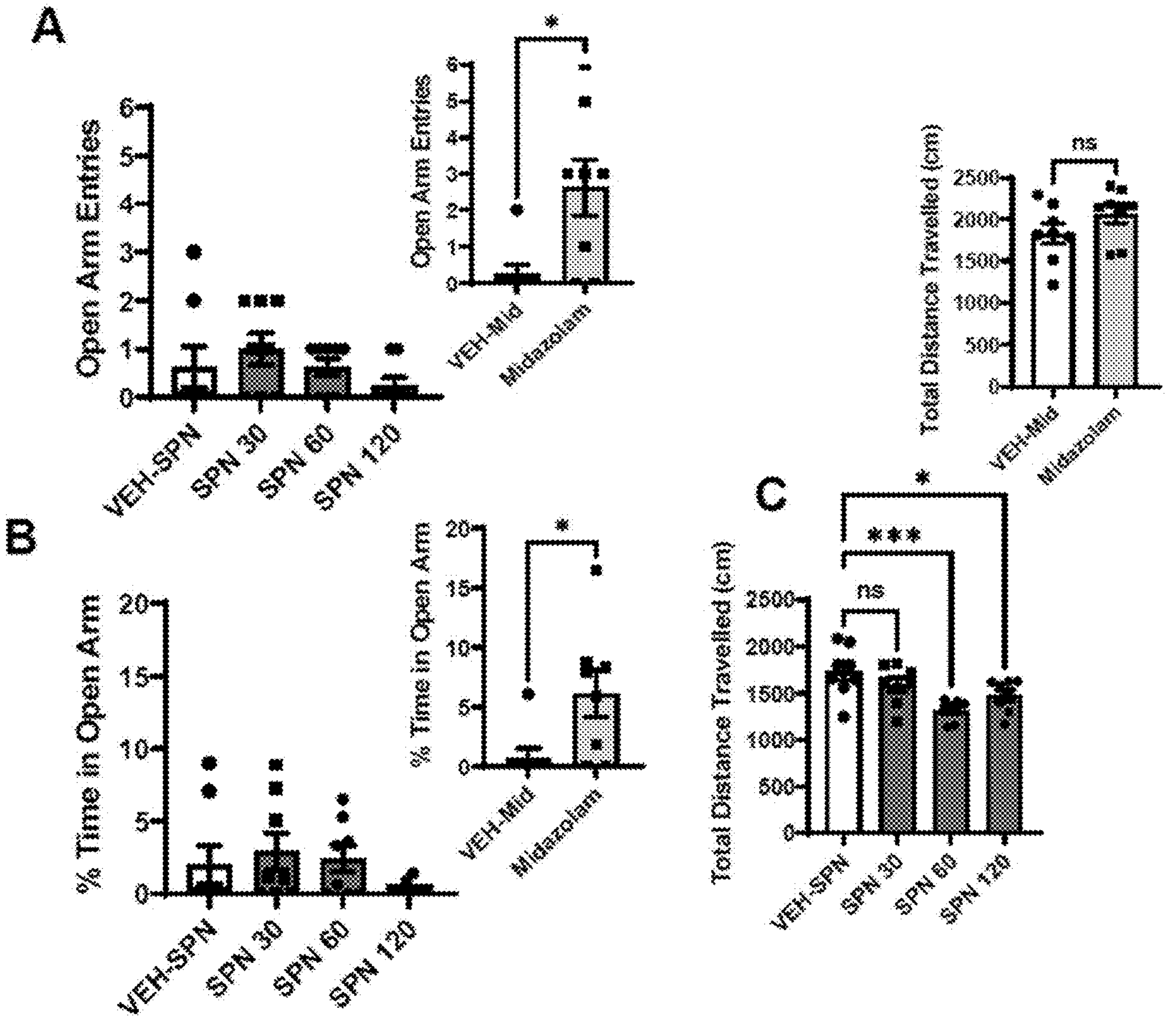
FIGS. 69*a*-69*c* show effects of COMPOUND A (abbreviated in the Figure legend as "SPN") in the Elevated Plus Maze (EPM) in rats. The effects of 3 doses of COMPOUND A, 30, 60, and 120 mg/kg p.o. on (FIG. 69*a*) the number of open arm entries, (FIG. 69*b*) the % of time spent in the open arms, and (FIG. 69*c*) the total distance travelled are illustrated. In the insets, the effects of a single dose of the positive control compound midazolam (0.5 mg/kg i.p.) are illustrated. Bars represent mean±S.E.M. for each treatment (N=8). VEH=vehicle; SPN=COMPOUND A, Mid=midazolam. *=significantly different (p<0.05) from the VEH-associated response; ***=p<0.001.

COMPOUND A Study. The effects of COMPOUND A in the EPM are illustrated in FIG. 69 and Tables 12 and 13. Of all of the outcome measures analyzed, the only statistically significant difference between COMPOUND A and vehicle was in the total distance traveled, [$F(3,28)=6.28$, $p=0.002$]. Post hoc analysis indicated that the rats administered the 60 and 120 mg/kg doses of COMPOUND A travelled a significantly shorter distance than the vehicle-treated animals ($p<0.001$ and $p<0.05$ for the 60 and 120 mg/kg doses, respectively).

The effects of the midazolam in study 1 are illustrated in the insets in FIG. 69 and in Tables 12 and 13. Compared to vehicle, midazolam exhibited significant ($p<0.05$) anxiolytic activity as indicated by the following outcomes: increased number of open arm entries, $t=2.9$, $df=14$, $p=0.01$; time in the open arms, $t=2.6$, $df=14$, $p=0.02$, % time in the open arms, $t=2.6$, $df=14$, $p=0.02$; head dips in the open arms, $t=2.3$, $df=14$, $p=0.04$; and decreased time in the closed arms, $t=3.5$, $df=14$, $p=0.003$.

Figures 70A, 70B, 70C:
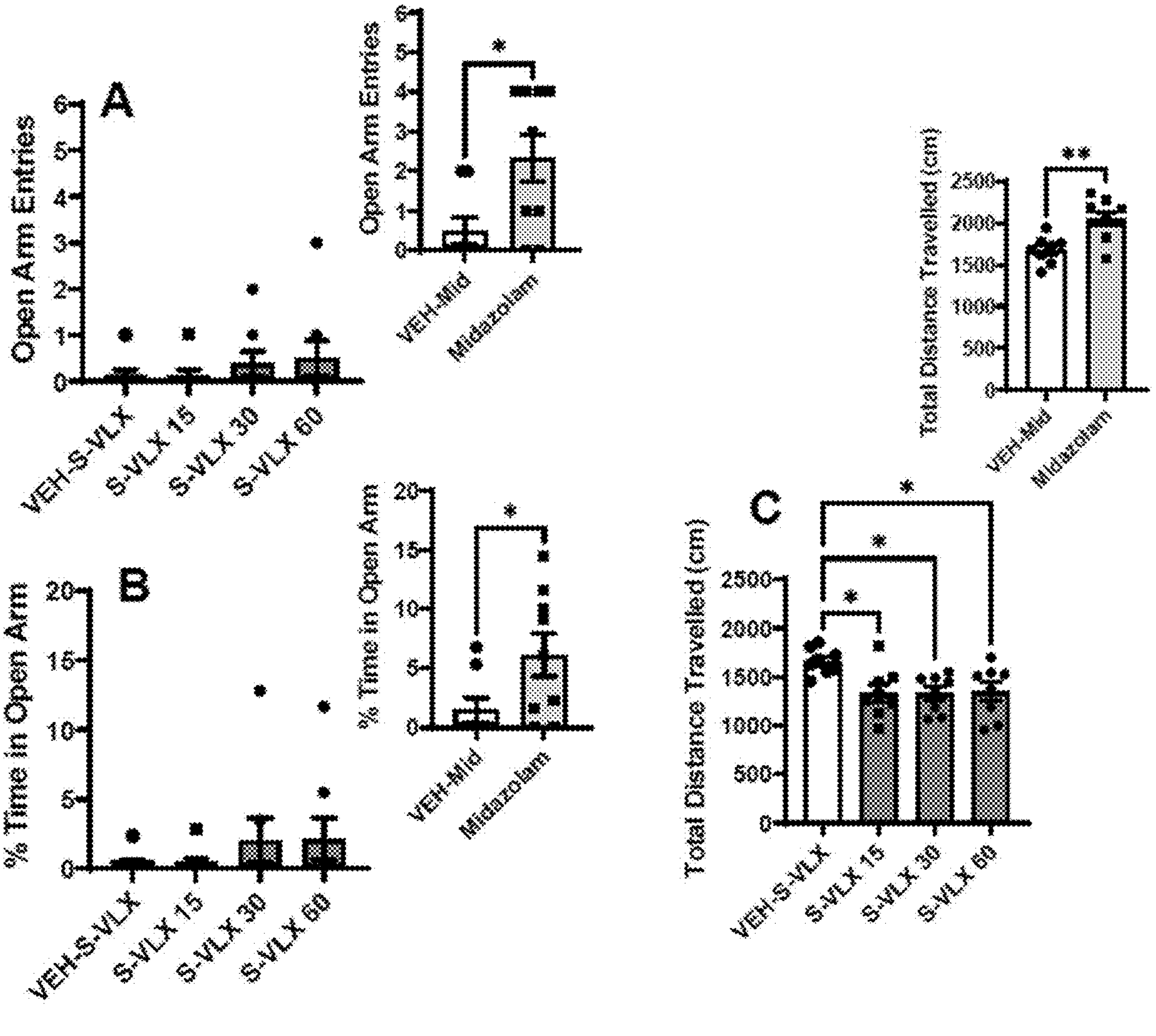
FIGS. 70*a*-70*c* show effects of S-Viloxazine (S-VLX) in the Elevated Plus Maze (EPM) in rats. The effects of 3 doses of S-VLX, 15, 30, and 60 mg/kg p.o. on (FIG. 70*a*) the number of open arm entries.

S-Viloxazine Study. The effects of S-Viloxazine (S-VLX) in the EPM are illustrated in FIG. 70 and Tables 12 and 13. As in the case of COMPOUND A, of all of the outcome measures analyzed, the only statistically significant difference between S-VLX and vehicle was in the total distance traveled, [$F(3,28)=4.22$, $p=0.1$]. Post hoc analysis indicated that the rats administered the 15, 30, and 60 mg/kg doses of S-VLX travelled a significantly shorter distance than the vehicle-treated animals ($p<0.05$ for all three doses compared to vehicle).

The effects of the midazolam in study 2 are illustrated in the insets in FIG. 70 and in Tables 12 and 13. Compared to vehicle, midazolam exhibited significant ($p<6.66$) anxiolytic activity as indicated by the following outcomes: increased number of open arm entries, $t=2.6$, $df=15$, $p=0.02$; time in the open arms, $t=2.2$, $df=15$, $p=0.047$, % time in the open arms, $t=2.2$, $df=15$, $p=0.047$; head dips in the open arms, $t=2.3$, $df=15$, $p=0.04$; and decreased time in the closed arms, $t=2.7$, $df=15$, $p=0.02$. Interestingly, in study 2 midazolam was also associated with an increased number of closed arm entries, $t=2.9$, $df=15$, $p=0.01$; decreased closed arm returns, $t=3.7$, $df=15$, $p=0.002$; increased total arm entries, $t=3.7$, $df=15$, $p=0.002$; and increased total distance travelled, $t=3.7$, $df=15$, $p=0.002$

TABLE 12

Effects of compounds on anxiety-like behaviors in rats in the elevated plus maze (primary outcome measures)

| | Treatment | N | Open Arm Entries | % Time in open arms | Total distance travelled (cm) |
|---|---|---|---|---|---|
| Study 1 COMPOUND A | Midazolam VEH | 8 | 0.25 ± 0.25 | 2.76 ± 0.76 | 1826.99 ± 122.14 |
| | Midazolam | 8 | 2.63 ± 0.78* | 6.16 ± 1.96* | 2064.55 ± 111.02 |
| | COMPOUND A VEH | 8 | 0.63 ± 0.42 | 2.01 ± 1.33 | 1733.69 ± 95.38 |
| | COMPOUND A 30 | 8 | 1.00 ± 0.33 | 2.91 ± 1.28 | 1591.15 ± 73.52 |
| | COMPOUND A 60 | 8 | 0.63 ± 0.18 | 2.42 ± 0.92 | 1318.06 ± 39.58* |
| | COMPOUND A 120 | 8 | 0.25 ± 0.16 | 0.28 ± 0.19 | 1476.54 ± 60.73* |
| Study 2 S-viloxazine | Midazolam VEH | 8 | 0.50 ± 0.33 | 1.51 ± 1.00 | 1681.11 ± 57.95 |
| | Midazolam | 9 | 2.33 ± 0.60* | 6.13 ± 1.80* | 2052.96 ± 791.05* |
| | S-VLX VEH | 8 | 0.13 ± 0.13 | 0.30 ± 0.30 | 1660.22 ± 47.20 |
| | S-VLX 15 | 8 | 0.13 ± 0.13 | 0.36 ± 0.36 | 1334.42 ± 90.911* |
| | S-VLX 30 | 8 | 0.38 ± 0.26 | 2.04 ± 1.60 | 1334.22 ± 68.23* |
| | S-VLX 60 | 8 | 0.50 ± 0.38 | 2.14 ± 1.52 | 1350.11 ± 96.17* |

VEH = vehicle;
S-VLX = S-viloxazine
*= sig different (<0.05) from the VEH-VEH associated response

TABLE 13

Effects of Compounds on Additional Anxiety-like Behaviors In Rats in the Elevated Plus Maze

| | Treatment | N | Time in open arms (sec) | Time in closed arms (sec) | Head dips in open arms | Closed arm entries | Closed arm returns | Stretch-attend postures | Total arm entries |
|---|---|---|---|---|---|---|---|---|---|
| Study 1 COMPOUND A | Midazolam VEH | 8 | 2.28 ± 2.28 | 288.21 ± 5.69 | 1.75 ± 1.37 | 10.38 ± 1.71 | 2.88 ± 0.85 | 19.38 ± 1.02 | 10.63 ± 1.86 |
| | Midazolam | 8 | 18.47 ± 5.88* | 247.54 ± 9.95* | 7.00 ± 1.83* | 14.13 ± 1.44 | 1.38 ± 0.71 | 18.88 ± 2.53 | 16.75 ± 1.77* |
| | COMPOUND AVEH | 8 | 6.02 ± 3.98 | 283.00 ± 5.75 | 2.62 ± 1.33 | 9.63 ± 1.39 | 2.50 ± 0.53 | 19.25 ± 1.16 | 10.25 ± 1.56 |
| | COMPOUND A 30 | 8 | 8.74 ± 3.83 | 282.58 ± 4.96 | 2.25 ± 0.96 | 10.00 ± 1.30 | 2.00 ± 0.76 | 18.00 ± 1.36 | 11.00 ± 1.57 |
| | COMPOUND A 60 | 8 | 7.25 ± 2.77 | 281.10 ± 4.55 | 3.63 ± 1.32 | 7.00 ± 0.82 | 2.13 ± 0.48 | 18.63 ± 1.16 | 7.63 ± 0.91 |
| | COMPOUND A 120 | 8 | 0.85 ± 0.58 | 283.06 ± 4.83 | 2.25 ± 0.77 | 9.63 ± 0.86 | 2.00 ± 0.38 | 20.38 ± 1.50 | 9.88 ± 0.88 |
| Study 2 S-viloxazine | Midazolam VEH | 8 | 4.54 ± 3.00 | 282.91 ± 4.28 | 2.00 ± 0.80 | 8.50 ± 1.24 | 4.63 ± 0.84 | 25.63 ± 1.79 | 9.00 ± 1.41 |
| | Midazolam | 9 | 18.38 ± 5.40* | 259.11 ± 7.30* | 5.67 ± 1.32* | 13.89 ± 1.34* | 1.44 ± 0.29* | 20.33 ± 2.29 | 16.22 ± 1.39* |
| | S-VLX VEH | 8 | 0.89 ± 0.89 | 287.78 ± 1.77 | 1.63 ± 0.42 | 9.00 ± 1.10 | 2.25 ± 0.45 | 19.00 ± 1.31 | 9.13 ± 1.09 |
| | S-VLX 15 | 8 | 1.08 ± 1.08 | 289.33 ± 2.84 | 1.38 ± 0.73 | 7.13 ± 1.48 | 2.13 ± 0.58 | 17.13 ± 1.08 | 7.25 ± 1.47 |
| | S-VLX 30 | 8 | 6.11 ± 4.79 | 277.60 ± 11.39 | 3.38 ± 1.90 | 7.88 ± 1.19 | 2.75 ± 0.70 | 19.38 ± 1.02 | 8.25 ± 1.26 |

TABLE 13-continued

Effects of Compounds on Additional Anxiety-like Behaviors In Rats in the Elevated Plus Maze

| Treatment | N | Time in open arms (sec) | Time in closed arms (sec) | Head dips in open arms | Closed arm entries | Closed arm returns | Stretch-attend postures | Total arm entries |
|---|---|---|---|---|---|---|---|---|
| S-VLX 60 | 8 | 6.43 ± 4.56 | 279.11 ± 12.13 | 2.88 ± 1.88 | 6.00 ± 2.01 | 3.50 ± 0.94 | 16.38 ± 1.71 | 6.50 ± 2.18 |

VEH = vehicle; S-VLX = S-viloxazine

*= sig different (<0.05) from the VEH-VEH associated response

In sum, none of the doses of COMPOUND A were associated with anxiolytic activity. The higher two doses of COMPOUND A were associated with decreases in the total distance travelled on the EPM. None of the doses of S-Viloxazine were associated with anxiolytic activity. All three doses of S-Viloxazine were associated with modest decreases in the total distance travelled on the EPM. In both studies, the positive control/reference compound midazolam exhibited anxiolytic activity as indicated by a significantly increased number of open arm entries, time (and % of time) in the open arms, head dips in the open arms, and decreased time in the closed arms. The EPM task validity was demonstrated by the anxiolytic effects of the benzodiazepine, midazolam.

Example 22. Effects of COMPOUND A on Novel Object Recognition in Rats

A study was conducted to evaluate COMPOUND A, in a Spontaneous Novel Object Recognition (NOR) task in rats. Studies included a 48 hr retention interval version of the task and a scopolamine-impairment model with a 3 hr retention interval. NOR is a rodent model of (non-spatial) recognition memory that is commonly used for the preclinical evaluation of new compounds that have potential pro-cognitive effects. The test is based on the natural tendency of rodents to investigate a novel object instead of a familiar one. During the dose-effect evaluation of COMPOUND A, a single dose of the acetylcholinesterase inhibitor and Alzheimer's disease treatment, donepezil, was evaluated in the 48 hr retention interval version of the task as a positive control/reference compound. A single dose of the antidepressant compound, vortioxetine, was evaluated in the scopolamine-impairment version of the task as a positive control/reference compound. The principal readout parameters for this study were time spent with the novel and familiar objects and the discrimination (d2) ratios in the A/B sessions.

Methods and Materials

Study subjects. One hundred forty-three (143) adult (approx. 3 months old) male Wistar rats (Envigo, Inc, Indianapolis, IN) were used in the study. Subjects were double housed in polycarbonate cages (45×30×18 cm) with corncob bedding in a vivarium of constant temperature (21-23° C.) and humidity (40-50%). Lighting was maintained on a 12-hr light-dark cycle (7:00 a.m.-7:00 p.m.) and the subjects had free access to water and food throughout the study. All behavioral testing was performed during the light portion (9 a.m.-5 p.m.) of the light/dark cycle (Monday through Friday).

Method. The NOR task is adapted from Ennaceur and Delacour (1988) as we have published previously. (Callahan et al, Neuropharmacology 67:201-212; Callahan et al, Psychopharmacology 231, 3695-3706; Callahan et al, Neuropharmacology 117:422-433.) Briefly, test subjects were acclimated to laboratory conditions (i.e., tail marking, daily handling, and weighing) for at least 3 days prior to experimentation. During experimentation, the animals were transported to the laboratory and acclimated for 30 min prior to initiating the experimental phase; the animals remained in the laboratory for 15 min following study completion.

Habituation—The animals were acclimated, weighed, and individually placed in a dimly lit (10-lux) training/testing environment (an opaque plastic chamber, 78.7 cm×39.4 cm×31.7 cm with bedding on the floor) for 10 min of chamber exploration. The NOR chamber was placed on a table positioned along the short wall of the laboratory. HVAC ventilation provided masking noise to reduce any extraneous background noise, and there were no room orienting cues or wall-mounted visual cues (except for the small camera positioned above the NOR chamber). At the beginning of each series of NOR experiments, fresh bedding material was placed in the chamber prior to habituation and allowed to become saturated with animal odors. Animal droppings were removed between experimental sessions; however, the same bedding was used for the remainder of each study (i.e., during training and testing), thus preventing any specific olfactory cues over the course of experimentation.

Training trial—Twenty-four hours after the habituation session, the animals were acclimated, weighed, and injected with test compound (drug or vehicle) and after the appropriate pretreatment interval, placed in the chamber with their nose facing the center of a long wall and allowed to explore two identical objects for 10 min. The animal's behavior was observed and digitally recorded via a CCTV camera located 69 cm above the chamber; the investigator sat quietly 10-15 ft. away from the NOR chamber. For an experimental subject to move further in the study to the Test Trial, it was required to explore each individual object at least 4 sec and spend a minimum of 12 sec of total object exploration during the training session.

Test trial—For the standard version of NOR a delay interval that reliably resulted in forgetting of the familiar object (e.g., 48 hrs after the training session) was used. For the scopolamine impairment studies, a delay interval that reliably allowed for recollection of the familiar object (3 hr) under vehicle conditions was used. In the NOR task, two objects, one object identical to training (familiar) and a novel object, were placed in the chamber, and the animal was allowed to explore the objects for 5 min. Experimental objects to be discriminated were plastic multicolored Duplo-Lego block configured towers (12 cm in height, 6 cm in width) paired with ceramic conical-shaped green Christmas tree salt/pepper shakers (12 cm in height, 5 cm in diameter); all objects exist in duplicate. The objects were placed 19.3 cm from the sides of the two short walls and 19.3 cm from the sides of the long walls of the chamber; distance between the two objects was approximately 40 cm. The role of familiar and novel object as well as chamber position of objects were randomly assigned across subjects and treatments, and objects were cleaned between sessions with a dilute 50% (vol/vol) ethanol solution to eliminate olfactory cues. The criteria for the observer to classify an object interaction as exploratory (investigative) behavior was direct interaction with nostrils or head positioning towards the object from a maximum distance of 2 cm. Physically climbing, rearing and digging around an object was not scored as object exploration. The primary behavioral measure was time (s) spent investigating each object. A discrimination index (d2) was calculated on each test trial and defined as the difference in time spent exploring the novel and familiar objects divided by the total exploration time for both objects: d2 index=(novel−familiar)/(novel+familiar). This measure is considered as an index of recognition memory and takes into account individual differences in the total amount of exploration time. For data inclusion, the rat had to explore each individual object at least 4 sec and spend a minimum of 12 sec of total object exploration. Experimental groups contained a minimum of 8 rats per treatment (or testing) condition which provides sufficient sample size to observe statistical significance. Animals were tested only once, and object exploration times were scored both live and from video recordings under blind testing methods (i.e., the investigator was unaware of treatment assignment).

Drug Dosing. COMPOUND A was administered by oral gavage in a volume of 2.0 mL/kg (to remain consistent with vortioxetine, see below). The doses were calculated based on the free base of the compound. Based on previous in vivo pharmacology studies, it was found that COMPOUND A exhibited a pro-cognitive phenotypic signature at 90 and 120 mg/kg (po), as well as antidepressant-like effects on the tail suspension test at 32 mg/kg (po), in mice. In addition, improved mental function was noted with racemic viloxazine at a daily dose of 400 mg in humans. Using allometric scaling of this therapeutic dose to obtain the human equivalent can result in 34 mg/kg of racemic viloxazine. At 40 mg/kg (po) in rats, racemic viloxazine produces a $C_{max}$ of S-VLX of 1600 ng/mL. COMPOUND A would require higher doses to obtain a similar plasma concentration of S-VLX in rats. Moreover, mice exhibited a higher $C_{max}$ at 20 mg/kg than rats did at 60 mg/kg when treated with COMPOUND A orally. Thus, based on these data, the doses for COMPOUND A in rats, delivered orally for the 48 hr delay version of NOR this study were 15, 30, 60, and 90 mg/kg. The effects of those doses were assessed and subsequently three doses were selected for additional testing in the scopolamine impairment model (see below).

Based on PK data, COMPOUND A when dosed at 60 mg/kg has a $t_{max}$ of 0.33 h. A higher dose of COMPOUND A (120 mg/kg), though, exhibited a $t_{max}$ of 0.67 h. Thus, due to the quick nature of the NOR training session (10 min to complete), the lower doses of COMPOUND A (15, 30, and 60 mg/kg) were orally dosed 20 min prior to the training session of the NOR task. The higher dose of COMPOUND A (90 mg/kg) was dosed 40 min prior to the training session of the task.

For the 48 hr delay version of NOR, the positive control compound donepezil was dissolved in physiologic saline (0.9% NaCl) and administered by intraperitoneal (i.p.) injection in a volume of 1.0 ml/kg 30 minutes before the A/A session as we have published previously. (Terry et al., The Journal of Pharmacology and Experimental Therapeutics, 352(2), 405-418).

COMPOUND A Preparation. COMPOUND A was weighed and prepared in the appropriate volume of vehicle, which was 0.8% DMSO, 6% PEG 400, 93.2% HPβCD (6% in H2O). COMPOUND A's vehicle formulation, 0.8% DMSO, 6% PEG 400, 93.2% HPβCD (6% in H2O), was diluted in water (1 vol stock solution+4 vol H2O) from a five-time concentrated (5×) stock solution in 4% DMSO+30% PEG400+66% HβCD (30%). The stock solution was dissolved in 0.8% DMSO, 6% PEG 400, and then diluted with water containing 6% HPβCD to a desired final concentration. Dosing was completed within 1 hour of formulation/re-mixing on each dosing day. Notes were made on the appearance of the formulation, including appearance (solution vs. suspension), color, precipitations, etc. COMPOUND A was protected from light and kept on ice until dosing. The vehicle for COMPOUND A was 0.8% DMSO, 6% PEG 400, 93.2% HPβCD (6% in H2O).

Scopolamine: Dosing and Formulation. For the scopolamine-reversal studies, (−)-scopolamine hydrobromide (CAS No. 6533-68-2) was obtained from Sigma-Aldrich (St. Louis, MO, USA). Scopolamine was dissolved in normal saline and administered by intraperitoneal (i.p.) injection at a dose of 0.2 mg/kg 30 min before the training session. This scopolamine dosing approach is based on our recently published study (Callahan et al., Scientific Reports 11(1): 9843).

Vortioxetine, which has demonstrated pro-cognitive capacities in healthy rodents, pharmacologically challenged rodents, and animal models of depression, served as the positive control for the scopolamine-reversal study. The dose of vortioxetine (10 mg/kg, s.c.) was based on previously published studies demonstrating persistent memory following a 24 hour delay, as well as in a scopolamine-challenged model (Mork et al., Pharmacology, Biochemistry and Behavior, 105, 41-50; Pehrson et al., J Pharmacol Exp Ther, 358, 472-482). Vortioxetine was dissolved (w/v) in 20% aqueous hydroxypropyl-β-cyclodextrin and administered in a volume of 2.0 mL/kg, 1 hour before the training session of NOR.

Results

The data were imported into SigmaPlot® 11.0 or GraphPad Prism 9 for statistical analyses. Unpaired t-tests, as well as one or two factor analysis of variance (ANOVA) was used (when appropriate) followed by Dunnett's or Student-Newman-Keuls post-hoc tests, respectively. All results were expressed as the mean±standard error of the mean (S.E.M.). Differences between means from experimental groups were considered significant at the $p<0.05$ level.

Figure 71:
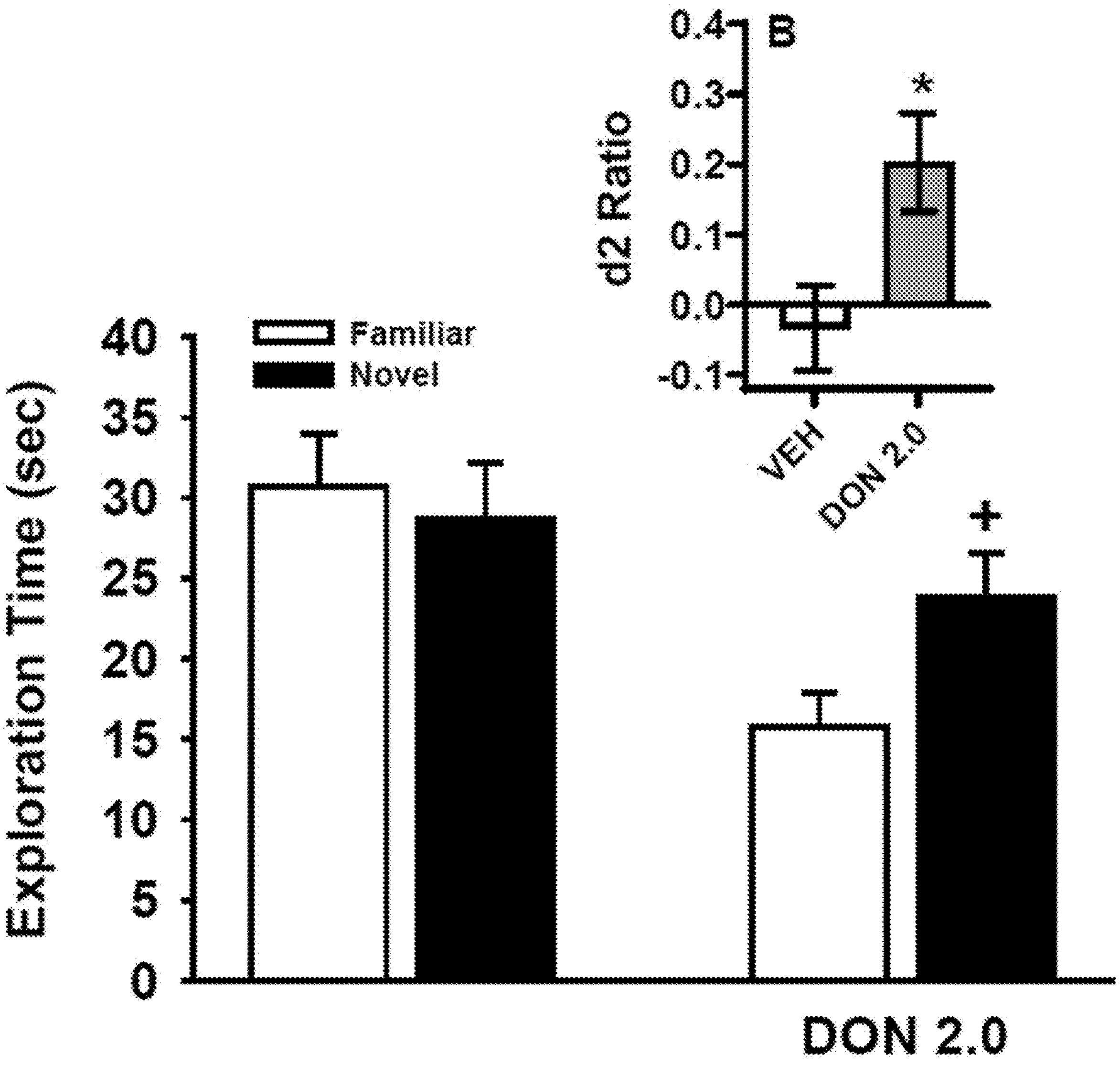
FIG. 71 shows effects of donepezil (2.0 mg/kg) in young-adult Wistar rats on performance of a spontaneous novel object recognition task. Mean (±S.E.M) exploration times of the familiar and novel objects after 48 hr delays (A/B retention sessions) are illustrated in the main Fig (A). The inset (B) illustrates the mean (±S.E.M) discrimination (d2) ratios. d2 ratio=(novel−familiar)/(novel+familiar). +p<0.02, novel vs familiar object; *p<0.05 vs VEH. N=10-13 for each group. VEH=Vehicle; DON=Donepezil.

48 hr Delay Studies. The effects of the AD treatment, donepezil (2.0 mg/kg) in the NOR task (A/B retention sessions) after a 48-hour retention interval are illustrated in FIG. 71. As shown, donepezil was associated with an increase in preference for the novel object: main effect of treatment [$F(1,21)=8.60$, $p=0.008$]; object type [$F(1,21)=1.68$, $p=0.209$]; treatment by object type interaction [$F(1,21)=4.61$, $p=0.044$]. Post-hoc analysis indicated that donepezil was associated with a significant preference for the novel object ($p=0.017$ versus familiar). This effect of donepezil was also observed when the d2 ratios were analyzed, [$t(21)=2.466$ $p=0.02$].

Figure 72:
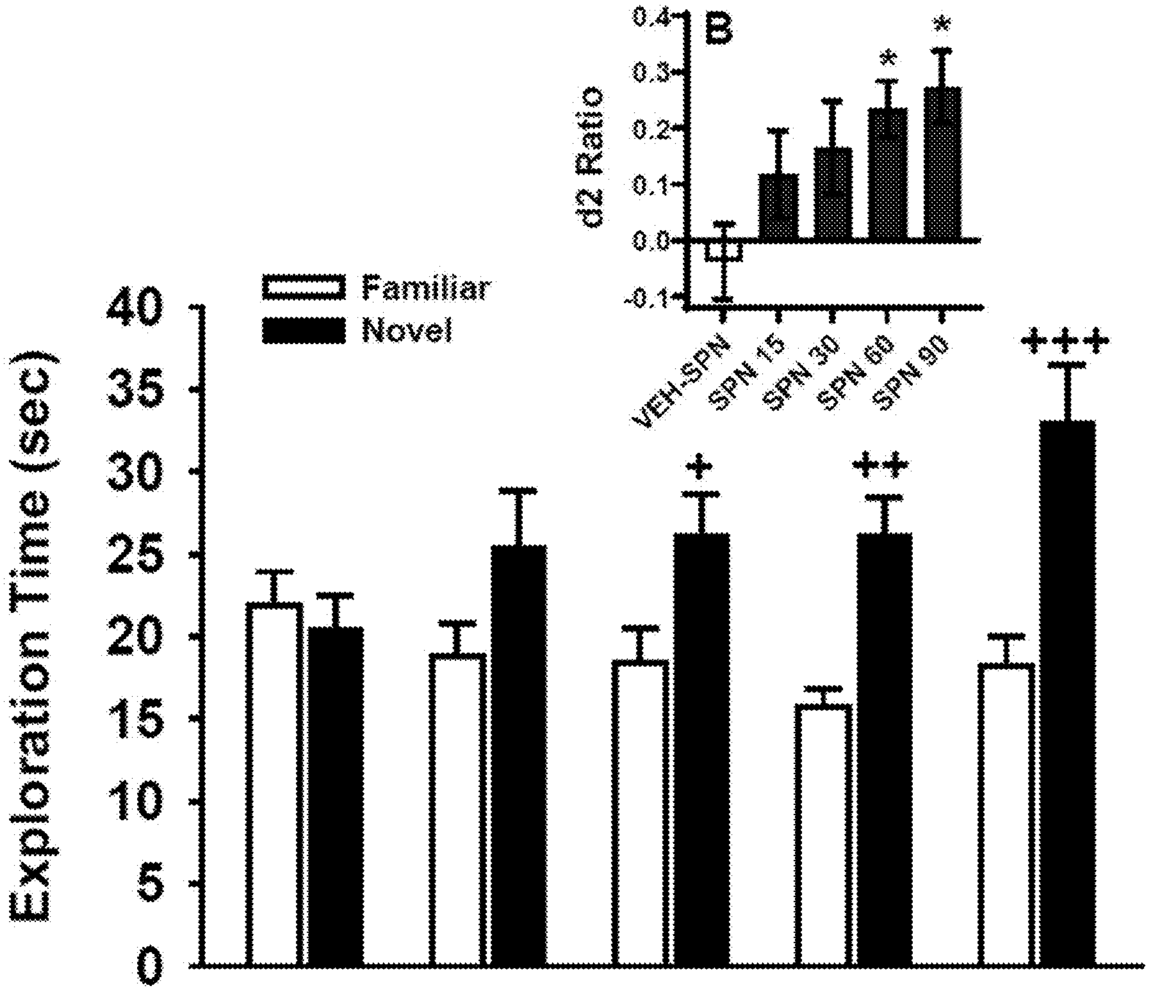
FIG. 72 shows dose-related effects of COMPOUND A (abbreviated as "SPN" in the figure) in young-adult Wistar rats on performance of a spontaneous novel object recognition task. Mean (±S.E.M) exploration times of the familiar and novel objects after 48 hr delays (A/B retention sessions) are illustrated in the main Fig (A). The inset (B) illustrates the mean (±S.E.M) discrimination (d2) ratios. d2 ratio=(novel−familiar)/(novel+familiar). +p<0.05, ++p<0.01, +++p<0.001, novel vs familiar object; *p<0.05 vs VEH. N=11-12 for each group. VEH=Vehicle.

The effects of COMPOUND A in the NOR task (A/B retention sessions) after a 48-hour retention interval are illustrated in FIG. 72. As shown, COMPOUND A was associated with a dose dependent increase in preference for the novel object: main effect of dose [$F(4,54)=1.18$, $p=0.329$]; object type [$F(1,54)=25.06$, $p<0.001$]; dose by object type interaction [$F(4,54)=2.96$, $p=0.028$]. Post-hoc analysis indicated that COMPOUND A 15 mg/kg was associated with a non-significant trend toward a preference for the novel object ($p=0.054$) versus the familiar object compared to vehicle control. The 30, 60, and the 90 mg/kg doses were associated with a significant ($p<0.05$) preference for the novel object versus the familiar object. When the d2 ratios were analyzed, the following statistical results were obtained: effect of dose [$F(4,54)=2.91$, $p=0.030$]. Post hoc analysis indicated that that the 60 and the 90 mg/kg doses were associated with a significant difference ($p<0.05$) from the vehicle-control response.

Figure 73:
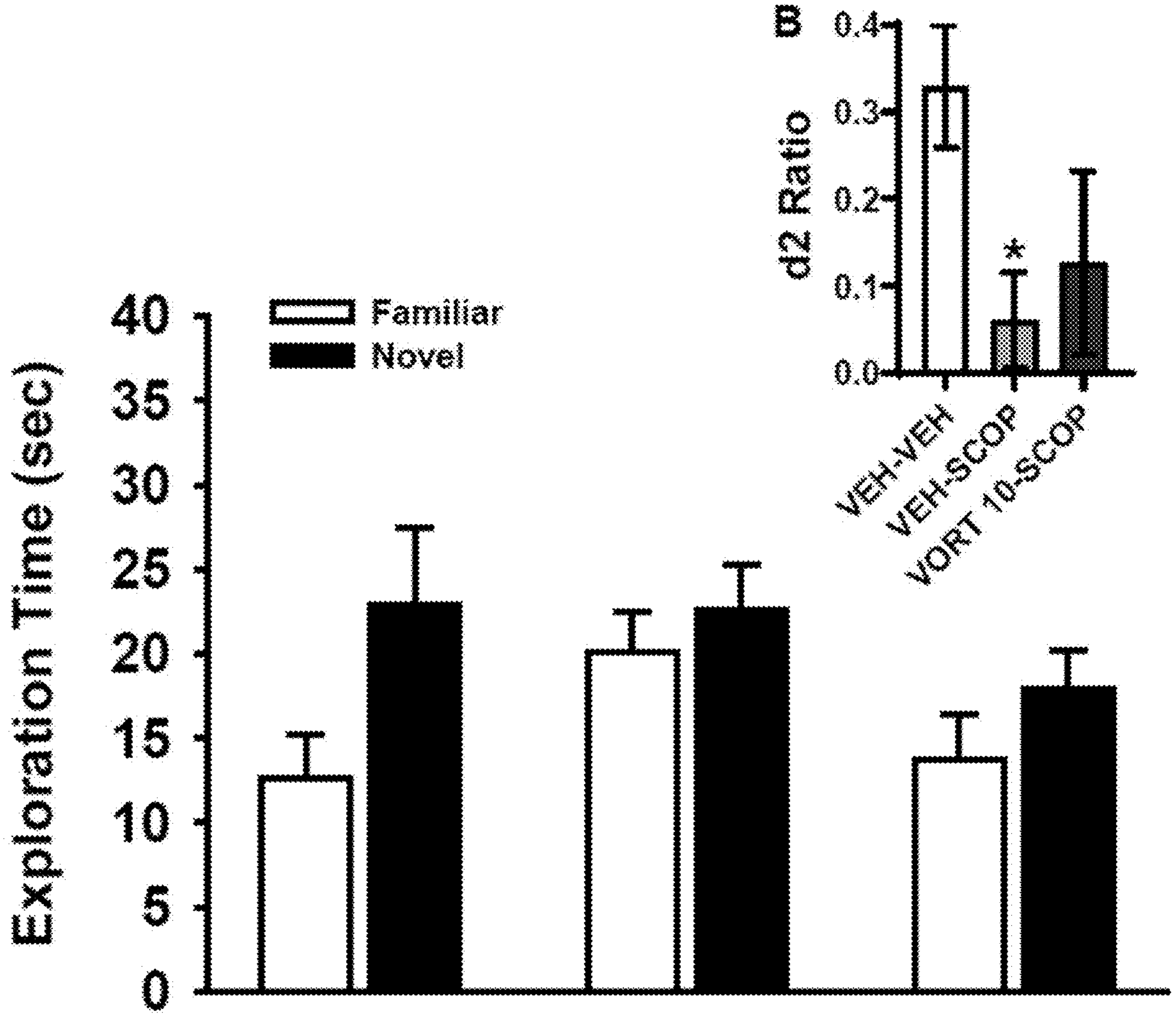
FIG. 73 shows effects of vortioxetine (10.0 mg/kg) in young-adult Wistar rats on performance of a spontaneous novel object recognition task scopolamine impairment model. Mean (±S.E.M) exploration times of the familiar and novel objects after 3 hr delays (A/B retention sessions) are illustrated in the main Fig (A). The inset (B) illustrates the mean (±S.E.M) discrimination (d2) ratios. d2 ratio=(novel−familiar)/(novel+familiar). +++p<0.001, novel vs familiar object; *p<0.05 vs VEH-VEH. N=9-11 for each group. VEH=vehicle; SCOP=scopolamine; VORT=vortioxetine.

Scopolamine Reversal Studies. The effects of the antidepressant treatment, vortioxetine (10.0 mg/kg) in the scopolamine reversal task (A/B retention sessions) after a 3-hour retention interval are illustrated in FIG. 73. In the analysis of the exploration times, the effect of treatment and the treatment x object type interaction were not significant ($p>0.05$). There was a significant effect of the object type [$F(1,26)=12.43$, $p=0.002$], however. Post hoc analysis indicated that there was a significant ($p=0.002$) preference for the novel object in the vehicle-treated subjects, but not those administered the vehicle-scopolamine or the vortioxetine-scopolamine combination. When the d2 ratios were analyzed, the following statistical results were obtained: effect of treatment, [$F(2,26)=3.26$, $p=0.055$]. Post hoc analysis indicated a significant difference from the vehicle-control response in the vehicle-scopolamine treated animals ($p=0.04$), but not the vortioxetine-scopolamine combination. It is also important to note that three of the twelve rats that were administered the vortioxetine-scopolamine combination exhibited adverse reactions during the A/A session (thigmotaxis, vocalizations, labored breathing) and were not evaluated further.

Figure 74:
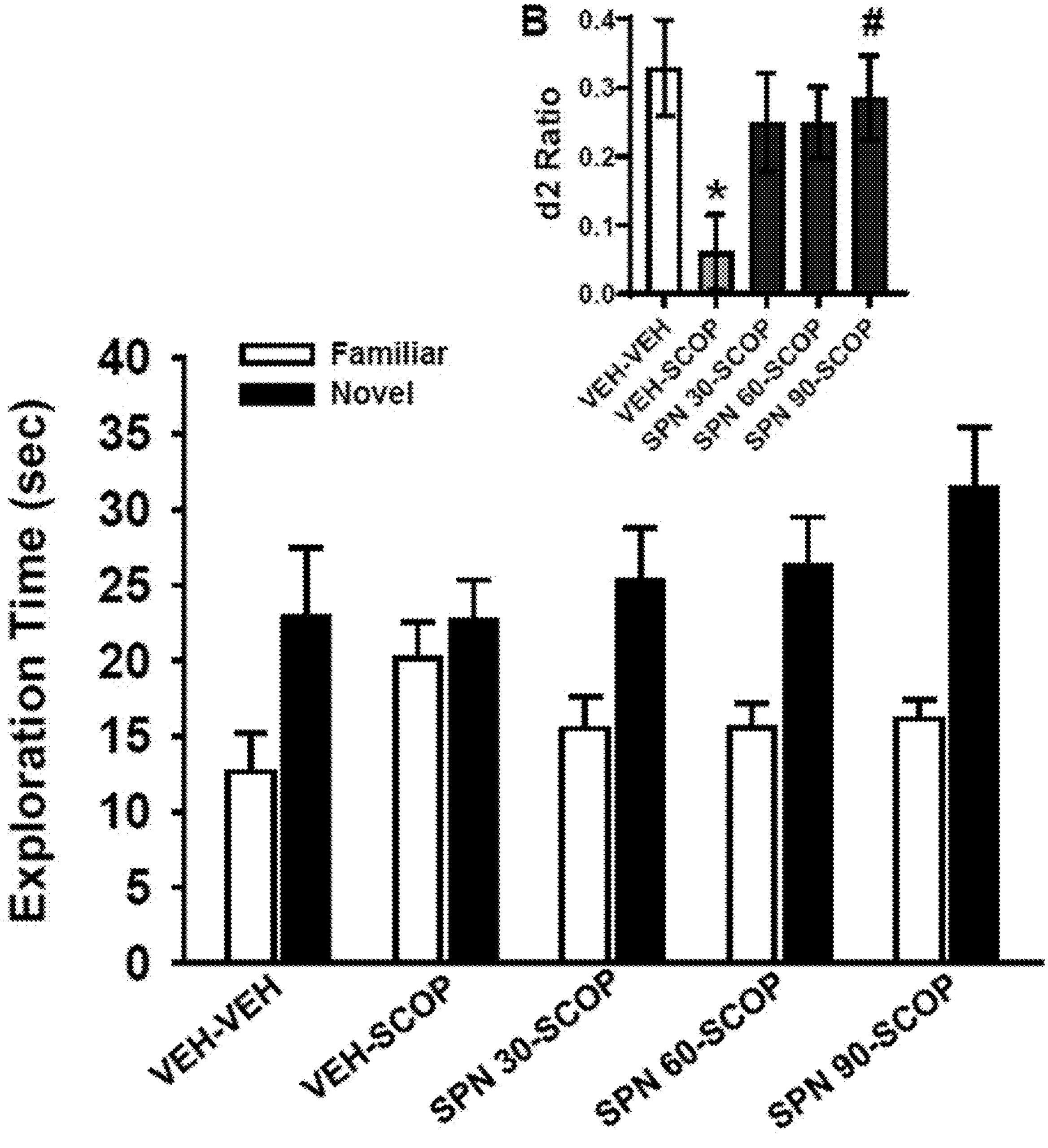
FIG. 74 shows dose-related effects of COMPOUND A (abbreviated as "SPN" in the figure) in young-adult Wistar rats on performance of a spontaneous novel object recognition task scopolamine impairment model. Mean (±S.E.M) exploration times of the familiar and novel objects after 3 hr delays (A/B retention sessions) are illustrated in the main Fig (A). The inset (B) illustrates the mean (±S.E.M) discrimination (d2) ratios. d2 ratio=(novel−familiar)/(novel+familiar). ++p<0.01, +++p<0.001, novel vs familiar object; *p<0.05 vs VEH-VEH; #p<0.05 vs VEH-SCOP. N=9-11 for each group. VEH=vehicle; SCOP=scopolamine.

The effects of COMPOUND A in the scopolamine reversal task (A/B retention sessions) after a 3-hour retention interval are illustrated in FIG. 74. In the analysis of the exploration times, the following statistical results were obtained: main effect of treatment [$F(4,47)=0.60$, $p=0.67$]; object type, [$F(1,47)=55.48$, $p<0.001$]; treatment by object type interaction, [$F(4,47)=2.66$, $p=0.044$]. In the post hoc analysis, subjects administered vehicle and the 30, 60, and 90 mg/kg COMPOUND A doses+scopolamine were associated with a significant ($p<0.05$) preference for the novel object versus the familiar object. In contrast, the subjects administered the vehicle-scopolamine combination did not exhibit a significant preference for the novel object. When the d2 ratios were analyzed, the following statistical results were obtained: effect of dose [$F(4,47)=2.75$, $p=0.039$]. Post hoc analysis indicated that the subjects administered the vehicle-scopolamine combination were significantly impaired compared to the vehicle-controls ($p<0.05$) and that the highest dose of COMPOUND A (90 mg/kg) significantly attenuated this effect of scopolamine.

In sum, the positive control/reference compound, donepezil, evaluated in the 48 hr delay version of NOR was associated with significant memory enhancement in both the object exploration analysis as well the d2 ratio analysis of the A/B sessions. These results demonstrate the validity of the NOR task for detecting pro-cognitive effects in rats. COMPOUND A was associated with statistically significant and dose-dependent improvements in NOR performance in the 48 hr delay version of NOR. In the object exploration analysis in the A/B sessions, the 3 higher doses of COMPOUND A were statistically different from vehicle control, while in the d2 ratio analysis, the highest two doses (60 and 90 mg/kg) were significantly different from vehicle control. In the scopolamine-reversal version of NOR, the reference compound vortioxetine was not associated with significant memory enhancement (i.e., attenuation of the scopolamine impairment). Three of the twelve rats that were administered the vortioxetine-scopolamine combination exhibited adverse reactions during the A/A session and were not evaluated further. COMPOUND A was associated with statistically significant improvements in NOR performance in the scopolamine-reversal version of NOR. In the object exploration analysis in the A/B sessions all 3 doses of COMPOUND A evaluated (30, 60, and 90 mg/kg) were associated with a statistically different response (i.e., preference for the novel object) compared to the vehicle-scopolamine treatment response, while in the d2 ratio analysis, the highest dose (90 mg/kg) of COMPOUND A was associated with a significant attenuation of the scopolamine impairment effect. These studies conducted in two versions of the NOR task support the potential of COMPOUND A for further development as a memory enhancing compound.

Example 23. Evaluation of the Effects of COMPOUND A on Sleep/Wake and EEG Parameters During the Active Period in the Orexin/Tta; Tet-O/Diphtheria Toxin A Mouse Model of Narcolepsy A study was conducted to investigate the dose-related effects of the test compound COMPOUND A in a novel inducible mouse model of narcolepsy. Telemetry-based electroencephalography (EEG) was employed to determine whether COMPOUND A had a therapeutic effect on symptoms following the induction of the narcolepsy phenotype. EEG patterns, electromyograph (EMG), core body temperature (Tb), and gross locomotor activity (LMA) were collected and analyzed.

Methods and Materials

Animals were housed in a temperature-controlled recording room under a 12/12 light/dark cycle and had food and water available ad libitum. Room temperature (24±2° C.), humidity (50±20% relative humidity), and lighting conditions were monitored and recorded daily.

Breeding of Orexin/tTA; Tet-O Diphtheria Toxin A ("DTA") mice. A conditional model of hypocretin neuron ablation (orexin/tTA; Tet-O diphtheria toxin A or "DTA mice") was used in this study. In this model of narcolepsy, degeneration of hypocretin/orexin neurons occurs when the neurotoxic diphtheria toxin subunit A (DTA) protein is synthesized in these cells. Expression of the DTA transgene is controlled through the tetracycline transactivator (Tet-off) system. When doxycycline (Dox) is in the diet, it binds the tetracycline transactivator (tTA) which prevents tTA from binding to the Tet-O regulatory site upstream of the prepro-hypocretin/DTA transgene. Removal of Dox from the diet enables tTA to bind Tet-O, thereby initiating transgene transcription. Because the Tet-O binding site is located exclusively in hypocretin/orexin (Hcrt) neurons, removal of dietary Dox (Dox(−)) results in accumulation of the neurotoxic DTA protein within these cells and degeneration of the Hcrt neurons occurs. After 6 weeks of Dox(−), >97% of Hcrt cells have degenerated and key features of narcolepsy, including wakefulness fragmentation and cataplexy, are readily evident.

Male DTA mice used in this study were bred at SRI and confirmed via genotyping. Mice were maintained on Dox+ chow to approximately 14 weeks of age before entering a 6-week period of degeneration by removal of dietary Dox. Therefore, mice were approximately 20 weeks of age at the start of the experimental period.

Surgical Procedures. For this study, 8 male DTA mice were implanted with chronic recording devices for continuous recordings of EEG, EMG, Tb, and LMA via telemetry. Under isoflurane anesthesia (1-4%), the fur was shaved from the top of the head and from the midabdominal region. After the skin had been disinfected with chlorhexidine and sterile water, a ~2.5 cm dorsal midline incision on top of the head was made. A subcutaneous pocket was blunt dissected along the left dorsal flank, and then irrigated with 1.5-3.0 ml of sterile saline. A sterile miniature transmitter (HD-X02, Data Sciences Inc., St Paul, MN) was then inserted through the incision placed into the subcutaneous pocket. The temporalis muscle was then retracted, and the skull was cauterized and thoroughly cleaned with a 3% hydrogen peroxide solution. Holes were drilled through the skull at the coordinates of −2.0 mm AP from bregma and 2.0 mm ML and at −1 mm AP from lambda on the midline. The two biopotential leads that were used as EEG electrodes were inserted into the holes and affixed to the skull with dental acrylic. The two biopotential leads that were used as EMG electrodes were sutured into the neck musculature. The incision was closed with absorbable suture.

Animals were administered an anti-inflammatory (NSAID, e.g., meloxicam), an analgesic (opioid, e.g., buprenorphine), and saline after surgery during the anesthetic recovery. Animals were closely monitored during anesthetic recovery until they were ambulatory. Subsequently, they were carefully observed daily (~5 min/day) until the incision was healed and the sutures were removed (1-2 wk post-surgery). NSAIDs were then administered once per day 72 h and opioids once per day for 24 hours following surgery, or as needed for signs of pain. Signs of pain included decreased activity, decreased food/water consumption, weight loss, hunched posture, abnormal respiratory rate or character, chattering/grinding teeth, piloerection, changes in facial expression (e.g., position/status of ears, eyes, whiskers), failure to groom, or overgrooming.

Experimental Design. Using a repeated-measures counter-balanced design, COMPOUND A (10, 30, 90 and 120 mg/kg, p.o.) and amphetamine (Amph; 2 mg/kg, i.p.) were administered at 10 ml/kg and tested for their effects on cataplexy, sleep/wake parameters, Tb, and LMA compared to a vehicle control (Veh; 4% DMSO, 30% PEG400, 66% HPβCD [30% in H2O]) in DTA mice. Injections occurred just prior to the start of the dark period (before the start of Zeitgeber Hour [ZT] 12). Amph was dissolved in physiological saline rather than the vehicle control. EEG, EMG, Tb, and LMA were recorded via telemetry along with video recordings using Ponemah 6.41 software (Data Sciences Inc., St Paul, MN). A minimum of 3 days elapsed between treatments and the 6 dosings per animal were completed over a 3-week period. Animals were acclimated to the handling procedures and were administered multiple 0.2 ml water dosing (p.o) during the week before the first experimental day.

Results

Figure 82:
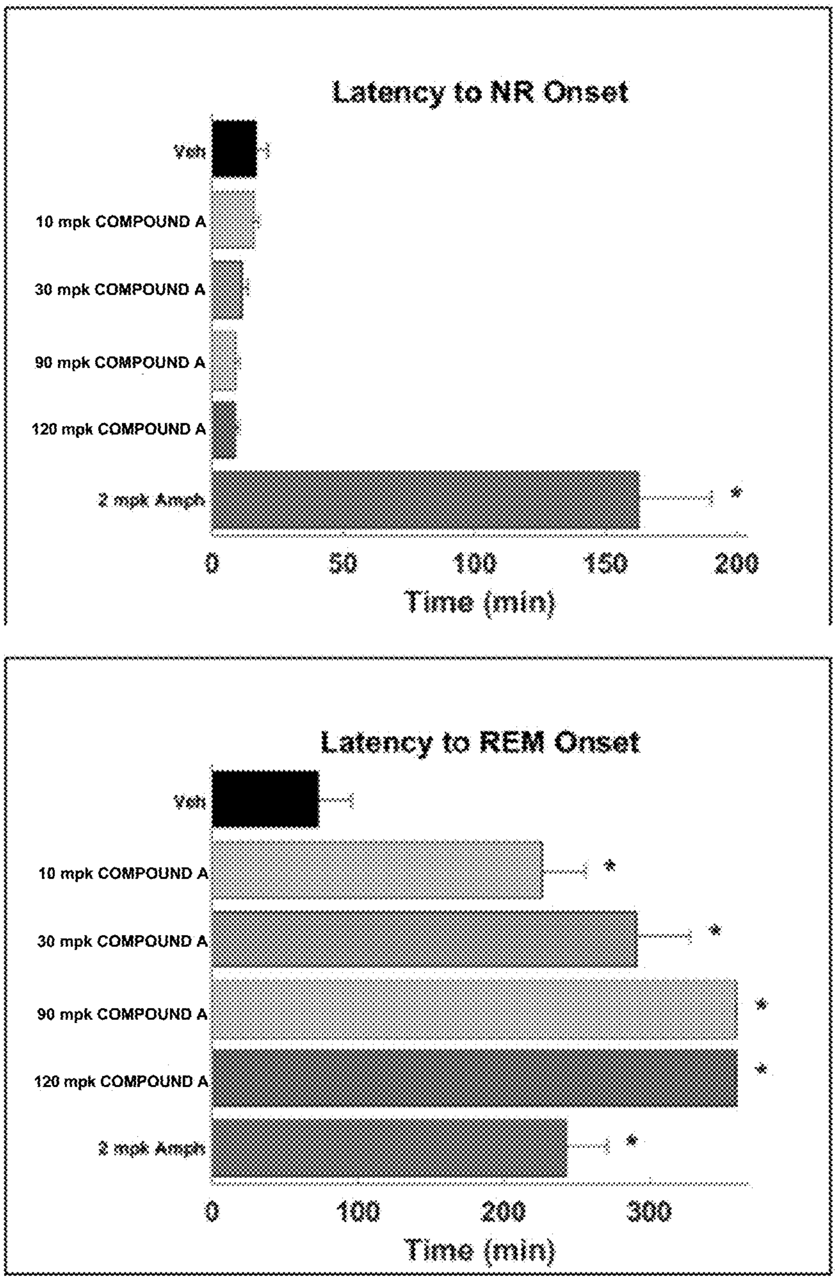
FIG. 82 shows latency (mean±SEM in this and all following figures) to the first 6 continuous epochs of NR (top panel) and the first 3 continuous epochs of REM (bottom panel). *=condition is significantly different from Veh (p<0.05).
Figure 83:
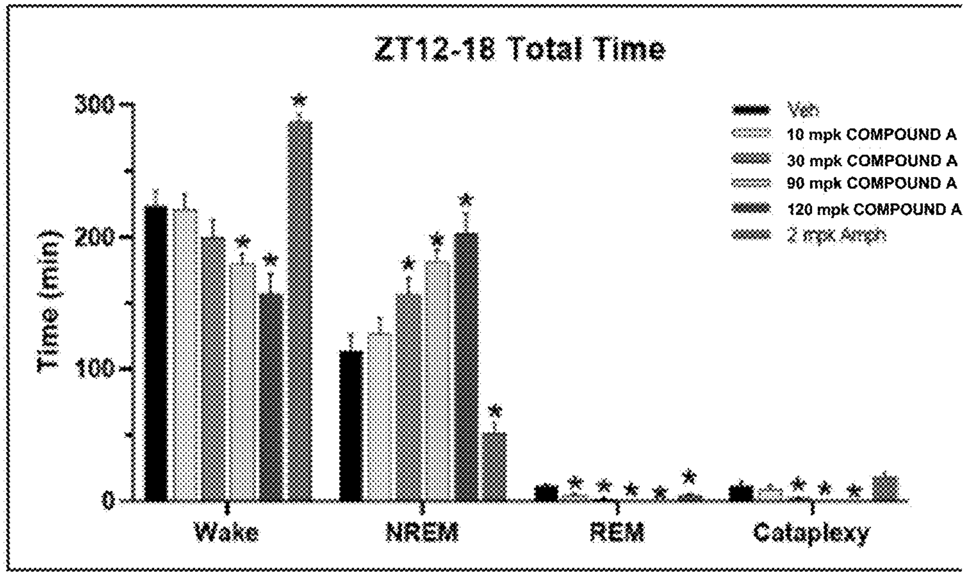
FIG. 83 shows the average time in Wake, NREM, REM, and C and the REM:NR ratios for the entire 6 h recording period. Top panel: The average time in W, NREM, REM, and C. Bottom panel: REM:NR ratios. *=significantly different from Veh (p<0.05).
Figure 83:
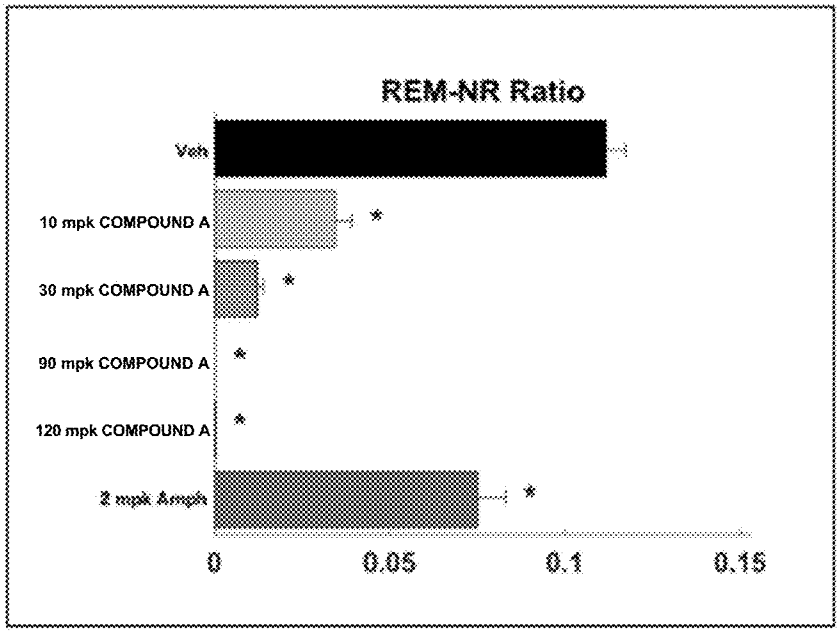

COMPOUND A: Administration of COMPOUND A was followed by strong, dose-related effects on most of the parameters studied here. All concentrations of COMPOUND A increased the latency to REM (FIG. 82). Total W time decreased following COMPOUND A at the two highest doses (90 and 120 mg/kg) and total NREM time increased following COMPOUND A at the three highest doses (30, 90 and 120 mg/kg) (FIG. 83). All concentrations of COMPOUND A decreased total time in REM and total time in C decreased following COMPOUND A at 30, 90 and 120 mg/kg. REM:NR ratios decreased following all test conditions (FIG. 83), reflecting the suppression of REM sleep.

Figure 84:
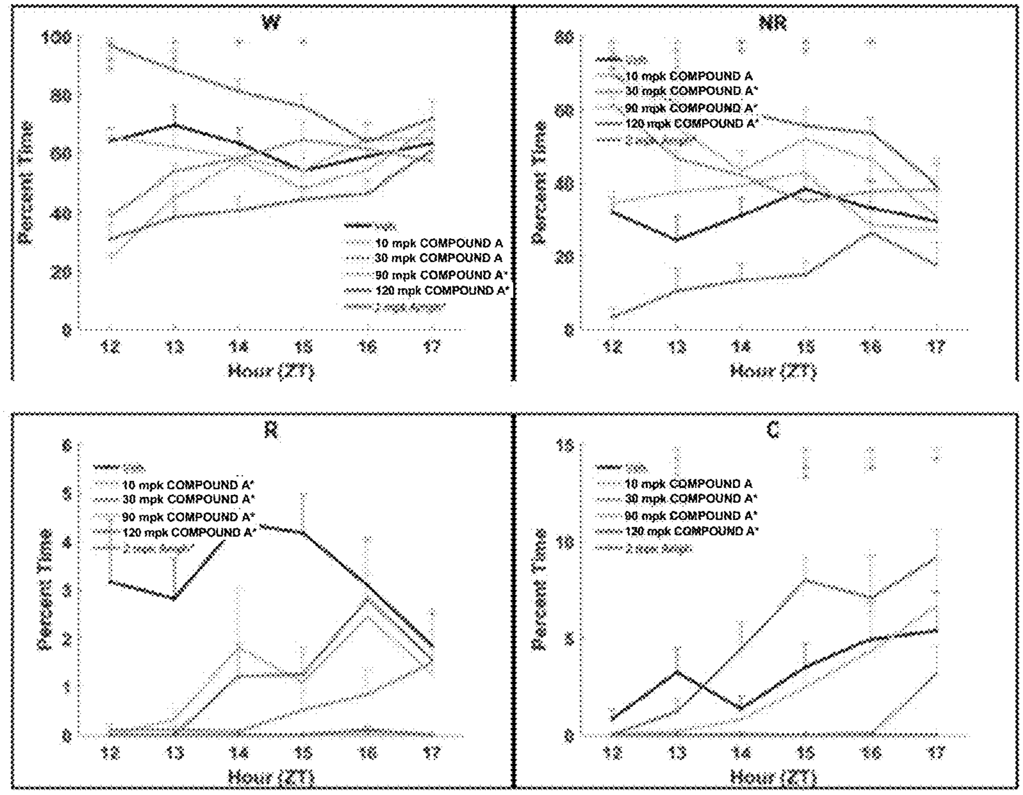
FIG. 84 shows hourly percent time spent in W, NR, REM, and C following Amph at 2 mg/kg and COMPOUND A at 10, 30, 90 and 120 mg/kg vs. Veh. Dosing occurred just prior to the start of ZT12. The asterisks above the graphs (color-coded to match the condition) represent time points with significant differences from Veh (p<0.05). The asterisks in the legends represent overall condition effects with significant differences from Veh (p<0.05). Top left: Percent time in W. ANOVA is significant for treatment and for treatment by time. Top right: Percent time in NR. ANOVA is significant for treatment and for treatment by time. Bottom left: Percent time in REM. ANOVA is significant for treatment only. Bottom right: Percent time in C. ANOVA is significant for treatment and for treatment by time.

W decreased during ZT12-14 and overall (treatment effect) following COMPOUND A at 120 mg/kg as well as ZT12-13 and overall following COMPOUND A at 90 mg/kg (FIG. 84). W also decreased during ZT12 following COMPOUND A at 30 mg/kg. NREM increased overall following COMPOUND A at 30, 60 and 120 mg/kg. During ZT12-ZT13, COMPOUND A at 30 and 90 mg/kg increased NREM, at 10 mg/kg NREM increased during ZT13. The highest dose, 120 mg/kg increased NREM during ZT12-ZT16. REM decreased overall following all concentrations of COMPOUND A and C decreased overall following all but the 10 mg/kg concentration of COMPOUND A. C also decreased during ZT13 and ZT15-ZT17 following COMPOUND A at 90 and 120 mg/kg, during ZT13 and ZT15-16 following COMPOUND A at 30 mg/kg, and during ZT13 following COMPOUND A at 10 mg/kg.

Figure 85:
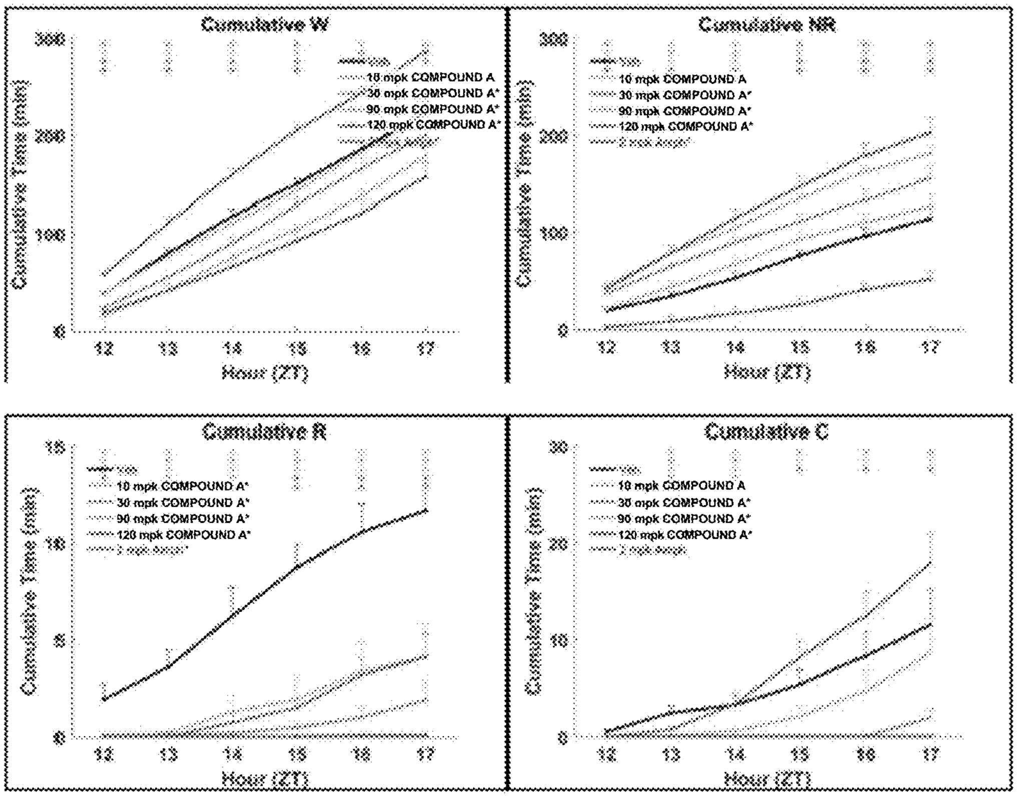
FIG. 85 shows cumulative time spent in W, NR, REM, and C following Amph at 2 mg/kg and COMPOUND A at 10, 30, 90 and 120 mg/kg vs. Veh. Dosing occurred just prior to the start of ZT12. The asterisks above the graphs (color-coded to match the condition) represent time points with significant differences from Veh ($p<0.05$). The asterisks in the legends represent overall condition effects with significant differences from Veh ($p<0.05$). Top left: Cumulative time in W. ANOVA is significant for treatment and for treatment by time. Top right: Cumulative time in NR. ANOVA is significant for treatment and for treatment by time. Bottom left: Cumulative time in REM. ANOVA is significant for treatment and for treatment by time. Bottom right: Cumulative time in C. ANOVA is significant for treatment and for treatment by time.

Cumulative NREM increased overall while cumulative W, REM and C decreased overall following COMPOUND A at 30, 90 and 120 mg/kg (FIG. 85). Cumulative REM also decreased following COMPOUND A at 10 mg/kg. Cumulative W and REM decreased and cumulative NREM increased during every hour of the recording period following COMPOUND A at 90 and 120 mg/kg. Following COMPOUND A at 30 mg/kg, cumulative W decreased during ZT12-ZT15, cumulative NREM increased during ZT12-ZT17, and cumulative REM decreased during ZT13-ZT17. Cumulative NREM increased during ZT13-ZT14 and cumulative REM decreased during ZT12-ZT17 following the lowest concentration of COMPOUND A. Cumulative C decreased during ZT13-ZT17 following COMPOUND A at 30, 90 and 120 mg/kg and during ZT13-ZT14 following COMPOUND A at 10 mg/kg.

Figure 86:
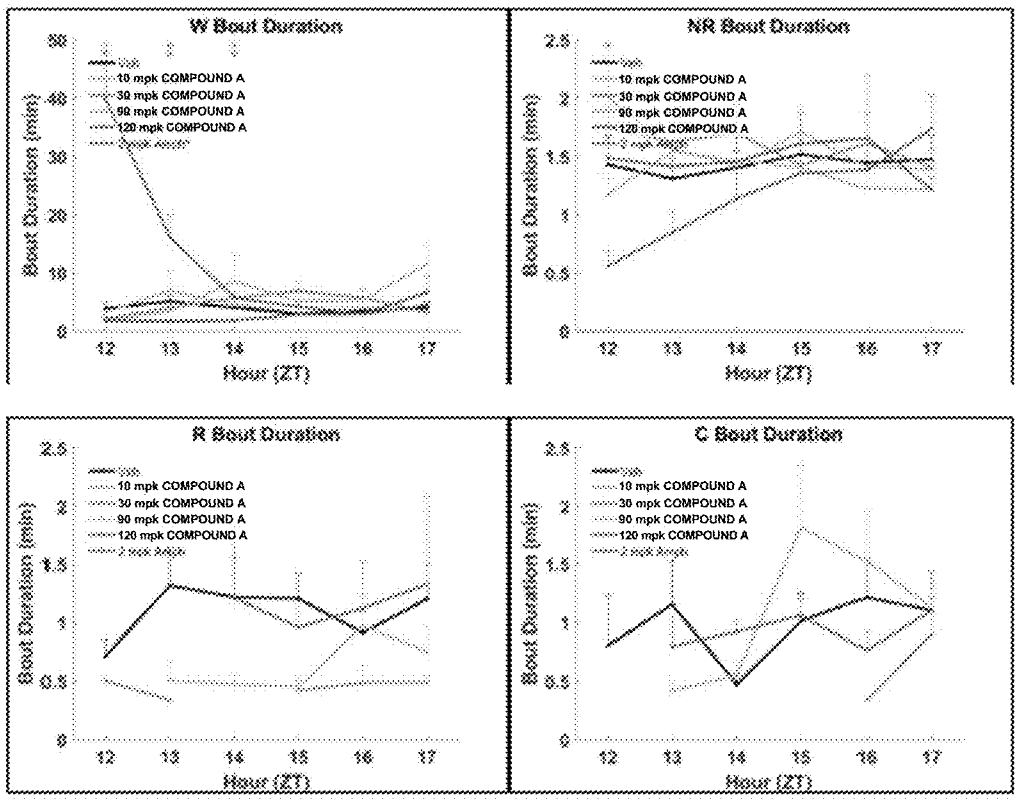
FIG. 86 shows average bout durations following Amph at 2 mg/kg and COMPOUND A at 10, 30, 90 and 120 mg/kg vs. Veh. Dosing occurred just prior to the start of ZT12. The asterisks above the graphs (color-coded to match the condition) represent time points with significant differences from Veh ($p<0.05$). The asterisks in the legends represent overall condition effects with significant differences from Veh ($p<0.05$). Top left panel: The average hourly W bout duration. ANOVA is significant for treatment and for treatment by time. Top right panel: The average hourly NR bout duration. ANOVA is significant for treatment by time only. Bottom left panel: The average hourly REM bout duration. ANOVA could not be performed due to the absence of REM during some hours for some conditions. Bottom right panel: The average hourly C bout duration. ANOVA could not be performed due to the lack of C during some hours for some conditions.
Figure 87:
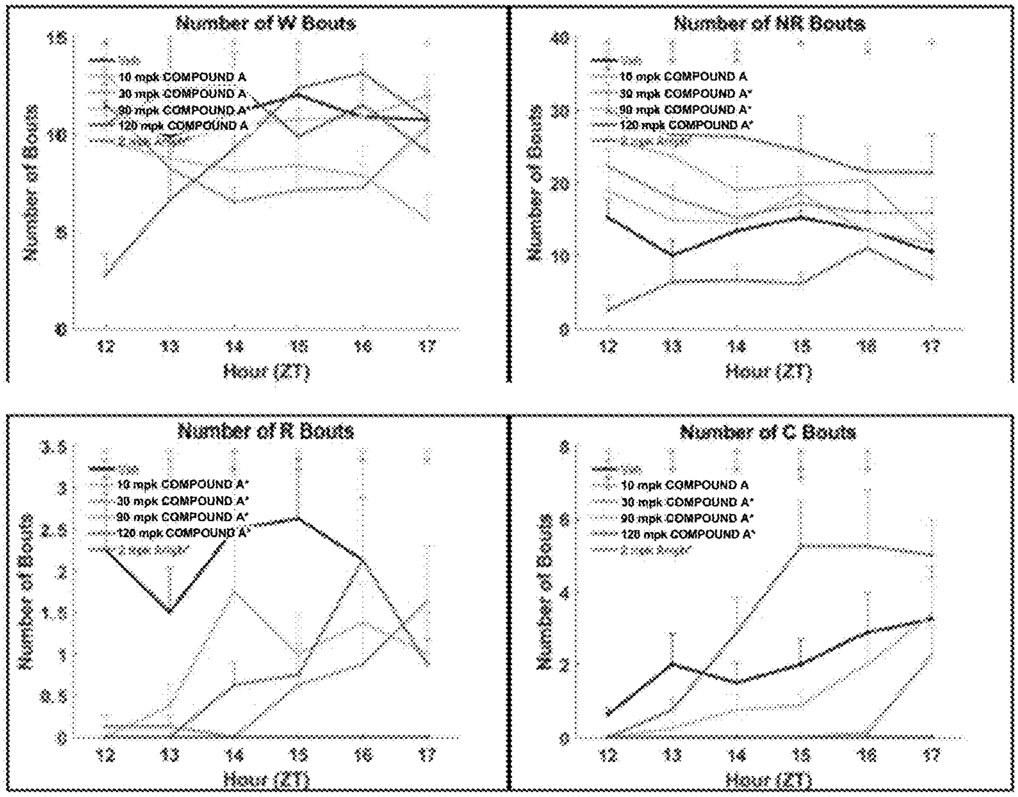
FIG. 87 shows average number of bouts following Amph at 2 mg/kg and COMPOUND A at 10, 30, 90 and 120 mg/kg vs. Veh. Dosing occurred just prior to the start of ZT12. The asterisks above the graphs (color-coded to match the condition) represent time points with significant differences from Veh ($p<0.05$). The asterisks in the legends represent overall condition effects with significant differences from Veh ($p<0.05$). Top left panel: The average hourly number of W bouts. ANOVA is significant for treatment and for treatment by time. Top right panel: The average hourly number of NR bouts. ANOVA is significant for treatment and for treatment by time. Bottom left panel: The average hourly number of REM bouts. ANOVA is significant for treatment and for treatment by time. Bottom right panel: The average hourly number of C bouts. ANOVA is significant for treatment and for treatment by time.
Figure 88:
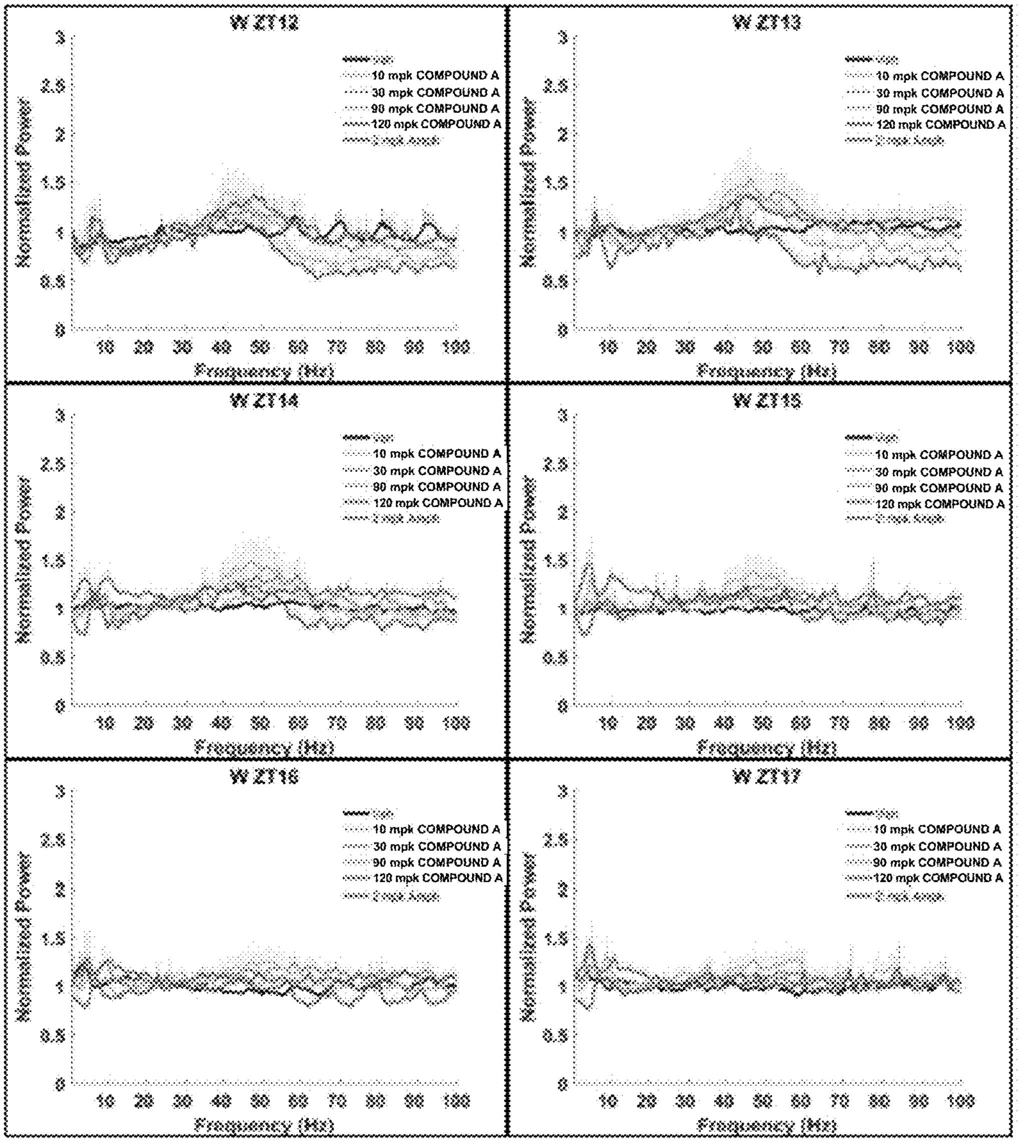
FIG. 88 shows the full normalized EEG spectrum (0.3-100 Hz) in W following Amph at 2 mg/kg and COMPOUND A at 10, 30, 90 and 120 mg/kg vs. Veh. Top left panel: The normalized W EEG spectrum for the 1st h following dosing. Top right panel: The normalized W EEG spectrum for the 2nd h following dosing. Middle left panel: The normalized W EEG spectrum for the 3rd h following dosing. Middle right panel: The normalized W EEG spectrum for the 4th h following dosing. Bottom left panel: The normalized W EEG spectrum for the 5th h following dosing. Bottom right panel: The normalized W EEG spectrum for the 6th h following dosing.

Changes in sleep-wake amounts following COMPOUND A administration occurred primarily via changes in the number of sleep-wake bouts rather than through altered bout durations (FIGS. 86-87). W bout duration decreased during ZT13-ZT14 following COMPOUND A at 120 mg/kg and during ZT12 following COMPOUND A at 90 mg/kg but increased during ZT14 following COMPOUND A at 30 mg/kg (FIG. 86). The number of W bouts decreased overall following COMPOUND A at 90 mg/kg and the number of NREM bouts increased overall following COMPOUND A at 30, 90 and 120 mg/kg (FIG. 87). The number of REM bouts decreased overall following all concentrations of COMPOUND A and the number of C bouts decreased overall following COMPOUND A at 30, 90 and 120 mg/kg. The number of W bouts also decreased during ZT15 and ZT17 following COMPOUND A at 90 mg/kg and during ZT14-ZT15 following COMPOUND A at 30 mg/kg. The number of NR bouts increased during ZT12-ZT14 and ZT16 following COMPOUND A at 90 and 120 mg/kg and during ZT12-ZT13 and ZT17 following COMPOUND A at 30 mg/kg. The number of REM bouts decreased during ZT12-ZT16 following 3466 at 90 and 120 mg/kg, during ZT12-ZT14 following 3466 at 30 mg/kg, and during ZT12-ZT13 following COMPOUND A at 10 mg/kg. The number of C bouts decreased during ZT12-ZT16 following COMPOUND A at 30, 90 and 120 mg/kg and during ZT12 following COMPOUND A at 10 mg/kg.

Figure 89:
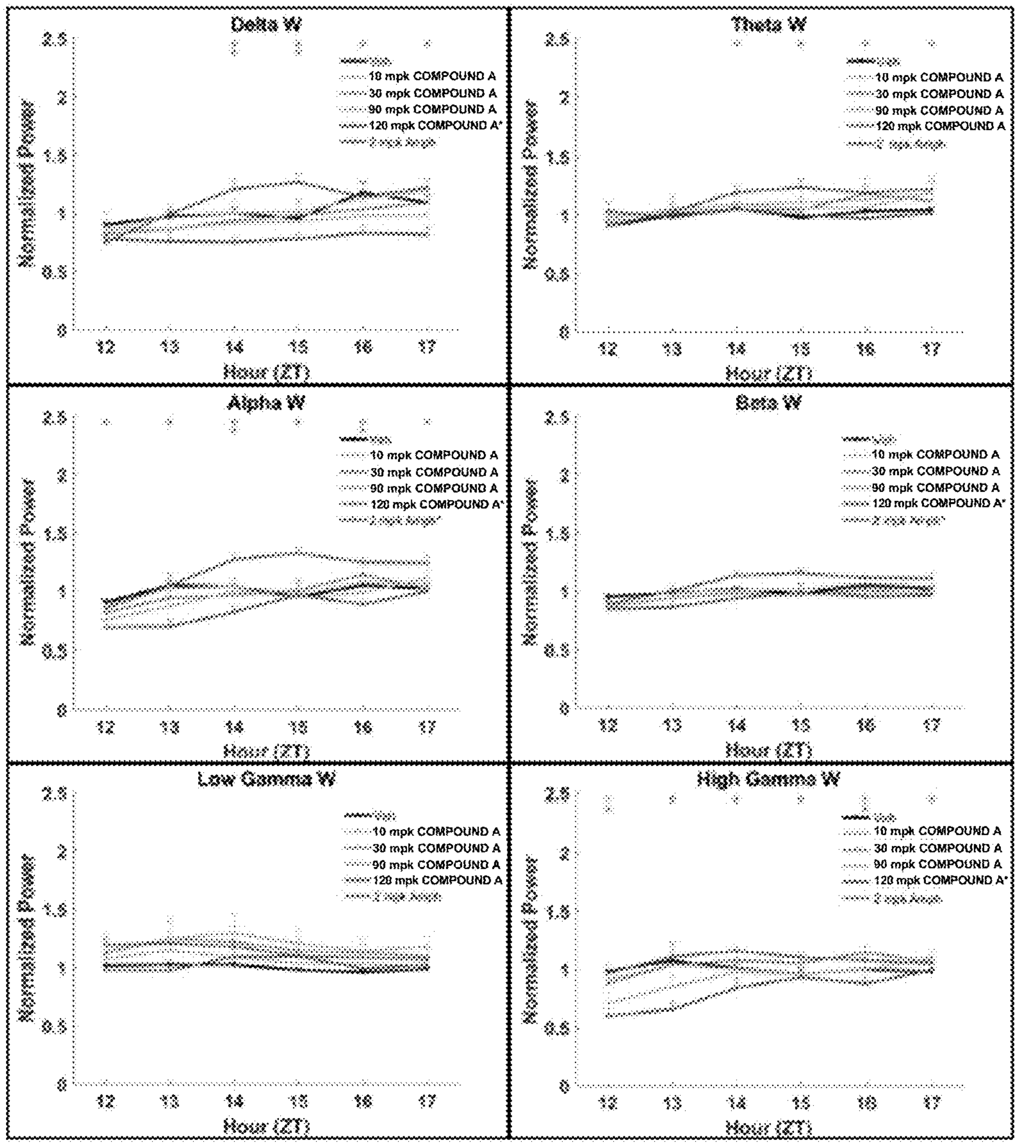
FIG. 89 shows average hourly EEG power in W for 6 standard frequency bands (delta, theta, alpha, beta, low gamma, and high gamma) following Amph at 2 mg/kg and COMPOUND A at 10, 30, 90 and 120 mg/kg vs. Veh. Data were normalized to the 6 h average following Veh control. The asterisks above the graphs (color-coded to match the condition) represent time points with significant differences from Veh. The asterisks in the legends represent overall condition effects with significant differences from Veh. Top left panel: The average hourly power during W in the delta frequency range. ANOVA is significant for treatment and for treatment by time. Top right panel: The average hourly power during W in the theta frequency range. ANOVA is significant for treatment by time only. Middle left panel: The average hourly power during W in the alpha frequency range. ANOVA is significant for treatment and for treatment by time. Middle right panel: The average hourly power during W in the beta frequency range. ANOVA is significant for treatment only. Bottom left panel: The average hourly power during W in the low gamma frequency range. ANOVA is not significant. Bottom right panel: The average hourly power during W in the high gamma frequency range. ANOVA is significant for treatment and for treatment by time.
Figure 90:
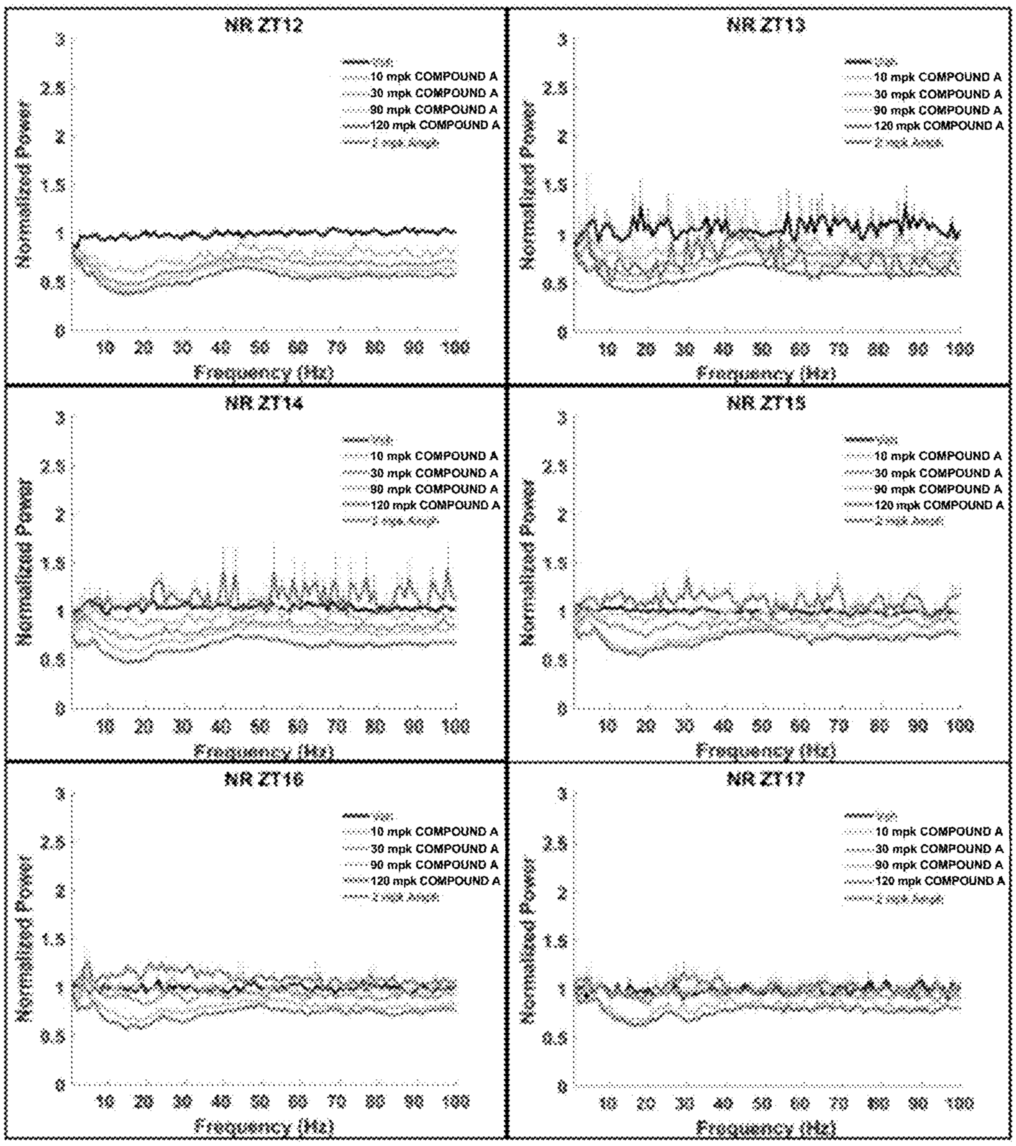
FIG. 90 shows the full normalized EEG spectrum (0.3-100 Hz) in NR following Amph at 2 mg/kg and COMPOUND A at 10, 30, 90 and 120 mg/kg vs. Veh. Top left panel: The normalized NR EEG spectrum for the 1st h following dosing. Top right panel: The normalized NR EEG spectrum for the 2nd h following dosing. Middle left panel: The normalized NR EEG spectrum for the 3rd h following dosing. Middle right panel: The normalized NR EEG spectrum for the 4th h following dosing. Bottom left panel: The normalized NR EEG spectrum for the 5th h following dosing. Bottom right panel: The normalized NR EEG spectrum for the 6th h following dosing.
Figure 91:
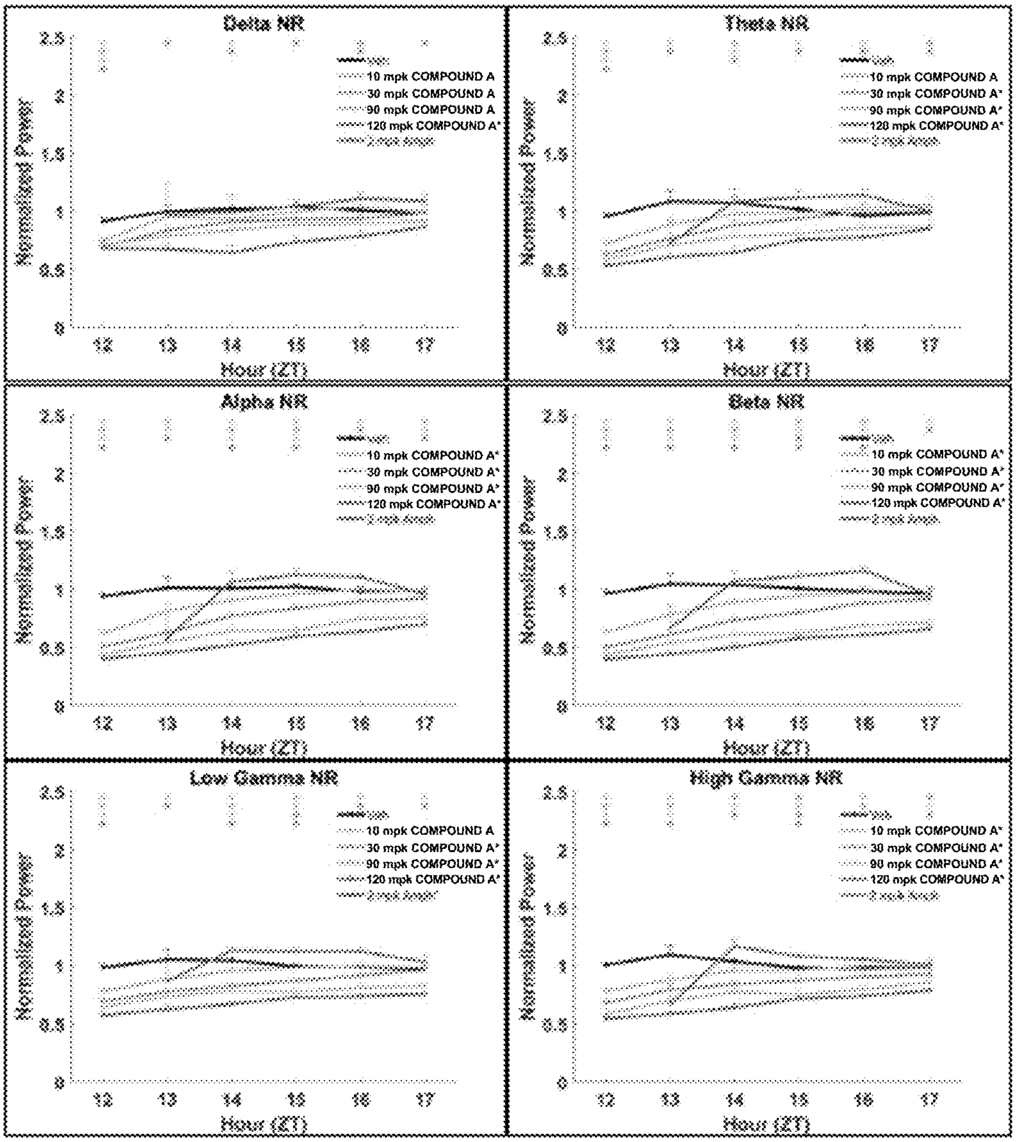
FIG. 91 shows average hourly EEG power in NR for 6 standard frequency bands (delta, theta, alpha, beta, low gamma, and high gamma) following Amph at 2 mg/kg and COMPOUND A at 10, 30, 90 and 120 mg/kg vs. Veh. Data were normalized to the 6 h average following Veh control. The asterisks above the graphs (color-coded to match the condition) represent time points with significant differences from Veh. The asterisks in the legends represent overall condition effects with significant differences from Veh. Top left panel: The average hourly power during NR in the delta frequency range. ANOVA is significant for treatment and for treatment by time. Top right panel: The average hourly power during NR in the theta frequency range. ANOVA is significant for treatment and for treatment by time. Middle left panel: The average hourly power during NR in the alpha frequency range. ANOVA is significant for treatment and for treatment by time. Middle right panel: The average hourly power during NR in the beta frequency range. ANOVA is significant for treatment and for treatment by time. Bottom left panel: The average hourly power during NR in the low gamma frequency range. ANOVA is significant for treatment and for treatment by time. Bottom right panel: The average hourly power during NR in the high gamma frequency range. ANOVA is significant for treatment and for treatment by time.
Figure 92:
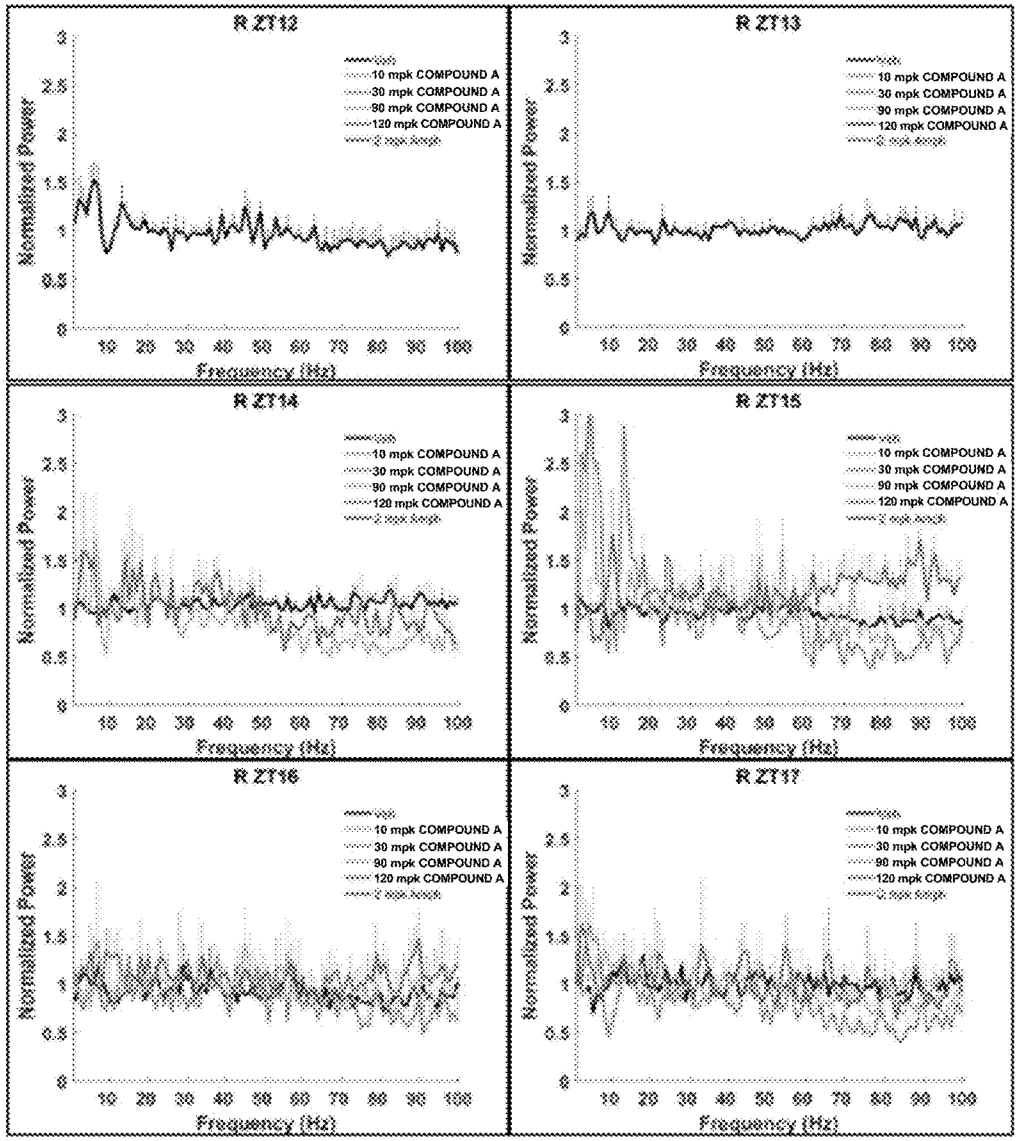
FIG. 92 shows the full normalized EEG spectrum (0.3-100 Hz) in REM following Amph at 2 mg/kg and COMPOUND A at 10, 30, 90 and 120 mg/kg vs. Veh. Top left panel: The normalized REM EEG spectrum for the 1st h following dosing. Top right panel: The normalized REM EEG spectrum for the 2nd h following dosing. Middle left panel: The normalized REM EEG spectrum for the 3rd h following dosing. Middle right panel: The normalized REM EEG spectrum for the 4th h following dosing. Bottom left panel: The normalized REM EEG spectrum for the 5th h following dosing. Bottom right panel: The normalized REM EEG spectrum for the 6th h following dosing.
Figure 93:
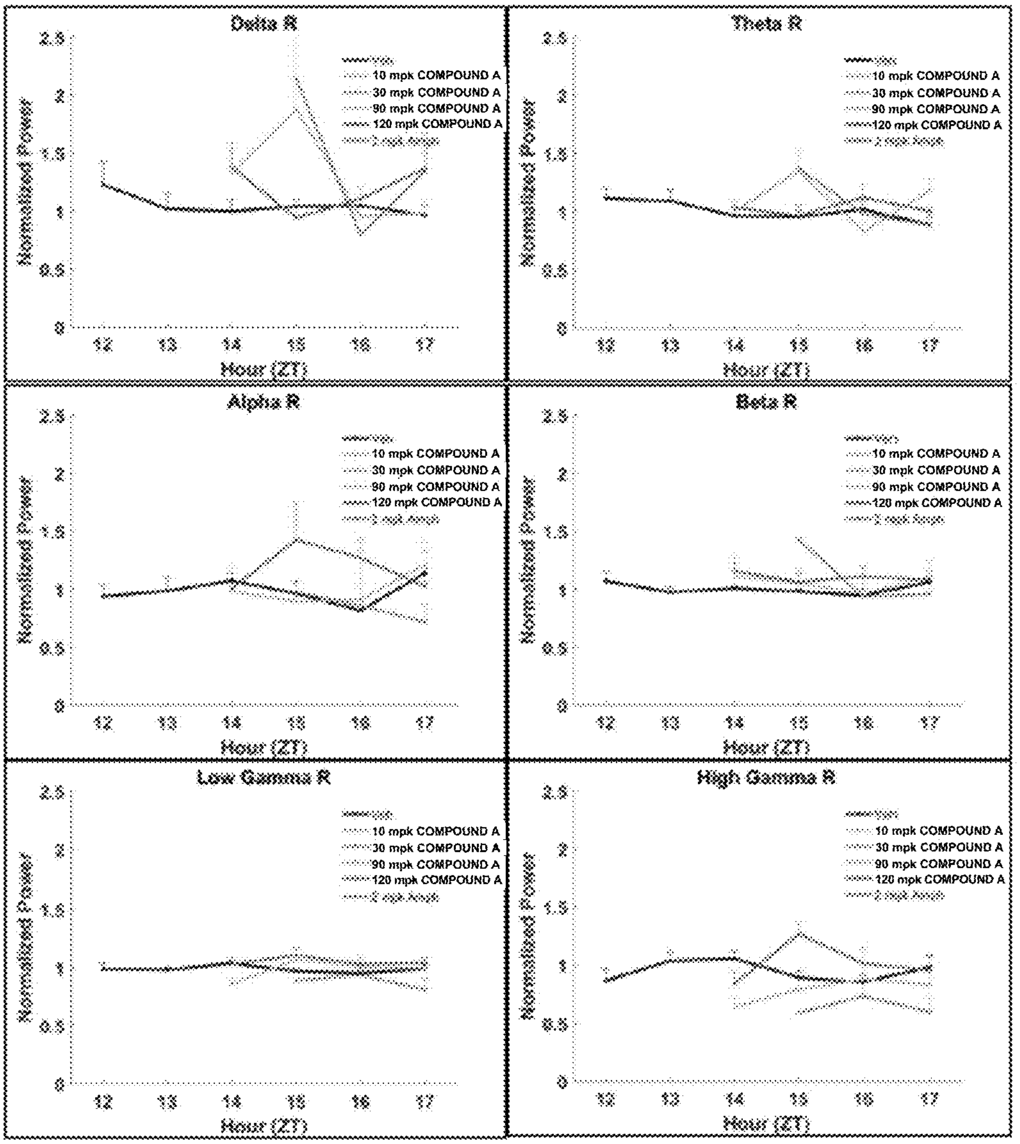
FIG. 93 shows average hourly EEG power in REM for 6 standard frequency bands (delta, theta, alpha, beta, low gamma, and high gamma) following Amph at 2 mg/kg and COMPOUND A at 10, 30, 90 and 120 mg/kg vs. Veh. Data were normalized to the 6 h average following Veh control.

EEG spectra also changed significantly following COMPOUND A administration (FIGS. 88-95). During W, significant overall decreases in EEG power were found for the delta, alpha, beta and high gamma frequency bands following COMPOUND A at 120 mg/kg (FIG. 89). Following COMPOUND A at 120 mg/kg, W delta decreased during ZT14-ZT17, W alpha decreased during ZT12-ZT14 and ZT16, and W high gamma decreased during ZT12-ZT13 and ZT16. During NREM sleep, large decreases in EEG power were observed across the entire spectrum (FIGS. 90-91). NREM delta power decreased overall following COMPOUND A at 120 mg/kg, NREM theta and low gamma decreased overall following COMPOUND A at 30, 90 and 120 mg/kg, and NREM alpha, beta and high gamma decreased overall following all concentrations of COMPOUND A. In addition, many hourly time points had significantly decreased power across all power bands following COMPOUND A, including every hour for every power band following COMPOUND A at 120 mg/kg (FIG. 91). For REM and C, too little time was spent in these states following COMPOUND A administration to be able to perform statistical analyses on these power spectra (FIGS. 92-95).

LMA decreased overall following COMPOUND A at 90 and 120 mg/kg and Tb decreased following 3466 at 120 mg/kg (FIG. 96).

Amphetamine: The results expected with amphetamine were obtained, namely, increased latency to the onset of both NREM and REM sleep (FIG. 82), increased W and decreased NREM (FIG. 83), and an overall increase in LMA (FIG. 96). Levels of C were generally unaffected by Amph (FIGS. 83-85). Although not designed to be a quantitative comparator to COMPOUND A, together, these observations demonstrate the efficacy of the bioassay.

In sum, administration of COMPOUND A was followed by very strong suppression of both REM and Cataplexy while significantly increasing NREM and decreasing W in a dose-related manner. Following the two highest concentrations of COMPOUND A, 90 and 120 mg/kg, REM and C were practically eliminated during the 6-h recording which effectively reduced REM:NR ratios to zero. The changes in time spent in each state occurred primarily via changes in the number of bouts of each state. Highly significant decreases in EEG power during NREM sleep were found across the entire power spectrum, indicative of brain penetration by COMPOUND A and engagement of molecular targets that underlie brain networks that contribute to EEG activity. Significant decreases in NREM EEG power were even found following the lowest concentration of COMPOUND A tested. Since few other measures were affected by the 10 mg/kg concentration, both REM sleep time and NREM EEG power could be particularly sensitive to the effects of COMPOUND A on the brain network that contributes to ongoing EEG activity. It should be noted the 30 mg/kg dose had no significant effect on the total amount of W across the 6 h period analyzed and the effect on NREM sleep was transient and significant only during the first hour post-dosing.

The highest doses of COMPOUND A reduced spectral activity in the high gamma range during W for the first 1-2 hours after administration; this EEG band is often associated with cognition in conjoint electrophysiological and behavioral tasks. Although it is unclear whether cognition assessed in other environments would be affected, at least when measured in the familiar home cage environment, the overwhelming effect of COMPOUND A is to increase NR sleep and suppress EEG spectral power, particularly at the 120 mg/kg concentration.

The strong suppression of C following COMPOUND A supports treatment of narcolepsy. The strong promotion of NREM suggests this compound would preferably be administered during the inactive or sleep phase.

Example 24. Additional Analyses on the In Vivo Effect of Viloxazine Derivative COMPOUND a in Orexin-DTA Transgenic Mice A study was conducted to evaluate the in vivo effect of viloxazine derivative COMPOUND A in Orexin-DTA transgenic mice. Six (6) dosing conditions were administered: one (1) positive control d-Amphetamine sulfate (2 mg/kg), 4 doses of the test compound COMPOUND A (10, 30, 90 and 120 mg/kg), and one (1) vehicle control. EEG, electromyography (EMG), body temperature (Tb, s.c.) and locomotor activity (LMA) were collected via telemetry using a DSI data collection system (N=8 mice). Dose administration occurred just prior to light offset, the major activity period for nocturnal rodents such as mice. Only the first six (6) hours just following dose administration were scored and analyzed initially for the report. Based on the results, further analyses were warranted to determine the time course for the suppression of cataplexy. Since cataplexy was at baseline levels following the administration of d-Amphetamine and the 10 mg/kg concentration of COMPOUND A at the end of the first 6 hours, no further analyses of these conditions were performed. Therefore, for the second 6-h period further analyses were performed on four (4) conditions: COMPOUND A at 30, 90, and 120 mg/kg and a vehicle control.

Latency to sleep onset, hourly and cumulative sleep/wake amounts, and sleep/wake/cataplexy consolidation measures (bout duration and number of bouts per hour) were assessed for the last 6 h of the dark period (Zeitgeber Hour [ZT] 19-ZT24). The EEG and EMG recordings were scored in 10 s epochs for wake (W), rapid eye movement sleep (REM), non-rapid eye movement sleep (NREM), and cataplexy (C).

Figure 75:
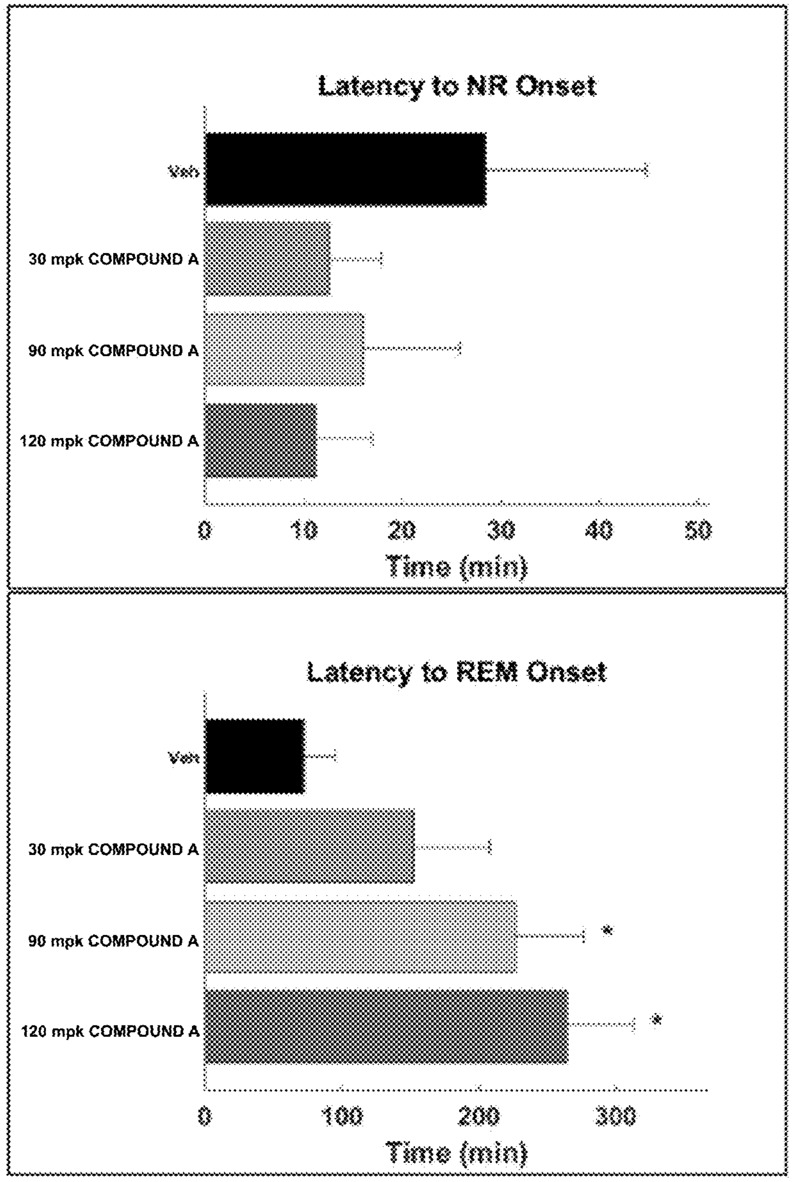
FIG. 75 shows latency (mean±SEM) to the first 6 continuous epochs of NR (top panel) and the first 3 continuous epochs of REM (bottom panel) for hours ZT19-ZT24 (the last half of the dark period). *=condition is significantly different from Veh (p<0.05).
Figure 76:
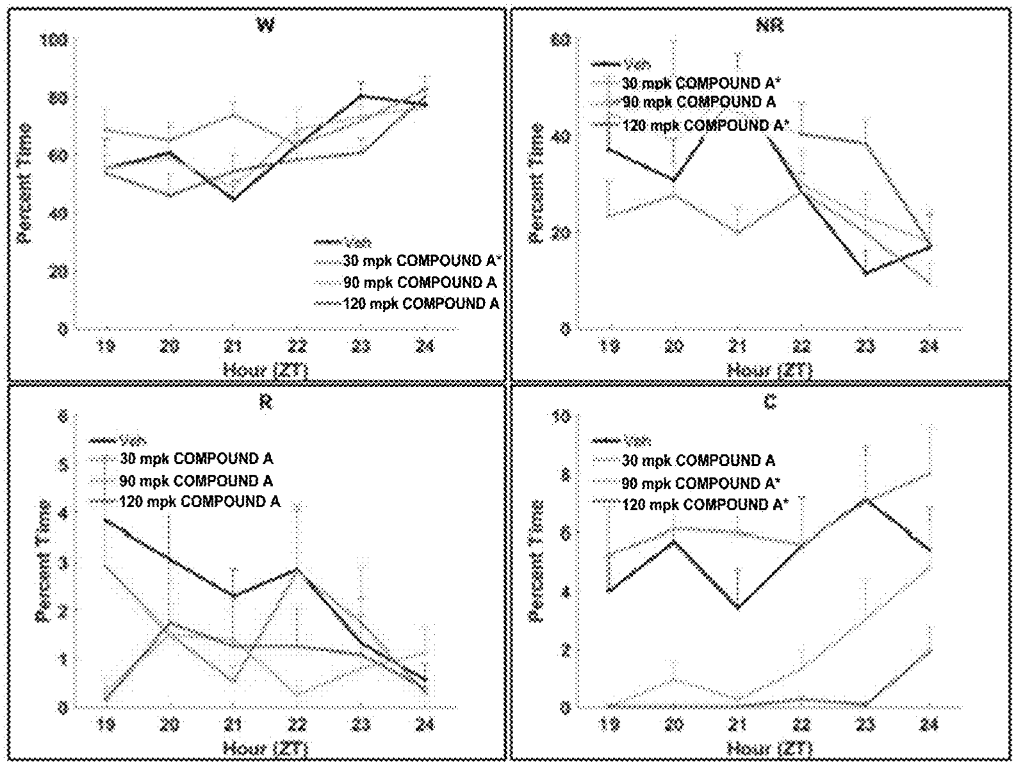
FIG. 76 shows hourly percent time spent in W, NR, REM, and C following COMPOUND A at 30, 90 and 120 mg/kg vs. Veh for hours ZT19-ZT24 (the last half of the dark period). Dosing occurred just prior to ZT12 (the start of hour ZT13). The asterisks in the legends represent overall condition effects with significant differences from Veh (p<0.05). Top left: Percent time in W. ANOVA is significant for treatment only. Top right: Percent time in NR. ANOVA is significant for treatment only. Bottom left: Percent time in REM. ANOVA is N.S. Bottom right: Percent time in C. ANOVA is significant for treatment only.
Figure 77:
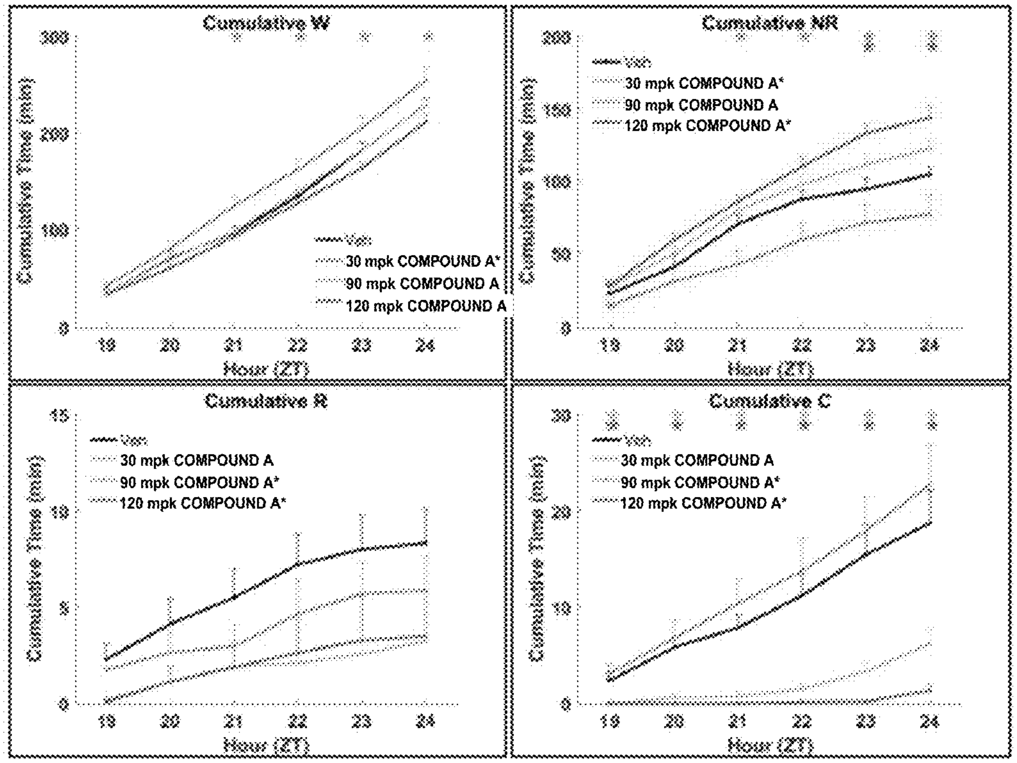
FIG. 77 shows cumulative time spent in W, NR, REM, and C following COMPOUND A at 30, 90 and 120 mg/kg vs. Veh for hours ZT19-ZT24 (the last half of the dark period). Dosing occurred just prior to ZT12 (the start of hour ZT13). The asterisks above the graphs (color-coded to match the condition) represent time points with significant differences from Veh (p<0.05). The asterisks in the legends represent overall condition effects with significant differences from Veh (p<0.05). Top left: Cumulative time in W. ANOVA is significant for treatment and for treatment by time. Top right: Cumulative time in NR. ANOVA is significant for treatment and for treatment by time. Bottom left: Cumulative time in REM. ANOVA is significant for treatment only. Bottom right: Cumulative time in C. ANOVA is significant for treatment and for treatment by time.
Figure 78:
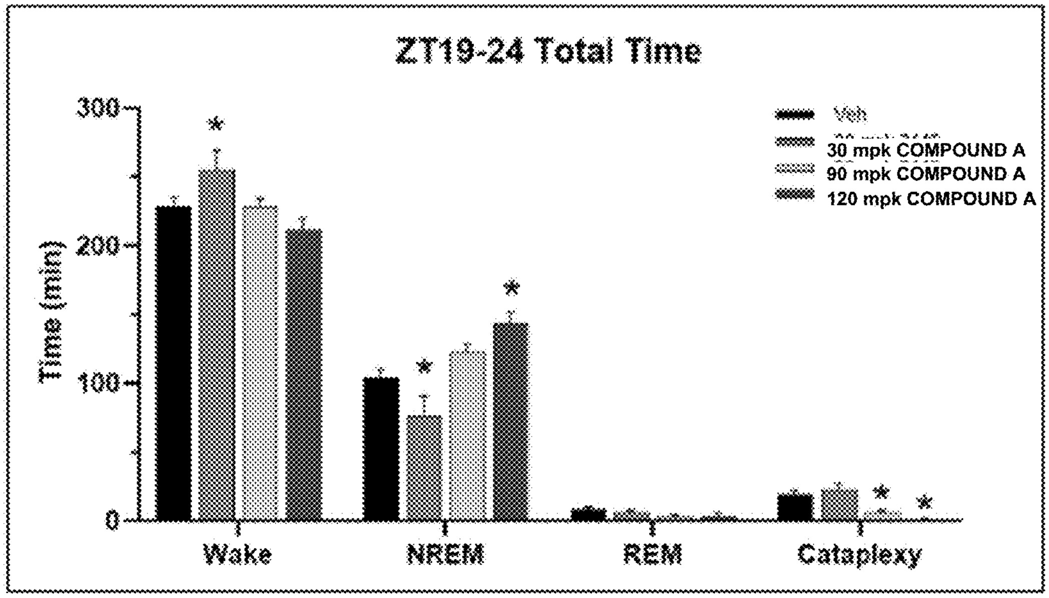
FIG. 78 shows the total time in Wake, NREM, REM, and C (top panel) and the REM:NR ratios (bottom panel) for the entire 6 h period from ZT19-ZT24 (the last half of the dark period). Top panel: The total time in W, NREM, REM, and C. Bottom panel: The REM:NR ratios. *=significantly different from Veh (p<0.05).
Figure 78:
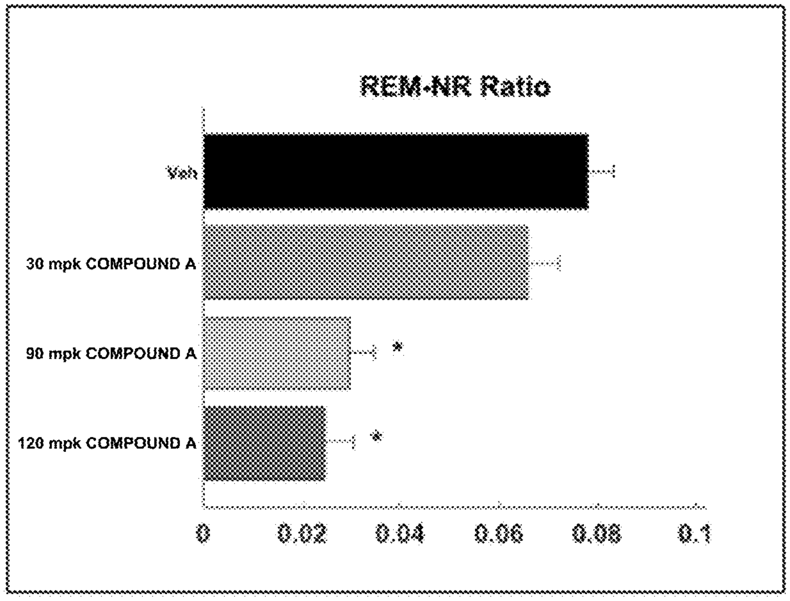

The latency to REM increased following COMPOUND A at 90 and 120 mg/kg (FIG. 75). W increased overall (treatment effect) and NREM decreased overall for hourly, cumulative and total time effects following COMPOUND A at 30 mg/kg (FIGS. 76-78). NREM increased overall for hourly, cumulative and total time effects following COMPOUND A at 120 mg/kg. C continued to be significantly decreased following COMPOUND A at the two highest concentrations and was decreased overall for both hourly and cumulative data as well as for total time. Cumulative REM was decreased overall following COMPOUND A at 90 and 120 mg/kg. REM:NR ratios decreased following COMPOUND A at 90 and 120 mg/kg (FIG. 78).

Figure 79:
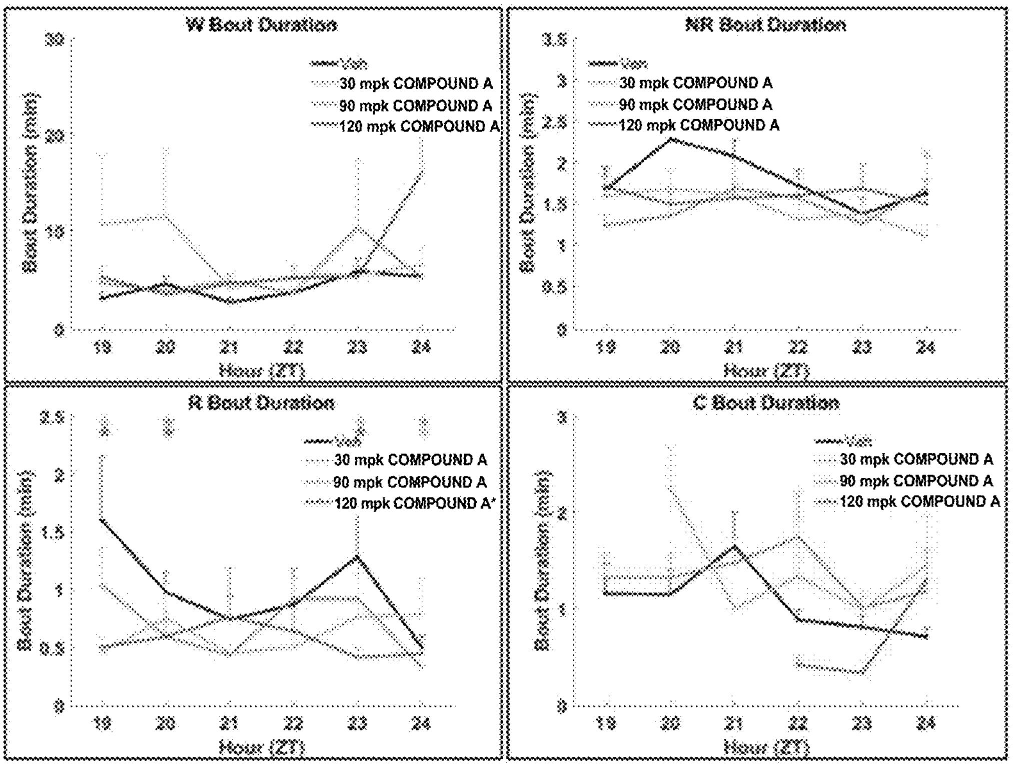
FIG. 79 shows average bout durations following COMPOUND A at 30, 90 and 120 mg/kg vs. Veh for hours ZT19-ZT24 (the last half of the dark period). Dosing occurred just prior to ZT12 (the start of hour ZT13). The asterisks above the graphs (color-coded to match the condition) represent time points with significant differences from Veh (p<0.05). The asterisks in the legends represent overall condition effects with significant differences from Veh (p<0.05). Top left panel: The average hourly W bout duration. ANOVA is N.S. Top right panel: The average hourly NR bout duration. ANOVA is N.S. Bottom left panel: The average hourly REM bout duration. ANOVA is significant for treatment and for treatment by time. Bottom right panel: The average hourly C bout duration. ANOVA could not be performed due to the lack of C during some hours for some conditions.
Figure 80:
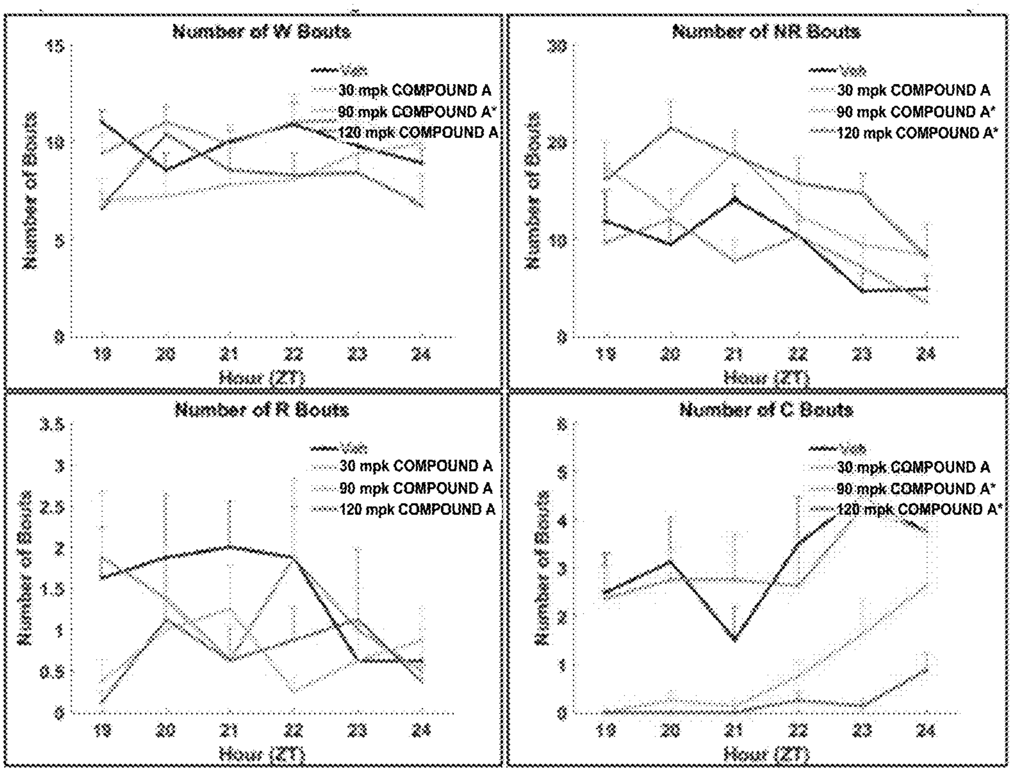
FIG. 80 shows average number of bouts following COMPOUND A at 30, 90 and 120 mg/kg vs. Veh for hours ZT19-ZT24 (the last half of the dark period). Dosing occurred just prior to ZT12 (the start of hour ZT13). The asterisks in the legends represent overall condition effects with significant differences from Veh (p<0.05). Top left panel: The average hourly number of W bouts. ANOVA is significant for treatment only. Top right panel: The average hourly number of NR bouts. ANOVA is significant for treatment only. Bottom left panel: The average hourly number of REM bouts. ANOVA is N.S. Bottom right panel: The average hourly number of C bouts. ANOVA is significant for treatment only.

REM bout durations decreased overall following COMPOUND A at 120 mg/kg (FIG. 79). The number of W bouts decreased overall following COMPOUND A at 90 mg/kg (FIG. 80). The number of C bouts decreased while the number of NREM bouts increased following COMPOUND A at 90 and 120 mg/kg.

Figure 81:
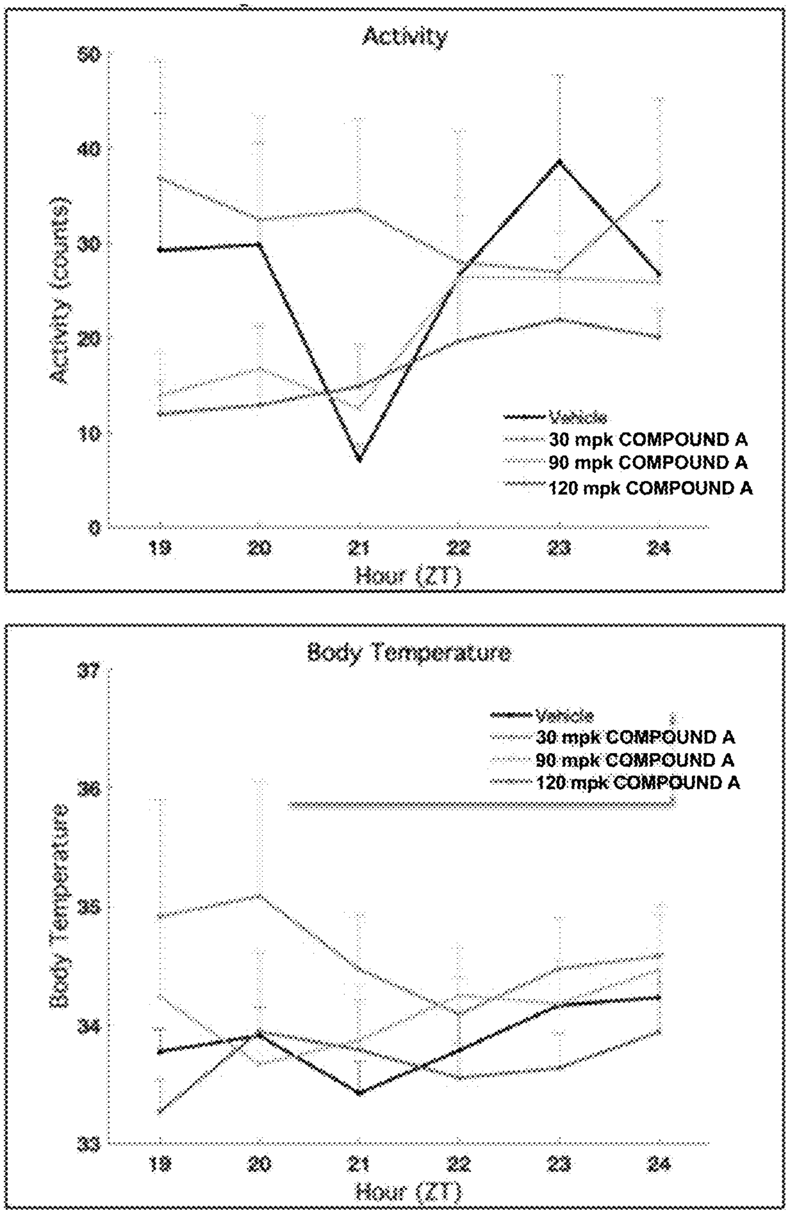
FIG. 81 shows average hourly LMA and Body Temperature following COMPOUND A at 30, 90 and 120 mg/kg vs. Veh for hours ZT19-ZT24 (the last half of the dark period). Dosing occurred just prior to ZT12 (the start of hour ZT13). Top panel: The average hourly Activity. ANOVA is N.S. Bottom panel: The average hourly Temperature. ANOVA is N.S.

No significant effects on s.c. body temperature or LMA were observed (FIG. 81).

In sum, many of the effects on sleep/wake parameters described in the first report were either diminished or absent during the second half of the dark period although C remained reduced for the two highest concentrations of COMPOUND A for ZT19-24. C was at vehicle levels following COMPOUND A at 30 mg/kg. However, W increased and NREM decreased following COMPOUND A at 30 mg/kg suggesting a rebound in wakefulness during this period. Interestingly, during the final hour of the recording period analyzed here (ZT24), most parameters for all COMPOUND A conditions were comparable to vehicle values. The exception was for C following the highest concentration of COMPOUND A. Although C occurred during ZT24 following COMPOUND A at 120 mg/kg, the levels were approximately half of vehicle levels (FIG. 76).

In Vitro Assays

Example 25. In Vitro Pharmacology for Compounds COMPOUND D, COMPOUND E, COMPOUND A, COMPOUND B and COMPOUND C A study was conducted to test 5 compounds in cellular and nuclear receptor functional and enzyme and uptake assays.

Methods and Materials

In Vitro Pharmacology: Cellular and Nuclear Receptor Functional Assays

| Assay Receptors | Source | Stimulus | Incubation | Measured Component | Detection Method | Bibl. |
|---|---|---|---|---|---|---|
| $5\text{-}HT_{2B}$ (h) (agonist effect) | human recombinant (CHO cells) | none (1 μM serotonin for control) | 30 min 37° C. | IP1 | HTRF | 782 |
| $5\text{-}HT_{2B}$ (h) (antagonist effect) | human recombinant (CHO cells) | serotonin (30 nM) | 30 min 37° C. | IP1 | HTRF | 782 |

-continued

| Assay Receptors | Source | Stimulus | Incubation | Measured Component | Detection Method | Bibl. |
|---|---|---|---|---|---|---|
| $5\text{-}HT_{2C}$ (h) (agonist effect) | human recombinant (HEK-293 cells) | none (1 μM serotonin for control) | 30 min 37° C. | $IP_1$ | HTRF | 782 |
| $5\text{-}HT_{2C}$ (h) (antagonist effect) | human recombinant (HEK-293 cells) | serotonin (10 nM) | 30 min 37° C. | $IP_1$ | HTRF | 782 |

The results are expressed as a percent of control agonist response or inverse agonist response $$\frac{\text{measured response}}{\text{control response}} * 100$$

and as a percent inhibition of control agonist response $$100 - \left(\frac{\text{measured response}}{\text{control response}} * 100\right)$$

obtained in the presence of the test compounds.

The EC50 values (concentration producing a half-maximal response) and IC50 values (concentration causing a half-maximal inhibition of the control agonist response) were determined by non-linear regression analysis of the concentration-response curves generated with mean replicate values using Hill equation curve fitting $$Y = D + \left[\frac{A - D}{1 + (C/C_{50})^{nH}}\right]$$

where Y=response, A=left asymptote of the curve, D=right asymptote of the curve, C=compound concentration, and C50=EC50 or IC50, and nH=slope factor. This analysis was performed using software developed at Cerep (Hill software) and validated by comparison with data generated by the commercial software SigmaPlot® 4.0 for Windows® (© 1997 by SPSS Inc.).

For the antagonists, the apparent dissociation constants (KB) were calculated using the modified Cheng Prusoff equation $$K_B = \frac{IC_{50}}{1 + (A/EC_{50A})}$$

where A=concentration of reference agonist in the assay, and EC50A=EC50 value of the reference agonist.

In Vitro Pharmacology: Enzyme and Uptake Assays

| Assay Transporters | Source | Substrate/ Stimulus/Tracer | Incubation | Measured Component | Detection Method | Bibl. |
|---|---|---|---|---|---|---|
| Norepinephrine transporter uptake (h) | human recombinant | norepinephrine hydrochloride, DL-[7-3H(N)] (500 nM) | 120 min RT | [3H]NE incorporation into cells | Scintillation counting | 184 |

The results are expressed as a percent of control specific activity $$\frac{\text{measured specific activity}}{\text{control specific activity}} * 100$$

and as a percent inhibition of control specific activity $$100 - \left(\frac{\text{measured specific activity}}{\text{control specific activity}} * 100\right)$$

obtained in the presence of the test compounds.

The IC50 values (concentration causing a half-maximal inhibition of control specific activity), EC50 values (concentration producing a half-maximal increase in control basal activity), and Hill coefficients (nH) were determined by non-linear regression analysis of the inhibition/concentration-response curves generated with mean replicate values using Hill equation curve fitting $$Y = D + \left[\frac{A - D}{1 + (C/C_{50})^{nH}}\right]$$

where Y=specific activity, A=left asymptote of the curve, D=right asymptote of the curve, C=compound concentration, C50=IC50 or EC50, and nH=slope factor. This analysis was performed using software developed at Cerep (Hill software) and validated by comparison with data generated by the commercial software SigmaPlot® 4.0 for Windows® (© 1997 by SPSS Inc.).

Results

In Vitro Pharmacology. Results showing an inhibition (or stimulation for assays run in basal conditions) higher than 50% were considered to represent significant effects of the test compounds. Results showing an inhibition (or stimulation) between 25% and 50% are indicative of weak to moderate effects. Results showing an inhibition (or stimulation) lower than 25% were not considered significant and mostly attributable to variability of the signal around the control level.

Results showing an inhibition or stimulation higher than 50% were considered to represent significant effects of the test compounds. Such effects were observed and are listed in Table 14

TABLE 14

| Assay | $IC_{50}$ | $k_B$ |
|---|---|---|
| COMPOUND D | | |
| 5-$HT_{2B}$(h) (antagonist effect) | 4.9E−06 M | 7.5E−07 M |
| Norepinephrine transporter uptake (h) | 8.7E−07 M | |
| COMPOUND E | | |
| 5-$HT_{2B}$(h) (antagonist effect) | 4.2E−06 M | 6.3E−07 M |
| Norepinephrine transporter uptake (h) | 2.6E−06 M | |
| COMPOUND A | | |
| 5-$HT_{2B}$(h) (antagonist effect) | 6.9E−06 M | 1.0E−06 M |
| Norepinephrine transporter uptake (h) | 3.9E−07 M | |
| COMPOUND B | | |
| 5-$HT_{2B}$(h) (antagonist effect) | 1.4E−05 M | 2.1E−06 M |
| Norepinephrine transporter uptake (h) | 1.9E−06 M | |
| COMPOUND C | | |
| 5-$HT_{2B}$(h) (antagonist effect) | 1.3E−05 M | 2.0E−06 M |
| Norepinephrine transporter uptake (h) | 1.8E−06 M | |

Example 26. hNav1.5 In Vitro Functional Assay for Compounds COMPOUND D, COMPOUND E, COMPOUND A, COMPOUND B, and COMPOUND C Electrophysiological assays were conducted to profile five compounds for activities on the ion channel target using the QPatch HT electrophysiological platform.

Methods and Materials

CYL6004QP2DR Nav1.5 Human Sodium Ion Channel Cell Based Automated Patch Clamp Assay. Cells were held at −120 mV for 100 ms, stepped to −130 mV for 100 ms, and stepped back to −120 mV for 100 ms to measure the leak current. Na channels exist in a) resting or closed state at −120 mV, b) a transient open state that inactivates to c) inactivated state at −10 mV. Na current inhibition within 1-2 ms of channel opening at −10 mV is open channel inhibition (pulse 1). In order to completely inactivate the Na channels and facilitate inactivated state-dependent binding of the drug, the channels were kept at open state (−10 mV) longer (pulsed for 500 ms) and then stepped back to −120 mV for 20 ms to recover from inactivation into resting or closed state (but the channels that had drug bound to them will not recover from inactivation and will not open) before stepping to −10 mV for 50 ms (pulse 2) to measure Na channels that are available to open. The higher inhibition seen at Pulse 2 is due to inactivated state-dependent inhibition. Pulse 1 and 2 are used to investigate drug binding to the open state and inactivated state of the Na channels, respectively. Each concentration of compound was applied for 5 minutes.

Data Analysis and Results

Current amplitudes more than 200 pA at the control stage were analyzed. The amplitude of the current was calculated by measuring the difference between the peak inward current on stepping to −10 mV (i.e. peak of the current) and remaining current at the end of the step. The current was assessed in vehicle control conditions and then at the end of each five (5) minute compound application. Reference standards were run as an integral part of each assay to ensure the validity of the results obtained. Results are summarized in Tables 15-16

TABLE 15

QPatch HT Estimated $IC_{50}$ Summary Data Table

| Compound Name | Target | Mode | Estimated $IC_{50}$ (μM) |
|---|---|---|---|
| COMPOUND D | Nav1.5 Human Sodium Ion Channel | Antagonist | >100 (Pulse 1) 14.1 (Pulse 2) |
| COMPOUND E | Nav1.5 Human Sodium Ion Channel | Antagonist | 92.6(Pulse 1) 5.7 (Pulse 2) |
| COMPOUND A | Nav1.5 Human Sodium Ion Channel | Antagonist | >100(Pulse 1) 19.6 (Pulse 2) |
| COMPOUND B | Nav1.5 Human Sodium Ion Channel | Antagonist | >100(Pulse 1) 7.6 (Pulse 2) |
| COMPOUND C | Nav1.5 Human Sodium Ion Channel | Antagonist | >100(Pulse 1) 8.5 (Pulse 2) |

TABLE 16

QPatch HT Reference Compound Data Table

| ITEM | Assay Name | Mode | Reference Compound | Estimated $IC_{50}$ (μM) |
|---|---|---|---|---|
| CYL6004QP2DR | Nav1.5 Human Sodium Ion Channel Cell Based Automated Patch Clamp Assay | Antag-onist | Tetracaine | 48.4 (Pulse 1) 0.77 (Pulse 2) |

Example 27. Study of COMPOUND D and COMPOUND E

A study was conducted to test COMPOUND D and COMPOUND E in Binding and enzyme and uptake assays.

COMPOUND D and COMPOUND E were tested at 1.0E-05 M.

The results are expressed as a percent of control specific binding $$\frac{\text{measured specific binding}}{\text{control specific binding}} * 100$$

and as a percent inhibition of control specific binding $$100 - \left(\frac{\text{measured specific binding}}{\text{control specific binding}} * 100\right)$$

obtained in the presence of the test compounds.

The IC50 values (concentration causing a half-maximal inhibition of control specific binding) and Hill coefficients (nH) were determined by non-linear regression analysis of the competition curves generated with mean replicate values using Hill equation curve fitting $$Y = D + \left[\frac{A - D}{1 + (C/C_{50})^{nH}}\right]$$

where Y=specific binding, A=left asymptote of the curve, D=right asymptote of the curve, C=compound concentration, C50=IC50, and nH=slope factor. This analysis was performed using software developed at Cerep (Hill software) and validated by comparison with data generated by the commercial software SigmaPlot® 4.0 for Windows® (© 1997 by SPSS Inc.).

The inhibition constants (Ki) were calculated using the Cheng Prusoff equation $$K_i = \frac{IC_{50}}{(1 + L/K_D)}$$

where L=concentration of radioligand in the assay, and KD=affinity of the radioligand for the receptor. A scatchard plot is used to determine the KD.

In Vitro Pharmacology: Enzyme and Uptake Assays

The results are expressed as a percent of control specific activity $$\frac{\text{measured specific activity}}{\text{control specific activity}} * 100$$

and as a percent inhibition of control specific activity $$100 - \left(\frac{\text{measured specific activity}}{\text{control specific activity}} * 100\right)$$

obtained in the presence of the test compounds.

The IC50 values (concentration causing a half-maximal inhibition of control specific activity), EC50 values (concentration producing a half-maximal increase in control basal activity), and Hill coefficients (nH) were determined by non-linear regression analysis of the inhibition/concentration-response curves generated with mean replicate values using Hill equation curve fitting $$Y = D + \left[\frac{A - D}{1 + (C/C_{50})^{nH}}\right]$$

where Y=specific activity, A=left asymptote of the curve, D=right asymptote of the curve, C=compound concentration, C50=IC50 or EC50, and nH=slope factor. This analysis was performed using software developed at Cerep (Hill software) and validated by comparison with data generated by the commercial software SigmaPlot® 4.0 for Windows® (© 1997 by SPSS Inc.).

Results

In Vitro Pharmacology. Results showing an inhibition (or stimulation for assays run in basal conditions) higher than 500 were considered to represent significant effects of the test compounds. Results showing an inhibition (or stimulation) between 25% and 50% are indicative of weak to moderate effects. Results showing an inhibition (or stimulation) lower than 25M were not considered significant and mostly attributable to variability of the signal around the control level.

Results showing an inhibition or stimulation higher than 50% were considered to represent significant effects of the test compounds. Such effects were observed and are listed in Table 17

TABLE 17

| Assay | 1.0E−05 M |
|---|---|
| COMPOUND D | |
| 5-$HT_{2B}$(h) (antagonist effect) | 81.5% |
| 5-$HT_{2c}$(h) (antagonist effect) | 72.4% |
| 5-$HT_{4e}$(h) (antagonist radioligand) | 78.6% |
| norepinephrine transporter(h) (antagonist radioligand) | 78.4% |
| COMPOUND E | |
| $MT_3$ ($ML_2$) (agonist radioligand) | 51.1% |
| 5-$HT_{2B}$(h) (agonist radioligand) | 80.2% |
| 5-$HT_{2C}$(h) (agonist radioligand) | 54.1% |
| $Ca^{2+}$ channel (L, diltiazem site) (benzothiazepines) (antagonist radioligand) | 78.9% |
| $Ca^{2+}$ channel (L, verapamil site) (phenylalkylamine) (antagonist radioligand) | 50.7% |
| $Na^+$ channel (site 2) (antagonist radioligand) | 84.5% |

Example 28a. Preclinical PK of COMPOUND D and COMPOUND E

A study was conducted for preclinical PK performance of COMPOUND D and COMPOUND E. Please see below for details on the study, with fasted mice orally dosed with COMPOUND D or COMPOUND E.

Study Details

| Administered compound | COMPOUND D | COMPOUND E |
|---|---|---|
| Species | Male CD-1 Mouse, fasted overnight, food returned 2 hours post dosing | |
| Study Group | 1.00 | 2.00 |
| Dosing route | PO | PO |
| Nominal dose (mg/kg) | 19.7 | 21.0 |
| Administered dose (mg/kg) | 21.3 | 21.0 |
| Formulation | 4% DMSO, 30% PEG400, 66% HPβCD (30% in $H_2O$) | 4% DMSO, 30% PEG400, 66% HPβCD (30% in $H_2O$) |

Results

Results are shown in FIGS. 97-98. Relevant data are summarized in below tables (ND=Not determined (Parameters not determined due to inadequately defined terminal elimination phase. BQL=Below the lower limit of quantitation (LLOQ). If the adjusted rsq (linear regression coefficient of the concentration value on the terminal phase) is less than 0.9, T1/2 might not be accurately estimated. If the % $AUC_{Extra}$>20%, $AUC_{0\text{-}inf}$, Cl, $MRT_{0\text{-}inf}$ and Vdss might not be accurately estimated. If the % $AUMC_{Extra}$>20%, $MRT_{0\text{-}inf}$ and $Vd_{ss}$ might not be accurately estimated. a: Bioavailability (%) was calculated using AUC0-inf (% $AUC_{Extra}$<20%) or AUC0-last (% $AUC_{Extra}$>20%) with nominal dose)

| Plasma concentration of Viloxazine in the Mouse (ng/mL) Group 1, COMPOUND D PO (19.74 mg/kg) | | | | | | | |
|---|---|---|---|---|---|---|---|
| | M1 | M2 | M3 | Mean | | SD | CV (%) |
| Time (h) | | | | | | | |
| 0.250 | 799 | 1040 | 958 | 932 | ± | 123 | 13.1 |
| 0.500 | 878 | 1120 | 824 | 941 | ± | 158 | 16.8 |
| 1.00 | 677 | 633 | 706 | 672 | ± | 36.8 | 5.47 |
| 2.00 | 262 | 273 | 339 | 291 | ± | 41.6 | 14.3 |
| 4.00 | 75.4 | 42.4 | 67.6 | 61.8 | ± | 17.2 | 27.9 |
| 8.00 | BQL | BQL | BQL | ND | ± | ND | ND |
| 24.0 | BQL | BQL | BQL | ND | | ND | ND |
| PK Parameters | | | | | | | |
| Rsq_adj | 0.975 | 0.999 | 0.999 | 0.991 | ± | 0.0139 | 1.40 |
| No. points used for $T_{1/2}$ | 3.00 | 3.00 | 3.00 | 3.00 | ± | 0.000 | 0.0 |
| $C_{max}$ (ng/g) | 878 | 1120 | 958 | 985 | ± | 123 | 12.5 |
| $T_{max}$ (h) | 0.500 | 0.500 | 0.250 | 0.417 | ± | 0.144 | 34.6 |
| $T_{1/2}$ (h) | 0.968 | 0.766 | 0.882 | 0.872 | ± | 0.102 | 11.7 |
| $T_{last}$ (h) | 4.00 | 4.00 | 4.00 | 4.00 | ± | 0.00 | 0.0 |
| $AUC_{0-last}$ (ng · h/g) | 1433 | 1502 | 1561 | 1499 | ± | 64.0 | 4.27 |
| $AUC_{0-inf}$ (ng · h/g) | 1538 | 1549 | 1647 | 1578 | ± | 59.8 | 3.79 |
| $MRT_{0-last}$ (h) | 1.29 | 1.15 | 1.31 | 1.25 | ± | 0.0866 | 6.93 |
| $MRT_{0-inf}$ (h) | 1.57 | 1.27 | 1.51 | 1.45 | ± | 0.161 | 11.1 |
| $AUC_{Extra}$ (%) | 6.85 | 3.02 | 5.23 | 5.03 | ± | 1.92 | 38.1 |
| $AUMC_{Extra}$ (%) | 23.5 | 12.2 | 18.2 | 17.9 | ± | 5.67 | 31.6 |

| Plasma concentration of Viloxazine in the Mouse (ng/mL) Group 2, COMPOUND E PO (20.99 mg/kg) | | | | | | | |
|---|---|---|---|---|---|---|---|
| | M4 | M5 | M6 | Mean | | SD | CV (%) |
| Time (h) | | | | | | | |
| 0.250 | 691 | 715 | 1310 | 905 | ± | 351 | 38.7 |
| 0.500 | 846 | 673 | 1300 | 940 | ± | 324 | 34.5 |
| 1.00 | 632 | 616 | 978 | 742 | ± | 205 | 27.6 |
| 2.00 | 268 | 246 | 361 | 292 | ± | 61.0 | 20.9 |
| 4.00 | 80.8 | 50.0 | 69.3 | 66.7 | ± | 15.6 | 23.3 |
| 8.00 | BQL | BQL | BQL | ND | ± | ND | ND |
| 24.0 | BQL | BQL | BQL | ND | ± | ND | ND |
| PK Parameters | | | | | | | |
| Rsq_adj | 0.982 | 0.997 | 0.996 | 0.992 | ± | 0.00847 | 0.854 |
| No. points used for $T_{1/2}$ | 3.00 | 3.00 | 4.00 | 3.33 | ± | 0.577 | 17.3 |
| $C_{max}$ (ng/g) | 846 | 715 | 1310 | 957 | ± | 313 | 32.7 |
| $T_{max}$ (h) | 0.500 | 0.250 | 0.250 | 0.333 | ± | 0.144 | 43.3 |
| $T_{1/2}$ (h) | 1.03 | 0.834 | 0.811 | 0.892 | ± | 0.120 | 13.5 |
| $T_{last}$ (h) | 4.00 | 4.00 | 4.00 | 4.00 | ± | 0.00 | 0.0 |
| $AUC_{0-last}$ (ng · h/g) | 1382 | 1234 | 2028 | 1548 | ± | 422 | 27.3 |
| $AUC_{0-inf}$ (ng · h/g) | 1502 | 1294 | 2109 | 1635 | ± | 424 | 25.9 |
| $MRT_{0-last}$ (h) | 1.34 | 1.28 | 1.20 | 1.27 | ± | 0.0712 | 5.60 |
| $MRT_{0-inf}$ (h) | 1.67 | 1.46 | 1.35 | 1.49 | ± | 0.163 | 10.9 |
| $AUC_{Extra}$ (%) | 7.99 | 4.65 | 3.85 | 5.49 | ± | 2.20 | 40.0 |
| $AUMC_{Extra}$ (%) | 26.3 | 16.6 | 14.7 | 19.2 | ± | 6.19 | 32.3 |

Example 28b. Preclinical PK of COMPOUND D, COMPOUND B and Viloxazine

A study was conducted for preclinical PK performance of COMPOUND D and COMPOUND B. Please see below for study details on intraperitoneal injections of COMPOUND B and COMPOUND D in fasted mice.

Study Details

| | Administered compound | | |
|---|---|---|---|
| | COMPOUND D | COMPOUND B | Viloxazine |
| Species | Male CD-1 Mouse, fasted overnight, food returned 2 hours post dosing | | |
| Study Group | 1.00 | 2.00 | 3.00 |
| Dosing route | IP | IP | IP |
| Nominal dose (mg/kg) | 11.0 | 10.9 | 11.8 |
| Administered dose (mg/kg) | 6.15 | 12.1 | 12.7 |
| Formulation | 4% DMSO, 30% PEG400, 66% HPβCD (30% in $H_2O$) | 4% DMSO, 30% PEG400, 66% HPβCD (30% in $H_2O$) | 4% DMSO, 30% PEG400, 66% HPβCD (30% in $H_2O$) |

Results

Results are shown in FIGS. 99*a*-99*f*. Relevant data are summarized in below tables (ND=Not determined due to inadequately defined terminal elimination phase or insufficient number of values. BQL=Below the lower limit of quantitation (LLOQ). If the adjusted rsq (linear regression coefficient of the concentration value on the terminal phase) is less than 0.9, T1/2 might not be accurately estimated. If the % $AUC_{Extra}$>20%, $AUC_{0-inf}$, Cl, $MRT_{0-inf}$ and Vdss might not be accurately estimated. If the % $AUMC_{Extra}$>20%, $MRT_{0-inf}$ and $Vd_{ss}$ might not be accurately estimated. a: Bioavailability (%) was calculated using AUC0-inf (% $AUC_{Extra}$<20%) or AUC0-last (% $AUC_{Extra}$>20%) with nominal dose).

Plasma concentration of COMPOUND D in the Mouse (ng/mL)
Group 1, IP (10.978 mg/kg)

| | M1 | M2 | M3 | Mean | | SD | CV (%) |
|---|---|---|---|---|---|---|---|
| Time (h) | | | | | | | |
| 0.250 | BQL | BQL | 3.44 | ND | ± | ND | ND |
| 0.500 | 1.12 | BQL | BQL | ND | ± | ND | ND |
| 1.00 | 5.74 | BQL | BQL | ND | ± | ND | ND |
| 2.00 | BQL | BQL | BQL | ND | ± | ND | ND |
| 4.00 | BQL | BQL | BQL | ND | ± | ND | ND |
| 8.00 | BQL | BQL | BQL | ND | ± | ND | ND |
| 24.0 | BQL | BQL | 3.48 | ND | ± | ND | ND |
| PK Parameters | | | | | | | |
| Rsq_adj | ND | ND | ND | ND | ± | ND | ND |
| No. points used for $T_{1/2}$ | 0.00 | ND | 0.00 | 0.00 | ± | ND | ND |
| $C_{max}$ (ng/mL) | 5.74 | ND | 3.48 | 4.61 | ± | ND | ND |
| $T_{max}$ (h) | 1.00 | ND | 24.0 | 12.5 | ± | ND | ND |
| $T_{1/2}$ (h) | ND | ND | ND | ND | ± | ND | ND |
| $T_{last}$ (h) | 1.00 | ND | 24.0 | 12.5 | ± | ND | ND |
| $AUC_{0-last}$ (ng · h/mL) | 2.00 | ND | 82.6 | 42.3 | ± | ND | ND |
| $AUC_{0-inf}$ (ng · h/mL) | ND | ND | ND | ND | ± | ND | ND |
| $MRT_{0-last}$ (h) | 0.860 | ND | 12.1 | 6.50 | ± | ND | ND |
| $MRT_{0-inf}$ (h) | ND | ND | ND | ND | ± | ND | ND |
| $AUC_{Extra}$ (%) | ND | ND | ND | ND | ± | ND | ND |
| $AUMC_{Extra}$ (%) | ND | ND | ND | ND | ± | ND | ND |

Plasma concentration of Viloxazine in the mouse following administration of COMPOUND D (ng/mL)
Group 1, IP (10.978 mg/kg)

| | M1 | M2 | M3 | Mean | | SD | CV (%) |
|---|---|---|---|---|---|---|---|
| Time (h) | | | | | | | |
| 0.250 | 747 | 270 | 353 | 457 | ± | 255 | 55.8 |
| 0.500 | 575 | 604 | 378 | 519 | ± | 123 | 23.7 |
| 1.00 | 135 | 487 | 237 | 286 | ± | 181 | 63.3 |
| 2.00 | 177 | 290 | 126 | 198 | ± | 83.9 | 42.5 |
| 4.00 | 34.5 | 53.2 | 16.7 | 34.8 | ± | 18.3 | 52.4 |
| 8.00 | 2.15 | 1.51 | BQL | 1.83 | ± | ND | ND |
| 24.0 | BQL | BQL | BQL | ND | ± | ND | ND |
| PK Parameters | | | | | | | |
| Rsq_adj | 0.996 | 1.000 | 0.979 | 0.992 | ± | 0.0113 | 1.14 |
| No. points used for $T_{1/2}$ | 3.00 | 3.00 | 3.00 | 3.00 | ± | 0.00 | 0 |
| $C_{max}$ (ng/mL) | 747 | 604 | 378 | 576 | ± | 186 | 32.3 |
| $T_{max}$ (h) | 0.250 | 0.500 | 0.500 | 0.417 | ± | 0.144 | 34.6 |
| $T_{1/2}$ (h) | 0.951 | 0.789 | 0.768 | 0.836 | ± | 0.0998 | 11.9 |
| $T_{last}$ (h) | 8.00 | 8.00 | 4.00 | 6.67 | ± | 2.31 | 34.6 |
| $AUC_{0-last}$ (ng · h/mL) | 785 | 1132 | 570 | 829 | ± | 283 | 34.2 |
| $AUC_{0-inf}$ (ng · h/mL) | 788 | 1134 | 589 | 837 | ± | 276 | 32.9 |
| $MRT_{0-last}$ (h) | 1.46 | 1.65 | 1.23 | 1.44 | ± | 0.209 | 14.5 |
| $MRT_{0-inf}$ (h) | 1.49 | 1.66 | 1.35 | 1.50 | ± | 0.154 | 10.2 |
| $AUC_{Extra}$ (%) | 0.374 | 0.152 | 3.14 | 1.22 | ± | 1.67 | 136 |
| $AUMC_{Extra}$ (%) | 2.36 | 0.836 | 11.9 | 5.03 | ± | 5.99 | 119 |

Plasma concentration of COMPOUND B in the Mouse (ng/mL)
Group 2, IP (10.948 mg/kg)

| | M4 | M5 | M6 | Mean | | SD | CV (%) |
|---|---|---|---|---|---|---|---|
| Time (h) | | | | | | | |
| 0.250 | 25.4 | BQL | 17.7 | 21.6 | ± | ND | ND |
| 0.500 | 5.75 | 4.88 | 8.44 | 6.36 | ± | 1.86 | 29.2 |
| 1.00 | BQL | BQL | BQL | ND | ± | ND | ND |
| 2.00 | BQL | BQL | BQL | ND | ± | ND | ND |
| 4.00 | BQL | BQL | BQL | ND | ± | ND | ND |
| 8.00 | BQL | BQL | BQL | ND | ± | ND | ND |
| 24.0 | BQL | BQL | BQL | ND | ± | ND | ND |
| PK Parameters | | | | | | | |
| Rsq_adj | ND | ND | ND | ND | ± | ND | ND |
| No. points used for $T_{1/2}$ | 0.00 | 0.00 | 0.00 | 0.00 | ± | 0.00 | 0.0 |
| $C_{max}$ (ng/mL) | 25.4 | 4.88 | 17.7 | 16.0 | ± | 10.4 | 64.8 |
| $T_{max}$ (h) | 0.250 | 0.500 | 0.250 | 0.333 | ± | 0.144 | 43.3 |
| $T_{1/2}$ (h) | ND | ND | ND | ND | ± | ND | ND |
| $T_{last}$ (h) | 0.500 | 0.500 | 0.500 | 0.500 | ± | 0.00 | 0.0 |
| $AUC_{0-last}$ (ng · h/mL) | 6.48 | 1.22 | 5.34 | 4.35 | ± | 2.77 | 63.7 |
| $AUC_{0-inf}$ (ng · h/mL) | ND | ND | ND | ND | ± | ND | ND |
| $MRT_{0-last}$ (h) | 0.299 | 0.500 | 0.314 | 0.371 | ± | 0.112 | 30.2 |
| $MRT_{0-inf}$ (h) | ND | ND | ND | ND | ± | ND | ND |
| $AUC_{Extra}$ (%) | ND | ND | ND | ND | ± | ND | ND |
| $AUMC_{Extra}$ (%) | ND | ND | ND | ND | ± | ND | ND |

Plasma concentration of Viloxazine in the mouse following administration of COMPOUND B (ng/mL)
Group 2, IP (10.948 mg/kg)

| | M4 | M5 | M6 | Mean | | SD | CV (%) |
|---|---|---|---|---|---|---|---|
| Time (h) | | | | | | | |
| 0.250 | 461 | 35.4 | 285 | 260 | ± | 214 | 82.1 |
| 0.500 | 386 | 344 | 357 | 362 | ± | 21.5 | 5.93 |
| 1.00 | 322 | 113 | 341 | 259 | ± | 127 | 48.9 |
| 2.00 | 196 | 172 | 162 | 177 | ± | 17.5 | 9.89 |
| 4.00 | 45.9 | BQL | 37.8 | 41.9 | ± | ND | ND |
| 8.00 | BQL | BQL | 1.67 | ND | ± | ND | ND |
| 24.0 | BQL | BQL | BQL | ND | ± | ND | ND |
| PK Parameters | | | | | | | |
| Rsq_adj | 0.985 | ND | 1.000 | 0.992 | ± | ND | ND |
| No. points used for $T_{1/2}$ | 3.00 | 0.00 | 4.00 | 2.33 | ± | 2.08 | 89.2 |
| $C_{max}$ (ng/mL) | 461 | 344 | 357 | 387 | ± | 64.1 | 16.6 |
| $T_{max}$ (h) | 0.250 | 0.500 | 0.500 | 0.417 | ± | 0.144 | 34.6 |
| $T_{1/2}$ (h) | 1.05 | ND | 0.912 | 0.981 | ± | ND | ND |
| $T_{last}$ (h) | 4.00 | 2.00 | 8.00 | 4.67 | ± | 3.06 | 65.5 |
| $AUC_{0-last}$ (ng · h/mL) | 800 | 296 | 748 | 615 | ± | 277 | 45.1 |
| $AUC_{0-inf}$ (ng · h/mL) | 870 | ND | 750 | 810 | ± | ND | ND |
| $MRT_{0-last}$ (h) | 1.41 | 1.06 | 1.64 | 1.37 | ± | 0.293 | 21.5 |
| $MRT_{0-inf}$ (h) | 1.74 | ND | 1.66 | 1.70 | ± | ND | ND |
| $AUC_{Extra}$ (%) | 7.99 | ND | 0.293 | 4.14 | ± | ND | ND |
| $AUMC_{Extra}$ (%) | 25.4 | ND | 1.64 | 13.5 | ± | ND | ND |

Plasma concentration of Viloxazine in the Mouse (ng/mL)
Group 3, IP (11.82 mg/kg)

| | M7 | M8 | M9 | Mean | | SD | CV (%) |
|---|---|---|---|---|---|---|---|
| Time (h) | | | | | | | |
| 0.250 | 1070 | 1160 | 1250 | 1160 | ± | 90.0 | 7.76 |
| 0.500 | 862 | 1370 | 1470 | 1234 | ± | 326 | 26.4 |
| 1.00 | 892 | 1120 | 319 | 777 | ± | 413 | 53.1 |
| 2.00 | 519 | 713 | 513 | 582 | ± | 114 | 19.6 |
| 4.00 | 156 | BQL | 88.4 | 122 | ± | ND | ND |
| 8.00 | 3.92 | 4.12 | 4.60 | 4.21 | ± | 0.349 | 8.29 |
| 24.0 | BQL | BQL | BQL | ND | ± | ND | ND |
| PK Parameters | | | | | | | |
| Rsq_adj | 0.982 | 0.993 | 0.996 | 0.990 | ± | 0.00738 | 0.746 |
| No. points used for $T_{1/2}$ | 3.00 | 3.00 | 3.00 | 3.00 | ± | 0.00 | 0.0 |
| $C_{max}$ (ng/mL) | 1070 | 1370 | 1470 | 1303 | ± | 208 | 16.0 |
| $T_{max}$ (h) | 0.250 | 0.500 | 0.500 | 0.417 | ± | 0.144 | 34.6 |
| $T_{1/2}$ (h) | 0.836 | 0.844 | 0.890 | 0.857 | ± | 0.0291 | 3.40 |
| $T_{last}$ (h) | 8.00 | 8.00 | 8.00 | 8.00 | ± | 0.00 | 0.0 |
| $AUC_{0-last}$ (ng · h/mL) | 2271 | 2808 | 1878 | 2319 | ± | 467 | 20.1 |
| $AUC_{0-inf}$ (ng · h/mL) | 2275 | 2813 | 1884 | 2324 | ± | 467 | 20.1 |
| $MRT_{0-last}$ (h) | 1.75 | 1.61 | 1.57 | 1.64 | ± | 0.0926 | 5.64 |
| $MRT_{0-inf}$ (h) | 1.76 | 1.62 | 1.60 | 1.66 | ± | 0.0898 | 5.41 |
| $AUC_{Extra}$ (%) | 0.208 | 0.178 | 0.313 | 0.233 | ± | 0.0711 | 30.5 |
| $AUMC_{Extra}$ (%) | 1.08 | 1.01 | 1.82 | 1.31 | ± | 0.448 | 34.3 |

Example 29. Metabolic Stability of Test Compounds at 1 μM in Liver S9 Fractions

Test Compounds: COMPOUND D, COMPOUND E, and Viloxazine. Positive controls: 7-ethoxycoumarin and 7-hydroxycoumarin.

Test System

| Species | Description | Final Conc. |
|---|---|---|
| Rat liver S9 | Pooled male | 0.5 mg/mL |
| Dog Liver S9 | Pooled 8 male | 0.5 mg/mL |
| Human Liver S9 | Pooled 8 male | 0.5 mg/mL |

10 mM stock.
1 mM intermediate: 10 μL of 10 mM stock added 90 μL of 90% MeOH/water (10% DMSO/90% MeOH).
10 μM working solution: 10 μL of 1 mM added 990 μL 50 mM PPB (1.0% DMSO/9.0% MeOH)

Data Analysis $$\%\ \text{Remaining} = \frac{\text{Peak area ratio of analyte to } IS \text{ at each time point}}{\text{Peak area ratio of analyte to } IS \text{ at } t = 0} \times 100\%$$

Results

Results are shown in FIGS. 100*a*-100*d*, FIGS. 101*a*-101*d*, and FIGS. 102*a*-102*d*. Relevant data are summarized in below tables

| Summary of Metabolic Stability of Test Compounds at 1 μM in Liver S9 Fractions | | | | | | Formation of viloxazine in Liver S9 Fractions Analyte Peak Area/ IS Peak Area | |
|---|---|---|---|---|---|---|---|
| Compound ID | Species | $R^2$ | $t_{1/2}$ (min) | $CL_{int(mic.)}$ (μL/min/mg) | % Remaining at 60 min | (Mean of Ratio) 0 min | 60 min |
| COMPOUND D | SD Rat | 0.8658 | 9.4 | 148 | 0.48% | 0.12 | 0.45 |
| COMPOUND E | SD Rat | 0.8996 | 4.8 | 290 | 0.00% | 0.04 | 0.36 |
| COMPOUND D | Beagle Dog | 0.8739 | 12.6 | 110 | 3.10% | 0.13 | 0.42 |
| COMPOUND E | Beagle Dog | 0.8504 | 8.3 | 167 | 0.25% | 0.04 | 0.41 |
| COMPOUND D | Human | 0.8165 | 1.86 | 746 | 0.00% | 0.12 | 0.43 |
| COMPOUND E | Human | 0.8734 | 8.9 | 155 | 0.76% | 0.04 | 0.36 |

$t_{1/2}$ = 0.693/ke
$CL_{int\ (mic)}$ = 0.693/half life/mg microsome protein per mL Example 30. Plasma Stability A study was conducted to examine the plasma stability. Test Compounds: COMPOUND D, COMPOUND E, and Viloxazine. Positive controls: Enalapril and Propantheline.

Test System

| Species/Matrix | No. of Individuals | Anticoagulant Used |
|---|---|---|
| Rat Plasma | Male pooled | EDTA-K2 |
| Human plasma | Mixed gender | EDTA-K2 |

50 μM working solution: Aliquot 25 μL of 2 mM stock into 975 μL 20% MeOH/water to achieve 50 μM working solution (2.5% DMSO; 20% MeOH)

Data Analysis $$\%\ \text{Remaining} = \frac{\text{Peak area ratio of analyte to } IS \text{ at each time point}}{\text{Peak area ratio of analyte to } IS \text{ at } t = 0} \times 100\%$$

Results for COMPOUND D stability in rat plasma is shown in FIG. 103*a*. Results for COMPOUND E stability in rat plasma is shown in FIG. 103*b*. Results for the positive control in rat plasma is shown in FIG. 103*c*. Results for COMPOUND D stability in human plasma is shown in FIG. 103*d*. Results for COMPOUND E stability in human plasma is shown in FIG. 103*e*. Results for the positive control in human plasma is shown in FIG. 103*f*. Relevant data are also summarized in below table

| Summary of Plasma Stability | | | | Formation of viloxazine in Plasma Analyte Peak Area/IS | |
|---|---|---|---|---|---|
| Com-pound ID | Final Concen-tration (μM) | Species/ Matrix | % Re-maining at 60 min (Mean) | Peak Area (Mean of Ratio) 0 min | 60 min |
| COMPOUND D | 2 | Rat plasma | 0.0 | 0.477 | 0.837 |
| | | Human plasma | 77.1 | 0.501 | 0.658 |
| COMPOUND E | | Rat plasma | 0.0 | 0.100 | 0.685 |
| | | Human plasma | 90.3 | 0.095 | 0.276 |

Example 31. Metabolic Stability of Test Compounds in Human Intestinal Homogenates A study was conducted to examine the metabolic stability. Test Compounds: COMPOUND D, COMPOUND E, and Viloxazine. Positive controls: 7-hydroxycoumarin and Testosterone.

Test System

| Species | Description | Final Conc. |
|---|---|---|
| Human intestinal homogenates | pooled male | 0.5 mg/mL |

10 mM stock:

1 mM intermediate: 10 μL of 10 mM stock added 90 μL of 90% MeOH/water (10% DMSO/90% MeOH)

10 μM working solution: 10 μL of 1 mM added 990 μL 50 mM PPB (1.0% DMSO/9.0% MeOH)

Data Analysis $$\%\ \text{Remaining} = \frac{\text{Peak area ratio of analyte to } IS \text{ at each time point}}{\text{Peak area ratio of analyte to } IS \text{ at } t = 0} \times 100\%$$

Results for the stability of COMPOUND D, COMPOUND E, and positive controls are shown in FIGS. 104*a*-104*d*. Relevant data are also summarized in below table

| Summary of Metabolic Stability of Test Compounds in Human Intestinal homogenates Fractions | | | | | Formation of viloxazine in human intestinal homogenates Fractions Analyte Peak Area/ IS Peak Area | |
|---|---|---|---|---|---|---|
| Compound ID | Species | $t_{1/2}$ (min) | $CL_{int(mic.)}$ (μL/min/mg) | % Remaining at 60 min | (Mean of Ratio) 0 min | 60 min |
| COMPOUND D | Human intestinal homogenates | 0.85 | 1626 | 0.00 | 0.127 | 0.60 |
| COMPOUND E | | 10.8 | 128 | 0.90 | 0.036 | 0.55 |

Note:

If the remaining is >80% at 60 min then the t½ will be reported as >187 min.

If the remaining is 0% at 5 min then the t½ will be reported as <2.5 min.

$R^2$ is the correlation coefficient of the linear regression for the determination of kinetic constant (see raw data worksheet).

$t_{1/2}$ = 0.693/ke.

$CL_{int\ (mic)}$ = 0.693/half life/mg protein per mL

Example 32. Bioanalytical Data for Compounds in Rat Plasma

A study was conducted to examine the bioanalytical data for compounds in Rat plasma. Results are summarized in below tables. Frozen Sprague Dawley rat (male pooled) and human (mixed gender) plasma was utilized for the study. Test compounds were dissolved in dimethyl sulfoxide (DMSO) to make a 10 mM stock solution. A working solution was made with MeOH/water. COMPOUND E (2 M) was incubated with plasma in duplicates at 37° C. in a water bath. Sampling timepoints included 0, 5, 15, 30, and 60 min Enalapril and propantheline were used as positive control for rat and human plasma at 2 μM TABLE 18a Bench-top stability of COMPOUND E in Rat plasma at wet ice bath (No stabilizer)

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.00631 | 0.00103 | 0.00030 | 1.47 | 0.35 | 0.04 |
| | 0.00435 | 0.00141 | 0.00036 | 1.60 | 0.30 | 0.04 |
| | 0.00432 | 0.00151 | 0.00000 | 1.60 | 0.35 | 0.04 |
| | 0.00389 | 0.00136 | 0.00034 | 1.65 | 0.33 | 0.04 |
| Mean peak area ratio | 0.00472 | 0.00133 | 0.00025 | 1.58 | 0.33 | 0.04 |
| % stability | NA | 28.2 | 5.3 | NA | 20.9 | 2.5 |

TABLE 19a

Bench-top stability of COMPOUND E in Rat plasma at wet ice bath with 5% Paraoxon ethyl as stabilizer.

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.00838 | 0.00544 | 0.00522 | 3.28 | 2.85 | 2.1 |
| | 0.00933 | 0.00682 | 0.00546 | 3.46 | 2.7 | 2.22 |
| | 0.00862 | 0.00593 | 0.00579 | 3.51 | 2.62 | 1.98 |
| | 0.00896 | 0.00590 | 0.00600 | 3.28 | 2.58 | 2.21 |
| Mean peak area ratio | 0.00882 | 0.00602 | 0.00562 | 3.38 | 2.69 | 2.13 |
| % stability | NA | 68.3 | 63.7 | NA | 79.5 | 62.9 |

TABLE 20a

Bench-top stability of COMPOUND E in mice Blood at wet ice bath with 5% Paraoxon ethyl as stabilizer.

| Stability | Peak area of 0 hr sample | Peak area of 0.5 hr sample | Peak area of 0 hr sample | Peak area of 0.5 hr sample |
|---|---|---|---|---|
| | Wet ice bath | | | |
| duration | LQC | | HQC | |
| 0.5 hour | 0.0118 | 0.00799 | 2.910 | 2.79 |
| | 0.00924 | 0.00867 | 2.750 | 2.99 |
| | 0.01020 | 0.00783 | 3.12 | 3.29 |
| | 0.00856 | 0.00773 | 2.830 | 2.93 |
| Mean peak area | 0.00933 | 0.00806 | 2.903 | 3.00 |
| % stability | NA | 86.3 | NA | 103 |

TABLE 18b

Bench-top stability of Viloxazine in Rat plasma at wet ice bath (No stabilizer)

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.0114 | 0.00875 | 0.00851 | 2.49 | 3.00 | 2.64 |
| | 0.0106 | 0.00811 | 0.00824 | 2.69 | 2.68 | 2.84 |
| | 0.00941 | 0.00870 | 0.00853 | 2.50 | 2.81 | 2.84 |
| | 0.00794 | 0.00815 | 0.00894 | 2.54 | 2.79 | 2.85 |
| Mean peak area ratio | 0.00932 | 0.00843 | 0.00856 | 2.56 | 2.82 | 2.79 |
| % stability | NA | 90.5 | 91.8 | NA | 110 | 109 |

TABLE 19b

Bench-top stability of Viloxazine in Rat plasma at wet ice bath with 5% Paraoxon ethyl as stabilizer.

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.00627 | 0.00588 | 0.00599 | 2.23 | 2.19 | 2.36 |
| | 0.00670 | 0.00581 | 0.00653 | 2.29 | 2.26 | 2.42 |
| | 0.00620 | 0.00522 | 0.00649 | 2.40 | 2.23 | 2.33 |
| | 0.00689 | 0.00577 | 0.00684 | 2.26 | 2.29 | 2.40 |
| Mean peak area ratio | 0.00652 | 0.00567 | 0.00646 | 2.30 | 2.24 | 2.38 |
| % stability | NA | 87.0 | 99.2 | NA | 98 | 104 |

TABLE 20b

Bench-top stability of Viloxazine in mice Blood at wet ice bath with 5% Paraoxon ethyl as stabilizer.

| Stability | Peak area of 0 hr sample | Peak area of 0.5 hr sample | Peak area of 0 hr sample | Peak area of 0.5 hr sample |
|---|---|---|---|---|
| | Wet ice bath | | | |
| duration | LQC | | HQC | |
| 0.5 hour | 0.00906 | 0.00631 | 1.94 | 2.14 |
| | 0.00863 | 0.00701 | 2.08 | 2.25 |
| | 0.00737 | 0.00686 | 2.10 | 2.34 |
| | 0.00680 | 0.00632 | 1.90 | 2.27 |
| Mean peak area | 0.00760 | 0.00663 | 2.005 | 2.25 |
| % stability | NA | 87.2 | NA | 112 |

Example 33. Bioanalytical Data for Compounds in Rat Plasma

A study was conducted to examine the bioanalytical data for compounds in Rat plasma. Results are summarized in below tables. Frozen Sprague Dawley rat (male pooled) and human (mixed gender) plasma was utilized for the study. Test compounds were dissolved in dimethyl sulfoxide (DMSO) to make a 10 mM stock solution. A working solution was made with MeOH/water. COMPOUND E (2 M) was incubated with plasma in duplicates at 37° C. in a water bath. Sampling timepoints included 0, 5, 15, 30, and 60 min Enalapril and propantheline were used as positive control for rat and human plasma at 2 μM TABLE 21a Bench-top stability of COMPOUND D in Rat plasma at wet ice bath (No stabilizer)

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.00352 | 0.00083 | 0.00035 | 0.617 | 0.199 | 0.0519 |
| | 0.00299 | 0.00078 | 0.00045 | 0.688 | 0.203 | 0.0522 |
| | 0.00269 | 0.00106 | 0.00000 | 0.713 | 0.201 | 0.0541 |
| | 0.00248 | 0.00085 | 0.00000 | 0.652 | 0.229 | 0.0566 |
| Mean peak area ratio | 0.00292 | 0.00088 | 0.00020 | 0.67 | 0.21 | 0.05 |
| % stability | NA | 30.1 | 6.8 | NA | 31.2 | 8.0 |

TABLE 22a

Bench-top stability of COMPOUND D in Rat plasma at wet ice bath with 5% Paraoxon ethyl as stabilizer.

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.00547 | 0.00272 | 0.00158 | 1.75 | 0.95 | 0.36 |
| | 0.00629 | 0.00356 | 0.00163 | 1.94 | 1.08 | 0.45 |
| | 0.00602 | 0.00378 | 0.00330 | 1.92 | 1.17 | 0.48 |
| | 0.00653 | 0.00386 | 0.00245 | 1.69 | 1.08 | 0.61 |
| Mean peak area ratio | 0.00608 | 0.00348 | 0.00224 | 1.83 | 1.07 | 0.47 |
| % stability | NA | 57.3 | 36.9 | NA | 58.7 | 26.0 |

TABLE 23a

Bench-top stability of COMPOUND D in mice Blood at wet ice bath with 5% Paraoxon ethyl as stabilizer.

| Stability | Peak area of 0 hr sample | Peak area of 0.5 hr sample | Peak area of 0 hr sample | Peak area of 0.5 hr sample |
|---|---|---|---|---|
| | Wet ice bath | | | |
| duration | LQC | | HQC | |
| 0.5 hour | 0.00507 | 0.00264 | 1.290 | 0.675 |
| | 0.00442 | 0.00283 | 1.360 | 0.648 |
| | 0.00539 | 0.00263 | 1.45 | 0.731 |
| | 0.00426 | 0.00236 | 1.160 | 0.675 |
| Mean peak area | 0.00479 | 0.00262 | 1.315 | 0.682 |
| % stability | NA | 54.7 | NA | 52 |

TABLE 21b

Bench-top stability of Viloxazine in Rat plasma at wet ice bath (No stabilizer)

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.0068 | 0.0059 | 0.0068 | 2.45 | 2.58 | 2.63 |
| | 0.0061 | 0.0074 | 0.0074 | 2.52 | 2.71 | 2.79 |
| | 0.0063 | 0.0073 | 0.0068 | 2.51 | 2.65 | 2.84 |
| | 0.0064 | 0.0067 | 0.0069 | 2.44 | 2.89 | 2.90 |

TABLE 21b-continued

Bench-top stability of Viloxazine in Rat plasma at wet ice bath (No stabilizer)

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| Mean peak area ratio | 0.0064 | 0.0068 | 0.0070 | 2.48 | 2.71 | 2.79 |
| % stability | NA | 106.4 | 108.8 | NA | 109 | 113 |

TABLE 22b

Bench-top stability of Viloxazine in Rat plasma at wet ice bath with 5% Paraoxon ethyl as stabilizer.

| Stability duration | Peak area of 0 hr sample | Peak area of 1 hr sample LQC | Peak area of 2 hr sample | Peak area of 0 hr sample | Peak area of 1 hr sample HQC | Peak area of 2 hr sample |
|---|---|---|---|---|---|---|
| 2 hour | 0.0066 | 0.0063 | 0.0062 | 2.25 | 2.42 | 2.54 |
| | 0.0066 | 0.0065 | 0.0069 | 2.22 | 2.54 | 2.66 |
| | 0.0074 | 0.0067 | 0.0061 | 2.31 | 2.62 | 2.66 |
| | 0.0063 | 0.0072 | 0.0073 | 2.32 | 2.49 | 2.58 |
| Mean peak area ratio | 0.0067 | 0.0067 | 0.0066 | 2.28 | 2.52 | 2.61 |
| % stability | NA | 98.9 | 98.5 | NA | 111 | 115 |

TABLE 23b

Bench-top stability of Viloxazine in mice Blood at wet ice bath with 5% Paraoxon ethyl as stabilizer.

| Stability | Peak area of 0 hr sample | Peak area of 0.5 hr sample | Peak area of 0 hr sample | Peak area of 0.5 hr sample |
|---|---|---|---|---|
| | Wet ice bath | | | |
| duration | LQC | | HQC | |
| 0.5 hour | 0.00840 | 0.00604 | 2.39 | 2.62 |
| | 0.00701 | 0.00714 | 2.28 | 2.68 |
| | 0.00764 | 0.00737 | 2.29 | 2.67 |
| | 0.00634 | 0.00577 | o2.15 | o2.88 |
| Mean peak area | 0.00735 | 0.00658 | 2.320 | 2.66 |
| % stability | NA | 89.6 | NA | 115 |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can of course vary. It is also to be understood that the terminology used herein is for the purpose of describing particular embodiments only and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

In an embodiment, a process for preparing 2-((2-ethoxyphenoxy)methyl)morpholine-4-carbonyl chloride (Intermediate 1) is provided, comprising:

reacting 2-((2-ethoxyphenoxy)methyl)-morpholine with a reaction mixture comprising triphosgene

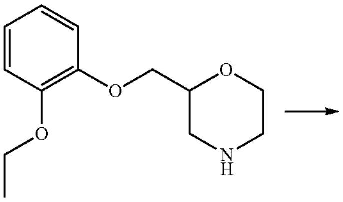

-continued

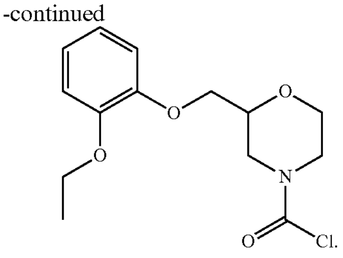

Intermediate I

In further embodiments, the reaction mixture comprises dichloromethane. In other embodiments, the reaction mixture comprises sodium bicarbonate.

In some embodiments, Intermediate 1 is used to prepare 2-chloropyridin-4-yl 2-((2-ethoxyphenoxy)methyl)morpholine-4-carboxylate (SP-20), comprising:

reacting 2-((2-ethoxyphenoxy)methyl)morpholine-4-carbonyl chloride (Intermediate 1) and a reaction mixture comprising 2-chloro-4-hydroxy pyridine

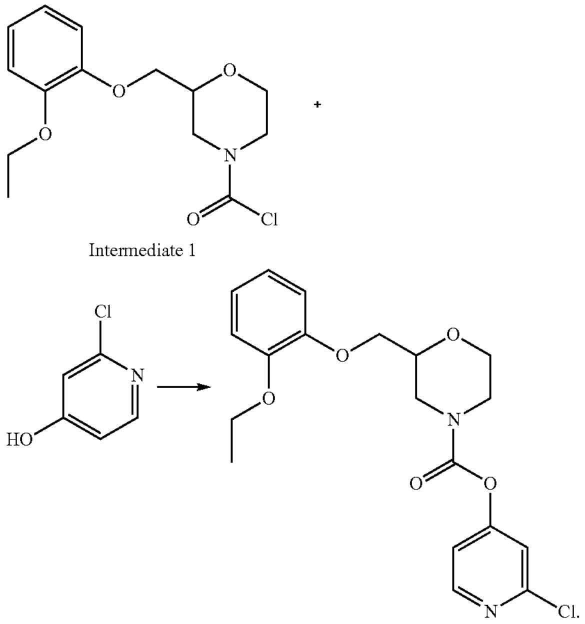

Intermediate 1

SP-20

In further embodiments, this reaction mixture further comprises anhydrous tetrahydrofuran.

In some embodiments, a process for preparing chloromethyl 2-((2-ethoxyphenoxy)methyl)morpholine-4-carboxylate (Intermediate 2) is provided, comprising: reacting 2-((2-ethoxyphenoxy)methyl)-morpholine with a reaction mixture comprising 1-chloromethyl chloroformate

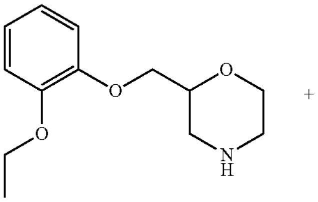

-continued

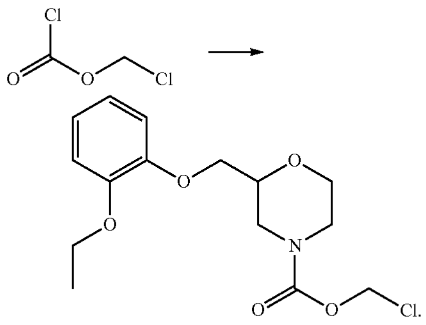

Intermediate 2

In further embodiments, this reaction mixture comprises trimethylamine. In other embodiments, this reaction mixture comprises dichloromethane.

In some embodiments, Intermediate 2 is used to prepare ((D-valyl)oxy)methyl 2-((2-ethoxyphenoxy)methyl)morpholine-4-carboxylate (SP-16), comprising:

(a) forming (SP-16A) by reacting Intermediate 2 with a reaction mixture comprising N-Boc-D-Valine; and

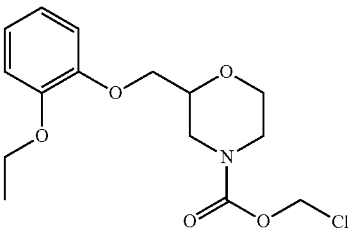

Intermediate 2

+

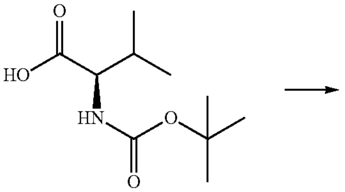

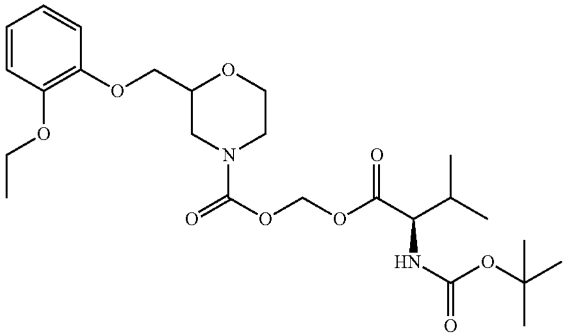

SP-16A (b) reacting SP-16A with dioxane in an organic acid

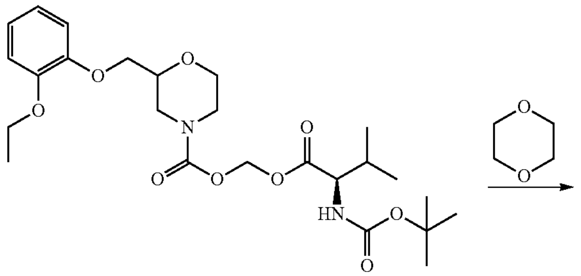

SP-16A

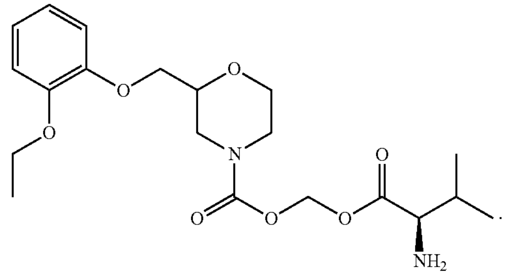

SP-16

In further embodiments, the reaction mixture comprises cesium carbonate. In other embodiments, the reaction mixture comprises methanol. In some embodiments, the organic acid is hydrochloric acid.

In some embodiments, Intermediate 2 is used to prepare (((R)-3-amino-4-methylpentanoyl)oxy)methyl 2-((2-ethoxyphenoxy)-methyl)morpholine-4-carboxylate (SP-29), comprising:

(a) forming SP-29A by reacting Intermediate 2 and a reaction mixture comprising Boc-L-β-leucine; and

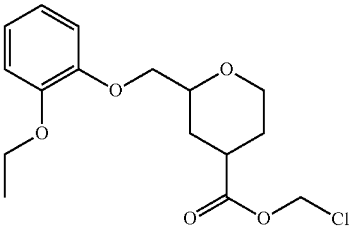

Intermediate 2

+

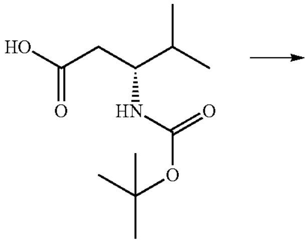

-continued

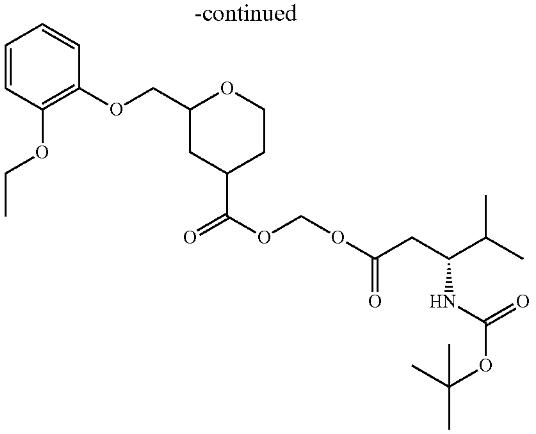

SP-29A (b) stirring SP-29A in chloroform and trifluoracetic acid

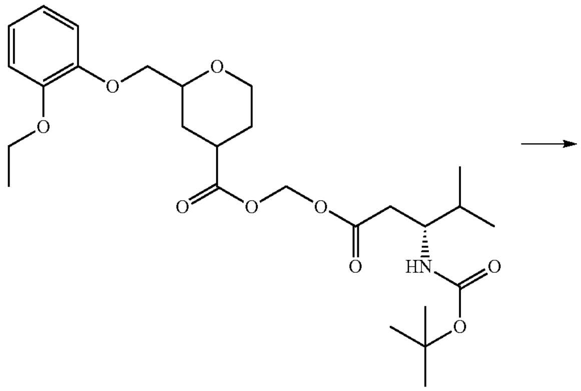

SP-29A

-continued

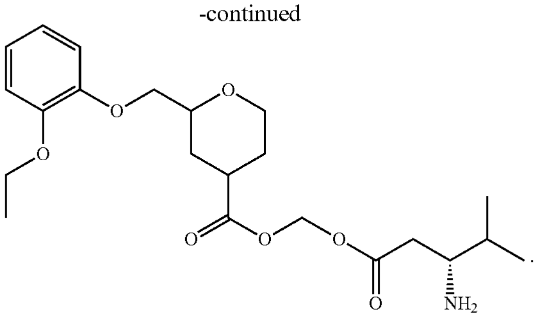

SP-29

In further embodiments, this reaction mixture comprises cesium carbonate. In other embodiments, the reaction mixture comprises methanol.

In other embodiments, Intermediate 2 is used to prepare bis(((2-((2-ethoxyphenoxy)methyl)morpholine-4-carbonyl)oxy)methyl)pyridine-3,5-dicarboxylate (SP-30), comprising:

reacting Intermediate 2 and a reaction mixture comprising 3,5-pyridinedicarboxylic acid

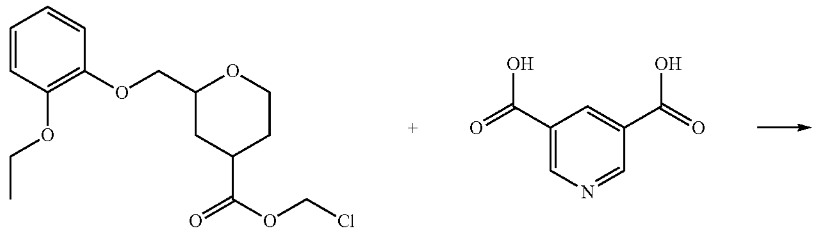

Intermediate 2

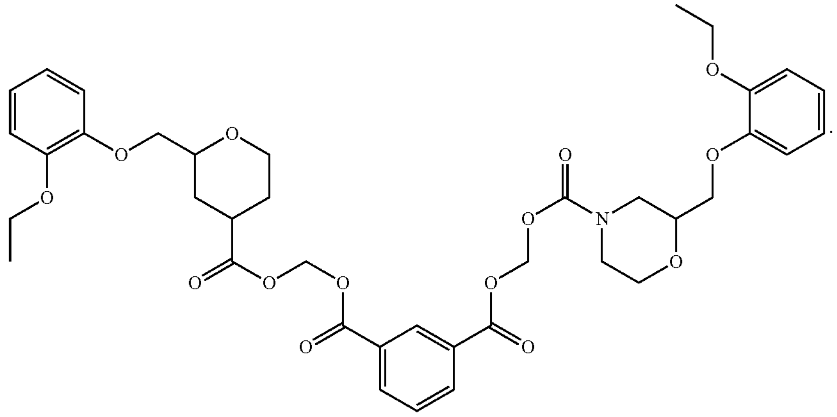

SP-30

In further embodiments, this reaction mixture comprises cesium carbonate. In other embodiments, the reaction mixture comprises methanol.

In some embodiments, Intermediate 2 is used to prepare ((2-2'-(methylazanediyl)bis(acetyl))bis(oxy))bis(methylene) bis(2-((2-ethoxyphenoxy)methyl)morpholine-4-carboxylate) (SP-31), comprising:

reacting chloromethyl 2-((2-ethoxyphenoxy)methyl)morpholine-4-carboxylate (Intermediate 2) and a reaction mixture comprising methyliminodiacetic acid

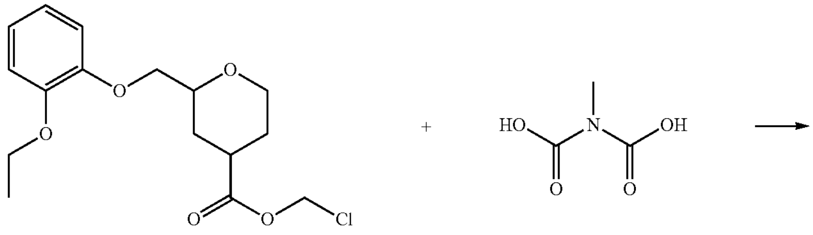

Intermediate 2

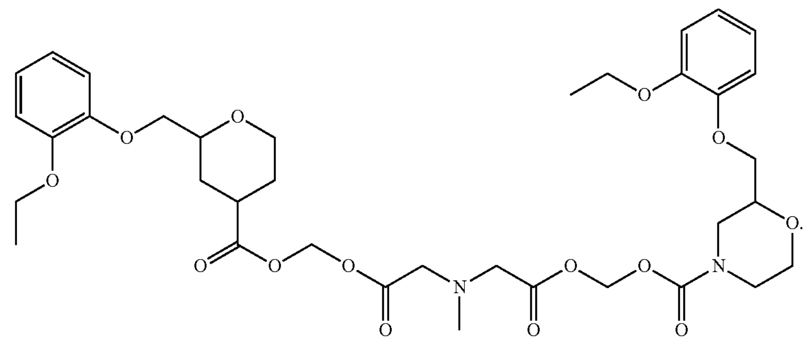

SP-31

In further embodiments, this reaction mixture comprises cesium carbonate. In other embodiments, the reaction mixture comprises methanol.

In other embodiments, Intermediate 2 is used to prepare (((R)-2-(aminomethyl)-3-methylbutanoyl)oxy)methyl 2-((2-ethoxyphenoxy)methyl)morpholine-4-carboxylate, trifluoroacetic acid salt (SP-32), comprising:

(a) forming SP-32A by reacting Intermediate 2 and a reaction mixture comprising N-Boc-3-amino-2-isopropylpropionic acid; and

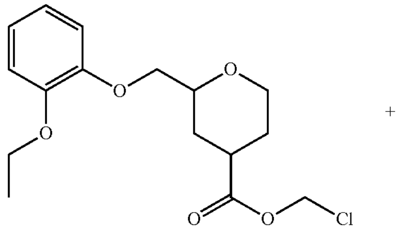

Intermediate 2

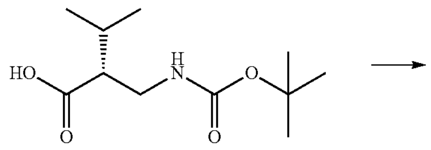

-continued

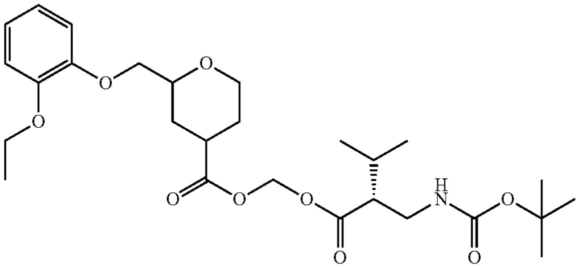

SP-32A (b) stirring SP-32A in chloroform and trifluoroacetic acid

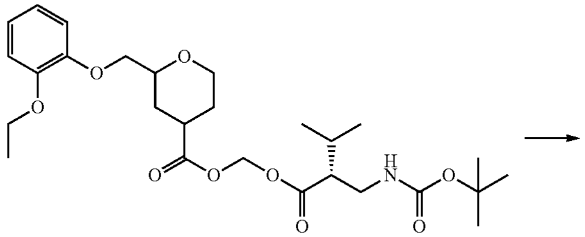

SP-32A

-continued

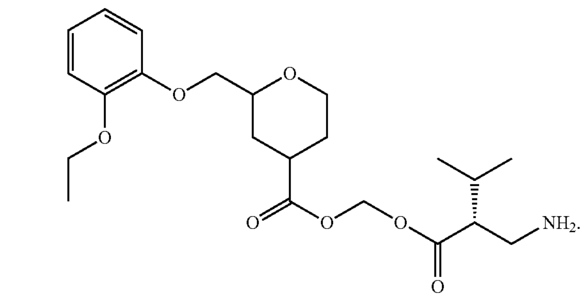

SP-32

In further embodiments, this reaction mixture comprises cesium carbonate. In other embodiments, the reaction mixture comprises methanol.

In another embodiment, a process for preparing 1-chloroethyl 2-((2-ethoxyphenoxy)methyl)morpholine-4-carboxylate (Intermediate 3) is provided, comprising:

reacting 2-((2-ethoxyphenoxy)methyl)morpholine with a reaction mixture comprising 1-chloroethyl chloroformate

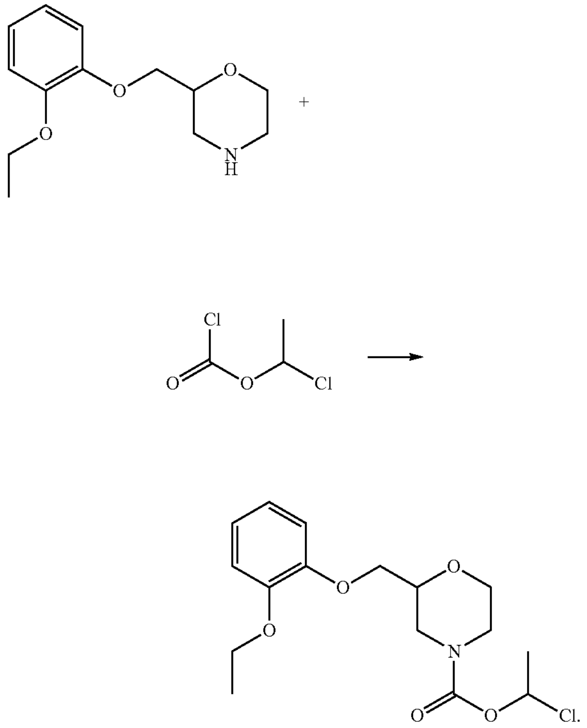

Intermediate 3

In further embodiments, this reaction mixture comprises trimethylamine. In other embodiments, the reaction mixture comprises dichloromethane.

In some embodiments, Intermediate 3 is used to prepare 1-((L-valyl)oxy)ethyl 2-((2-ethoxyphenoxy)methyl)morpholine-4-carboxylate (SP-17), comprising:

(a) forming SP-17A by reacting Intermediate 3 and a reaction mixture comprising N-Boc-L-Valine; and

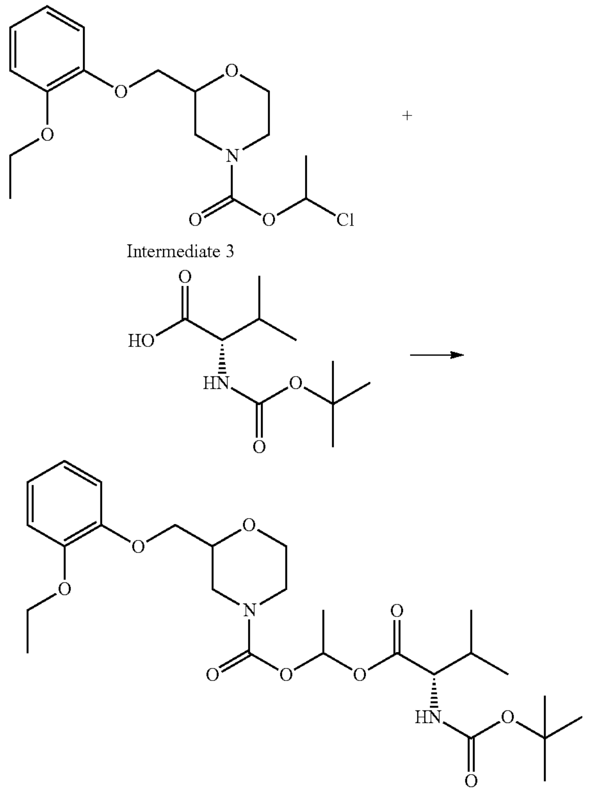

Intermediate 3

SP-17A (b) reacting SP-17A with dioxane in an organic acid

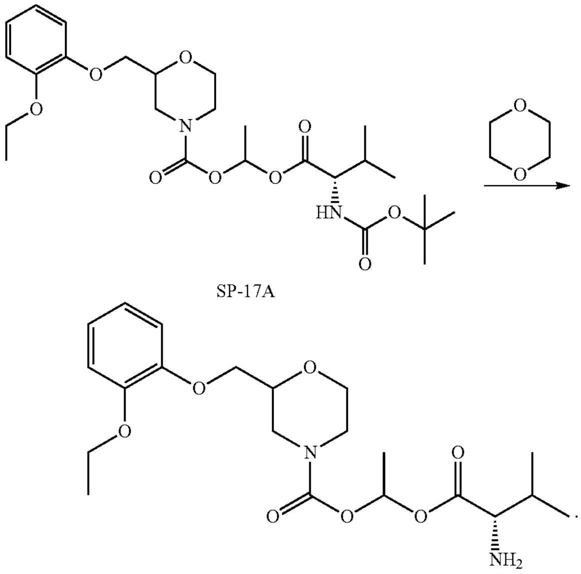

SP-17A

SP-17

In further embodiments, this reaction mixture comprises methanol. In other embodiments, the reaction mixture comprises cesium carbonate. In some further embodiments, the organic acid is hydrochloric acid.

In some embodiments, Intermediate 3 is used to prepare 1-((1-phenylalanyl)oxy)ethyl 2-((2-ethoxyphenoxy)methyl) morpholine-4-carboxylate (SP-22), comprising:

(a) forming SP-22A by reacting Intermediate 3 with a reaction mixture comprising N-Boc-phenylalanine; and

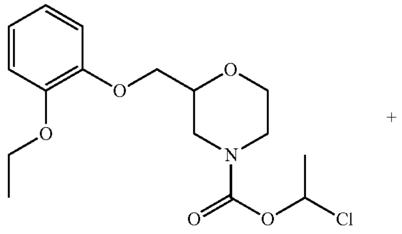

Intermediate 3

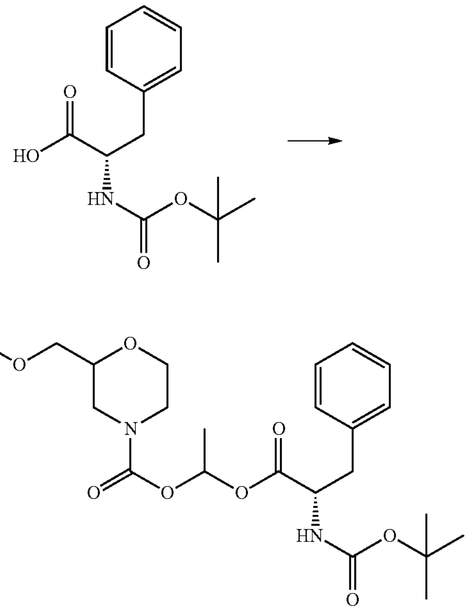

SP-22A (b) reacting SP-22A with dioxane in an organic acid

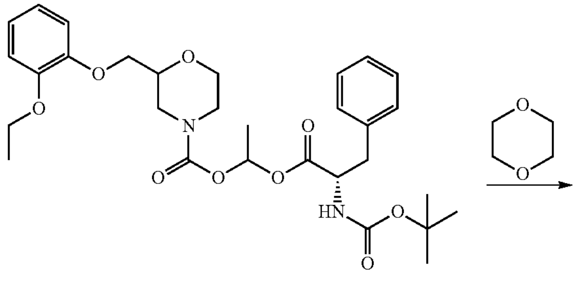

SP-22A

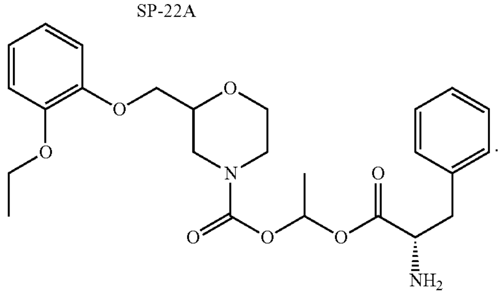

SP-22

In further embodiments, this reaction mixture further comprises cesium carbonate. In other embodiments, the reaction mixture further comprises methanol. In alternative embodiments, the organic acid is hydrochloric acid.

In some embodiments, Intermediate 3 is used to prepare 1-((dimethyl-L-valyl)oxy)ethyl 2-((2-ethoxyphenoxy)methyl)morpholine-4-carboxylate (SP-23), comprising: reacting Intermediate 3 with a reaction mixture comprising L-Val-N,N-dimethyl

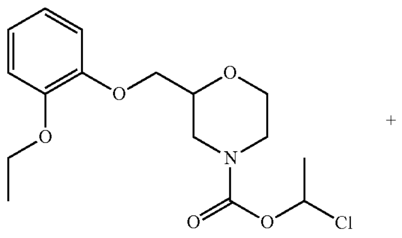

Intermediate 3

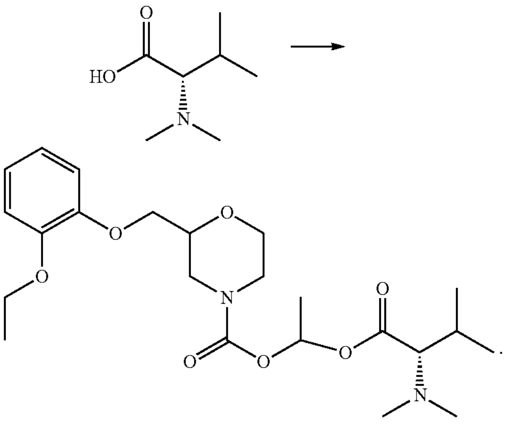

SP-23

In further embodiments, this reaction mixture comprises cesium carbonate. In some embodiments, the reaction mixture comprises methanol.

In some embodiments, Intermediate 3 is used to prepare 1-((Acetyl-L-valyl)oxy)ethyl 2-((2-ethoxyphenoxy)methyl)morpholine-4-carboxylate (SP-24), comprising:

reacting Intermediate 3 with a reaction mixture comprising N-acetylvaline

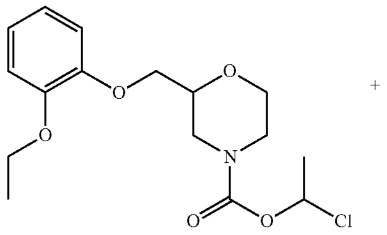

Intermediate 3

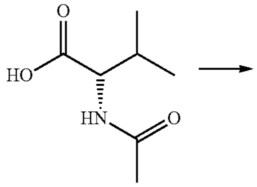

-continued

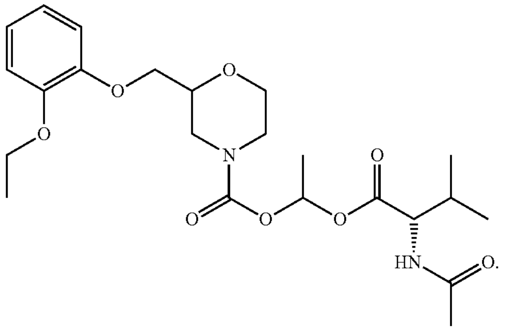

SP-24

In further embodiments, this reaction mixture comprises cesium carbonate. In some embodiments, the reaction mixture comprises methanol.

In some embodiments, Intermediate 3 is used to prepare 1-((methyl-D-valyl)oxy)ethyl 2-((2-ethoxyphenoxy)methyl) morpholine-4-carboxylate (SP-25), comprising:

(a) forming SP-25A by reacting Intermediate 3 with a reaction mixture comprising N-Boc-D-Valine; and

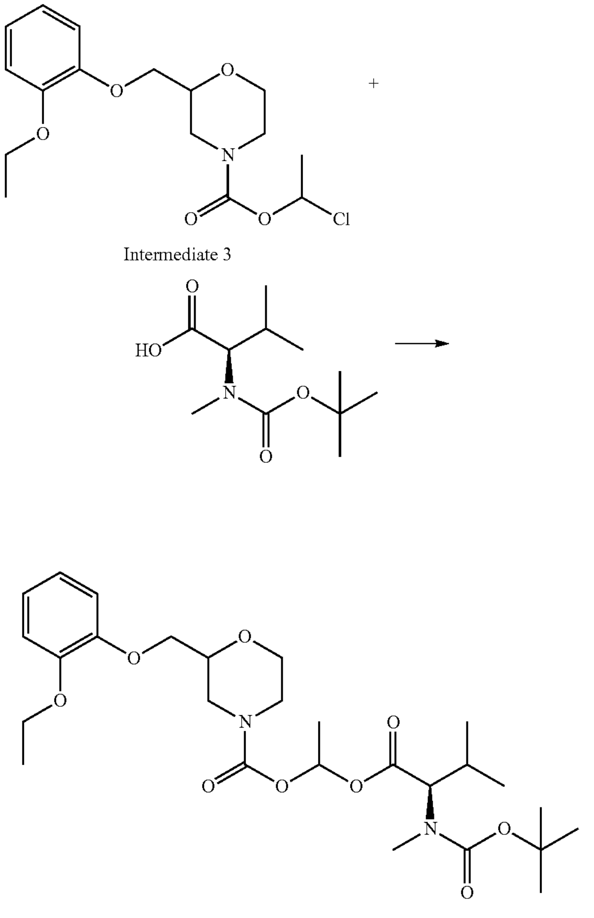

Intermediate 3

SP-25A (b) reacting SP-25A with dichloromethane and trifluoroacetic acid

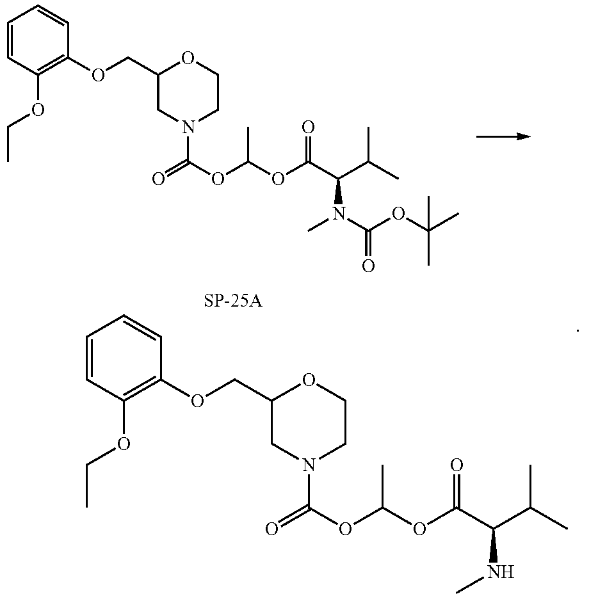

SP-25A

SP-25

In further embodiments, this reaction mixture comprises methanol. In some embodiments, the reaction mixture comprises cesium carbonate.

In some embodiments, Intermediate 3 is used to prepare 1-(((R)-2-(aminomethyl)-3-methylbutanoyl)oxy)ethyl 2-((2-ethoxyphenoxy)methyl)morpholine-4-carboxylate (SP-27), comprising:

(a) forming SP-27A by reacting Intermediate 3 and a reaction mixture comprising N-Boc-3-amino-2-isopropionic acid; and

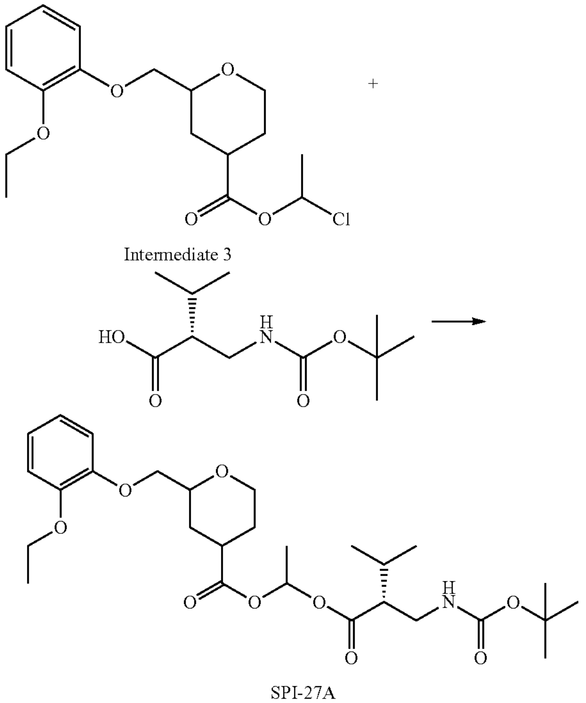

Intermediate 3

SPI-27A (b) stirring a solution of SP-27A in chloroform and trifluoroacetic acid

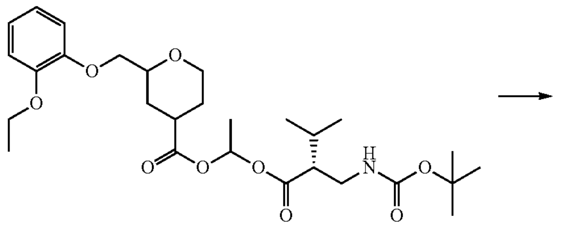

SPI-27A

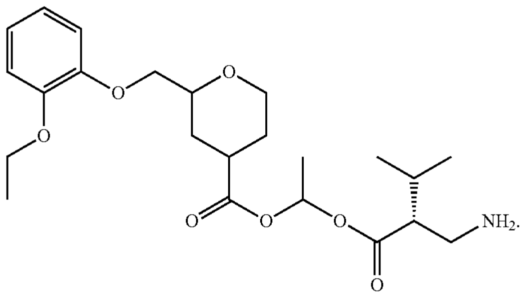

SP-27

In further embodiments, this reaction mixture further comprises cesium carbonate. In other embodiments, the reaction mixture further comprises methanol.

In some embodiments, Intermediate 3 is used to prepare 1-(((R)-2-(aminomethyl)-3-methylbutanoyl)oxy)ethyl 2-((2-ethoxyphenoxy)methyl)morpholine-4-carboxylate (SP-28), comprising:

(a) forming SP-28A by reacting Intermediate 3 with a reaction mixture comprising Boc-Val-Val; and

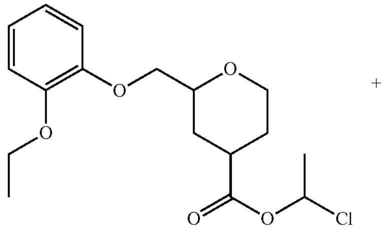

Intermediate 3

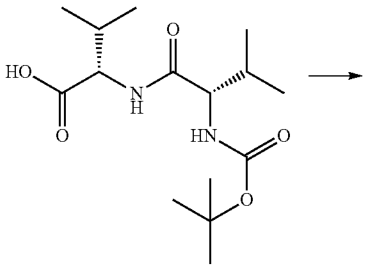

-continued

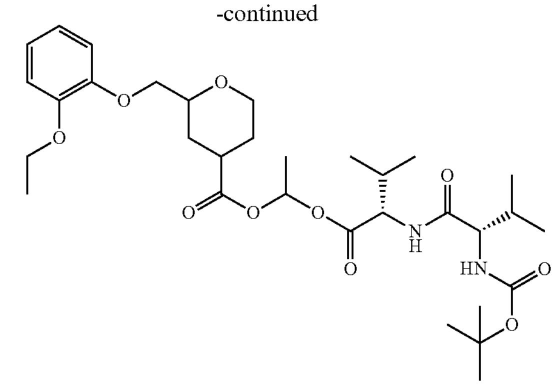

SP-28A (b) stirring a solution of SP-28A in chloroform and trifluoroacetic acid

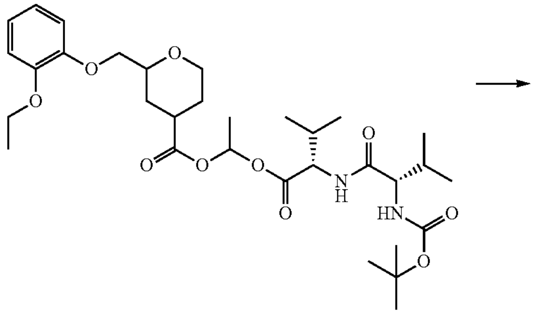

SP-28A

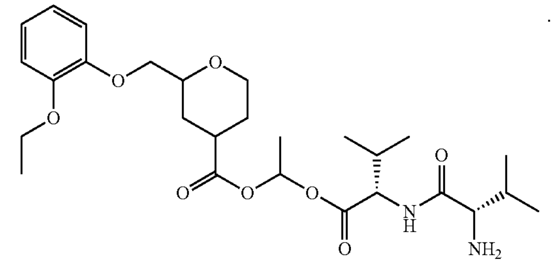

SP-28

In further embodiments, this reaction mixture further comprises cesium carbonate. In some embodiments, the reaction mixture further comprises methanol.

In one embodiment, a process for preparing (2R)-2-amino-N-((2-((2-ethoxyphenoxy)methyl)morpholino) methyl)-3-methylbutanamide (SP-18) is provided, comprising:

(a) forming SP-18A by reacting 2-((2-ethoxyphenoxy) methyl)morpholine and a reaction mixture comprising polyformaldehyde; and

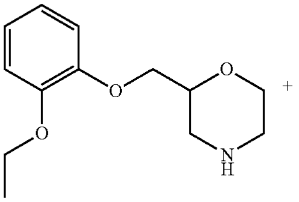

-continued

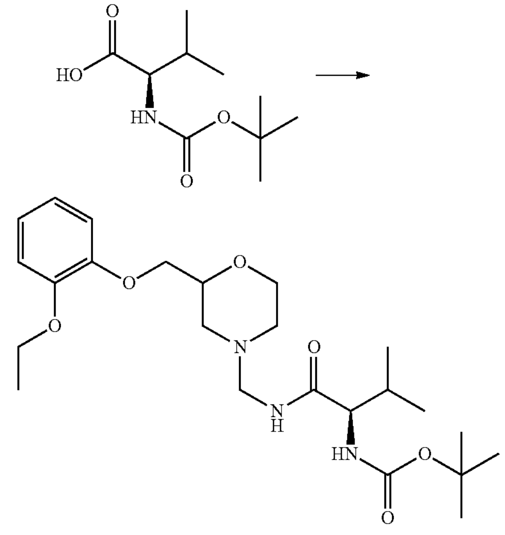

SP-18A (b) reacting SP-18A with dioxane in an organic acid

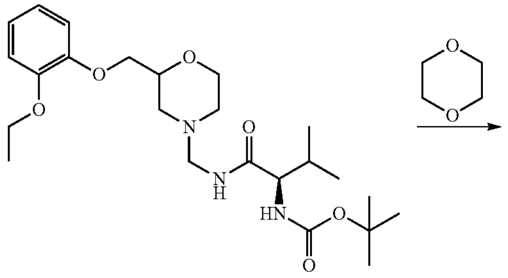

SP-18A

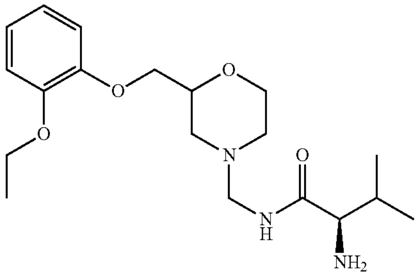

SP-18

In further embodiments, this reaction mixture further comprises tetrahydrofuran. In some embodiments, the organic acid is hydrochloric acid.

In another embodiment, a process for preparing pyridine-2-yl 2((2-ethoxyphenoxy)methyl)morpholine-4-carboxylate (SP-19) is provided, comprising:

(a) forming pyridine-2-yl carbonochloridate by reacting 2-hydroxypyridine with a reaction mixture comprising N,N-diisopropylethylamine; and

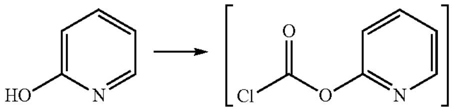

(b) reacting the pyridine-2-yl carbonochloridate with a second reaction mixture comprising 2-((2-ethoxyphenoxy)methyl)morpholine

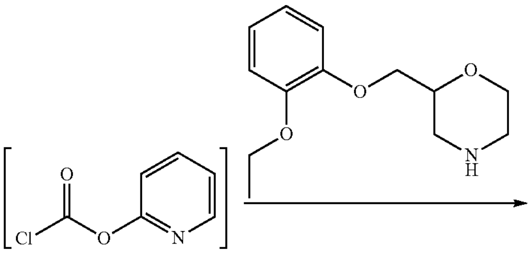

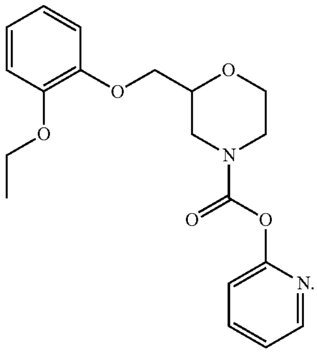

SP-19

In further embodiments, this reaction mixture comprises triphosgene. In some embodiments, the reaction mixture comprises dichloromethane. In other embodiments, the second reaction mixture comprises dichloromethane. In yet other embodiments, the second reaction mixture comprises triethylamine.

In one embodiment, a process for preparing methylene bis(2-((2-ethoxyphenoxy)methyl)morpholine-4-carboxylate (SP-21) is provided, comprising:

reacting (2-((2-ethoxyphenoxy)methyl)morpholine with a reaction mixture comprising methylene dibromide

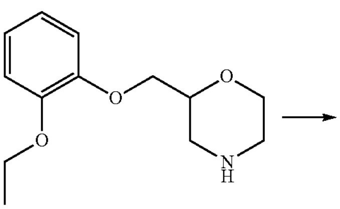

-continued

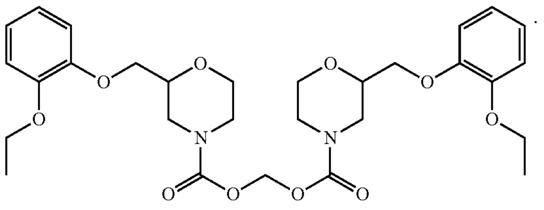

SP-21

In further embodiments, the reaction mixture comprises dimethyl formamide. In some embodiments, carbon dioxide gas is passed over the reaction mixture.

In another embodiment, a process for preparing 1-((D-valyl)oxy)-2-methylpropyl 2-((2-ethoxyphenoxy)methyl)-morphiline-4-carboxylate (SP-26) is provided, comprising:

(a) forming SP-26A by reacting (2-((2-ethoxyphenoxy)-methyl)morpholine and a first reaction mixture comprising 1-chloro-2-methylpropylchloroformate;

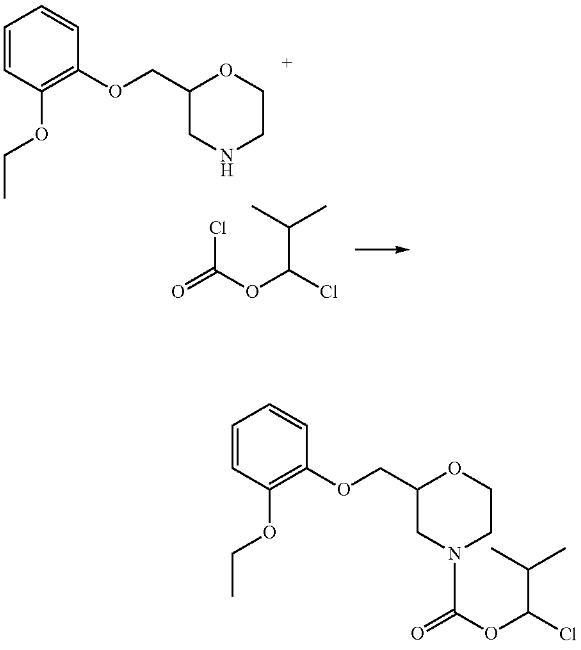

SP-26A (b) forming SP-26B by reacting SP-26A and a second reaction mixture comprising N-Boc-D-Valine; and

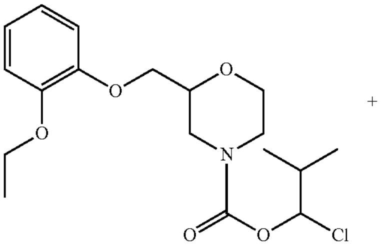

SP-26A

-continued

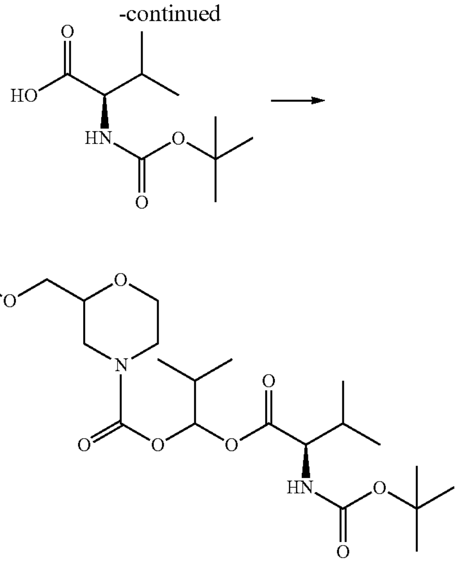

SP-26B (c) reacting SP-26B with dioxane in an organic acid

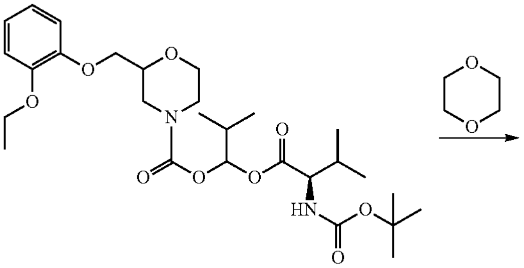

SP-26B

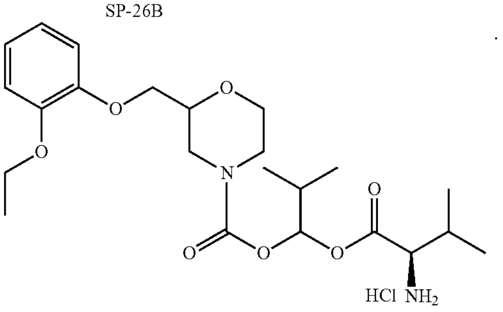

SP-26

In a further embodiment, the first reaction mixture comprises trimethylamine. In some embodiments, the first reaction mixture comprises dichloromethane. In other embodiments, the second reaction mixture comprises cesium carbonate. In some embodiments, the second reaction mixture comprises methanol. In other embodiments, the organic acid is hydrochloric acid.

Other embodiments are set forth in the following claims.

What is claimed is:

1. A method for treating a central nervous system disorder, the method comprising administering to a subject in need thereof a compound of Formula I, a stereoisomer thereof, or a salt thereof:

(I)

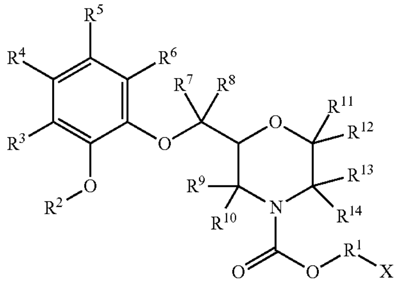

wherein:

$R^1$ is alkyl, heterocyclyl, or a pyridyl;

$R^2$ is alkyl, aryl, heteroaryl, or heterocyclyl;

$R^3$-$R^{14}$ are each independently H, F, Cl, Br, I, CN, $NO_2$, alkyl, aryl, heteroaryl, or heterocyclyl; and X is halogen, an amino acid residue, a substituted amino acid residue, or ester, wherein X may also be H but only when $R^1$ is pyridyl.

2. The method of claim 1, wherein X is an amino acid residue.

3. The method of claim 2, wherein the amino acid residue is valine.

4. The method of claim 3, wherein $R^1$ is $CH_2$, $CH_3CH$, or $(CH_3)_2CHCH$.

5. The method of claim 1, wherein the compound has the following structure:

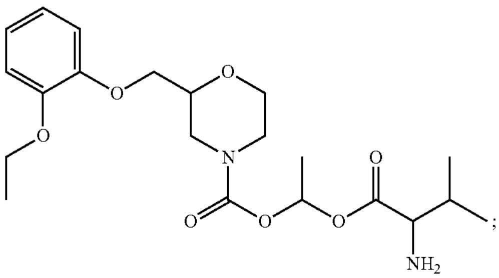

; or

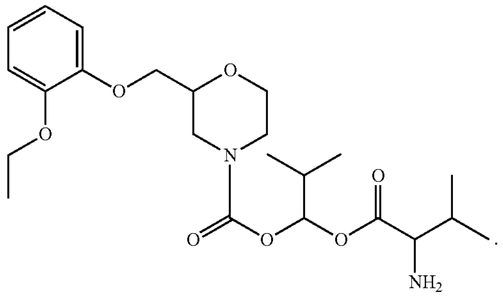

6. The method of claim 1, comprising administering to the subject a salt of a compound having the following structure:

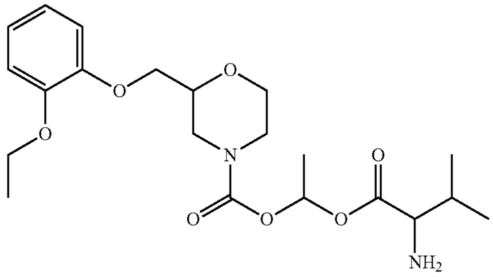

; or

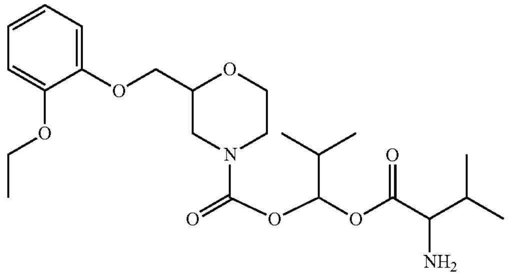

.

7. The method of claim 1, wherein the compound has the following structure:

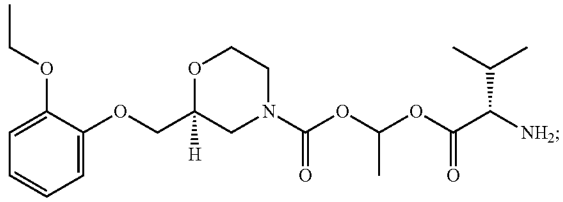

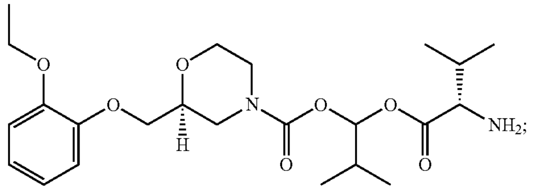

or

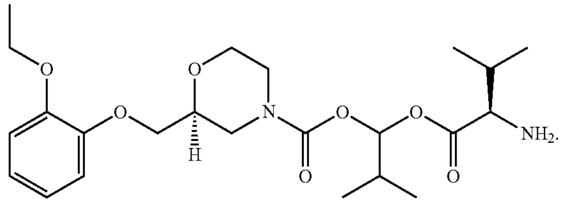

8. The method of claim 1, wherein the compound has the following structure:

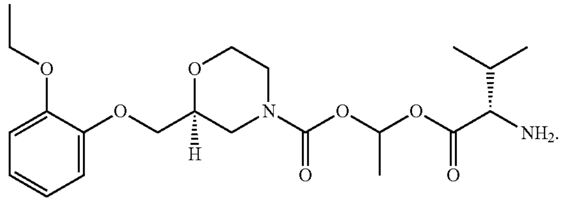 [SMILES: CCOc1ccccc1OC[C@@H]1CN(C(=O)OC(C)OC(=O)[C@@H](N)C(C)C)CCO1]

9. The method of claim 1, wherein the compound has the following structure:

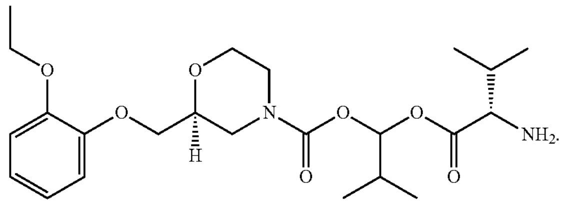 [SMILES: CCOc1ccccc1OC[C@@H]1CN(C(=O)OC(OC(=O)[C@@H](N)C(C)C)C(C)C)CCO1]

10. The method of claim 1, wherein the compound has the following structure:

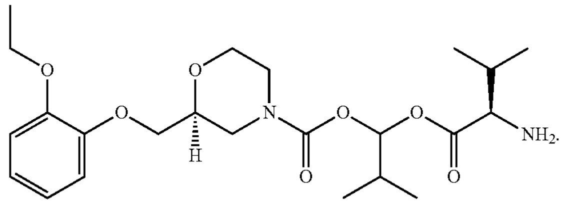 [SMILES: CCOc1ccccc1OC[C@@H]1CN(C(=O)OC(OC(=O)[C@H](N)C(C)C)C(C)C)CCO1]

11. The method of claim 1, wherein the disorder is selected from the group consisting of depression, attention deficit hyperactivity disorder (ADHD), sleep disorders, apathy, cognition, anxiety, orthostatic hypotension, pain, and neurological disorders.

12. The method of claim 1, wherein the disorder is a sleep disorder.

13. The method of claim 12, wherein the administering is performed during an inactive or sleep phase.

14. The method of claim 12, wherein the sleep disorder is narcolepsy, cataplexy, or a REM sleep behavior disorder.

15. The method of claim 1, wherein the disorder is ADHD.

16. The method of claim 1, wherein the disorder is a neurological disorder selected from the group consisting of Parkinson's disease, Alzheimer's disease, Lewy body dementia, and multiple system atrophy.

17. The method of claim 1, wherein the disorder comprises pain.

18. The method of claim 1, wherein the disorder is a neuropsychiatric disorder.

19. The method of claim 1, wherein the disorder is anxiety or depression.

* * * * *